US008642751B2

(12) United States Patent
Dalby et al.

(10) Patent No.: US 8,642,751 B2
(45) Date of Patent: Feb. 4, 2014

(54) MICRORNA INHIBITORS COMPRISING LOCKED NUCLEOTIDES

(75) Inventors: Christina Dalby, Boulder, CO (US);
William S. Marshall, Boulder, CO (US);
Eva van Rooij, Boulder, CO (US);
Rusty Montgomery, Boulder, CO (US)

(73) Assignee: miRagen Therapeutics, Boulder, CO (US)

( * ) Notice: Subject to any disclaimer, the term of this patent is extended or adjusted under 35 U.S.C. 154(b) by 0 days.

(21) Appl. No.: 13/327,507

(22) Filed: Dec. 15, 2011

(65) Prior Publication Data

US 2012/0184596 A1 Jul. 19, 2012

Related U.S. Application Data

(60) Provisional application No. 61/423,456, filed on Dec. 15, 2010, provisional application No. 61/495,224, filed on Jun. 9, 2011.

(51) Int. Cl.
*C07H 21/04* (2006.01)

(52) U.S. Cl.
USPC .......................................................... 536/24.5

(58) Field of Classification Search
None
See application file for complete search history.

(56) References Cited

U.S. PATENT DOCUMENTS

| | | | |
|---|---|---|---|
| 7,232,806 B2 | 6/2007 | Tuschl et al. | |
| 7,687,617 B2 | 3/2010 | Thrue et al. | |
| 8,222,221 B2 | 7/2012 | Corey et al. | |
| 8,304,397 B2* | 11/2012 | Olson et al. | 424/93.1 |
| 8,481,507 B2 | 7/2013 | Olson et al. | |
| 2005/0059005 A1 | 3/2005 | Tuschl et al. | |
| 2006/0185027 A1 | 8/2006 | Bartel et al. | |
| 2007/0287179 A1 | 12/2007 | Tuschl et al. | |
| 2007/0292878 A1 | 12/2007 | Raymond | |
| 2008/0050744 A1 | 2/2008 | Brown et al. | |
| 2008/0176766 A1 | 7/2008 | Brown et al. | |
| 2008/0214437 A1 | 9/2008 | Mohapatra et al. | |
| 2009/0105174 A1 | 4/2009 | Jayasena | |
| 2009/0137504 A1 | 5/2009 | Echwald et al. | |
| 2009/0143326 A1 | 6/2009 | Obad et al. | |
| 2009/0180957 A1* | 7/2009 | Olson et al. | 424/9.1 |
| 2009/0286969 A1 | 11/2009 | Esau et al. | |
| 2009/0291906 A1 | 11/2009 | Esau et al. | |
| 2009/0291907 A1 | 11/2009 | Esau et al. | |
| 2009/0293148 A1 | 11/2009 | Ren et al. | |
| 2009/0326049 A1 | 12/2009 | Aristarkhov et al. | |
| 2010/0004320 A1* | 1/2010 | Elmen et al. | 514/44 R |
| 2010/0029003 A1 | 2/2010 | Bartel et al. | |
| 2010/0173288 A1 | 7/2010 | Zhang et al. | |
| 2010/0210712 A1 | 8/2010 | Hansen et al. | |
| 2010/0269183 A1 | 10/2010 | Olson et al. | |
| 2010/0280094 A1 | 11/2010 | Beuvink et al. | |
| 2010/0292297 A1 | 11/2010 | Wang et al. | |
| 2010/0298410 A1 | 11/2010 | Obad et al. | |
| 2011/0071211 A1* | 3/2011 | Thum et al. | 514/44 A |
| 2011/0098338 A1 | 4/2011 | Hajjar et al. | |
| 2011/0105593 A1 | 5/2011 | Steel et al. | |
| 2011/0117560 A1 | 5/2011 | Spinale et al. | |
| 2011/0152352 A1 | 6/2011 | Hata et al. | |
| 2011/0160285 A1 | 6/2011 | Anderson et al. | |
| 2011/0224277 A1 | 9/2011 | Esau et al. | |
| 2011/0294869 A1 | 12/2011 | Petersen | |
| 2011/0313019 A1 | 12/2011 | Swayze et al. | |
| 2012/0035243 A1 | 2/2012 | Olson et al. | |
| 2012/0041052 A1 | 2/2012 | Beuvink et al. | |
| 2012/0083596 A1 | 4/2012 | Elmén et al. | |
| 2012/0114744 A1 | 5/2012 | Beuvink et al. | |
| 2012/0172416 A1 | 7/2012 | Velin et al. | |
| 2012/0322851 A1 | 12/2012 | Hardee et al. | |
| 2013/0078225 A1 | 3/2013 | Zeng et al. | |
| 2013/0079505 A1 | 3/2013 | Moeller et al. | |
| 2013/0096290 A1 | 4/2013 | Brown | |
| 2013/0109738 A1 | 5/2013 | Chang et al. | |
| 2013/0137753 A1 | 5/2013 | Samant et al. | |
| 2013/0150256 A1 | 6/2013 | Synnergren et al. | |
| 2013/0156845 A1 | 6/2013 | Manoharan et al. | |
| 2013/0157883 A1 | 6/2013 | Keller et al. | |
| 2013/0171242 A1 | 7/2013 | Lim et al. | |

FOREIGN PATENT DOCUMENTS

| | | |
|---|---|---|
| EP | 1959012 A2 | 8/2008 |
| EP | 2113567 A1 | 11/2009 |
| EP | 2194129 A2 | 6/2010 |
| EP | 2208798 A1 | 7/2010 |
| EP | 2388327 A1 | 11/2011 |
| EP | 2388328 A1 | 11/2011 |
| EP | 2447274 A2 | 5/2012 |

(Continued)

OTHER PUBLICATIONS

International Preliminary Report on Patentability, PCT appl..No. PCT/US2011/065121, 9 pages (Jun. 18, 2013).
International Search Report, PCT appl..No. PCT/US2011/065121, 5 pages (Jun. 5, 2012).
Montgomery et al., "Therapeutic Inhibition of miR-208a Improves Cardiac Function and Survival During Heart Failue," Circ. 124(14):1537-1547, Supplemental Material (2011).
Written Opinion of the International Searching Authority, PCT appl.. No. PCT/US2011/065121, 8 pages (Jun. 5, 2012).

*Primary Examiner* — Richard Schnizer
(74) *Attorney, Agent, or Firm* — Cooley LLP

(57) ABSTRACT

The invention provides chemically modified oligonucleotides capable of inhibiting the expression (e.g., abundance) of miR-208 family miRNAs, including miR-208a, miR-208b, and/or miR-499. The invention provides in some embodiments, oligonucleotides capable of inhibiting, in a specific fashion, the expression or abundance of each of miR-208a, miR-208b, and miR-499. The invention further provides pharmaceutical compositions comprising the oligonucleotides, and methods of treating patients having conditions or disorders relating to or involving a miR-208 family miRNA, such as a cardiovascular condition. In various embodiments, the oligonucleotides provide advantages in one or more of potency, efficiency of delivery, target specificity, toxicity, and/or stability.

13 Claims, 39 Drawing Sheets

(56) References Cited

FOREIGN PATENT DOCUMENTS

| | | |
|---|---|---|
| EP | 2205737 B1 | 2/2013 |
| EP | 2559442 A1 | 2/2013 |
| EP | 2604690 A1 | 6/2013 |
| EP | 2610342 A1 | 7/2013 |
| WO | WO 2005/013901 A2 | 2/2005 |
| WO | WO 2005/017145 A1 | 2/2005 |
| WO | WO 2005/078096 A2 | 8/2005 |
| WO | WO 2005/078139 A2 | 8/2005 |
| WO | WO 2005/079397 A2 | 9/2005 |
| WO | WO 2005/118806 A2 | 12/2005 |
| WO | WO 2006/063356 A1 | 6/2006 |
| WO | WO 2006/111512 A1 | 10/2006 |
| WO | WO 2006/137941 A2 | 12/2006 |
| WO | WO 2007/000668 A2 | 1/2007 |
| WO | WO 2007/070483 A2 | 6/2007 |
| WO | WO 2007/090073 A2 | 8/2007 |
| WO | WO 2007/112754 A2 | 10/2007 |
| WO | WO 2008/016924 A2 | 2/2008 |
| WO | WO 2008/042231 A2 | 4/2008 |
| WO | WO 2008/043521 A2 | 4/2008 |
| WO | WO 2008/061537 A2 | 5/2008 |
| WO | WO 2008/074328 A2 | 6/2008 |
| WO | WO 2008/076324 A2 | 6/2008 |
| WO | WO 2008/147839 A1 | 12/2008 |
| WO | WO 2009/026576 A1 | 2/2009 |
| WO | WO 2009/043353 A2 | 4/2009 |
| WO | WO 2009/058818 A2 | 5/2009 |
| WO | WO 2009/062169 A2 | 5/2009 |
| WO | WO 2009/114681 A2 | 9/2009 |
| WO | WO 2009/149182 A1 | 12/2009 |
| WO | WO 2010/048585 A2 | 4/2010 |
| WO | WO 2010/091204 A1 | 8/2010 |
| WO | WO 2010/144485 A1 | 12/2010 |
| WO | WO 2011/139911 A2 | 11/2011 |
| WO | WO 2011/154553 A2 | 12/2011 |
| WO | WO 2011/158191 A1 | 12/2011 |
| WO | WO 2012/006577 A2 | 1/2012 |
| WO | WO 2012/020307 A2 | 2/2012 |
| WO | WO 2012/027206 A1 | 3/2012 |
| WO | WO 2012/149646 A1 | 11/2012 |
| WO | WO 2013/052965 A2 | 4/2013 |
| WO | WO 2013/054113 A1 | 4/2013 |
| WO | WO 2013/057527 A2 | 4/2013 |
| WO | WO 2013/059496 A1 | 4/2013 |
| WO | WO 2013/087907 A1 | 6/2013 |
| WO | WO 2013/088338 A1 | 6/2013 |
| WO | WO 2013/090457 A2 | 6/2013 |

\* cited by examiner

FIGURE 9

| | | 1 | 2 | 3 | 4 | 5 | 6 | 7 | 8 | 9 | 10 | 11 | 12 | 13 | 14 | 15 | 16 | 17 | 18 | 19 | 20 | 21 | 22 |
|---|---|---|---|---|---|---|---|---|---|---|---|---|---|---|---|---|---|---|---|---|---|---|---|
| miR-208a | 5' | A | U | A | A | G | A | C | G | A | G | C | A | A | A | A | A | G | C | U | U | G | U |
| AUAAGACGAGCAAAAAGCUUGU (SEQ ID NO:94) | | | | | | | | | | | | | | | | | | | | | | | |
| miR-208a RC ACAAGCTTTTTGCTCGTCTTAT (SEQ ID NO:95) | 5' | | | | | | | C | T | T | T | T | G | C | T | T | G | T | C | T | T | A | T |
| | %LNA | | | | | | | 20% | 88% | 88% | 13% | 90% | 10% | 70% | 60% | 90% | 10% | 30% | 90% | 30% | 100% | 100% | 30% |
| | %DNA | | | | | | | 80% | 13% | 13% | 88% | 10% | 90% | 30% | 40% | 10% | 90% | 70% | 10% | 70% | 0% | 0% | 70% |

| | | 1 | 2 | 3 | 4 | 5 | 6 | 7 | 8 | 9 | 10 | 11 | 12 | 13 | 14 | 15 | 16 | 17 | 18 | 19 | 20 | 21 | 22 |
|---|---|---|---|---|---|---|---|---|---|---|---|---|---|---|---|---|---|---|---|---|---|---|---|
| miR-208b | 5' | A | U | A | A | G | A | C | G | A | A | C | A | A | A | A | G | G | U | U | U | G | U |
| AUAAGACGAACAAAAGGUUUGU (SEQ ID NO:97) | | | | | | | | | | | | | | | | | | | | | | | |
| miR-208b RC ACAAACCTTTTTGTTCGTCTTAT (SEQ ID NO:98) | 5' | | | | | | | C | C | T | T | T | G | T | T | C | G | T | C | T | T | A | T |
| | %LNA | | | | | | | 20% | 78% | 90% | 10% | 100% | 0% | 60% | 0% | 100% | 20% | 30% | 100% | 30% | 90% | 60% | 50% |
| | %DNA | | | | | | | 80% | 22% | 10% | 90% | 0% | 100% | 40% | 100% | 0% | 80% | 70% | 0% | 70% | 10% | 40% | 50% |

SEQUENCE LISTING

```
<160> NUMBER OF SEQ ID NOS: 99

<210> SEQ ID NO 1
<211> LENGTH: 11
<212> TYPE: DNA
<213> ORGANISM: Homo sapiens

<400> SEQUENCE: 1
tgctcgtctt a                                                         11

<210> SEQ ID NO 2
<211> LENGTH: 11
<212> TYPE: DNA
<213> ORGANISM: Homo sapiens

<400> SEQUENCE: 2
tgttcgtctt a                                                         11

<210> SEQ ID NO 3
<211> LENGTH: 16
<212> TYPE: DNA
<213> ORGANISM: Homo sapiens

<400> SEQUENCE: 3 cttttttgctc gtctta                                                    16

<210> SEQ ID NO 4
<211> LENGTH: 16
<212> TYPE: DNA
<213> ORGANISM: Homo sapiens

<400> SEQUENCE: 4 cctttttgttc gtctta                                                    16

<210> SEQ ID NO 5
<211> LENGTH: 71
<212> TYPE: RNA
<213> ORGANISM: Homo sapiens

<400> SEQUENCE: 5
acgggcgagc uuuuggcccg gguuauaccu gaugcucacg uauaagacga gcaaaaagcu     60
uguuggucag a                                                         71
```

<210> SEQ ID NO 6
<211> LENGTH: 22
<212> TYPE: RNA
<213> ORGANISM: Homo sapiens

<400> SEQUENCE: 6
auaagacgaa caaaagguuu gu                                              22

<210> SEQ ID NO 7
<211> LENGTH: 21
<212> TYPE: RNA
<213> ORGANISM: Homo sapiens

<400> SEQUENCE: 7
uuaagacuug cagugauguu u                                               21

<210> SEQ ID NO 8
<211> LENGTH: 16
<212> TYPE: RNA
<213> ORGANISM: Homo sapiens

<400> SEQUENCE: 8
uaagacgagc aaaaag                                                     16

<210> SEQ ID NO 9
<211> LENGTH: 16
<212> TYPE: RNA
<213> ORGANISM: Homo sapiens

<400> SEQUENCE: 9
uaagacgaac aaaaag                                                     16

<210> SEQ ID NO 10
<211> LENGTH: 16
<212> TYPE: DNA
<213> ORGANISM: Artificial Sequence
<220> FEATURE:
<223> OTHER INFORMATION: Anti-miR-208 oligonucleotide
<220> FEATURE:
<221> NAME/KEY: misc_feature
<222> LOCATION: (1)..(1)
<223> OTHER INFORMATION: May be locked nucleic acid cytidine
      phosphorothioate
<220> FEATURE:
<221> NAME/KEY: misc_feature
<222> LOCATION: (2)..(4)
<223> OTHER INFORMATION: May be deoxy thymidine phosphorothioate
<220> FEATURE:
<221> NAME/KEY: misc_feature
<222> LOCATION: (5)..(6)
<223> OTHER INFORMATION: May be locked nucleic acid thymidine
      phosphorothioate
<220> FEATURE:
<221> NAME/KEY: misc_feature
<222> LOCATION: (7)..(7)
<223> OTHER INFORMATION: May be deoxy guanosine phosphorothioate
<220> FEATURE:
<221> NAME/KEY: misc_feature
<222> LOCATION: (8)..(8)
<223> OTHER INFORMATION: May be locked nucleic acid cytidine
      phosphorothioate
<220> FEATURE:
<221> NAME/KEY: misc_feature
<222> LOCATION: (9)..(9)
<223> OTHER INFORMATION: May be deoxy thymidine phosphorothioate
<220> FEATURE:
<221> NAME/KEY: misc_feature
<222> LOCATION: (10)..(10)
<223> OTHER INFORMATION: May be locked nucleic acid cytidine
      phosphorothioate

```
<220> FEATURE:
<221> NAME/KEY: misc_feature
<222> LOCATION: (11)..(11)
<223> OTHER INFORMATION: May be locked nucleic acid guanosine
      phosphorothioate
<220> FEATURE:
<221> NAME/KEY: misc_feature
<222> LOCATION: (12)..(12)
<223> OTHER INFORMATION: May be deoxy thymidine phosphorothioate
<220> FEATURE:
<221> NAME/KEY: misc_feature
<222> LOCATION: (13)..(13)
<223> OTHER INFORMATION: May be locked nucleic acid cytidine
      phosphorothioate
<220> FEATURE:
<221> NAME/KEY: misc_feature
<222> LOCATION: (14)..(14)
<223> OTHER INFORMATION: May be deoxy thymidine phosphorothioate
<220> FEATURE:
<221> NAME/KEY: misc_feature
<222> LOCATION: (15)..(15)
<223> OTHER INFORMATION: May be locked nucleic acid thymidine
      phosphorothioate
<220> FEATURE:
<221> NAME/KEY: misc_feature
<222> LOCATION: (16)..(16)
<223> OTHER INFORMATION: May be locked nucleic acid adenosine

<400> SEQUENCE: 10 cttttgctc gtctta                                                    16

<210> SEQ ID NO 11
<211> LENGTH: 11
<212> TYPE: DNA
<213> ORGANISM: Artificial Sequence
<220> FEATURE:
<223> OTHER INFORMATION: Anti-miR-208 oligonucleotide
<220> FEATURE:
<221> NAME/KEY: misc_feature
<222> LOCATION: (1)..(1)
<223> OTHER INFORMATION: May be locked nucleic acid thymidine
      phosphorothioate
<220> FEATURE:
<221> NAME/KEY: misc_feature
<222> LOCATION: (2)..(2)
<223> OTHER INFORMATION: May be deoxy guanosine phosphorothioate
<220> FEATURE:
<221> NAME/KEY: misc_feature
<222> LOCATION: (3)..(3)
<223> OTHER INFORMATION: May be locked nucleic acid cytidine
      phosphorothioate
<220> FEATURE:
<221> NAME/KEY: misc_feature
<222> LOCATION: (4)..(4)
<223> OTHER INFORMATION: May be locked nucleic acid thymidine
      phosphorothioate
<220> FEATURE:
<221> NAME/KEY: misc_feature
<222> LOCATION: (5)..(5)
<223> OTHER INFORMATION: May be locked nucleic acid cytidine
      phosphorothioate
<220> FEATURE:
<221> NAME/KEY: misc_feature
<222> LOCATION: (6)..(6)
<223> OTHER INFORMATION: May be deoxy guanosine phosphorothioate
<220> FEATURE:
<221> NAME/KEY: misc_feature
<222> LOCATION: (7)..(7)
<223> OTHER INFORMATION: May be locked nucleic acid thymidine
      phosphorothioate
<220> FEATURE:
<221> NAME/KEY: misc_feature
<222> LOCATION: (8)..(8)
<223> OTHER INFORMATION: May be locked nucleic acid cytidine
      phosphorothioate
<220> FEATURE:
<221> NAME/KEY: misc_feature
<222> LOCATION: (9)..(9)
```

```
<223> OTHER INFORMATION: May be deoxy thymidine phosphorothioate
<220> FEATURE:
<221> NAME/KEY: misc_feature
<222> LOCATION: (10)..(10)
<223> OTHER INFORMATION: May be locked nucleic acid thymidine
      phosphorothioate
<220> FEATURE:
<221> NAME/KEY: misc_feature
<222> LOCATION: (11)..(11)
<223> OTHER INFORMATION: May be locked nucleic acid adenosine

<400> SEQUENCE: 11
tgctcgtctt a                                                           11

<210> SEQ ID NO 12
<211> LENGTH: 11
<212> TYPE: DNA
<213> ORGANISM: Artificial Sequence
<220> FEATURE:
<223> OTHER INFORMATION: Anti-miR-208 oligonucleotide
<220> FEATURE:
<221> NAME/KEY: misc_feature
<222> LOCATION: (1)..(1)
<223> OTHER INFORMATION: May be locked nucleic acid thymidine
      phosphorothioate
<220> FEATURE:
<221> NAME/KEY: misc_feature
<222> LOCATION: (2)..(2)
<223> OTHER INFORMATION: May be deoxy guanosine phosphorothioate
<220> FEATURE:
<221> NAME/KEY: misc_feature
<222> LOCATION: (3)..(3)
<223> OTHER INFORMATION: May be locked nucleic acid cytidine
      phosphorothioate
<220> FEATURE:
<221> NAME/KEY: misc_feature
<222> LOCATION: (4)..(4)
<223> OTHER INFORMATION: May be locked nucleic acid thymidine
      phosphorothioate
<220> FEATURE:
<221> NAME/KEY: misc_feature
<222> LOCATION: (5)..(5)
<223> OTHER INFORMATION: May be locked nucleic acid cytidine
      phosphorothioate
<220> FEATURE:
<221> NAME/KEY: misc_feature
<222> LOCATION: (6)..(6)
<223> OTHER INFORMATION: May be deoxy guanosine phosphorothioate
<220> FEATURE:
<221> NAME/KEY: misc_feature
<222> LOCATION: (7)..(7)
<223> OTHER INFORMATION: May be deoxy thymidine phosphorothioate
<220> FEATURE:
<221> NAME/KEY: misc_feature
<222> LOCATION: (8)..(8)
<223> OTHER INFORMATION: May be locked nucleic acid cytidine
      phosphorothioate
<220> FEATURE:
<221> NAME/KEY: misc_feature
<222> LOCATION: (9)..(9)
<223> OTHER INFORMATION: May be deoxy thymidine phosphorothioate
<220> FEATURE:
<221> NAME/KEY: misc_feature
<222> LOCATION: (10)..(10)
<223> OTHER INFORMATION: May be locked nucleic acid thymidine
      phosphorothioate
<220> FEATURE:
<221> NAME/KEY: misc_feature
<222> LOCATION: (11)..(11)
<223> OTHER INFORMATION: May be locked nucleic acid adenosine

<400> SEQUENCE: 12
tgctcgtctt a                                                           11

<210> SEQ ID NO 13
<211> LENGTH: 11
```

```
<212> TYPE: DNA
<213> ORGANISM: Artificial Sequence
<220> FEATURE:
<223> OTHER INFORMATION: Anti-miR-208 oligonucleotide
<220> FEATURE:
<221> NAME/KEY: misc_feature
<222> LOCATION: (1)..(1)
<223> OTHER INFORMATION: May be locked nucleic acid thymidine
      phosphorothioate
<220> FEATURE:
<221> NAME/KEY: misc_feature
<222> LOCATION: (2)..(2)
<223> OTHER INFORMATION: May be deoxy guanosine phosphorothioate
<220> FEATURE:
<221> NAME/KEY: misc_feature
<222> LOCATION: (3)..(3)
<223> OTHER INFORMATION: May be locked nucleic acid cytidine
      phosphorothioate
<220> FEATURE:
<221> NAME/KEY: misc_feature
<222> LOCATION: (4)..(4)
<223> OTHER INFORMATION: May be deoxy adenosine phosphorothioate
<220> FEATURE:
<221> NAME/KEY: misc_feature
<222> LOCATION: (5)..(5)
<223> OTHER INFORMATION: May be locked nucleic acid cytidine
      phosphorothioate
<220> FEATURE:
<221> NAME/KEY: misc_feature
<222> LOCATION: (6)..(6)
<223> OTHER INFORMATION: May be deoxy guanosine phosphorothioate
<220> FEATURE:
<221> NAME/KEY: misc_feature
<222> LOCATION: (7)..(7)
<223> OTHER INFORMATION: May be locked nucleic acid thymidine
      phosphorothioate
<220> FEATURE:
<221> NAME/KEY: misc_feature
<222> LOCATION: (8)..(8)
<223> OTHER INFORMATION: May be deoxy cytidine phosphorothioate
<220> FEATURE:
<221> NAME/KEY: misc_feature
<222> LOCATION: (9)..(10)
<223> OTHER INFORMATION: May be locked nucleic acid thymidine
      phosphorothioate
<220> FEATURE:
<221> NAME/KEY: misc_feature
<222> LOCATION: (11)..(11)
<223> OTHER INFORMATION: May be locked nucleic acid adenosine

<400> SEQUENCE: 13
tgcacgtctt a                                                          11

<210> SEQ ID NO 14
<211> LENGTH: 11
<212> TYPE: DNA
<213> ORGANISM: Artificial Sequence
<220> FEATURE:
<223> OTHER INFORMATION: Anti-miR-208 oligonucleotide
<220> FEATURE:
<221> NAME/KEY: misc_feature
<222> LOCATION: (1)..(1)
<223> OTHER INFORMATION: May be locked nucleic acid thymidine
      phosphorothioate
<220> FEATURE:
<221> NAME/KEY: misc_feature
<222> LOCATION: (2)..(2)
<223> OTHER INFORMATION: May be locked nucleic acid guanosine
      phosphorothioate
<220> FEATURE:
<221> NAME/KEY: misc_feature
<222> LOCATION: (3)..(3)
<223> OTHER INFORMATION: May be deoxy cytidine phosphorothioate
<220> FEATURE:
<221> NAME/KEY: misc_feature
<222> LOCATION: (4)..(4)
<223> OTHER INFORMATION: May be deoxy adenosine phosphorothioate
<220> FEATURE:
```

```
<221> NAME/KEY: misc_feature
<222> LOCATION: (5)..(5)
<223> OTHER INFORMATION: May be locked nucleic acid cytidine
      phosphorothioate
<220> FEATURE:
<221> NAME/KEY: misc_feature
<222> LOCATION: (6)..(6)
<223> OTHER INFORMATION: May be locked nucleic acid guanosine
      phosphorothioate
<220> FEATURE:
<221> NAME/KEY: misc_feature
<222> LOCATION: (7)..(7)
<223> OTHER INFORMATION: May be deoxy thymidine phosphorothioate
<220> FEATURE:
<221> NAME/KEY: misc_feature
<222> LOCATION: (8)..(8)
<223> OTHER INFORMATION: May be locked nucleic acid cytidine
      phosphorothioate
<220> FEATURE:
<221> NAME/KEY: misc_feature
<222> LOCATION: (9)..(9)
<223> OTHER INFORMATION: May be deoxy thymidine phosphorothioate
<220> FEATURE:
<221> NAME/KEY: misc_feature
<222> LOCATION: (10)..(10)
<223> OTHER INFORMATION: May be locked nucleic acid thymidine
      phosphorothioate
<220> FEATURE:
<221> NAME/KEY: misc_feature
<222> LOCATION: (11)..(11)
<223> OTHER INFORMATION: May be locked nucleic acid adenosine

<400> SEQUENCE: 14
tgcacgtctt a                                                          11

<210> SEQ ID NO 15
<211> LENGTH: 16
<212> TYPE: DNA
<213> ORGANISM: Artificial Sequence
<220> FEATURE:
<223> OTHER INFORMATION: Anti-miR-208 oligonucleotide
<220> FEATURE:
<221> NAME/KEY: misc_feature
<222> LOCATION: (1)..(1)
<223> OTHER INFORMATION: May be locked nucleic acid cytidine
      phosphorothioate
<220> FEATURE:
<221> NAME/KEY: misc_feature
<222> LOCATION: (2)..(2)
<223> OTHER INFORMATION: May be deoxy thymidine phosphorothioate
<220> FEATURE:
<221> NAME/KEY: misc_feature
<222> LOCATION: (3)..(6)
<223> OTHER INFORMATION: May be locked nucleic acid thymidine
      phosphorothioate
<220> FEATURE:
<221> NAME/KEY: misc_feature
<222> LOCATION: (7)..(7)
<223> OTHER INFORMATION: May be deoxy guanosine phosphorothioate
<220> FEATURE:
<221> NAME/KEY: misc_feature
<222> LOCATION: (8)..(8)
<223> OTHER INFORMATION: May be locked nucleic acid cytidine
      phosphorothioate
<220> FEATURE:
<221> NAME/KEY: misc_feature
<222> LOCATION: (9)..(9)
<223> OTHER INFORMATION: May be deoxy thymidine phosphorothioate
<220> FEATURE:
<221> NAME/KEY: misc_feature
<222> LOCATION: (10)..(10)
<223> OTHER INFORMATION: May be locked nucleic acid cytidine
      phosphorothioate
<220> FEATURE:
<221> NAME/KEY: misc_feature
<222> LOCATION: (11)..(11)
<223> OTHER INFORMATION: May be deoxy guanosine phosphorothioate
<220> FEATURE:
```

```
<221> NAME/KEY: misc_feature
<222> LOCATION: (12)..(12)
<223> OTHER INFORMATION: May be deoxy thymidine phosphorothioate
<220> FEATURE:
<221> NAME/KEY: misc_feature
<222> LOCATION: (13)..(13)
<223> OTHER INFORMATION: May be locked nucleic acid cytidine
      phosphorothioate
<220> FEATURE:
<221> NAME/KEY: misc_feature
<222> LOCATION: (14)..(14)
<223> OTHER INFORMATION: May be deoxy thymidine phosphorothioate
<220> FEATURE:
<221> NAME/KEY: misc_feature
<222> LOCATION: (15)..(15)
<223> OTHER INFORMATION: May be locked nucleic acid thymidine
      phosphorothioate
<220> FEATURE:
<221> NAME/KEY: misc_feature
<222> LOCATION: (16)..(16)
<223> OTHER INFORMATION: May be deoxy adenosine

<400> SEQUENCE: 15 cttttttgctc gtctta                                                     16

<210> SEQ ID NO 16
<211> LENGTH: 16
<212> TYPE: DNA
<213> ORGANISM: Artificial Sequence
<220> FEATURE:
<223> OTHER INFORMATION: Anti-miR-208 oligonucleotide
<220> FEATURE:
<221> NAME/KEY: misc_feature
<222> LOCATION: (1)..(1)
<223> OTHER INFORMATION: May be locked nucleic acid cytidine
      phosphorothioate
<220> FEATURE:
<221> NAME/KEY: misc_feature
<222> LOCATION: (2)..(3)
<223> OTHER INFORMATION: May be deoxy thymidine phosphorothioate
<220> FEATURE:
<221> NAME/KEY: misc_feature
<222> LOCATION: (4)..(6)
<223> OTHER INFORMATION: May be locked nucleic acid thymidine
      phosphorothioate
<220> FEATURE:
<221> NAME/KEY: misc_feature
<222> LOCATION: (7)..(7)
<223> OTHER INFORMATION: May be deoxy guanosine phosphorothioate
<220> FEATURE:
<221> NAME/KEY: misc_feature
<222> LOCATION: (8)..(8)
<223> OTHER INFORMATION: May be locked nucleic acid cytidine
      phosphorothioate
<220> FEATURE:
<221> NAME/KEY: misc_feature
<222> LOCATION: (9)..(9)
<223> OTHER INFORMATION: May be locked nucleic acid thymidine
      phosphorothioate
<220> FEATURE:
<221> NAME/KEY: misc_feature
<222> LOCATION: (10)..(10)
<223> OTHER INFORMATION: May be locked nucleic acid cytidine
      phosphorothioate
<220> FEATURE:
<221> NAME/KEY: misc_feature
<222> LOCATION: (11)..(11)
<223> OTHER INFORMATION: May be deoxy guanosine phosphorothioate
<220> FEATURE:
<221> NAME/KEY: misc_feature
<222> LOCATION: (12)..(12)
<223> OTHER INFORMATION: May be locked nucleic acid thymidine
      phosphorothioate
<220> FEATURE:
<221> NAME/KEY: misc_feature
<222> LOCATION: (13)..(13)
<223> OTHER INFORMATION: May be locked nucleic acid cytidine
      phosphorothioate
```

```
<220> FEATURE:
<221> NAME/KEY: misc_feature
<222> LOCATION: (14)..(15)
<223> OTHER INFORMATION: May be locked nucleic acid thymidine
      phosphorothioate
<220> FEATURE:
<221> NAME/KEY: misc_feature
<222> LOCATION: (16)..(16)
<223> OTHER INFORMATION: May be deoxy adenosine

<400> SEQUENCE: 16 cttttttgctc gtctta                                                      16

<210> SEQ ID NO 17
<211> LENGTH: 16
<212> TYPE: DNA
<213> ORGANISM: Artificial Sequence
<220> FEATURE:
<223> OTHER INFORMATION: Anti-miR-208 oligonucleotide
<220> FEATURE:
<221> NAME/KEY: misc_feature
<222> LOCATION: (1)..(1)
<223> OTHER INFORMATION: May be locked nucleic acid cytidine
      phosphorothioate
<220> FEATURE:
<221> NAME/KEY: misc_feature
<222> LOCATION: (2)..(6)
<223> OTHER INFORMATION: May be locked nucleic acid thymidine
      phosphorothioate
<220> FEATURE:
<221> NAME/KEY: misc_feature
<222> LOCATION: (7)..(7)
<223> OTHER INFORMATION: May be deoxy guanosine phosphorothioate
<220> FEATURE:
<221> NAME/KEY: misc_feature
<222> LOCATION: (8)..(8)
<223> OTHER INFORMATION: May be locked nucleic acid cytidine
      phosphorothioate
<220> FEATURE:
<221> NAME/KEY: misc_feature
<222> LOCATION: (9)..(9)
<223> OTHER INFORMATION: May be locked nucleic acid thymidine
      phosphorothioate
<220> FEATURE:
<221> NAME/KEY: misc_feature
<222> LOCATION: (10)..(10)
<223> OTHER INFORMATION: May be locked nucleic acid cytidine
      phosphorothioate
<220> FEATURE:
<221> NAME/KEY: misc_feature
<222> LOCATION: (11)..(11)
<223> OTHER INFORMATION: May be deoxy guanosine phosphorothioate
<220> FEATURE:
<221> NAME/KEY: misc_feature
<222> LOCATION: (12)..(12)
<223> OTHER INFORMATION: May be locked nucleic acid thymidine
      phosphorothioate
<220> FEATURE:
<221> NAME/KEY: misc_feature
<222> LOCATION: (13)..(13)
<223> OTHER INFORMATION: May be locked nucleic acid cytidine
      phosphorothioate
<220> FEATURE:
<221> NAME/KEY: misc_feature
<222> LOCATION: (14)..(15)
<223> OTHER INFORMATION: May be locked nucleic acid thymidine
      phosphorothioate
<220> FEATURE:
<221> NAME/KEY: misc_feature
<222> LOCATION: (16)..(16)
<223> OTHER INFORMATION: May be deoxy adenosine

<400> SEQUENCE: 17 cttttttgctc gtctta                                                      16

<210> SEQ ID NO 18
```

```
<211> LENGTH: 16
<212> TYPE: DNA
<213> ORGANISM: Artificial Sequence
<220> FEATURE:
<223> OTHER INFORMATION: Anti-miR-208 oligonucleotide
<220> FEATURE:
<221> NAME/KEY: misc_feature
<222> LOCATION: (1)..(1)
<223> OTHER INFORMATION: May be locked nucleic acid cytidine
      phosphorothioate
<220> FEATURE:
<221> NAME/KEY: misc_feature
<222> LOCATION: (2)..(2)
<223> OTHER INFORMATION: May be deoxy thymidine phosphorothioate
<220> FEATURE:
<221> NAME/KEY: misc_feature
<222> LOCATION: (3)..(3)
<223> OTHER INFORMATION: May be locked nucleic acid thymidine
      phosphorothioate
<220> FEATURE:
<221> NAME/KEY: misc_feature
<222> LOCATION: (4)..(4)
<223> OTHER INFORMATION: May be deoxy thymidine phosphorothioate
<220> FEATURE:
<221> NAME/KEY: misc_feature
<222> LOCATION: (5)..(6)
<223> OTHER INFORMATION: May be locked nucleic acid thymidine
      phosphorothioate
<220> FEATURE:
<221> NAME/KEY: misc_feature
<222> LOCATION: (7)..(7)
<223> OTHER INFORMATION: May be deoxy guanosine phosphorothioate
<220> FEATURE:
<221> NAME/KEY: misc_feature
<222> LOCATION: (8)..(8)
<223> OTHER INFORMATION: May be locked nucleic acid cytidine
      phosphorothioate
<220> FEATURE:
<221> NAME/KEY: misc_feature
<222> LOCATION: (9)..(9)
<223> OTHER INFORMATION: May be deoxy thymidine phosphorothioate
<220> FEATURE:
<221> NAME/KEY: misc_feature
<222> LOCATION: (10)..(10)
<223> OTHER INFORMATION: May be locked nucleic acid cytidine
      phosphorothioate
<220> FEATURE:
<221> NAME/KEY: misc_feature
<222> LOCATION: (11)..(11)
<223> OTHER INFORMATION: May be deoxy guanosine phosphorothioate
<220> FEATURE:
<221> NAME/KEY: misc_feature
<222> LOCATION: (12)..(12)
<223> OTHER INFORMATION: May be locked nucleic acid thymidine
      phosphorothioate
<220> FEATURE:
<221> NAME/KEY: misc_feature
<222> LOCATION: (13)..(13)
<223> OTHER INFORMATION: May be deoxy cytidine phosphorothioate
<220> FEATURE:
<221> NAME/KEY: misc_feature
<222> LOCATION: (14)..(15)
<223> OTHER INFORMATION: May be locked nucleic acid thymidine
      phosphorothioate
<220> FEATURE:
<221> NAME/KEY: misc_feature
<222> LOCATION: (16)..(16)
<223> OTHER INFORMATION: May be deoxy adenosine

<400> SEQUENCE: 18 cttttt gctc gtctta                                                16

<210> SEQ ID NO 19
<211> LENGTH: 16
<212> TYPE: DNA
<213> ORGANISM: Artificial Sequence
<220> FEATURE:
<223> OTHER INFORMATION: Anti-miR-208 oligonucleotide
```

```
<220> FEATURE:
<221> NAME/KEY: misc_feature
<222> LOCATION: (1)..(1)
<223> OTHER INFORMATION: May be locked nucleic acid cytidine
      phosphorothioate
<220> FEATURE:
<221> NAME/KEY: misc_feature
<222> LOCATION: (2)..(2)
<223> OTHER INFORMATION: May be deoxy thymidine phosphorothioate
<220> FEATURE:
<221> NAME/KEY: misc_feature
<222> LOCATION: (3)..(6)
<223> OTHER INFORMATION: May be locked nucleic acid thymidine
      phosphorothioate
<220> FEATURE:
<221> NAME/KEY: misc_feature
<222> LOCATION: (7)..(7)
<223> OTHER INFORMATION: May be deoxy guanosine phosphorothioate
<220> FEATURE:
<221> NAME/KEY: misc_feature
<222> LOCATION: (8)..(8)
<223> OTHER INFORMATION: May be locked nucleic acid cytidine
      phosphorothioate
<220> FEATURE:
<221> NAME/KEY: misc_feature
<222> LOCATION: (9)..(9)
<223> OTHER INFORMATION: May be deoxy thymidine phosphorothioate
<220> FEATURE:
<221> NAME/KEY: misc_feature
<222> LOCATION: (10)..(10)
<223> OTHER INFORMATION: May be locked nucleic acid cytidine
      phosphorothioate
<220> FEATURE:
<221> NAME/KEY: misc_feature
<222> LOCATION: (11)..(11)
<223> OTHER INFORMATION: May be deoxy guanosine phosphorothioate
<220> FEATURE:
<221> NAME/KEY: misc_feature
<222> LOCATION: (12)..(12)
<223> OTHER INFORMATION: May be deoxy thymidine phosphorothioate
<220> FEATURE:
<221> NAME/KEY: misc_feature
<222> LOCATION: (13)..(13)
<223> OTHER INFORMATION: May be locked nucleic acid cytidine
      phosphorothioate
<220> FEATURE:
<221> NAME/KEY: misc_feature
<222> LOCATION: (14)..(15)
<223> OTHER INFORMATION: May be deoxy thymidine phosphorothioate
<220> FEATURE:
<221> NAME/KEY: misc_feature
<222> LOCATION: (16)..(16)
<223> OTHER INFORMATION: May be locked nucleic acid adenosine

<400> SEQUENCE: 19 cttttttgctc gtctta                                                  16

<210> SEQ ID NO 20
<211> LENGTH: 16
<212> TYPE: DNA
<213> ORGANISM: Artificial Sequence
<220> FEATURE:
<223> OTHER INFORMATION: Anti-miR-208 oligonucleotide
<220> FEATURE:
<221> NAME/KEY: misc_feature
<222> LOCATION: (1)..(1)
<223> OTHER INFORMATION: May be locked nucleic acid cytidine
      phosphorothioate
<220> FEATURE:
<221> NAME/KEY: misc_feature
<222> LOCATION: (2)..(2)
<223> OTHER INFORMATION: May be deoxy thymidine phosphorothioate
<220> FEATURE:
<221> NAME/KEY: misc_feature
<222> LOCATION: (3)..(4)
<223> OTHER INFORMATION: May be locked nucleic acid thymidine
      phosphorothioate
<220> FEATURE:
```

```
<221> NAME/KEY: misc_feature
<222> LOCATION: (5)..(5)
<223> OTHER INFORMATION: May be deoxy thymidine phosphorothioate
<220> FEATURE:
<221> NAME/KEY: misc_feature
<222> LOCATION: (6)..(6)
<223> OTHER INFORMATION: May be locked nucleic acid thymidine
      phosphorothioate
<220> FEATURE:
<221> NAME/KEY: misc_feature
<222> LOCATION: (7)..(7)
<223> OTHER INFORMATION: May be deoxy guanosine phosphorothioate
<220> FEATURE:
<221> NAME/KEY: misc_feature
<222> LOCATION: (8)..(8)
<223> OTHER INFORMATION: May be locked nucleic acid cytidine
      phosphorothioate
<220> FEATURE:
<221> NAME/KEY: misc_feature
<222> LOCATION: (9)..(9)
<223> OTHER INFORMATION: May be locked nucleic acid thymidine
      phosphorothioate
<220> FEATURE:
<221> NAME/KEY: misc_feature
<222> LOCATION: (10)..(10)
<223> OTHER INFORMATION: May be locked nucleic acid cytidine
      phosphorothioate
<220> FEATURE:
<221> NAME/KEY: misc_feature
<222> LOCATION: (11)..(11)
<223> OTHER INFORMATION: May be deoxy guanosine phosphorothioate
<220> FEATURE:
<221> NAME/KEY: misc_feature
<222> LOCATION: (12)..(12)
<223> OTHER INFORMATION: May be deoxy thymidine phosphorothioate
<220> FEATURE:
<221> NAME/KEY: misc_feature
<222> LOCATION: (13)..(13)
<223> OTHER INFORMATION: May be locked nucleic acid cytidine
      phosphorothioate
<220> FEATURE:
<221> NAME/KEY: misc_feature
<222> LOCATION: (14)..(14)
<223> OTHER INFORMATION: May be deoxy thymidine phosphorothioate
<220> FEATURE:
<221> NAME/KEY: misc_feature
<222> LOCATION: (15)..(15)
<223> OTHER INFORMATION: May be locked nucleic acid thymidine
      phosphorothioate
<220> FEATURE:
<221> NAME/KEY: misc_feature
<222> LOCATION: (16)..(16)
<223> OTHER INFORMATION: May be deoxy adenosine

<400> SEQUENCE: 20 cttttttgctc gtctta                                                    16

<210> SEQ ID NO 21
<211> LENGTH: 16
<212> TYPE: DNA
<213> ORGANISM: Artificial Sequence
<220> FEATURE:
<223> OTHER INFORMATION: Anti-miR-208 oligonucleotide
<220> FEATURE:
<221> NAME/KEY: misc_feature
<222> LOCATION: (1)..(1)
<223> OTHER INFORMATION: May be locked nucleic acid cytidine
      phosphorothioate
<220> FEATURE:
<221> NAME/KEY: misc_feature
<222> LOCATION: (2)..(2)
<223> OTHER INFORMATION: May be deoxy thymidine phosphorothioate
<220> FEATURE:
<221> NAME/KEY: misc_feature
<222> LOCATION: (3)..(3)
<223> OTHER INFORMATION: May be locked nucleic acid thymidine
      phosphorothioate
<220> FEATURE:
```

```
<221> NAME/KEY: misc_feature
<222> LOCATION: (4)..(4)
<223> OTHER INFORMATION: May be deoxy thymidine phosphorothioate
<220> FEATURE:
<221> NAME/KEY: misc_feature
<222> LOCATION: (5)..(5)
<223> OTHER INFORMATION: May be locked nucleic acid thymidine
      phosphorothioate
<220> FEATURE:
<221> NAME/KEY: misc_feature
<222> LOCATION: (6)..(6)
<223> OTHER INFORMATION: May be deoxy thymidine phosphorothioate
<220> FEATURE:
<221> NAME/KEY: misc_feature
<222> LOCATION: (7)..(7)
<223> OTHER INFORMATION: May be locked nucleic acid guanosine
      phosphorothioate
<220> FEATURE:
<221> NAME/KEY: misc_feature
<222> LOCATION: (8)..(8)
<223> OTHER INFORMATION: May be deoxy cytidine phosphorothioate
<220> FEATURE:
<221> NAME/KEY: misc_feature
<222> LOCATION: (9)..(9)
<223> OTHER INFORMATION: May be locked nucleic acid thymidine
      phosphorothioate
<220> FEATURE:
<221> NAME/KEY: misc_feature
<222> LOCATION: (10)..(10)
<223> OTHER INFORMATION: May be deoxy cytidine phosphorothioate
<220> FEATURE:
<221> NAME/KEY: misc_feature
<222> LOCATION: (11)..(11)
<223> OTHER INFORMATION: May be locked nucleic acid guanosine
      phosphorothioate
<220> FEATURE:
<221> NAME/KEY: misc_feature
<222> LOCATION: (12)..(12)
<223> OTHER INFORMATION: May be deoxy thymidine phosphorothioate
<220> FEATURE:
<221> NAME/KEY: misc_feature
<222> LOCATION: (13)..(13)
<223> OTHER INFORMATION: May be locked nucleic acid cytidine
      phosphorothioate
<220> FEATURE:
<221> NAME/KEY: misc_feature
<222> LOCATION: (14)..(14)
<223> OTHER INFORMATION: May be deoxy thymidine phosphorothioate
<220> FEATURE:
<221> NAME/KEY: misc_feature
<222> LOCATION: (15)..(15)
<223> OTHER INFORMATION: May be locked nucleic acid thymidine
      phosphorothioate
<220> FEATURE:
<221> NAME/KEY: misc_feature
<222> LOCATION: (16)..(16)
<223> OTHER INFORMATION: May be locked nucleic acid adenosine

<400> SEQUENCE: 21
cttttgtctc gtctta                                                   16

<210> SEQ ID NO 22
<211> LENGTH: 16
<212> TYPE: DNA
<213> ORGANISM: Artificial Sequence
<220> FEATURE:
<223> OTHER INFORMATION: Anti-miR-208 oligonucleotide
<220> FEATURE:
<221> NAME/KEY: misc_feature
<222> LOCATION: (1)..(1)
<223> OTHER INFORMATION: May be locked nucleic acid cytidine
      phosphorothioate
<220> FEATURE:
<221> NAME/KEY: misc_feature
<222> LOCATION: (2)..(3)
<223> OTHER INFORMATION: May be deoxy thymidine phosphorothioate
<220> FEATURE:
<221> NAME/KEY: misc_feature
```

-continued

```
<222> LOCATION: (4)..(5)
<223> OTHER INFORMATION: May be locked nucleic acid thymidine
      phosphorothioate
<220> FEATURE:
<221> NAME/KEY: misc_feature
<222> LOCATION: (6)..(6)
<223> OTHER INFORMATION: May be deoxy thymidine phosphorothioate
<220> FEATURE:
<221> NAME/KEY: misc_feature
<222> LOCATION: (7)..(7)
<223> OTHER INFORMATION: May be locked nucleic acid guanosine
      phosphorothioate
<220> FEATURE:
<221> NAME/KEY: misc_feature
<222> LOCATION: (8)..(8)
<223> OTHER INFORMATION: May be deoxy cytidine phosphorothioate
<220> FEATURE:
<221> NAME/KEY: misc_feature
<222> LOCATION: (9)..(9)
<223> OTHER INFORMATION: May be locked nucleic acid thymidine
      phosphorothioate
<220> FEATURE:
<221> NAME/KEY: misc_feature
<222> LOCATION: (10)..(10)
<223> OTHER INFORMATION: May be locked nucleic acid cytidine
      phosphorothioate
<220> FEATURE:
<221> NAME/KEY: misc_feature
<222> LOCATION: (11)..(11)
<223> OTHER INFORMATION: May be deoxy guanosine phosphorothioate
<220> FEATURE:
<221> NAME/KEY: misc_feature
<222> LOCATION: (12)..(12)
<223> OTHER INFORMATION: May be locked nucleic acid thymidine
      phosphorothioate
<220> FEATURE:
<221> NAME/KEY: misc_feature
<222> LOCATION: (13)..(13)
<223> OTHER INFORMATION: May be deoxy cytidine phosphorothioate
<220> FEATURE:
<221> NAME/KEY: misc_feature
<222> LOCATION: (14)..(14)
<223> OTHER INFORMATION: May be locked nucleic acid thymidine
      phosphorothioate
<220> FEATURE:
<221> NAME/KEY: misc_feature
<222> LOCATION: (15)..(15)
<223> OTHER INFORMATION: May be deoxy thymidine phosphorothioate
<220> FEATURE:
<221> NAME/KEY: misc_feature
<222> LOCATION: (16)..(16)
<223> OTHER INFORMATION: May be locked nucleic acid adenosine

<400> SEQUENCE: 22 cttttttgctc gtctta                                                  16

<210> SEQ ID NO 23
<211> LENGTH: 16
<212> TYPE: DNA
<213> ORGANISM: Artificial Sequence
<220> FEATURE:
<223> OTHER INFORMATION: Anti-miR-208 oligonucleotide
<220> FEATURE:
<221> NAME/KEY: misc_feature
<222> LOCATION: (1)..(1)
<223> OTHER INFORMATION: May be locked nucleic acid cytidine
      phosphorothioate
<220> FEATURE:
<221> NAME/KEY: misc_feature
<222> LOCATION: (2)..(2)
<223> OTHER INFORMATION: May be deoxy cytidine phosphorothioate
<220> FEATURE:
<221> NAME/KEY: misc_feature
<222> LOCATION: (3)..(4)
<223> OTHER INFORMATION: May be deoxy thymidine phosphorothioate
<220> FEATURE:
<221> NAME/KEY: misc_feature
<222> LOCATION: (5)..(6)
```

-continued

```
<223> OTHER INFORMATION: May be locked nucleic acid thymidine
      phosphorothioate
<220> FEATURE:
<221> NAME/KEY: misc_feature
<222> LOCATION: (7)..(7)
<223> OTHER INFORMATION: May be deoxy guanosine phosphorothioate
<220> FEATURE:
<221> NAME/KEY: misc_feature
<222> LOCATION: (8)..(8)
<223> OTHER INFORMATION: May be locked nucleic acid thymidine
      phosphorothioate
<220> FEATURE:
<221> NAME/KEY: misc_feature
<222> LOCATION: (9)..(9)
<223> OTHER INFORMATION: May be deoxy thymidine phosphorothioate
<220> FEATURE:
<221> NAME/KEY: misc_feature
<222> LOCATION: (10)..(10)
<223> OTHER INFORMATION: May be locked nucleic acid cytidine
      phosphorothioate
<220> FEATURE:
<221> NAME/KEY: misc_feature
<222> LOCATION: (11)..(11)
<223> OTHER INFORMATION: May be locked nucleic acid guanosine
      phosphorothioate
<220> FEATURE:
<221> NAME/KEY: misc_feature
<222> LOCATION: (12)..(12)
<223> OTHER INFORMATION: May be deoxy thymidine phosphorothioate
<220> FEATURE:
<221> NAME/KEY: misc_feature
<222> LOCATION: (13)..(13)
<223> OTHER INFORMATION: May be locked nucleic acid cytidine
      phosphorothioate
<220> FEATURE:
<221> NAME/KEY: misc_feature
<222> LOCATION: (14)..(14)
<223> OTHER INFORMATION: May be deoxy thymidine phosphorothioate
<220> FEATURE:
<221> NAME/KEY: misc_feature
<222> LOCATION: (15)..(15)
<223> OTHER INFORMATION: May be locked nucleic acid thymidine
      phosphorothioate
<220> FEATURE:
<221> NAME/KEY: misc_feature
<222> LOCATION: (16)..(16)
<223> OTHER INFORMATION: May be locked nucleic acid adenosine

<400> SEQUENCE: 23
ccttttgttc gtctta                                                    16

<210> SEQ ID NO 24
<211> LENGTH: 15
<212> TYPE: DNA
<213> ORGANISM: Artificial Sequence
<220> FEATURE:
<223> OTHER INFORMATION: Anti-miR-208 oligonucleotide
<220> FEATURE:
<221> NAME/KEY: misc_feature
<222> LOCATION: (1)..(5)
<223> OTHER INFORMATION: May be locked nucleic acid thymidine
      phosphorothioate
<220> FEATURE:
<221> NAME/KEY: misc_feature
<222> LOCATION: (6)..(6)
<223> OTHER INFORMATION: May be deoxy guanosine phosphorothioate
<220> FEATURE:
<221> NAME/KEY: misc_feature
<222> LOCATION: (7)..(7)
<223> OTHER INFORMATION: May be locked nucleic acid cytidine
      phosphorothioate
<220> FEATURE:
<221> NAME/KEY: misc_feature
<222> LOCATION: (8)..(8)
<223> OTHER INFORMATION: May be deoxy thymidine phosphorothioate
<220> FEATURE:
<221> NAME/KEY: misc_feature
<222> LOCATION: (9)..(9)
```

```
<223> OTHER INFORMATION: May be locked nucleic acid cytidine
      phosphorothioate
<220> FEATURE:
<221> NAME/KEY: misc_feature
<222> LOCATION: (10)..(10)
<223> OTHER INFORMATION: May be deoxy guanosine phosphorothioate
<220> FEATURE:
<221> NAME/KEY: misc_feature
<222> LOCATION: (11)..(11)
<223> OTHER INFORMATION: May be deoxy thymidine phosphorothioate
<220> FEATURE:
<221> NAME/KEY: misc_feature
<222> LOCATION: (12)..(12)
<223> OTHER INFORMATION: May be locked nucleic acid cytidine
      phosphorothioate
<220> FEATURE:
<221> NAME/KEY: misc_feature
<222> LOCATION: (13)..(13)
<223> OTHER INFORMATION: May be deoxy thymidine phosphorothioate
<220> FEATURE:
<221> NAME/KEY: misc_feature
<222> LOCATION: (14)..(14)
<223> OTHER INFORMATION: May be locked nucleic acid thymidine
      phosphorothioate
<220> FEATURE:
<221> NAME/KEY: misc_feature
<222> LOCATION: (15)..(15)
<223> OTHER INFORMATION: May be deoxy adenosine

<400> SEQUENCE: 24
tttttgctcg tctta                                                    15

<210> SEQ ID NO 25
<211> LENGTH: 15
<212> TYPE: DNA
<213> ORGANISM: Artificial Sequence
<220> FEATURE:
<223> OTHER INFORMATION: Anti-miR-208 oligonucleotide
<220> FEATURE:
<221> NAME/KEY: misc_feature
<222> LOCATION: (1)..(2)
<223> OTHER INFORMATION: May be locked nucleic acid thymidine
      phosphorothioate
<220> FEATURE:
<221> NAME/KEY: misc_feature
<222> LOCATION: (3)..(3)
<223> OTHER INFORMATION: May be deoxy thymidine phosphorothioate
<220> FEATURE:
<221> NAME/KEY: misc_feature
<222> LOCATION: (4)..(5)
<223> OTHER INFORMATION: May be locked nucleic acid thymidine
      phosphorothioate
<220> FEATURE:
<221> NAME/KEY: misc_feature
<222> LOCATION: (6)..(6)
<223> OTHER INFORMATION: May be deoxy guanosine phosphorothioate
<220> FEATURE:
<221> NAME/KEY: misc_feature
<222> LOCATION: (7)..(7)
<223> OTHER INFORMATION: May be locked nucleic acid cytidine
      phosphorothioate
<220> FEATURE:
<221> NAME/KEY: misc_feature
<222> LOCATION: (8)..(8)
<223> OTHER INFORMATION: May be deoxy thymidine phosphorothioate
<220> FEATURE:
<221> NAME/KEY: misc_feature
<222> LOCATION: (9)..(9)
<223> OTHER INFORMATION: May be locked nucleic acid cytidine
      phosphorothioate
<220> FEATURE:
<221> NAME/KEY: misc_feature
<222> LOCATION: (10)..(10)
<223> OTHER INFORMATION: May be deoxy guanosine phosphorothioate
<220> FEATURE:
<221> NAME/KEY: misc_feature
<222> LOCATION: (11)..(11)
<223> OTHER INFORMATION: May be deoxy thymidine phosphorothioate
```

-continued

```
<220> FEATURE:
<221> NAME/KEY: misc_feature
<222> LOCATION: (12)..(12)
<223> OTHER INFORMATION: May be locked nucleic acid cytidine
      phosphorothioate
<220> FEATURE:
<221> NAME/KEY: misc_feature
<222> LOCATION: (13)..(13)
<223> OTHER INFORMATION: May be deoxy thymidine phosphorothioate
<220> FEATURE:
<221> NAME/KEY: misc_feature
<222> LOCATION: (14)..(14)
<223> OTHER INFORMATION: May be locked nucleic acid thymidine
      phosphorothioate
<220> FEATURE:
<221> NAME/KEY: misc_feature
<222> LOCATION: (15)..(15)
<223> OTHER INFORMATION: May be deoxy adenosine

<400> SEQUENCE: 25
tttttgctcg tctta                                                     15

<210> SEQ ID NO 26
<211> LENGTH: 15
<212> TYPE: DNA
<213> ORGANISM: Artificial Sequence
<220> FEATURE:
<223> OTHER INFORMATION: Anti-miR-208 oligonucleotide
<220> FEATURE:
<221> NAME/KEY: misc_feature
<222> LOCATION: (1)..(5)
<223> OTHER INFORMATION: May be locked nucleic acid thymidine
      phosphorothioate
<220> FEATURE:
<221> NAME/KEY: misc_feature
<222> LOCATION: (6)..(6)
<223> OTHER INFORMATION: May be deoxy guanosine phosphorothioate
<220> FEATURE:
<221> NAME/KEY: misc_feature
<222> LOCATION: (7)..(7)
<223> OTHER INFORMATION: May be deoxy cytidine phosphorothioate
<220> FEATURE:
<221> NAME/KEY: misc_feature
<222> LOCATION: (8)..(8)
<223> OTHER INFORMATION: May be deoxy thymidine phosphorothioate
<220> FEATURE:
<221> NAME/KEY: misc_feature
<222> LOCATION: (9)..(9)
<223> OTHER INFORMATION: May be locked nucleic acid cytidine
      phosphorothioate
<220> FEATURE:
<221> NAME/KEY: misc_feature
<222> LOCATION: (10)..(10)
<223> OTHER INFORMATION: May be deoxy guanosine phosphorothioate
<220> FEATURE:
<221> NAME/KEY: misc_feature
<222> LOCATION: (11)..(11)
<223> OTHER INFORMATION: May be locked nucleic acid thymidine
      phosphorothioate
<220> FEATURE:
<221> NAME/KEY: misc_feature
<222> LOCATION: (12)..(12)
<223> OTHER INFORMATION: May be locked nucleic acid cytidine
      phosphorothioate
<220> FEATURE:
<221> NAME/KEY: misc_feature
<222> LOCATION: (13)..(13)
<223> OTHER INFORMATION: May be deoxy thymidine phosphorothioate
<220> FEATURE:
<221> NAME/KEY: misc_feature
<222> LOCATION: (14)..(14)
<223> OTHER INFORMATION: May be locked nucleic acid thymidine
      phosphorothioate
<220> FEATURE:
<221> NAME/KEY: misc_feature
<222> LOCATION: (15)..(15)
<223> OTHER INFORMATION: May be deoxy adenosine
```

-continued

```
<400> SEQUENCE: 26
tttttgctcg tctta                                                      15

<210> SEQ ID NO 27
<211> LENGTH: 15
<212> TYPE: DNA
<213> ORGANISM: Artificial Sequence
<220> FEATURE:
<223> OTHER INFORMATION: Anti-miR-208 oligonucleotide
<220> FEATURE:
<221> NAME/KEY: misc_feature
<222> LOCATION: (1)..(1)
<223> OTHER INFORMATION: May be locked nucleic acid thymidine
      phosphorothioate
<220> FEATURE:
<221> NAME/KEY: misc_feature
<222> LOCATION: (2)..(2)
<223> OTHER INFORMATION: May be deoxy thymidine phosphorothioate
<220> FEATURE:
<221> NAME/KEY: misc_feature
<222> LOCATION: (3)..(5)
<223> OTHER INFORMATION: May be locked nucleic acid thymidine
      phosphorothioate
<220> FEATURE:
<221> NAME/KEY: misc_feature
<222> LOCATION: (6)..(6)
<223> OTHER INFORMATION: May be deoxy guanosine phosphorothioate
<220> FEATURE:
<221> NAME/KEY: misc_feature
<222> LOCATION: (7)..(7)
<223> OTHER INFORMATION: May be locked nucleic acid cytidine
      phosphorothioate
<220> FEATURE:
<221> NAME/KEY: misc_feature
<222> LOCATION: (8)..(8)
<223> OTHER INFORMATION: May be deoxy thymidine phosphorothioate
<220> FEATURE:
<221> NAME/KEY: misc_feature
<222> LOCATION: (9)..(9)
<223> OTHER INFORMATION: May be locked nucleic acid cytidine
      phosphorothioate
<220> FEATURE:
<221> NAME/KEY: misc_feature
<222> LOCATION: (10)..(10)
<223> OTHER INFORMATION: May be deoxy guanosine phosphorothioate
<220> FEATURE:
<221> NAME/KEY: misc_feature
<222> LOCATION: (11)..(11)
<223> OTHER INFORMATION: May be deoxy thymidine phosphorothioate
<220> FEATURE:
<221> NAME/KEY: misc_feature
<222> LOCATION: (12)..(12)
<223> OTHER INFORMATION: May be locked nucleic acid cytidine
      phosphorothioate
<220> FEATURE:
<221> NAME/KEY: misc_feature
<222> LOCATION: (13)..(14)
<223> OTHER INFORMATION: May be locked nucleic acid thymidine
      phosphorothioate
<220> FEATURE:
<221> NAME/KEY: misc_feature
<222> LOCATION: (15)..(15)
<223> OTHER INFORMATION: May be deoxy adenosine

<400> SEQUENCE: 27
tttttgctcg tctta                                                      15

<210> SEQ ID NO 28
<211> LENGTH: 15
<212> TYPE: DNA
<213> ORGANISM: Artificial Sequence
<220> FEATURE:
<223> OTHER INFORMATION: Anti-miR-208 oligonucleotide
<220> FEATURE:
<221> NAME/KEY: misc_feature
<222> LOCATION: (1)..(5)
```

<223> OTHER INFORMATION: May be locked nucleic acid thymidine
      phosphorothioate
<220> FEATURE:
<221> NAME/KEY: misc_feature
<222> LOCATION: (6)..(6)
<223> OTHER INFORMATION: May be deoxy guanosine phosphorothioate
<220> FEATURE:
<221> NAME/KEY: misc_feature
<222> LOCATION: (7)..(7)
<223> OTHER INFORMATION: May be locked nucleic acid cytidine
      phosphorothioate
<220> FEATURE:
<221> NAME/KEY: misc_feature
<222> LOCATION: (8)..(8)
<223> OTHER INFORMATION: May be deoxy thymidine phosphorothioate
<220> FEATURE:
<221> NAME/KEY: misc_feature
<222> LOCATION: (9)..(9)
<223> OTHER INFORMATION: May be locked nucleic acid cytidine
      phosphorothioate
<220> FEATURE:
<221> NAME/KEY: misc_feature
<222> LOCATION: (10)..(10)
<223> OTHER INFORMATION: May be deoxy guanosine phosphorothioate
<220> FEATURE:
<221> NAME/KEY: misc_feature
<222> LOCATION: (11)..(11)
<223> OTHER INFORMATION: May be deoxy thymidine phosphorothioate
<220> FEATURE:
<221> NAME/KEY: misc_feature
<222> LOCATION: (12)..(12)
<223> OTHER INFORMATION: May be locked nucleic acid cytidine
      phosphorothioate
<220> FEATURE:
<221> NAME/KEY: misc_feature
<222> LOCATION: (13)..(14)
<223> OTHER INFORMATION: May be locked nucleic acid thymidine
      phosphorothioate
<220> FEATURE:
<221> NAME/KEY: misc_feature
<222> LOCATION: (15)..(15)
<223> OTHER INFORMATION: May be locked nucleic acid adenosine

<400> SEQUENCE: 28
tttttgctcg tctta                                                      15

<210> SEQ ID NO 29
<211> LENGTH: 15
<212> TYPE: DNA
<213> ORGANISM: Artificial Sequence
<220> FEATURE:
<223> OTHER INFORMATION: Anti-miR-208 oligonucleotide
<220> FEATURE:
<221> NAME/KEY: misc_feature
<222> LOCATION: (1)..(1)
<223> OTHER INFORMATION: May be locked nucleic acid thymidine
      phosphorothioate
<220> FEATURE:
<221> NAME/KEY: misc_feature
<222> LOCATION: (2)..(2)
<223> OTHER INFORMATION: May be deoxy thymidine phosphorothioate
<220> FEATURE:
<221> NAME/KEY: misc_feature
<222> LOCATION: (3)..(5)
<223> OTHER INFORMATION: May be locked nucleic acid thymidine
      phosphorothioate
<220> FEATURE:
<221> NAME/KEY: misc_feature
<222> LOCATION: (6)..(6)
<223> OTHER INFORMATION: May be deoxy guanosine phosphorothioate
<220> FEATURE:
<221> NAME/KEY: misc_feature
<222> LOCATION: (7)..(7)
<223> OTHER INFORMATION: May be locked nucleic acid cytidine
      phosphorothioate
<220> FEATURE:
<221> NAME/KEY: misc_feature
<222> LOCATION: (8)..(8)

```
<223> OTHER INFORMATION: May be deoxy thymidine phosphorothioate
<220> FEATURE:
<221> NAME/KEY: misc_feature
<222> LOCATION: (9)..(9)
<223> OTHER INFORMATION: May be locked nucleic acid cytidine
      phosphorothioate
<220> FEATURE:
<221> NAME/KEY: misc_feature
<222> LOCATION: (10)..(10)
<223> OTHER INFORMATION: May be deoxy guanosine phosphorothioate
<220> FEATURE:
<221> NAME/KEY: misc_feature
<222> LOCATION: (11)..(11)
<223> OTHER INFORMATION: May be deoxy thymidine phosphorothioate
<220> FEATURE:
<221> NAME/KEY: misc_feature
<222> LOCATION: (12)..(12)
<223> OTHER INFORMATION: May be locked nucleic acid cytidine
      phosphorothioate
<220> FEATURE:
<221> NAME/KEY: misc_feature
<222> LOCATION: (13)..(14)
<223> OTHER INFORMATION: May be locked nucleic acid thymidine
      phosphorothioate
<220> FEATURE:
<221> NAME/KEY: misc_feature
<222> LOCATION: (15)..(15)
<223> OTHER INFORMATION: May be locked nucleic acid adenosine

<400> SEQUENCE: 29
tttttgctcg tctta                                                    15

<210> SEQ ID NO 30
<211> LENGTH: 15
<212> TYPE: DNA
<213> ORGANISM: Artificial Sequence
<220> FEATURE:
<223> OTHER INFORMATION: Anti-miR-208 oligonucleotide
<220> FEATURE:
<221> NAME/KEY: misc_feature
<222> LOCATION: (1)..(1)
<223> OTHER INFORMATION: May be locked nucleic acid cytidine
      phosphorothioate
<220> FEATURE:
<221> NAME/KEY: misc_feature
<222> LOCATION: (2)..(5)
<223> OTHER INFORMATION: May be locked nucleic acid thymidine
      phosphorothioate
<220> FEATURE:
<221> NAME/KEY: misc_feature
<222> LOCATION: (6)..(6)
<223> OTHER INFORMATION: May be deoxy guanosine phosphorothioate
<220> FEATURE:
<221> NAME/KEY: misc_feature
<222> LOCATION: (7)..(7)
<223> OTHER INFORMATION: May be locked nucleic acid cytidine
      phosphorothioate
<220> FEATURE:
<221> NAME/KEY: misc_feature
<222> LOCATION: (8)..(8)
<223> OTHER INFORMATION: May be deoxy thymidine phosphorothioate
<220> FEATURE:
<221> NAME/KEY: misc_feature
<222> LOCATION: (9)..(9)
<223> OTHER INFORMATION: May be locked nucleic acid cytidine
      phosphorothioate
<220> FEATURE:
<221> NAME/KEY: misc_feature
<222> LOCATION: (10)..(10)
<223> OTHER INFORMATION: May be deoxy guanosine phosphorothioate
<220> FEATURE:
<221> NAME/KEY: misc_feature
<222> LOCATION: (11)..(11)
<223> OTHER INFORMATION: May be deoxy thymidine phosphorothioate
<220> FEATURE:
<221> NAME/KEY: misc_feature
<222> LOCATION: (12)..(12)
<223> OTHER INFORMATION: May be locked nucleic acid cytidine
```

-continued

```
      phosphorothioate
<220> FEATURE:
<221> NAME/KEY: misc_feature
<222> LOCATION: (13)..(13)
<223> OTHER INFORMATION: May be deoxy thymidine phosphorothioate
<220> FEATURE:
<221> NAME/KEY: misc_feature
<222> LOCATION: (14)..(14)
<223> OTHER INFORMATION: May be locked nucleic acid thymidine
      phosphorothioate
<220> FEATURE:
<221> NAME/KEY: misc_feature
<222> LOCATION: (15)..(15)
<223> OTHER INFORMATION: May be deoxy adenosine

<400> SEQUENCE: 30
cttttgctcg tctta                                                    15

<210> SEQ ID NO 31
<211> LENGTH: 15
<212> TYPE: DNA
<213> ORGANISM: Artificial Sequence
<220> FEATURE:
<223> OTHER INFORMATION: Anti-miR-208 oligonucleotide
<220> FEATURE:
<221> NAME/KEY: misc_feature
<222> LOCATION: (1)..(1)
<223> OTHER INFORMATION: May be locked nucleic acid cytidine
      phosphorothioate
<220> FEATURE:
<221> NAME/KEY: misc_feature
<222> LOCATION: (2)..(2)
<223> OTHER INFORMATION: May be locked nucleic acid thymidine
      phosphorothioate
<220> FEATURE:
<221> NAME/KEY: misc_feature
<222> LOCATION: (3)..(3)
<223> OTHER INFORMATION: May be deoxy thymidine phosphorothioate
<220> FEATURE:
<221> NAME/KEY: misc_feature
<222> LOCATION: (4)..(5)
<223> OTHER INFORMATION: May be locked nucleic acid thymidine
      phosphorothioate
<220> FEATURE:
<221> NAME/KEY: misc_feature
<222> LOCATION: (6)..(6)
<223> OTHER INFORMATION: May be deoxy guanosine phosphorothioate
<220> FEATURE:
<221> NAME/KEY: misc_feature
<222> LOCATION: (7)..(7)
<223> OTHER INFORMATION: May be locked nucleic acid cytidine
      phosphorothioate
<220> FEATURE:
<221> NAME/KEY: misc_feature
<222> LOCATION: (8)..(8)
<223> OTHER INFORMATION: May be deoxy thymidine phosphorothioate
<220> FEATURE:
<221> NAME/KEY: misc_feature
<222> LOCATION: (9)..(9)
<223> OTHER INFORMATION: May be locked nucleic acid cytidine
      phosphorothioate
<220> FEATURE:
<221> NAME/KEY: misc_feature
<222> LOCATION: (10)..(10)
<223> OTHER INFORMATION: May be deoxy guanosine phosphorothioate
<220> FEATURE:
<221> NAME/KEY: misc_feature
<222> LOCATION: (11)..(11)
<223> OTHER INFORMATION: May be deoxy thymidine phosphorothioate
<220> FEATURE:
<221> NAME/KEY: misc_feature
<222> LOCATION: (12)..(12)
<223> OTHER INFORMATION: May be locked nucleic acid cytidine
      phosphorothioate
<220> FEATURE:
<221> NAME/KEY: misc_feature
<222> LOCATION: (13)..(13)
<223> OTHER INFORMATION: May be deoxy thymidine phosphorothioate
```

```
<220> FEATURE:
<221> NAME/KEY: misc_feature
<222> LOCATION: (14)..(14)
<223> OTHER INFORMATION: May be locked nucleic acid thymidine
      phosphorothioate
<220> FEATURE:
<221> NAME/KEY: misc_feature
<222> LOCATION: (15)..(15)
<223> OTHER INFORMATION: May be deoxy adenosine

<400> SEQUENCE: 31
cttttgctcg tctta                                                    15

<210> SEQ ID NO 32
<211> LENGTH: 15
<212> TYPE: DNA
<213> ORGANISM: Artificial Sequence
<220> FEATURE:
<223> OTHER INFORMATION: Anti-miR-208 oligonucleotide
<220> FEATURE:
<221> NAME/KEY: misc_feature
<222> LOCATION: (1)..(1)
<223> OTHER INFORMATION: May be locked nucleic acid cytidine
      phosphorothioate
<220> FEATURE:
<221> NAME/KEY: misc_feature
<222> LOCATION: (2)..(2)
<223> OTHER INFORMATION: May be deoxy thymidine phosphorothioate
<220> FEATURE:
<221> NAME/KEY: misc_feature
<222> LOCATION: (3)..(5)
<223> OTHER INFORMATION: May be locked nucleic acid thymidine
      phosphorothioate
<220> FEATURE:
<221> NAME/KEY: misc_feature
<222> LOCATION: (6)..(6)
<223> OTHER INFORMATION: May be deoxy guanosine phosphorothioate
<220> FEATURE:
<221> NAME/KEY: misc_feature
<222> LOCATION: (7)..(7)
<223> OTHER INFORMATION: May be locked nucleic acid cytidine
      phosphorothioate
<220> FEATURE:
<221> NAME/KEY: misc_feature
<222> LOCATION: (8)..(8)
<223> OTHER INFORMATION: May be deoxy thymidine phosphorothioate
<220> FEATURE:
<221> NAME/KEY: misc_feature
<222> LOCATION: (9)..(9)
<223> OTHER INFORMATION: May be locked nucleic acid cytidine
      phosphorothioate
<220> FEATURE:
<221> NAME/KEY: misc_feature
<222> LOCATION: (10)..(10)
<223> OTHER INFORMATION: May be deoxy guanosine phosphorothioate
<220> FEATURE:
<221> NAME/KEY: misc_feature
<222> LOCATION: (11)..(11)
<223> OTHER INFORMATION: May be deoxy thymidine phosphorothioate
<220> FEATURE:
<221> NAME/KEY: misc_feature
<222> LOCATION: (12)..(12)
<223> OTHER INFORMATION: May be locked nucleic acid cytidine
      phosphorothioate
<220> FEATURE:
<221> NAME/KEY: misc_feature
<222> LOCATION: (13)..(14)
<223> OTHER INFORMATION: May be locked nucleic acid thymidine
      phosphorothioate
<220> FEATURE:
<221> NAME/KEY: misc_feature
<222> LOCATION: (15)..(15)
<223> OTHER INFORMATION: May be deoxy adenosine

<400> SEQUENCE: 32
cttttgctcg tctta                                                    15
```

-continued

```
<210> SEQ ID NO 33
<211> LENGTH: 15
<212> TYPE: DNA
<213> ORGANISM: Artificial Sequence
<220> FEATURE:
<223> OTHER INFORMATION: Anti-miR-208 oligonucleotide
<220> FEATURE:
<221> NAME/KEY: misc_feature
<222> LOCATION: (1)..(1)
<223> OTHER INFORMATION: May be locked nucleic acid cytidine
      phosphorothioate
<220> FEATURE:
<221> NAME/KEY: misc_feature
<222> LOCATION: (2)..(5)
<223> OTHER INFORMATION: May be locked nucleic acid thymidine
      phosphorothioate
<220> FEATURE:
<221> NAME/KEY: misc_feature
<222> LOCATION: (6)..(6)
<223> OTHER INFORMATION: May be deoxy guanosine phosphorothioate
<220> FEATURE:
<221> NAME/KEY: misc_feature
<222> LOCATION: (7)..(7)
<223> OTHER INFORMATION: May be locked nucleic acid cytidine
      phosphorothioate
<220> FEATURE:
<221> NAME/KEY: misc_feature
<222> LOCATION: (8)..(8)
<223> OTHER INFORMATION: May be deoxy thymidine phosphorothioate
<220> FEATURE:
<221> NAME/KEY: misc_feature
<222> LOCATION: (9)..(9)
<223> OTHER INFORMATION: May be locked nucleic acid cytidine
      phosphorothioate
<220> FEATURE:
<221> NAME/KEY: misc_feature
<222> LOCATION: (10)..(10)
<223> OTHER INFORMATION: May be deoxy guanosine phosphorothioate
<220> FEATURE:
<221> NAME/KEY: misc_feature
<222> LOCATION: (11)..(11)
<223> OTHER INFORMATION: May be deoxy thymidine phosphorothioate
<220> FEATURE:
<221> NAME/KEY: misc_feature
<222> LOCATION: (12)..(12)
<223> OTHER INFORMATION: May be locked nucleic acid cytidine
      phosphorothioate
<220> FEATURE:
<221> NAME/KEY: misc_feature
<222> LOCATION: (13)..(13)
<223> OTHER INFORMATION: May be deoxy thymidine phosphorothioate
<220> FEATURE:
<221> NAME/KEY: misc_feature
<222> LOCATION: (14)..(14)
<223> OTHER INFORMATION: May be locked nucleic acid thymidine
      phosphorothioate
<220> FEATURE:
<221> NAME/KEY: misc_feature
<222> LOCATION: (15)..(15)
<223> OTHER INFORMATION: May be locked nucleic acid adenosine

<400> SEQUENCE: 33
cttttgctcg tctta                                               15

<210> SEQ ID NO 34
<211> LENGTH: 15
<212> TYPE: DNA
<213> ORGANISM: Artificial Sequence
<220> FEATURE:
<223> OTHER INFORMATION: Anti-miR-208 oligonucleotide
<220> FEATURE:
<221> NAME/KEY: misc_feature
<222> LOCATION: (1)..(1)
<223> OTHER INFORMATION: May be locked nucleic acid cytidine
      phosphorothioate
<220> FEATURE:
<221> NAME/KEY: misc_feature
```

```
<222> LOCATION: (2)..(2)
<223> OTHER INFORMATION: May be deoxy thymidine phosphorothioate
<220> FEATURE:
<221> NAME/KEY: misc_feature
<222> LOCATION: (3)..(5)
<223> OTHER INFORMATION: May be locked nucleic acid thymidine
      phosphorothioate
<220> FEATURE:
<221> NAME/KEY: misc_feature
<222> LOCATION: (6)..(6)
<223> OTHER INFORMATION: May be deoxy guanosine phosphorothioate
<220> FEATURE:
<221> NAME/KEY: misc_feature
<222> LOCATION: (7)..(7)
<223> OTHER INFORMATION: May be locked nucleic acid cytidine
      phosphorothioate
<220> FEATURE:
<221> NAME/KEY: misc_feature
<222> LOCATION: (8)..(8)
<223> OTHER INFORMATION: May be deoxy thymidine phosphorothioate
<220> FEATURE:
<221> NAME/KEY: misc_feature
<222> LOCATION: (9)..(9)
<223> OTHER INFORMATION: May be locked nucleic acid cytidine
      phosphorothioate
<220> FEATURE:
<221> NAME/KEY: misc_feature
<222> LOCATION: (10)..(10)
<223> OTHER INFORMATION: May be deoxy guanosine phosphorothioate
<220> FEATURE:
<221> NAME/KEY: misc_feature
<222> LOCATION: (11)..(11)
<223> OTHER INFORMATION: May be deoxy thymidine phosphorothioate
<220> FEATURE:
<221> NAME/KEY: misc_feature
<222> LOCATION: (12)..(12)
<223> OTHER INFORMATION: May be locked nucleic acid cytidine
      phosphorothioate
<220> FEATURE:
<221> NAME/KEY: misc_feature
<222> LOCATION: (13)..(13)
<223> OTHER INFORMATION: May be deoxy thymidine phosphorothioate
<220> FEATURE:
<221> NAME/KEY: misc_feature
<222> LOCATION: (14)..(14)
<223> OTHER INFORMATION: May be locked nucleic acid thymidine
      phosphorothioate
<220> FEATURE:
<221> NAME/KEY: misc_feature
<222> LOCATION: (15)..(15)
<223> OTHER INFORMATION: May be locked nucleic acid adenosine

<400> SEQUENCE: 34
cttttgctcg tctta                                                    15

<210> SEQ ID NO 35
<211> LENGTH: 15
<212> TYPE: DNA
<213> ORGANISM: Artificial Sequence
<220> FEATURE:
<223> OTHER INFORMATION: Anti-miR-208 oligonucleotide
<220> FEATURE:
<221> NAME/KEY: misc_feature
<222> LOCATION: (1)..(1)
<223> OTHER INFORMATION: May be locked nucleic acid cytidine
      phosphorothioate
<220> FEATURE:
<222> LOCATION: (2)..(5)
<223> OTHER INFORMATION: May be locked nucleic acid thymidine
      phosphorothioate
<220> FEATURE:
<221> NAME/KEY: misc_feature
<222> LOCATION: (6)..(6)
<223> OTHER INFORMATION: May be deoxy guanosine phosphorothioate
<220> FEATURE:
<221> NAME/KEY: misc_feature
<222> LOCATION: (7)..(7)
```

-continued

<223> OTHER INFORMATION: May be deoxy cytidine phosphorothioate
<220> FEATURE:
<221> NAME/KEY: misc_feature
<222> LOCATION: (8)..(8)
<223> OTHER INFORMATION: May be deoxy thymidine phosphorothioate
<220> FEATURE:
<221> NAME/KEY: misc_feature
<222> LOCATION: (9)..(9)
<223> OTHER INFORMATION: May be locked nucleic acid cytidine
      phosphorothioate
<220> FEATURE:
<221> NAME/KEY: misc_feature
<222> LOCATION: (10)..(10)
<223> OTHER INFORMATION: May be deoxy guanosine phosphorothioate
<220> FEATURE:
<221> NAME/KEY: misc_feature
<222> LOCATION: (11)..(11)
<223> OTHER INFORMATION: May be locked nucleic acid thymidine
      phosphorothioate
<220> FEATURE:
<221> NAME/KEY: misc_feature
<222> LOCATION: (12)..(12)
<223> OTHER INFORMATION: May be locked nucleic acid cytidine
      phosphorothioate
<220> FEATURE:
<221> NAME/KEY: misc_feature
<222> LOCATION: (13)..(13)
<223> OTHER INFORMATION: May be deoxy thymidine phosphorothioate
<220> FEATURE:
<221> NAME/KEY: misc_feature
<222> LOCATION: (14)..(14)
<223> OTHER INFORMATION: May be locked nucleic acid thymidine
      phosphorothioate
<220> FEATURE:
<221> NAME/KEY: misc_feature
<222> LOCATION: (15)..(15)
<223> OTHER INFORMATION: May be deoxy adenosine

<400> SEQUENCE: 35
cttttgctcg tctta                                                    15

<210> SEQ ID NO 36
<211> LENGTH: 15
<212> TYPE: DNA
<213> ORGANISM: Artificial Sequence
<220> FEATURE:
<223> OTHER INFORMATION: Anti-miR-208 oligonucleotide
<220> FEATURE:
<221> NAME/KEY: misc_feature
<222> LOCATION: (1)..(1)
<223> OTHER INFORMATION: May be locked nucleic acid cytidine
      phosphorothioate
<220> FEATURE:
<221> NAME/KEY: misc_feature
<222> LOCATION: (2)..(5)
<223> OTHER INFORMATION: May be locked nucleic acid thymidine
      phosphorothioate
<220> FEATURE:
<221> NAME/KEY: misc_feature
<222> LOCATION: (6)..(6)
<223> OTHER INFORMATION: May be deoxy guanosine phosphorothioate
<220> FEATURE:
<221> NAME/KEY: misc_feature
<222> LOCATION: (7)..(7)
<223> OTHER INFORMATION: May be locked nucleic acid thymidine
      phosphorothioate
<220> FEATURE:
<221> NAME/KEY: misc_feature
<222> LOCATION: (8)..(8)
<223> OTHER INFORMATION: May be deoxy thymidine phosphorothioate
<220> FEATURE:
<221> NAME/KEY: misc_feature
<222> LOCATION: (9)..(9)
<223> OTHER INFORMATION: May be locked nucleic acid cytidine
      phosphorothioate
<220> FEATURE:
<221> NAME/KEY: misc_feature
<222> LOCATION: (10)..(10)

<223> OTHER INFORMATION: May be deoxy guanosine phosphorothioate
<220> FEATURE:
<221> NAME/KEY: misc_feature
<222> LOCATION: (11)..(11)
<223> OTHER INFORMATION: May be deoxy thymidine phosphorothioate
<220> FEATURE:
<221> NAME/KEY: misc_feature
<222> LOCATION: (12)..(12)
<223> OTHER INFORMATION: May be locked nucleic acid cytidine
      phosphorothioate
<220> FEATURE:
<221> NAME/KEY: misc_feature
<222> LOCATION: (13)..(13)
<223> OTHER INFORMATION: May be deoxy thymidine phosphorothioate
<220> FEATURE:
<221> NAME/KEY: misc_feature
<222> LOCATION: (14)..(14)
<223> OTHER INFORMATION: May be locked nucleic acid thymidine
      phosphorothioate
<220> FEATURE:
<221> NAME/KEY: misc_feature
<222> LOCATION: (15)..(15)
<223> OTHER INFORMATION: May be deoxy adenosine

<400> SEQUENCE: 36
cttttgttcg tctta                                                    15

<210> SEQ ID NO 37
<211> LENGTH: 15
<212> TYPE: DNA
<213> ORGANISM: Artificial Sequence
<220> FEATURE:
<223> OTHER INFORMATION: Anti-miR-208 oligonucleotide
<220> FEATURE:
<221> NAME/KEY: misc_feature
<222> LOCATION: (1)..(1)
<223> OTHER INFORMATION: May be locked nucleic acid cytidine
      phosphorothioate
<220> FEATURE:
<221> NAME/KEY: misc_feature
<222> LOCATION: (2)..(5)
<223> OTHER INFORMATION: May be locked nucleic acid thymidine
      phosphorothioate
<220> FEATURE:
<221> NAME/KEY: misc_feature
<222> LOCATION: (6)..(6)
<223> OTHER INFORMATION: May be deoxy guanosine phosphorothioate
<220> FEATURE:
<221> NAME/KEY: misc_feature
<222> LOCATION: (7)..(7)
<223> OTHER INFORMATION: May be locked nucleic acid thymidine
      phosphorothioate
<220> FEATURE:
<221> NAME/KEY: misc_feature
<222> LOCATION: (8)..(8)
<223> OTHER INFORMATION: May be deoxy thymidine phosphorothioate
<220> FEATURE:
<221> NAME/KEY: misc_feature
<222> LOCATION: (9)..(9)
<223> OTHER INFORMATION: May be locked nucleic acid cytidine
      phosphorothioate
<220> FEATURE:
<221> NAME/KEY: misc_feature
<222> LOCATION: (10)..(10)
<223> OTHER INFORMATION: May be deoxy guanosine phosphorothioate
<220> FEATURE:
<221> NAME/KEY: misc_feature
<222> LOCATION: (11)..(11)
<223> OTHER INFORMATION: May be deoxy thymidine phosphorothioate
<220> FEATURE:
<221> NAME/KEY: misc_feature
<222> LOCATION: (12)..(12)
<223> OTHER INFORMATION: May be locked nucleic acid cytidine
      phosphorothioate
<220> FEATURE:
<221> NAME/KEY: misc_feature
<222> LOCATION: (13)..(13)
<223> OTHER INFORMATION: May be deoxy thymidine phosphorothioate

```
<220> FEATURE:
<221> NAME/KEY: misc_feature
<222> LOCATION: (14)..(14)
<223> OTHER INFORMATION: May be locked nucleic acid thymidine
      phosphorothioate
<220> FEATURE:
<221> NAME/KEY: misc_feature
<222> LOCATION: (15)..(15)
<223> OTHER INFORMATION: May be locked nucleic acid adenosine

<400> SEQUENCE: 37
cttttgttcg tctta                                                        15

<210> SEQ ID NO 38
<211> LENGTH: 15
<212> TYPE: DNA
<213> ORGANISM: Artificial Sequence
<220> FEATURE:
<223> OTHER INFORMATION: Anti-miR-208 oligonucleotide
<220> FEATURE:
<221> NAME/KEY: misc_feature
<222> LOCATION: (1)..(1)
<223> OTHER INFORMATION: May be locked nucleic acid cytidine
      phosphorothioate
<220> FEATURE:
<221> NAME/KEY: misc_feature
<222> LOCATION: (2)..(5)
<223> OTHER INFORMATION: May be locked nucleic acid thymidine
      phosphorothioate
<220> FEATURE:
<221> NAME/KEY: misc_feature
<222> LOCATION: (6)..(6)
<223> OTHER INFORMATION: May be deoxy guanosine phosphorothioate
<220> FEATURE:
<221> NAME/KEY: misc_feature
<222> LOCATION: (7)..(7)
<223> OTHER INFORMATION: May be locked nucleic acid thymidine
      phosphorothioate
<220> FEATURE:
<221> NAME/KEY: misc_feature
<222> LOCATION: (8)..(8)
<223> OTHER INFORMATION: May be deoxy thymidine phosphorothioate
<220> FEATURE:
<221> NAME/KEY: misc_feature
<222> LOCATION: (9)..(9)
<223> OTHER INFORMATION: May be locked nucleic acid cytidine
      phosphorothioate
<220> FEATURE:
<221> NAME/KEY: misc_feature
<222> LOCATION: (10)..(10)
<223> OTHER INFORMATION: May be deoxy guanosine phosphorothioate
<220> FEATURE:
<221> NAME/KEY: misc_feature
<222> LOCATION: (11)..(11)
<223> OTHER INFORMATION: May be locked nucleic acid thymidine
      phosphorothioate
<220> FEATURE:
<221> NAME/KEY: misc_feature
<222> LOCATION: (12)..(12)
<223> OTHER INFORMATION: May be locked nucleic acid cytidine
      phosphorothioate
<220> FEATURE:
<221> NAME/KEY: misc_feature
<222> LOCATION: (13)..(13)
<223> OTHER INFORMATION: May be deoxy thymidine phosphorothioate
<220> FEATURE:
<221> NAME/KEY: misc_feature
<222> LOCATION: (14)..(14)
<223> OTHER INFORMATION: May be locked nucleic acid thymidine
      phosphorothioate
<220> FEATURE:
<221> NAME/KEY: misc_feature
<222> LOCATION: (15)..(15)
<223> OTHER INFORMATION: May be deoxy adenosine

<400> SEQUENCE: 38
cttttgttcg tctta                                                        15
```

```
<210> SEQ ID NO 39
<211> LENGTH: 15
<212> TYPE: DNA
<213> ORGANISM: Artificial Sequence
<220> FEATURE:
<223> OTHER INFORMATION: Anti-miR-208 oligonucleotide
<220> FEATURE:
<221> NAME/KEY: misc_feature
<222> LOCATION: (1)..(1)
<223> OTHER INFORMATION: May be locked nucleic acid thymidine
      phosphorothioate
<220> FEATURE:
<221> NAME/KEY: misc_feature
<222> LOCATION: (2)..(2)
<223> OTHER INFORMATION: May be deoxy thymidine phosphorothioate
<220> FEATURE:
<221> NAME/KEY: misc_feature
<222> LOCATION: (3)..(3)
<223> OTHER INFORMATION: May be locked nucleic acid thymidine
      phosphorothioate
<220> FEATURE:
<221> NAME/KEY: misc_feature
<222> LOCATION: (4)..(4)
<223> OTHER INFORMATION: May be deoxy thymidine phosphorothioate
<220> FEATURE:
<221> NAME/KEY: misc_feature
<222> LOCATION: (5)..(5)
<223> OTHER INFORMATION: May be locked nucleic acid thymidine
      phosphorothioate
<220> FEATURE:
<221> NAME/KEY: misc_feature
<222> LOCATION: (6)..(6)
<223> OTHER INFORMATION: May be deoxy guanosine phosphorothioate
<220> FEATURE:
<221> NAME/KEY: misc_feature
<222> LOCATION: (7)..(7)
<223> OTHER INFORMATION: May be deoxy cytidine phosphorothioate
<220> FEATURE:
<221> NAME/KEY: misc_feature
<222> LOCATION: (8)..(8)
<223> OTHER INFORMATION: May be deoxy thymidine phosphorothioate
<220> FEATURE:
<221> NAME/KEY: misc_feature
<222> LOCATION: (9)..(9)
<223> OTHER INFORMATION: May be locked nucleic acid cytidine
      phosphorothioate
<220> FEATURE:
<221> NAME/KEY: misc_feature
<222> LOCATION: (10)..(10)
<223> OTHER INFORMATION: May be locked nucleic acid guanosine
      phosphorothioate
<220> FEATURE:
<221> NAME/KEY: misc_feature
<222> LOCATION: (11)..(11)
<223> OTHER INFORMATION: May be locked nucleic acid thymidine
      phosphorothioate
<220> FEATURE:
<221> NAME/KEY: misc_feature
<222> LOCATION: (12)..(12)
<223> OTHER INFORMATION: May be locked nucleic acid cytidine
      phosphorothioate
<220> FEATURE:
<221> NAME/KEY: misc_feature
<222> LOCATION: (13)..(14)
<223> OTHER INFORMATION: May be locked nucleic acid thymidine
      phosphorothioate
<220> FEATURE:
<221> NAME/KEY: misc_feature
<222> LOCATION: (15)..(15)
<223> OTHER INFORMATION: May be locked nucleic acid adenosine

<400> SEQUENCE: 39
tttttgctcg tctta                                                   15

<210> SEQ ID NO 40
<211> LENGTH: 15
```

```
<212> TYPE: DNA
<213> ORGANISM: Artificial Sequence
<220> FEATURE:
<223> OTHER INFORMATION: Anti-miR-208 oligonucleotide
<220> FEATURE:
<221> NAME/KEY: misc_feature
<222> LOCATION: (1)..(1)
<223> OTHER INFORMATION: May be locked nucleic acid cytidine
      phosphorothioate
<220> FEATURE:
<221> NAME/KEY: misc_feature
<222> LOCATION: (2)..(2)
<223> OTHER INFORMATION: May be deoxy thymidine phosphorothioate
<220> FEATURE:
<221> NAME/KEY: misc_feature
<222> LOCATION: (3)..(3)
<223> OTHER INFORMATION: May be locked nucleic acid thymidine
      phosphorothioate
<220> FEATURE:
<221> NAME/KEY: misc_feature
<222> LOCATION: (4)..(4)
<223> OTHER INFORMATION: May be deoxy thymidine phosphorothioate
<220> FEATURE:
<221> NAME/KEY: misc_feature
<222> LOCATION: (5)..(5)
<223> OTHER INFORMATION: May be locked nucleic acid thymidine
      phosphorothioate
<220> FEATURE:
<221> NAME/KEY: misc_feature
<222> LOCATION: (6)..(6)
<223> OTHER INFORMATION: May be deoxy guanosine phosphorothioate
<220> FEATURE:
<221> NAME/KEY: misc_feature
<222> LOCATION: (7)..(7)
<223> OTHER INFORMATION: May be deoxy cytidine phosphorothioate
<220> FEATURE:
<221> NAME/KEY: misc_feature
<222> LOCATION: (8)..(8)
<223> OTHER INFORMATION: May be deoxy thymidine phosphorothioate
<220> FEATURE:
<221> NAME/KEY: misc_feature
<222> LOCATION: (9)..(9)
<223> OTHER INFORMATION: May be locked nucleic acid cytidine
      phosphorothioate
<220> FEATURE:
<221> NAME/KEY: misc_feature
<222> LOCATION: (10)..(10)
<223> OTHER INFORMATION: May be locked nucleic acid guanosine
      phosphorothioate
<220> FEATURE:
<221> NAME/KEY: misc_feature
<222> LOCATION: (11)..(11)
<223> OTHER INFORMATION: May be locked nucleic acid thymidine
      phosphorothioate
<220> FEATURE:
<221> NAME/KEY: misc_feature
<222> LOCATION: (12)..(12)
<223> OTHER INFORMATION: May be locked nucleic acid cytidine
      phosphorothioate
<220> FEATURE:
<221> NAME/KEY: misc_feature
<222> LOCATION: (13)..(14)
<223> OTHER INFORMATION: May be locked nucleic acid thymidine
      phosphorothioate
<220> FEATURE:
<221> NAME/KEY: misc_feature
<222> LOCATION: (15)..(15)
<223> OTHER INFORMATION: May be locked nucleic acid adenosine

<400> SEQUENCE: 40
cttttgctcg tctta                                                    15

<210> SEQ ID NO 41
<211> LENGTH: 15
<212> TYPE: DNA
<213> ORGANISM: Artificial Sequence
<220> FEATURE:
<223> OTHER INFORMATION: Anti-miR-208 oligonucleotide
```

```
<220> FEATURE:
<221> NAME/KEY: misc_feature
<222> LOCATION: (1)..(1)
<223> OTHER INFORMATION: May be locked nucleic acid cytidine
      phosphorothioate
<220> FEATURE:
<221> NAME/KEY: misc_feature
<222> LOCATION: (2)..(2)
<223> OTHER INFORMATION: May be deoxy thymidine phosphorothioate
<220> FEATURE:
<221> NAME/KEY: misc_feature
<222> LOCATION: (3)..(3)
<223> OTHER INFORMATION: May be locked nucleic acid thymidine
      phosphorothioate
<220> FEATURE:
<221> NAME/KEY: misc_feature
<222> LOCATION: (4)..(4)
<223> OTHER INFORMATION: May be deoxy thymidine phosphorothioate
<220> FEATURE:
<221> NAME/KEY: misc_feature
<222> LOCATION: (5)..(5)
<223> OTHER INFORMATION: May be locked nucleic acid thymidine
      phosphorothioate
<220> FEATURE:
<221> NAME/KEY: misc_feature
<222> LOCATION: (6)..(6)
<223> OTHER INFORMATION: May be deoxy guanosine phosphorothioate
<220> FEATURE:
<221> NAME/KEY: misc_feature
<222> LOCATION: (7)..(8)
<223> OTHER INFORMATION: May be deoxy thymidine phosphorothioate
<220> FEATURE:
<221> NAME/KEY: misc_feature
<222> LOCATION: (9)..(9)
<223> OTHER INFORMATION: May be locked nucleic acid cytidine
      phosphorothioate
<220> FEATURE:
<221> NAME/KEY: misc_feature
<222> LOCATION: (10)..(10)
<223> OTHER INFORMATION: May be locked nucleic acid guanosine
      phosphorothioate
<220> FEATURE:
<221> NAME/KEY: misc_feature
<222> LOCATION: (11)..(11)
<223> OTHER INFORMATION: May be locked nucleic acid thymidine
      phosphorothioate
<220> FEATURE:
<221> NAME/KEY: misc_feature
<222> LOCATION: (12)..(12)
<223> OTHER INFORMATION: May be locked nucleic acid cytidine
      phosphorothioate
<220> FEATURE:
<221> NAME/KEY: misc_feature
<222> LOCATION: (13)..(14)
<223> OTHER INFORMATION: May be locked nucleic acid thymidine
      phosphorothioate
<220> FEATURE:
<221> NAME/KEY: misc_feature
<222> LOCATION: (15)..(15)
<223> OTHER INFORMATION: May be locked nucleic acid adenosine

<400> SEQUENCE: 41
cttttgttcg tctta                                                     15

<210> SEQ ID NO 42
<211> LENGTH: 14
<212> TYPE: DNA
<213> ORGANISM: Artificial Sequence
<220> FEATURE:
<223> OTHER INFORMATION: Anti-miR-208 oligonucleotide
<220> FEATURE:
<221> NAME/KEY: misc_feature
<222> LOCATION: (1)..(4)
<223> OTHER INFORMATION: May be locked nucleic acid thymidine
      phosphorothioate
<220> FEATURE:
<221> NAME/KEY: misc_feature
<222> LOCATION: (5)..(5)
```

```
<223> OTHER INFORMATION: May be deoxy guanosine phosphorothioate
<220> FEATURE:
<221> NAME/KEY: misc_feature
<222> LOCATION: (6)..(6)
<223> OTHER INFORMATION: May be locked nucleic acid cytidine
      phosphorothioate
<220> FEATURE:
<221> NAME/KEY: misc_feature
<222> LOCATION: (7)..(7)
<223> OTHER INFORMATION: May be deoxy thymidine phosphorothioate
<220> FEATURE:
<221> NAME/KEY: misc_feature
<222> LOCATION: (8)..(8)
<223> OTHER INFORMATION: May be locked nucleic acid cytidine
      phosphorothioate
<220> FEATURE:
<221> NAME/KEY: misc_feature
<222> LOCATION: (9)..(9)
<223> OTHER INFORMATION: May be deoxy guanosine phosphorothioate
<220> FEATURE:
<221> NAME/KEY: misc_feature
<222> LOCATION: (10)..(10)
<223> OTHER INFORMATION: May be deoxy thymidine phosphorothioate
<220> FEATURE:
<221> NAME/KEY: misc_feature
<222> LOCATION: (11)..(11)
<223> OTHER INFORMATION: May be locked nucleic acid cytidine
      phosphorothioate
<220> FEATURE:
<221> NAME/KEY: misc_feature
<222> LOCATION: (12)..(12)
<223> OTHER INFORMATION: May be deoxy thymidine phosphorothioate
<220> FEATURE:
<221> NAME/KEY: misc_feature
<222> LOCATION: (13)..(13)
<223> OTHER INFORMATION: May be locked nucleic acid thymidine
      phosphorothioate
<220> FEATURE:
<221> NAME/KEY: misc_feature
<222> LOCATION: (14)..(14)
<223> OTHER INFORMATION: May be deoxy adenosine

<400> SEQUENCE: 42
ttttgctcgt ctta                                                      14

<210> SEQ ID NO 43
<211> LENGTH: 14
<212> TYPE: DNA
<213> ORGANISM: Artificial Sequence
<220> FEATURE:
<223> OTHER INFORMATION: Anti-miR-208 oligonucleotide
<220> FEATURE:
<221> NAME/KEY: misc_feature
<222> LOCATION: (1)..(4)
<223> OTHER INFORMATION: May be locked nucleic acid thymidine
      phosphorothioate
<220> FEATURE:
<221> NAME/KEY: misc_feature
<222> LOCATION: (5)..(5)
<223> OTHER INFORMATION: May be deoxy guanosine phosphorothioate
<220> FEATURE:
<221> NAME/KEY: misc_feature
<222> LOCATION: (6)..(6)
<223> OTHER INFORMATION: May be locked nucleic acid cytidine
      phosphorothioate
<220> FEATURE:
<221> NAME/KEY: misc_feature
<222> LOCATION: (7)..(7)
<223> OTHER INFORMATION: May be deoxy thymidine phosphorothioate
<220> FEATURE:
<221> NAME/KEY: misc_feature
<222> LOCATION: (8)..(8)
<223> OTHER INFORMATION: May be locked nucleic acid cytidine
      phosphorothioate
<220> FEATURE:
<221> NAME/KEY: misc_feature
<222> LOCATION: (9)..(9)
<223> OTHER INFORMATION: May be deoxy guanosine phosphorothioate
```

```
<220> FEATURE:
<221> NAME/KEY: misc_feature
<222> LOCATION: (10)..(10)
<223> OTHER INFORMATION: May be deoxy thymidine phosphorothioate
<220> FEATURE:
<221> NAME/KEY: misc_feature
<222> LOCATION: (11)..(11)
<223> OTHER INFORMATION: May be locked nucleic acid cytidine
      phosphorothioate
<220> FEATURE:
<221> NAME/KEY: misc_feature
<222> LOCATION: (12)..(12)
<223> OTHER INFORMATION: May be deoxy thymidine phosphorothioate
<220> FEATURE:
<221> NAME/KEY: misc_feature
<222> LOCATION: (13)..(13)
<223> OTHER INFORMATION: May be locked nucleic acid thymidine
      phosphorothioate
<220> FEATURE:
<221> NAME/KEY: misc_feature
<222> LOCATION: (14)..(14)
<223> OTHER INFORMATION: May be locked nucleic acid adenosine

<400> SEQUENCE: 43
ttttgctcgt ctta                                                    14

<210> SEQ ID NO 44
<211> LENGTH: 14
<212> TYPE: DNA
<213> ORGANISM: Artificial Sequence
<220> FEATURE:
<223> OTHER INFORMATION: Anti-miR-208 oligonucleotide
<220> FEATURE:
<221> NAME/KEY: misc_feature
<222> LOCATION: (1)..(4)
<223> OTHER INFORMATION: May be locked nucleic acid thymidine
      phosphorothioate
<220> FEATURE:
<221> NAME/KEY: misc_feature
<222> LOCATION: (5)..(5)
<223> OTHER INFORMATION: May be deoxy guanosine phosphorothioate
<220> FEATURE:
<221> NAME/KEY: misc_feature
<222> LOCATION: (6)..(6)
<223> OTHER INFORMATION: May be deoxy cytidine phosphorothioate
<220> FEATURE:
<221> NAME/KEY: misc_feature
<222> LOCATION: (7)..(7)
<223> OTHER INFORMATION: May be deoxy thymidine phosphorothioate
<220> FEATURE:
<221> NAME/KEY: misc_feature
<222> LOCATION: (8)..(8)
<223> OTHER INFORMATION: May be locked nucleic acid cytidine
      phosphorothioate
<220> FEATURE:
<221> NAME/KEY: misc_feature
<222> LOCATION: (9)..(9)
<223> OTHER INFORMATION: May be deoxy guanosine phosphorothioate
<220> FEATURE:
<221> NAME/KEY: misc_feature
<222> LOCATION: (10)..(10)
<223> OTHER INFORMATION: May be deoxy thymidine phosphorothioate
<220> FEATURE:
<221> NAME/KEY: misc_feature
<222> LOCATION: (11)..(11)
<223> OTHER INFORMATION: May be locked nucleic acid cytidine
      phosphorothioate
<220> FEATURE:
<221> NAME/KEY: misc_feature
<222> LOCATION: (12)..(12)
<223> OTHER INFORMATION: May be deoxy thymidine phosphorothioate
<220> FEATURE:
<221> NAME/KEY: misc_feature
<222> LOCATION: (13)..(13)
<223> OTHER INFORMATION: May be locked nucleic acid thymidine
      phosphorothioate
<220> FEATURE:
<221> NAME/KEY: misc_feature
```

-continued

<222> LOCATION: (14)..(14)
<223> OTHER INFORMATION: May be locked nucleic acid adenosine

<400> SEQUENCE: 44
ttttgctcgt ctta                                                        14

<210> SEQ ID NO 45
<211> LENGTH: 14
<212> TYPE: DNA
<213> ORGANISM: Artificial Sequence
<220> FEATURE:
<223> OTHER INFORMATION: Anti-miR-208 oligonucleotide
<220> FEATURE:
<221> NAME/KEY: misc_feature
<222> LOCATION: (1)..(4)
<223> OTHER INFORMATION: May be locked nucleic acid thymidine
      phosphorothioate
<220> FEATURE:
<221> NAME/KEY: misc_feature
<222> LOCATION: (5)..(5)
<223> OTHER INFORMATION: May be deoxy guanosine phosphorothioate
<220> FEATURE:
<221> NAME/KEY: misc_feature
<222> LOCATION: (6)..(6)
<223> OTHER INFORMATION: May be deoxy cytidine phosphorothioate
<220> FEATURE:
<221> NAME/KEY: misc_feature
<222> LOCATION: (7)..(7)
<223> OTHER INFORMATION: May be deoxy thymidine phosphorothioate
<220> FEATURE:
<221> NAME/KEY: misc_feature
<222> LOCATION: (8)..(8)
<223> OTHER INFORMATION: May be locked nucleic acid cytidine
      phosphorothioate
<220> FEATURE:
<221> NAME/KEY: misc_feature
<222> LOCATION: (9)..(9)
<223> OTHER INFORMATION: May be deoxy guanosine phosphorothioate
<220> FEATURE:
<221> NAME/KEY: misc_feature
<222> LOCATION: (10)..(10)
<223> OTHER INFORMATION: May be locked nucleic acid thymidine
      phosphorothioate
<220> FEATURE:
<221> NAME/KEY: misc_feature
<222> LOCATION: (11)..(11)
<223> OTHER INFORMATION: May be locked nucleic acid cytidine
      phosphorothioate
<220> FEATURE:
<221> NAME/KEY: misc_feature
<222> LOCATION: (12)..(12)
<223> OTHER INFORMATION: May be deoxy thymidine phosphorothioate
<220> FEATURE:
<221> NAME/KEY: misc_feature
<222> LOCATION: (13)..(13)
<223> OTHER INFORMATION: May be locked nucleic acid thymidine
      phosphorothioate
<220> FEATURE:
<221> NAME/KEY: misc_feature
<222> LOCATION: (14)..(14)
<223> OTHER INFORMATION: May be locked nucleic acid adenosine

<400> SEQUENCE: 45
ttttgctcgt ctta                                                        14

<210> SEQ ID NO 46
<211> LENGTH: 14
<212> TYPE: DNA
<213> ORGANISM: Artificial Sequence
<220> FEATURE:
<223> OTHER INFORMATION: Anti-miR-208 oligonucleotide
<220> FEATURE:
<221> NAME/KEY: misc_feature
<222> LOCATION: (1)..(4)
<223> OTHER INFORMATION: May be locked nucleic acid thymidine
      phosphorothioate

```
<220> FEATURE:
<221> NAME/KEY: misc_feature
<222> LOCATION: (5)..(5)
<223> OTHER INFORMATION: May be deoxy guanosine phosphorothioate
<220> FEATURE:
<221> NAME/KEY: misc_feature
<222> LOCATION: (6)..(6)
<223> OTHER INFORMATION: May be deoxy cytidine phosphorothioate
<220> FEATURE:
<221> NAME/KEY: misc_feature
<222> LOCATION: (7)..(7)
<223> OTHER INFORMATION: May be locked nucleic acid thymidine
      phosphorothioate
<220> FEATURE:
<221> NAME/KEY: misc_feature
<222> LOCATION: (8)..(8)
<223> OTHER INFORMATION: May be locked nucleic acid cytidine
      phosphorothioate
<220> FEATURE:
<221> NAME/KEY: misc_feature
<222> LOCATION: (9)..(9)
<223> OTHER INFORMATION: May be deoxy guanosine phosphorothioate
<220> FEATURE:
<221> NAME/KEY: misc_feature
<222> LOCATION: (10)..(10)
<223> OTHER INFORMATION: May be locked nucleic acid thymidine
      phosphorothioate
<220> FEATURE:
<221> NAME/KEY: misc_feature
<222> LOCATION: (11)..(11)
<223> OTHER INFORMATION: May be deoxy cytidine phosphorothioate
<220> FEATURE:
<221> NAME/KEY: misc_feature
<222> LOCATION: (12)..(13)
<223> OTHER INFORMATION: May be locked nucleic acid thymidine
      phosphorothioate
<220> FEATURE:
<221> NAME/KEY: misc_feature
<222> LOCATION: (14)..(14)
<223> OTHER INFORMATION: May be deoxy adenosine

<400> SEQUENCE: 46
ttttgctcgt ctta                                                    14

<210> SEQ ID NO 47
<211> LENGTH: 14
<212> TYPE: DNA
<213> ORGANISM: Artificial Sequence
<220> FEATURE:
<223> OTHER INFORMATION: Anti-miR-208 oligonucleotide
<220> FEATURE:
<221> NAME/KEY: misc_feature
<222> LOCATION: (1)..(1)
<223> OTHER INFORMATION: May be locked nucleic acid thymidine
      phosphorothioate
<220> FEATURE:
<221> NAME/KEY: misc_feature
<222> LOCATION: (2)..(2)
<223> OTHER INFORMATION: May be deoxy thymidine phosphorothioate
<220> FEATURE:
<221> NAME/KEY: misc_feature
<222> LOCATION: (3)..(3)
<223> OTHER INFORMATION: May be locked nucleic acid thymidine
      phosphorothioate
<220> FEATURE:
<221> NAME/KEY: misc_feature
<222> LOCATION: (4)..(4)
<223> OTHER INFORMATION: May be deoxy thymidine phosphorothioate
<220> FEATURE:
<221> NAME/KEY: misc_feature
<222> LOCATION: (5)..(5)
<223> OTHER INFORMATION: May be deoxy guanosine phosphorothioate
<220> FEATURE:
<221> NAME/KEY: misc_feature
<222> LOCATION: (6)..(6)
<223> OTHER INFORMATION: May be locked nucleic acid cytidine
      phosphorothioate
<220> FEATURE:
```

```
<221> NAME/KEY: misc_feature
<222> LOCATION: (7)..(7)
<223> OTHER INFORMATION: May be deoxy thymidine phosphorothioate
<220> FEATURE:
<221> NAME/KEY: misc_feature
<222> LOCATION: (8)..(8)
<223> OTHER INFORMATION: May be locked nucleic acid cytidine
      phosphorothioate
<220> FEATURE:
<221> NAME/KEY: misc_feature
<222> LOCATION: (9)..(9)
<223> OTHER INFORMATION: May be locked nucleic acid guanosine
      phosphorothioate
<220> FEATURE:
<221> NAME/KEY: misc_feature
<222> LOCATION: (10)..(10)
<223> OTHER INFORMATION: May be locked nucleic acid thymidine
      phosphorothioate
<220> FEATURE:
<221> NAME/KEY: misc_feature
<222> LOCATION: (11)..(11)
<223> OTHER INFORMATION: May be locked nucleic acid cytidine
      phosphorothioate
<220> FEATURE:
<221> NAME/KEY: misc_feature
<222> LOCATION: (12)..(13)
<223> OTHER INFORMATION: May be locked nucleic acid thymidine
      phosphorothioate
<220> FEATURE:
<221> NAME/KEY: misc_feature
<222> LOCATION: (14)..(14)
<223> OTHER INFORMATION: May be locked nucleic acid adenosine

<400> SEQUENCE: 47
ttttgctcgt ctta                                                      14

<210> SEQ ID NO 48
<211> LENGTH: 14
<212> TYPE: DNA
<213> ORGANISM: Artificial Sequence
<220> FEATURE:
<223> OTHER INFORMATION: Anti-miR-208 oligonucleotide
<220> FEATURE:
<221> NAME/KEY: misc_feature
<222> LOCATION: (1)..(4)
<223> OTHER INFORMATION: May be locked nucleic acid thymidine
      phosphorothioate
<220> FEATURE:
<221> NAME/KEY: misc_feature
<222> LOCATION: (5)..(5)
<223> OTHER INFORMATION: May be deoxy guanosine phosphorothioate
<220> FEATURE:
<221> NAME/KEY: misc_feature
<222> LOCATION: (6)..(6)
<223> OTHER INFORMATION: May be locked nucleic acid thymidine
      phosphorothioate
<220> FEATURE:
<221> NAME/KEY: misc_feature
<222> LOCATION: (7)..(7)
<223> OTHER INFORMATION: May be deoxy thymidine phosphorothioate
<220> FEATURE:
<221> NAME/KEY: misc_feature
<222> LOCATION: (8)..(8)
<223> OTHER INFORMATION: May be locked nucleic acid cytidine
      phosphorothioate
<220> FEATURE:
<221> NAME/KEY: misc_feature
<222> LOCATION: (9)..(9)
<223> OTHER INFORMATION: May be deoxy guanosine phosphorothioate
<220> FEATURE:
<221> NAME/KEY: misc_feature
<222> LOCATION: (10)..(10)
<223> OTHER INFORMATION: May be deoxy thymidine phosphorothioate
<220> FEATURE:
<221> NAME/KEY: misc_feature
<222> LOCATION: (11)..(11)
<223> OTHER INFORMATION: May be locked nucleic acid cytidine
      phosphorothioate
```

```
<220> FEATURE:
<221> NAME/KEY: misc_feature
<222> LOCATION: (12)..(12)
<223> OTHER INFORMATION: May be deoxy thymidine phosphorothioate
<220> FEATURE:
<221> NAME/KEY: misc_feature
<222> LOCATION: (13)..(13)
<223> OTHER INFORMATION: May be locked nucleic acid thymidine
      phosphorothioate
<220> FEATURE:
<221> NAME/KEY: misc_feature
<222> LOCATION: (14)..(14)
<223> OTHER INFORMATION: May be deoxy adenosine

<400> SEQUENCE: 48
ttttgttcgt ctta                                                        14

<210> SEQ ID NO 49
<211> LENGTH: 14
<212> TYPE: DNA
<213> ORGANISM: Artificial Sequence
<220> FEATURE:
<223> OTHER INFORMATION: Anti-miR-208 oligonucleotide
<220> FEATURE:
<221> NAME/KEY: misc_feature
<222> LOCATION: (1)..(4)
<223> OTHER INFORMATION: May be locked nucleic acid thymidine
      phosphorothioate
<220> FEATURE:
<221> NAME/KEY: misc_feature
<222> LOCATION: (5)..(5)
<223> OTHER INFORMATION: May be deoxy guanosine phosphorothioate
<220> FEATURE:
<221> NAME/KEY: misc_feature
<222> LOCATION: (6)..(6)
<223> OTHER INFORMATION: May be locked nucleic acid thymidine
      phosphorothioate
<220> FEATURE:
<221> NAME/KEY: misc_feature
<222> LOCATION: (7)..(7)
<223> OTHER INFORMATION: May be deoxy thymidine phosphorothioate
<220> FEATURE:
<221> NAME/KEY: misc_feature
<222> LOCATION: (8)..(8)
<223> OTHER INFORMATION: May be locked nucleic acid cytidine
      phosphorothioate
<220> FEATURE:
<221> NAME/KEY: misc_feature
<222> LOCATION: (9)..(9)
<223> OTHER INFORMATION: May be deoxy guanosine phosphorothioate
<220> FEATURE:
<221> NAME/KEY: misc_feature
<222> LOCATION: (10)..(10)
<223> OTHER INFORMATION: May be deoxy thymidine phosphorothioate
<220> FEATURE:
<221> NAME/KEY: misc_feature
<222> LOCATION: (11)..(11)
<223> OTHER INFORMATION: May be locked nucleic acid cytidine
      phosphorothioate
<220> FEATURE:
<221> NAME/KEY: misc_feature
<222> LOCATION: (12)..(12)
<223> OTHER INFORMATION: May be deoxy thymidine phosphorothioate
<220> FEATURE:
<221> NAME/KEY: misc_feature
<222> LOCATION: (13)..(13)
<223> OTHER INFORMATION: May be locked nucleic acid thymidine
      phosphorothioate
<220> FEATURE:
<221> NAME/KEY: misc_feature
<222> LOCATION: (14)..(14)
<223> OTHER INFORMATION: May be locked nucleic acid adenosine

<400> SEQUENCE: 49
ttttgttcgt ctta                                                        14
```

```
<210> SEQ ID NO 50
<211> LENGTH: 14
<212> TYPE: DNA
<213> ORGANISM: Artificial Sequence
<220> FEATURE:
<223> OTHER INFORMATION: Anti-miR-208 oligonucleotide
<220> FEATURE:
<221> NAME/KEY: misc_feature
<222> LOCATION: (1)..(4)
<223> OTHER INFORMATION: May be locked nucleic acid thymidine
      phosphorothioate
<220> FEATURE:
<221> NAME/KEY: misc_feature
<222> LOCATION: (5)..(5)
<223> OTHER INFORMATION: May be deoxy guanosine phosphorothioate
<220> FEATURE:
<221> NAME/KEY: misc_feature
<222> LOCATION: (6)..(7)
<223> OTHER INFORMATION: May be deoxy thymidine phosphorothioate
<220> FEATURE:
<221> NAME/KEY: misc_feature
<222> LOCATION: (8)..(8)
<223> OTHER INFORMATION: May be locked nucleic acid cytidine
      phosphorothioate
<220> FEATURE:
<221> NAME/KEY: misc_feature
<222> LOCATION: (9)..(9)
<223> OTHER INFORMATION: May be deoxy guanosine phosphorothioate
<220> FEATURE:
<221> NAME/KEY: misc_feature
<222> LOCATION: (10)..(10)
<223> OTHER INFORMATION: May be deoxy thymidine phosphorothioate
<220> FEATURE:
<221> NAME/KEY: misc_feature
<222> LOCATION: (11)..(11)
<223> OTHER INFORMATION: May be locked nucleic acid cytidine
      phosphorothioate
<220> FEATURE:
<221> NAME/KEY: misc_feature
<222> LOCATION: (12)..(12)
<223> OTHER INFORMATION: May be deoxy thymidine phosphorothioate
<220> FEATURE:
<221> NAME/KEY: misc_feature
<222> LOCATION: (13)..(13)
<223> OTHER INFORMATION: May be locked nucleic acid thymidine
      phosphorothioate
<220> FEATURE:
<221> NAME/KEY: misc_feature
<222> LOCATION: (14)..(14)
<223> OTHER INFORMATION: May be locked nucleic acid adenosine

<400> SEQUENCE: 50
ttttgttcgt ctta                                                       14

<210> SEQ ID NO 51
<211> LENGTH: 14
<212> TYPE: DNA
<213> ORGANISM: Artificial Sequence
<220> FEATURE:
<223> OTHER INFORMATION: Anti-miR-208 oligonucleotide
<220> FEATURE:
<221> NAME/KEY: misc_feature
<222> LOCATION: (1)..(4)
<223> OTHER INFORMATION: May be locked nucleic acid thymidine
      phosphorothioate
<220> FEATURE:
<221> NAME/KEY: misc_feature
<222> LOCATION: (5)..(5)
<223> OTHER INFORMATION: May be deoxy guanosine phosphorothioate
<220> FEATURE:
<221> NAME/KEY: misc_feature
<222> LOCATION: (6)..(7)
<223> OTHER INFORMATION: May be deoxy thymidine phosphorothioate
<220> FEATURE:
<221> NAME/KEY: misc_feature
<222> LOCATION: (8)..(8)
<223> OTHER INFORMATION: May be locked nucleic acid cytidine
      phosphorothioate
```

-continued

```
<220> FEATURE:
<221> NAME/KEY: misc_feature
<222> LOCATION: (9)..(9)
<223> OTHER INFORMATION: May be deoxy guanosine phosphorothioate
<220> FEATURE:
<221> NAME/KEY: misc_feature
<222> LOCATION: (10)..(10)
<223> OTHER INFORMATION: May be locked nucleic acid thymidine
      phosphorothioate
<220> FEATURE:
<221> NAME/KEY: misc_feature
<222> LOCATION: (11)..(11)
<223> OTHER INFORMATION: May be locked nucleic acid cytidine
      phosphorothioate
<220> FEATURE:
<221> NAME/KEY: misc_feature
<222> LOCATION: (12)..(12)
<223> OTHER INFORMATION: May be deoxy thymidine phosphorothioate
<220> FEATURE:
<221> NAME/KEY: misc_feature
<222> LOCATION: (13)..(13)
<223> OTHER INFORMATION: May be locked nucleic acid thymidine
      phosphorothioate
<220> FEATURE:
<221> NAME/KEY: misc_feature
<222> LOCATION: (14)..(14)
<223> OTHER INFORMATION: May be locked nucleic acid adenosine

<400> SEQUENCE: 51
ttttgttcgt ctta                                                        14

<210> SEQ ID NO 52
<211> LENGTH: 14
<212> TYPE: DNA
<213> ORGANISM: Artificial Sequence
<220> FEATURE:
<223> OTHER INFORMATION: Anti-miR-208 oligonucleotide
<220> FEATURE:
<221> NAME/KEY: misc_feature
<222> LOCATION: (1)..(4)
<223> OTHER INFORMATION: May be locked nucleic acid thymidine
      phosphorothioate
<220> FEATURE:
<221> NAME/KEY: misc_feature
<222> LOCATION: (5)..(5)
<223> OTHER INFORMATION: May be deoxy guanosine phosphorothioate
<220> FEATURE:
<221> NAME/KEY: misc_feature
<222> LOCATION: (6)..(6)
<223> OTHER INFORMATION: May be deoxy thymidine phosphorothioate
<220> FEATURE:
<221> NAME/KEY: misc_feature
<222> LOCATION: (7)..(7)
<223> OTHER INFORMATION: May be locked nucleic acid thymidine
      phosphorothioate
<220> FEATURE:
<221> NAME/KEY: misc_feature
<222> LOCATION: (8)..(8)
<223> OTHER INFORMATION: May be locked nucleic acid cytidine
      phosphorothioate
<220> FEATURE:
<221> NAME/KEY: misc_feature
<222> LOCATION: (9)..(9)
<223> OTHER INFORMATION: May be deoxy guanosine phosphorothioate
<220> FEATURE:
<221> NAME/KEY: misc_feature
<222> LOCATION: (10)..(10)
<223> OTHER INFORMATION: May be locked nucleic acid thymidine
      phosphorothioate
<220> FEATURE:
<221> NAME/KEY: misc_feature
<222> LOCATION: (11)..(11)
<223> OTHER INFORMATION: May be deoxy cytidine phosphorothioate
<220> FEATURE:
<221> NAME/KEY: misc_feature
<222> LOCATION: (12)..(13)
<223> OTHER INFORMATION: May be locked nucleic acid thymidine
      phosphorothioate
```

```
<220> FEATURE:
<221> NAME/KEY: misc_feature
<222> LOCATION: (14)..(14)
<223> OTHER INFORMATION: May be deoxy adenosine

<400> SEQUENCE: 52
ttttgttcgt ctta                                                     14

<210> SEQ ID NO 53
<211> LENGTH: 14
<212> TYPE: DNA
<213> ORGANISM: Artificial Sequence
<220> FEATURE:
<223> OTHER INFORMATION: Anti-miR-208 oligonucleotide
<220> FEATURE:
<221> NAME/KEY: misc_feature
<222> LOCATION: (1)..(1)
<223> OTHER INFORMATION: May be locked nucleic acid thymidine
      phosphorothioate
<220> FEATURE:
<221> NAME/KEY: misc_feature
<222> LOCATION: (2)..(2)
<223> OTHER INFORMATION: May be deoxy thymidine phosphorothioate
<220> FEATURE:
<221> NAME/KEY: misc_feature
<222> LOCATION: (3)..(3)
<223> OTHER INFORMATION: May be locked nucleic acid thymidine
      phosphorothioate
<220> FEATURE:
<221> NAME/KEY: misc_feature
<222> LOCATION: (4)..(4)
<223> OTHER INFORMATION: May be deoxy thymidine phosphorothioate
<220> FEATURE:
<221> NAME/KEY: misc_feature
<222> LOCATION: (5)..(5)
<223> OTHER INFORMATION: May be deoxy guanosine phosphorothioate
<220> FEATURE:
<221> NAME/KEY: misc_feature
<222> LOCATION: (6)..(6)
<223> OTHER INFORMATION: May be locked nucleic acid thymidine
      phosphorothioate
<220> FEATURE:
<221> NAME/KEY: misc_feature
<222> LOCATION: (7)..(7)
<223> OTHER INFORMATION: May be deoxy thymidine phosphorothioate
<220> FEATURE:
<221> NAME/KEY: misc_feature
<222> LOCATION: (8)..(8)
<223> OTHER INFORMATION: May be locked nucleic acid cytidine
      phosphorothioate
<220> FEATURE:
<221> NAME/KEY: misc_feature
<222> LOCATION: (9)..(9)
<223> OTHER INFORMATION: May be locked nucleic acid guanosine
      phosphorothioate
<220> FEATURE:
<221> NAME/KEY: misc_feature
<222> LOCATION: (10)..(10)
<223> OTHER INFORMATION: May be locked nucleic acid thymidine
      phosphorothioate
<220> FEATURE:
<221> NAME/KEY: misc_feature
<222> LOCATION: (11)..(11)
<223> OTHER INFORMATION: May be locked nucleic acid cytidine
      phosphorothioate
<220> FEATURE:
<221> NAME/KEY: misc_feature
<222> LOCATION: (12)..(13)
<223> OTHER INFORMATION: May be locked nucleic acid thymidine
      phosphorothioate
<220> FEATURE:
<221> NAME/KEY: misc_feature
<222> LOCATION: (14)..(14)
<223> OTHER INFORMATION: May be locked nucleic acid adenosine

<400> SEQUENCE: 53
ttttgttcgt ctta                                                     14
```

```
<210> SEQ ID NO 54
<211> LENGTH: 13
<212> TYPE: DNA
<213> ORGANISM: Artificial Sequence
<220> FEATURE:
<223> OTHER INFORMATION: Anti-miR-208 oligonucleotide
<220> FEATURE:
<221> NAME/KEY: misc_feature
<222> LOCATION: (1)..(3)
<223> OTHER INFORMATION: May be locked nucleic acid thymidine
      phosphorothioate
<220> FEATURE:
<221> NAME/KEY: misc_feature
<222> LOCATION: (4)..(4)
<223> OTHER INFORMATION: May be deoxy guanosine phosphorothioate
<220> FEATURE:
<221> NAME/KEY: misc_feature
<222> LOCATION: (5)..(5)
<223> OTHER INFORMATION: May be locked nucleic acid cytidine
      phosphorothioate
<220> FEATURE:
<221> NAME/KEY: misc_feature
<222> LOCATION: (6)..(6)
<223> OTHER INFORMATION: May be deoxy thymidine phosphorothioate
<220> FEATURE:
<221> NAME/KEY: misc_feature
<222> LOCATION: (7)..(7)
<223> OTHER INFORMATION: May be locked nucleic acid cytidine
      phosphorothioate
<220> FEATURE:
<221> NAME/KEY: misc_feature
<222> LOCATION: (8)..(8)
<223> OTHER INFORMATION: May be deoxy guanosine phosphorothioate
<220> FEATURE:
<221> NAME/KEY: misc_feature
<222> LOCATION: (9)..(9)
<223> OTHER INFORMATION: May be deoxy thymidine phosphorothioate
<220> FEATURE:
<221> NAME/KEY: misc_feature
<222> LOCATION: (10)..(10)
<223> OTHER INFORMATION: May be locked nucleic acid cytidine
      phosphorothioate
<220> FEATURE:
<221> NAME/KEY: misc_feature
<222> LOCATION: (11)..(11)
<223> OTHER INFORMATION: May be deoxy thymidine phosphorothioate
<220> FEATURE:
<221> NAME/KEY: misc_feature
<222> LOCATION: (12)..(12)
<223> OTHER INFORMATION: May be locked nucleic acid thymidine
      phosphorothioate
<220> FEATURE:
<221> NAME/KEY: misc_feature
<222> LOCATION: (13)..(13)
<223> OTHER INFORMATION: May be deoxy adenosine

<400> SEQUENCE: 54
tttgctcgtc tta                                                          13

<210> SEQ ID NO 55
<211> LENGTH: 13
<212> TYPE: DNA
<213> ORGANISM: Artificial Sequence
<220> FEATURE:
<223> OTHER INFORMATION: Anti-miR-208 oligonucleotide
<220> FEATURE:
<221> NAME/KEY: misc_feature
<222> LOCATION: (1)..(3)
<223> OTHER INFORMATION: May be locked nucleic acid thymidine
      phosphorothioate
<220> FEATURE:
<221> NAME/KEY: misc_feature
<222> LOCATION: (4)..(4)
<223> OTHER INFORMATION: May be deoxy guanosine phosphorothioate
<220> FEATURE:
<221> NAME/KEY: misc_feature
```

```
<222> LOCATION: (5)..(5)
<223> OTHER INFORMATION: May be locked nucleic acid cytidine
      phosphorothioate
<220> FEATURE:
<221> NAME/KEY: misc_feature
<222> LOCATION: (6)..(6)
<223> OTHER INFORMATION: May be deoxy thymidine phosphorothioate
<220> FEATURE:
<221> NAME/KEY: misc_feature
<222> LOCATION: (7)..(7)
<223> OTHER INFORMATION: May be locked nucleic acid cytidine
      phosphorothioate
<220> FEATURE:
<221> NAME/KEY: misc_feature
<222> LOCATION: (8)..(8)
<223> OTHER INFORMATION: May be deoxy guanosine phosphorothioate
<220> FEATURE:
<221> NAME/KEY: misc_feature
<222> LOCATION: (9)..(9)
<223> OTHER INFORMATION: May be deoxy thymidine phosphorothioate
<220> FEATURE:
<221> NAME/KEY: misc_feature
<222> LOCATION: (10)..(10)
<223> OTHER INFORMATION: May be locked nucleic acid cytidine
      phosphorothioate
<220> FEATURE:
<221> NAME/KEY: misc_feature
<222> LOCATION: (11)..(11)
<223> OTHER INFORMATION: May be deoxy thymidine phosphorothioate
<220> FEATURE:
<221> NAME/KEY: misc_feature
<222> LOCATION: (12)..(12)
<223> OTHER INFORMATION: May be locked nucleic acid thymidine
      phosphorothioate
<220> FEATURE:
<221> NAME/KEY: misc_feature
<222> LOCATION: (13)..(13)
<223> OTHER INFORMATION: May be locked nucleic acid adenosine

<400> SEQUENCE: 55
tttgctcgtc tta                                                      13

<210> SEQ ID NO 56
<211> LENGTH: 13
<212> TYPE: DNA
<213> ORGANISM: Artificial Sequence
<220> FEATURE:
<223> OTHER INFORMATION: Anti-miR-208 oligonucleotide
<220> FEATURE:
<221> NAME/KEY: misc_feature
<222> LOCATION: (1)..(3)
<223> OTHER INFORMATION: May be locked nucleic acid thymidine
      phosphorothioate
<220> FEATURE:
<221> NAME/KEY: misc_feature
<222> LOCATION: (4)..(4)
<223> OTHER INFORMATION: May be deoxy guanosine phosphorothioate
<220> FEATURE:
<221> NAME/KEY: misc_feature
<222> LOCATION: (5)..(5)
<223> OTHER INFORMATION: May be locked nucleic acid cytidine
      phosphorothioate
<220> FEATURE:
<221> NAME/KEY: misc_feature
<222> LOCATION: (6)..(6)
<223> OTHER INFORMATION: May be deoxy thymidine phosphorothioate
<220> FEATURE:
<221> NAME/KEY: misc_feature
<222> LOCATION: (7)..(7)
<223> OTHER INFORMATION: May be locked nucleic acid cytidine
      phosphorothioate
<220> FEATURE:
<221> NAME/KEY: misc_feature
<222> LOCATION: (8)..(8)
<223> OTHER INFORMATION: May be locked nucleic acid guanosine
      phosphorothioate
<220> FEATURE:
<221> NAME/KEY: misc_feature
```

```
<222> LOCATION: (9)..(9)
<223> OTHER INFORMATION: May be locked nucleic acid thymidine
      phosphorothioate
<220> FEATURE:
<221> NAME/KEY: misc_feature
<222> LOCATION: (10)..(10)
<223> OTHER INFORMATION: May be locked nucleic acid cytidine
      phosphorothioate
<220> FEATURE:
<221> NAME/KEY: misc_feature
<222> LOCATION: (11)..(12)
<223> OTHER INFORMATION: May be locked nucleic acid thymidine
      phosphorothioate
<220> FEATURE:
<221> NAME/KEY: misc_feature
<222> LOCATION: (13)..(13)
<223> OTHER INFORMATION: May be locked nucleic acid adenosine

<400> SEQUENCE: 56
tttgctcgtc tta                                                       13

<210> SEQ ID NO 57
<211> LENGTH: 13
<212> TYPE: DNA
<213> ORGANISM: Artificial Sequence
<220> FEATURE:
<223> OTHER INFORMATION: Anti-miR-208 oligonucleotide
<220> FEATURE:
<221> NAME/KEY: misc_feature
<222> LOCATION: (1)..(1)
<223> OTHER INFORMATION: May be locked nucleic acid thymidine
      phosphorothioate
<220> FEATURE:
<221> NAME/KEY: misc_feature
<222> LOCATION: (2)..(2)
<223> OTHER INFORMATION: May be deoxy thymidine phosphorothioate
<220> FEATURE:
<221> NAME/KEY: misc_feature
<222> LOCATION: (3)..(3)
<223> OTHER INFORMATION: May be locked nucleic acid thymidine
      phosphorothioate
<220> FEATURE:
<221> NAME/KEY: misc_feature
<222> LOCATION: (4)..(4)
<223> OTHER INFORMATION: May be deoxy guanosine phosphorothioate
<220> FEATURE:
<221> NAME/KEY: misc_feature
<222> LOCATION: (5)..(5)
<223> OTHER INFORMATION: May be locked nucleic acid cytidine
      phosphorothioate
<220> FEATURE:
<221> NAME/KEY: misc_feature
<222> LOCATION: (6)..(6)
<223> OTHER INFORMATION: May be deoxy thymidine phosphorothioate
<220> FEATURE:
<221> NAME/KEY: misc_feature
<222> LOCATION: (7)..(7)
<223> OTHER INFORMATION: May be locked nucleic acid cytidine
      phosphorothioate
<220> FEATURE:
<221> NAME/KEY: misc_feature
<222> LOCATION: (8)..(8)
<223> OTHER INFORMATION: May be locked nucleic acid guanosine
      phosphorothioate
<220> FEATURE:
<221> NAME/KEY: misc_feature
<222> LOCATION: (9)..(9)
<223> OTHER INFORMATION: May be locked nucleic acid thymidine
      phosphorothioate
<220> FEATURE:
<221> NAME/KEY: misc_feature
<222> LOCATION: (10)..(10)
<223> OTHER INFORMATION: May be locked nucleic acid cytidine
      phosphorothioate
<220> FEATURE:
<221> NAME/KEY: misc_feature
<222> LOCATION: (11)..(12)
<223> OTHER INFORMATION: May be locked nucleic acid thymidine
``` phosphorothioate
<220> FEATURE:
<221> NAME/KEY: misc_feature
<222> LOCATION: (13)..(13)
<223> OTHER INFORMATION: May be locked nucleic acid adenosine

<400> SEQUENCE: 57
tttgctcgtc tta                                                          13

<210> SEQ ID NO 58
<211> LENGTH: 13
<212> TYPE: DNA
<213> ORGANISM: Artificial Sequence
<220> FEATURE:
<223> OTHER INFORMATION: Anti-miR-208 oligonucleotide
<220> FEATURE:
<221> NAME/KEY: misc_feature
<222> LOCATION: (1)..(3)
<223> OTHER INFORMATION: May be locked nucleic acid thymidine
      phosphorothioate
<220> FEATURE:
<221> NAME/KEY: misc_feature
<222> LOCATION: (4)..(4)
<223> OTHER INFORMATION: May be deoxy guanosine phosphorothioate
<220> FEATURE:
<221> NAME/KEY: misc_feature
<222> LOCATION: (5)..(5)
<223> OTHER INFORMATION: May be locked nucleic acid thymidine
      phosphorothioate
<220> FEATURE:
<221> NAME/KEY: misc_feature
<222> LOCATION: (6)..(6)
<223> OTHER INFORMATION: May be deoxy thymidine phosphorothioate
<220> FEATURE:
<221> NAME/KEY: misc_feature
<222> LOCATION: (7)..(7)
<223> OTHER INFORMATION: May be locked nucleic acid cytidine
      phosphorothioate
<220> FEATURE:
<221> NAME/KEY: misc_feature
<222> LOCATION: (8)..(8)
<223> OTHER INFORMATION: May be deoxy guanosine phosphorothioate
<220> FEATURE:
<221> NAME/KEY: misc_feature
<222> LOCATION: (9)..(9)
<223> OTHER INFORMATION: May be deoxy thymidine phosphorothioate
<220> FEATURE:
<221> NAME/KEY: misc_feature
<222> LOCATION: (10)..(10)
<223> OTHER INFORMATION: May be locked nucleic acid cytidine
      phosphorothioate
<220> FEATURE:
<221> NAME/KEY: misc_feature
<222> LOCATION: (11)..(11)
<223> OTHER INFORMATION: May be deoxy thymidine phosphorothioate
<220> FEATURE:
<221> NAME/KEY: misc_feature
<222> LOCATION: (12)..(12)
<223> OTHER INFORMATION: May be locked nucleic acid thymidine
      phosphorothioate
<220> FEATURE:
<221> NAME/KEY: misc_feature
<222> LOCATION: (13)..(13)
<223> OTHER INFORMATION: May be deoxy adenosine

<400> SEQUENCE: 58
tttgttcgtc tta                                                          13

<210> SEQ ID NO 59
<211> LENGTH: 13
<212> TYPE: DNA
<213> ORGANISM: Artificial Sequence
<220> FEATURE:
<223> OTHER INFORMATION: Anti-miR-208 oligonucleotide
<220> FEATURE:
<221> NAME/KEY: misc_feature

```
<222> LOCATION: (1)..(3)
<223> OTHER INFORMATION: May be locked nucleic acid thymidine
      phosphorothioate
<220> FEATURE:
<221> NAME/KEY: misc_feature
<222> LOCATION: (4)..(4)
<223> OTHER INFORMATION: May be deoxy guanosine phosphorothioate
<220> FEATURE:
<221> NAME/KEY: misc_feature
<222> LOCATION: (5)..(5)
<223> OTHER INFORMATION: May be locked nucleic acid thymidine
      phosphorothioate
<220> FEATURE:
<221> NAME/KEY: misc_feature
<222> LOCATION: (6)..(6)
<223> OTHER INFORMATION: May be deoxy thymidine phosphorothioate
<220> FEATURE:
<221> NAME/KEY: misc_feature
<222> LOCATION: (7)..(7)
<223> OTHER INFORMATION: May be locked nucleic acid cytidine
      phosphorothioate
<220> FEATURE:
<221> NAME/KEY: misc_feature
<222> LOCATION: (8)..(8)
<223> OTHER INFORMATION: May be deoxy guanosine phosphorothioate
<220> FEATURE:
<221> NAME/KEY: misc_feature
<222> LOCATION: (9)..(9)
<223> OTHER INFORMATION: May be deoxy thymidine phosphorothioate
<220> FEATURE:
<221> NAME/KEY: misc_feature
<222> LOCATION: (10)..(10)
<223> OTHER INFORMATION: May be locked nucleic acid cytidine
      phosphorothioate
<220> FEATURE:
<221> NAME/KEY: misc_feature
<222> LOCATION: (11)..(11)
<223> OTHER INFORMATION: May be deoxy thymidine phosphorothioate
<220> FEATURE:
<221> NAME/KEY: misc_feature
<222> LOCATION: (12)..(12)
<223> OTHER INFORMATION: May be locked nucleic acid thymidine
      phosphorothioate
<220> FEATURE:
<221> NAME/KEY: misc_feature
<222> LOCATION: (13)..(13)
<223> OTHER INFORMATION: May be locked nucleic acid adenosine

<400> SEQUENCE: 59
tttgttcgtc tta                                                        13

<210> SEQ ID NO 60
<211> LENGTH: 13
<212> TYPE: DNA
<213> ORGANISM: Artificial Sequence
<220> FEATURE:
<223> OTHER INFORMATION: Anti-miR-208 oligonucleotide
<220> FEATURE:
<221> NAME/KEY: misc_feature
<222> LOCATION: (1)..(3)
<223> OTHER INFORMATION: May be locked nucleic acid thymidine
      phosphorothioate
<220> FEATURE:
<221> NAME/KEY: misc_feature
<222> LOCATION: (4)..(4)
<223> OTHER INFORMATION: May be deoxy guanosine phosphorothioate
<220> FEATURE:
<221> NAME/KEY: misc_feature
<222> LOCATION: (5)..(5)
<223> OTHER INFORMATION: May be locked nucleic acid thymidine
      phosphorothioate
<220> FEATURE:
<221> NAME/KEY: misc_feature
<222> LOCATION: (6)..(6)
<223> OTHER INFORMATION: May be deoxy thymidine phosphorothioate
<220> FEATURE:
<221> NAME/KEY: misc_feature
<222> LOCATION: (7)..(7)
```

```
<223> OTHER INFORMATION: May be locked nucleic acid cytidine
      phosphorothioate
<220> FEATURE:
<221> NAME/KEY: misc_feature
<222> LOCATION: (8)..(8)
<223> OTHER INFORMATION: May be locked nucleic acid guanosine
      phosphorothioate
<220> FEATURE:
<221> NAME/KEY: misc_feature
<222> LOCATION: (9)..(9)
<223> OTHER INFORMATION: May be locked nucleic acid thymidine
      phosphorothioate
<220> FEATURE:
<221> NAME/KEY: misc_feature
<222> LOCATION: (10)..(10)
<223> OTHER INFORMATION: May be locked nucleic acid cytidine
      phosphorothioate
<220> FEATURE:
<221> NAME/KEY: misc_feature
<222> LOCATION: (11)..(12)
<223> OTHER INFORMATION: May be locked nucleic acid thymidine
      phosphorothioate
<220> FEATURE:
<221> NAME/KEY: misc_feature
<222> LOCATION: (13)..(13)
<223> OTHER INFORMATION: May be locked nucleic acid adenosine

<400> SEQUENCE: 60
tttgttcgtc tta                                                         13

<210> SEQ ID NO 61
<211> LENGTH: 13
<212> TYPE: DNA
<213> ORGANISM: Artificial Sequence
<220> FEATURE:
<223> OTHER INFORMATION: Anti-miR-208 oligonucleotide
<220> FEATURE:
<221> NAME/KEY: misc_feature
<222> LOCATION: (1)..(1)
<223> OTHER INFORMATION: May be locked nucleic acid thymidine
      phosphorothioate
<220> FEATURE:
<221> NAME/KEY: misc_feature
<222> LOCATION: (2)..(2)
<223> OTHER INFORMATION: May be deoxy thymidine phosphorothioate
<220> FEATURE:
<221> NAME/KEY: misc_feature
<222> LOCATION: (3)..(3)
<223> OTHER INFORMATION: May be locked nucleic acid thymidine
      phosphorothioate
<220> FEATURE:
<221> NAME/KEY: misc_feature
<222> LOCATION: (4)..(4)
<223> OTHER INFORMATION: May be deoxy guanosine phosphorothioate
<220> FEATURE:
<221> NAME/KEY: misc_feature
<222> LOCATION: (5)..(5)
<223> OTHER INFORMATION: May be locked nucleic acid thymidine
      phosphorothioate
<220> FEATURE:
<221> NAME/KEY: misc_feature
<222> LOCATION: (6)..(6)
<223> OTHER INFORMATION: May be deoxy thymidine phosphorothioate
<220> FEATURE:
<221> NAME/KEY: misc_feature
<222> LOCATION: (7)..(7)
<223> OTHER INFORMATION: May be locked nucleic acid cytidine
      phosphorothioate
<220> FEATURE:
<221> NAME/KEY: misc_feature
<222> LOCATION: (8)..(8)
<223> OTHER INFORMATION: May be locked nucleic acid guanosine
      phosphorothioate
<220> FEATURE:
<221> NAME/KEY: misc_feature
<222> LOCATION: (9)..(9)
<223> OTHER INFORMATION: May be locked nucleic acid thymidine
      phosphorothioate
```

```
<220> FEATURE:
<221> NAME/KEY: misc_feature
<222> LOCATION: (10)..(10)
<223> OTHER INFORMATION: May be locked nucleic acid cytidine
      phosphorothioate
<220> FEATURE:
<221> NAME/KEY: misc_feature
<222> LOCATION: (11)..(12)
<223> OTHER INFORMATION: May be locked nucleic acid thymidine
      phosphorothioate
<220> FEATURE:
<221> NAME/KEY: misc_feature
<222> LOCATION: (13)..(13)
<223> OTHER INFORMATION: May be locked nucleic acid adenosine

<400> SEQUENCE: 61
tttgttcgtc tta                                                        13

<210> SEQ ID NO 62
<211> LENGTH: 11
<212> TYPE: DNA
<213> ORGANISM: Artificial Sequence
<220> FEATURE:
<223> OTHER INFORMATION: Anti-miR-208 oligonucleotide
<220> FEATURE:
<221> NAME/KEY: misc_feature
<222> LOCATION: (1)..(1)
<223> OTHER INFORMATION: May be locked nucleic acid thymidine
      phosphorothioate
<220> FEATURE:
<221> NAME/KEY: misc_feature
<222> LOCATION: (2)..(2)
<223> OTHER INFORMATION: May be deoxy guanosine phosphorothioate
<220> FEATURE:
<221> NAME/KEY: misc_feature
<222> LOCATION: (3)..(3)
<223> OTHER INFORMATION: May be locked nucleic acid cytidine
      phosphorothioate
<220> FEATURE:
<221> NAME/KEY: misc_feature
<222> LOCATION: (4)..(4)
<223> OTHER INFORMATION: May be deoxy thymidine phosphorothioate
<220> FEATURE:
<221> NAME/KEY: misc_feature
<222> LOCATION: (5)..(5)
<223> OTHER INFORMATION: May be locked nucleic acid cytidine
      phosphorothioate
<220> FEATURE:
<221> NAME/KEY: misc_feature
<222> LOCATION: (6)..(6)
<223> OTHER INFORMATION: May be deoxy guanosine phosphorothioate
<220> FEATURE:
<221> NAME/KEY: misc_feature
<222> LOCATION: (7)..(7)
<223> OTHER INFORMATION: May be deoxy thymidine phosphorothioate
<220> FEATURE:
<221> NAME/KEY: misc_feature
<222> LOCATION: (8)..(8)
<223> OTHER INFORMATION: May be locked nucleic acid cytidine
      phosphorothioate
<220> FEATURE:
<221> NAME/KEY: misc_feature
<222> LOCATION: (9)..(9)
<223> OTHER INFORMATION: May be deoxy thymidine phosphorothioate
<220> FEATURE:
<221> NAME/KEY: misc_feature
<222> LOCATION: (10)..(10)
<223> OTHER INFORMATION: May be locked nucleic acid thymidine
      phosphorothioate
<220> FEATURE:
<221> NAME/KEY: misc_feature
<222> LOCATION: (11)..(11)
<223> OTHER INFORMATION: May be deoxy adenosine

<400> SEQUENCE: 62
tgctcgtctt a                                                          11
```

-continued

<210> SEQ ID NO 63
<211> LENGTH: 11
<212> TYPE: DNA
<213> ORGANISM: Artificial Sequence
<220> FEATURE:
<223> OTHER INFORMATION: Anti-miR-208 oligonucleotide
<220> FEATURE:
<221> NAME/KEY: misc_feature
<222> LOCATION: (1)..(1)
<223> OTHER INFORMATION: May be locked nucleic acid thymidine
      phosphorothioate
<220> FEATURE:
<221> NAME/KEY: misc_feature
<222> LOCATION: (2)..(2)
<223> OTHER INFORMATION: May be deoxy guanosine phosphorothioate
<220> FEATURE:
<221> NAME/KEY: misc_feature
<222> LOCATION: (3)..(3)
<223> OTHER INFORMATION: May be locked nucleic acid cytidine
      phosphorothioate
<220> FEATURE:
<221> NAME/KEY: misc_feature
<222> LOCATION: (4)..(4)
<223> OTHER INFORMATION: May be deoxy thymidine phosphorothioate
<220> FEATURE:
<221> NAME/KEY: misc_feature
<222> LOCATION: (5)..(5)
<223> OTHER INFORMATION: May be locked nucleic acid cytidine
      phosphorothioate
<220> FEATURE:
<221> NAME/KEY: misc_feature
<222> LOCATION: (6)..(6)
<223> OTHER INFORMATION: May be deoxy guanosine phosphorothioate
<220> FEATURE:
<221> NAME/KEY: misc_feature
<222> LOCATION: (7)..(7)
<223> OTHER INFORMATION: May be deoxy thymidine phosphorothioate
<220> FEATURE:
<221> NAME/KEY: misc_feature
<222> LOCATION: (8)..(8)
<223> OTHER INFORMATION: May be locked nucleic acid cytidine
      phosphorothioate
<220> FEATURE:
<221> NAME/KEY: misc_feature
<222> LOCATION: (9)..(9)
<223> OTHER INFORMATION: May be deoxy thymidine phosphorothioate
<220> FEATURE:
<221> NAME/KEY: misc_feature
<222> LOCATION: (10)..(10)
<223> OTHER INFORMATION: May be locked nucleic acid thymidine
      phosphorothioate
<220> FEATURE:
<221> NAME/KEY: misc_feature
<222> LOCATION: (11)..(11)
<223> OTHER INFORMATION: May be locked nucleic acid adenosine

<400> SEQUENCE: 63
tgctcgtctt a                                                          11

<210> SEQ ID NO 64
<211> LENGTH: 11
<212> TYPE: DNA
<213> ORGANISM: Artificial Sequence
<220> FEATURE:
<223> OTHER INFORMATION: Anti-miR-208 oligonucleotide
<220> FEATURE:
<221> NAME/KEY: misc_feature
<222> LOCATION: (1)..(1)
<223> OTHER INFORMATION: May be locked nucleic acid thymidine
      phosphorothioate
<220> FEATURE:
<221> NAME/KEY: misc_feature
<222> LOCATION: (2)..(2)
<223> OTHER INFORMATION: May be deoxy guanosine phosphorothioate
<220> FEATURE:
<221> NAME/KEY: misc_feature
<222> LOCATION: (3)..(3)

<223> OTHER INFORMATION: May be locked nucleic acid thymidine
      phosphorothioate
<220> FEATURE:
<221> NAME/KEY: misc_feature
<222> LOCATION: (4)..(4)
<223> OTHER INFORMATION: May be deoxy thymidine phosphorothioate
<220> FEATURE:
<221> NAME/KEY: misc_feature
<222> LOCATION: (5)..(5)
<223> OTHER INFORMATION: May be locked nucleic acid cytidine
      phosphorothioate
<220> FEATURE:
<221> NAME/KEY: misc_feature
<222> LOCATION: (6)..(6)
<223> OTHER INFORMATION: May be deoxy guanosine phosphorothioate
<220> FEATURE:
<221> NAME/KEY: misc_feature
<222> LOCATION: (7)..(7)
<223> OTHER INFORMATION: May be deoxy thymidine phosphorothioate
<220> FEATURE:
<221> NAME/KEY: misc_feature
<222> LOCATION: (8)..(8)
<223> OTHER INFORMATION: May be locked nucleic acid cytidine
      phosphorothioate
<220> FEATURE:
<221> NAME/KEY: misc_feature
<222> LOCATION: (9)..(9)
<223> OTHER INFORMATION: May be deoxy thymidine phosphorothioate
<220> FEATURE:
<221> NAME/KEY: misc_feature
<222> LOCATION: (10)..(10)
<223> OTHER INFORMATION: May be locked nucleic acid thymidine
      phosphorothioate
<220> FEATURE:
<221> NAME/KEY: misc_feature
<222> LOCATION: (11)..(11)
<223> OTHER INFORMATION: May be deoxy adenosine

<400> SEQUENCE: 64
tgttcgtctt a                                                          11

<210> SEQ ID NO 65
<211> LENGTH: 11
<212> TYPE: DNA
<213> ORGANISM: Artificial Sequence
<220> FEATURE:
<223> OTHER INFORMATION: Anti-miR-208 oligonucleotide
<220> FEATURE:
<221> NAME/KEY: misc_feature
<222> LOCATION: (1)..(1)
<223> OTHER INFORMATION: May be locked nucleic acid thymidine
      phosphorothioate
<220> FEATURE:
<221> NAME/KEY: misc_feature
<222> LOCATION: (2)..(2)
<223> OTHER INFORMATION: May be deoxy guanosine phosphorothioate
<220> FEATURE:
<221> NAME/KEY: misc_feature
<222> LOCATION: (3)..(3)
<223> OTHER INFORMATION: May be locked nucleic acid thymidine
      phosphorothioate
<220> FEATURE:
<221> NAME/KEY: misc_feature
<222> LOCATION: (4)..(4)
<223> OTHER INFORMATION: May be deoxy thymidine phosphorothioate
<220> FEATURE:
<221> NAME/KEY: misc_feature
<222> LOCATION: (5)..(5)
<223> OTHER INFORMATION: May be locked nucleic acid cytidine
      phosphorothioate
<220> FEATURE:
<221> NAME/KEY: misc_feature
<222> LOCATION: (6)..(6)
<223> OTHER INFORMATION: May be deoxy guanosine phosphorothioate
<220> FEATURE:
<221> NAME/KEY: misc_feature
<222> LOCATION: (7)..(7)
<223> OTHER INFORMATION: May be deoxy thymidine phosphorothioate

```
<220> FEATURE:
<221> NAME/KEY: misc_feature
<222> LOCATION: (8)..(8)
<223> OTHER INFORMATION: May be locked nucleic acid cytidine
      phosphorothioate
<220> FEATURE:
<221> NAME/KEY: misc_feature
<222> LOCATION: (9)..(9)
<223> OTHER INFORMATION: May be deoxy thymidine phosphorothioate
<220> FEATURE:
<221> NAME/KEY: misc_feature
<222> LOCATION: (10)..(10)
<223> OTHER INFORMATION: May be locked nucleic acid thymidine
      phosphorothioate
<220> FEATURE:
<221> NAME/KEY: misc_feature
<222> LOCATION: (11)..(11)
<223> OTHER INFORMATION: May be locked nucleic acid adenosine

<400> SEQUENCE: 65
tgttcgtctt a                                                            11

<210> SEQ ID NO 66
<211> LENGTH: 16
<212> TYPE: DNA
<213> ORGANISM: Artificial Sequence
<220> FEATURE:
<223> OTHER INFORMATION: Anti-miR-208 oligonucleotide
<220> FEATURE:
<221> NAME/KEY: misc_feature
<222> LOCATION: (1)..(1)
<223> OTHER INFORMATION: May be locked nucleic acid cytidine
      phosphorothioate
<220> FEATURE:
<221> NAME/KEY: misc_feature
<222> LOCATION: (2)..(2)
<223> OTHER INFORMATION: May be deoxy cytidine phosphorothioate
<220> FEATURE:
<221> NAME/KEY: misc_feature
<222> LOCATION: (3)..(6)
<223> OTHER INFORMATION: May be locked nucleic acid thymidine
      phosphorothioate
<220> FEATURE:
<221> NAME/KEY: misc_feature
<222> LOCATION: (7)..(7)
<223> OTHER INFORMATION: May be deoxy guanosine phosphorothioate
<220> FEATURE:
<221> NAME/KEY: misc_feature
<222> LOCATION: (8)..(8)
<223> OTHER INFORMATION: May be locked nucleic acid thymidine
      phosphorothioate
<220> FEATURE:
<221> NAME/KEY: misc_feature
<222> LOCATION: (9)..(9)
<223> OTHER INFORMATION: May be deoxy thymidine phosphorothioate
<220> FEATURE:
<221> NAME/KEY: misc_feature
<222> LOCATION: (10)..(10)
<223> OTHER INFORMATION: May be locked nucleic acid cytidine
      phosphorothioate
<220> FEATURE:
<221> NAME/KEY: misc_feature
<222> LOCATION: (11)..(11)
<223> OTHER INFORMATION: May be deoxy guanosine phosphorothioate
<220> FEATURE:
<221> NAME/KEY: misc_feature
<222> LOCATION: (12)..(12)
<223> OTHER INFORMATION: May be deoxy thymidine phosphorothioate
<220> FEATURE:
<221> NAME/KEY: misc_feature
<222> LOCATION: (13)..(13)
<223> OTHER INFORMATION: May be locked nucleic acid cytidine
      phosphorothioate
<220> FEATURE:
<221> NAME/KEY: misc_feature
<222> LOCATION: (14)..(14)
<223> OTHER INFORMATION: May be deoxy thymidine phosphorothioate
<220> FEATURE:
```

```
<221> NAME/KEY: misc_feature
<222> LOCATION: (15)..(15)
<223> OTHER INFORMATION: May be locked nucleic acid thymidine
      phosphorothioate
<220> FEATURE:
<221> NAME/KEY: misc_feature
<222> LOCATION: (16)..(16)
<223> OTHER INFORMATION: May be deoxy adenosine

<400> SEQUENCE: 66 cctttttgttc gtctta                                                   16

<210> SEQ ID NO 67
<211> LENGTH: 16
<212> TYPE: DNA
<213> ORGANISM: Artificial Sequence
<220> FEATURE:
<223> OTHER INFORMATION: Anti-miR-208 oligonucleotide
<220> FEATURE:
<221> NAME/KEY: misc_feature
<222> LOCATION: (1)..(1)
<223> OTHER INFORMATION: May be locked nucleic acid cytidine
      phosphorothioate
<220> FEATURE:
<221> NAME/KEY: misc_feature
<222> LOCATION: (2)..(2)
<223> OTHER INFORMATION: May be deoxy cytidine phosphorothioate
<220> FEATURE:
<221> NAME/KEY: misc_feature
<222> LOCATION: (3)..(3)
<223> OTHER INFORMATION: May be locked nucleic acid thymidine
      phosphorothioate
<220> FEATURE:
<221> NAME/KEY: misc_feature
<222> LOCATION: (4)..(4)
<223> OTHER INFORMATION: May be deoxy thymidine phosphorothioate
<220> FEATURE:
<221> NAME/KEY: misc_feature
<222> LOCATION: (5)..(6)
<223> OTHER INFORMATION: May be locked nucleic acid thymidine
      phosphorothioate
<220> FEATURE:
<221> NAME/KEY: misc_feature
<222> LOCATION: (7)..(7)
<223> OTHER INFORMATION: May be deoxy guanosine phosphorothioate
<220> FEATURE:
<221> NAME/KEY: misc_feature
<222> LOCATION: (8)..(8)
<223> OTHER INFORMATION: May be locked nucleic acid thymidine
      phosphorothioate
<220> FEATURE:
<221> NAME/KEY: misc_feature
<222> LOCATION: (9)..(9)
<223> OTHER INFORMATION: May be deoxy thymidine phosphorothioate
<220> FEATURE:
<221> NAME/KEY: misc_feature
<222> LOCATION: (10)..(10)
<223> OTHER INFORMATION: May be locked nucleic acid cytidine
      phosphorothioate
<220> FEATURE:
<221> NAME/KEY: misc_feature
<222> LOCATION: (11)..(11)
<223> OTHER INFORMATION: May be deoxy guanosine phosphorothioate
<220> FEATURE:
<221> NAME/KEY: misc_feature
<222> LOCATION: (12)..(12)
<223> OTHER INFORMATION: May be locked nucleic acid thymidine
      phosphorothioate
<220> FEATURE:
<221> NAME/KEY: misc_feature
<222> LOCATION: (13)..(13)
<223> OTHER INFORMATION: May be deoxy cytidine phosphorothioate
<220> FEATURE:
<221> NAME/KEY: misc_feature
<222> LOCATION: (14)..(15)
<223> OTHER INFORMATION: May be locked nucleic acid thymidine
      phosphorothioate
<220> FEATURE:
```

```
<221> NAME/KEY: misc_feature
<222> LOCATION: (16)..(16)
<223> OTHER INFORMATION: May be deoxy adenosine

<400> SEQUENCE: 67 cctttttgttc gtctta                                                    16

<210> SEQ ID NO 68
<211> LENGTH: 16
<212> TYPE: DNA
<213> ORGANISM: Artificial Sequence
<220> FEATURE:
<223> OTHER INFORMATION: Anti-miR-208 oligonucleotide
<220> FEATURE:
<221> NAME/KEY: misc_feature
<222> LOCATION: (1)..(1)
<223> OTHER INFORMATION: May be locked nucleic acid cytidine
      phosphorothioate
<220> FEATURE:
<221> NAME/KEY: misc_feature
<222> LOCATION: (2)..(2)
<223> OTHER INFORMATION: May be deoxy cytidine phosphorothioate
<220> FEATURE:
<221> NAME/KEY: misc_feature
<222> LOCATION: (3)..(6)
<223> OTHER INFORMATION: May be locked nucleic acid thymidine
      phosphorothioate
<220> FEATURE:
<221> NAME/KEY: misc_feature
<222> LOCATION: (7)..(7)
<223> OTHER INFORMATION: May be deoxy guanosine phosphorothioate
<220> FEATURE:
<221> NAME/KEY: misc_feature
<222> LOCATION: (8)..(8)
<223> OTHER INFORMATION: May be locked nucleic acid thymidine
      phosphorothioate
<220> FEATURE:
<221> NAME/KEY: misc_feature
<222> LOCATION: (9)..(9)
<223> OTHER INFORMATION: May be deoxy thymidine phosphorothioate
<220> FEATURE:
<221> NAME/KEY: misc_feature
<222> LOCATION: (10)..(10)
<223> OTHER INFORMATION: May be locked nucleic acid cytidine
      phosphorothioate
<220> FEATURE:
<221> NAME/KEY: misc_feature
<222> LOCATION: (11)..(11)
<223> OTHER INFORMATION: May be deoxy guanosine phosphorothioate
<220> FEATURE:
<221> NAME/KEY: misc_feature
<222> LOCATION: (12)..(12)
<223> OTHER INFORMATION: May be deoxy thymidine phosphorothioate
<220> FEATURE:
<221> NAME/KEY: misc_feature
<222> LOCATION: (13)..(13)
<223> OTHER INFORMATION: May be locked nucleic acid cytidine
      phosphorothioate
<220> FEATURE:
<221> NAME/KEY: misc_feature
<222> LOCATION: (14)..(15)
<223> OTHER INFORMATION: May be deoxy thymidine phosphorothioate
<220> FEATURE:
<221> NAME/KEY: misc_feature
<222> LOCATION: (16)..(16)
<223> OTHER INFORMATION: May be locked nucleic acid adenosine

<400> SEQUENCE: 68 cctttttgttc gtctta                                                    16

<210> SEQ ID NO 69
<211> LENGTH: 16
<212> TYPE: DNA
<213> ORGANISM: Artificial Sequence
<220> FEATURE:
<223> OTHER INFORMATION: Anti-miR-208 oligonucleotide
```

```
<220> FEATURE:
<221> NAME/KEY: misc_feature
<222> LOCATION: (1)..(1)
<223> OTHER INFORMATION: May be locked nucleic acid cytidine
      phosphorothioate
<220> FEATURE:
<221> NAME/KEY: misc_feature
<222> LOCATION: (2)..(2)
<223> OTHER INFORMATION: May be deoxy cytidine phosphorothioate
<220> FEATURE:
<221> NAME/KEY: misc_feature
<222> LOCATION: (3)..(6)
<223> OTHER INFORMATION: May be locked nucleic acid thymidine
      phosphorothioate
<220> FEATURE:
<221> NAME/KEY: misc_feature
<222> LOCATION: (7)..(7)
<223> OTHER INFORMATION: May be deoxy guanosine phosphorothioate
<220> FEATURE:
<221> NAME/KEY: misc_feature
<222> LOCATION: (8)..(8)
<223> OTHER INFORMATION: May be locked nucleic acid cytidine
      phosphorothioate
<220> FEATURE:
<221> NAME/KEY: misc_feature
<222> LOCATION: (9)..(9)
<223> OTHER INFORMATION: May be deoxy thymidine phosphorothioate
<220> FEATURE:
<221> NAME/KEY: misc_feature
<222> LOCATION: (10)..(10)
<223> OTHER INFORMATION: May be locked nucleic acid cytidine
      phosphorothioate
<220> FEATURE:
<221> NAME/KEY: misc_feature
<222> LOCATION: (11)..(11)
<223> OTHER INFORMATION: May be deoxy guanosine phosphorothioate
<220> FEATURE:
<221> NAME/KEY: misc_feature
<222> LOCATION: (12)..(12)
<223> OTHER INFORMATION: May be deoxy thymidine phosphorothioate
<220> FEATURE:
<221> NAME/KEY: misc_feature
<222> LOCATION: (13)..(13)
<223> OTHER INFORMATION: May be locked nucleic acid cytidine
      phosphorothioate
<220> FEATURE:
<221> NAME/KEY: misc_feature
<222> LOCATION: (14)..(14)
<223> OTHER INFORMATION: May be deoxy thymidine phosphorothioate
<220> FEATURE:
<221> NAME/KEY: misc_feature
<222> LOCATION: (15)..(15)
<223> OTHER INFORMATION: May be locked nucleic acid thymidine
      phosphorothioate
<220> FEATURE:
<221> NAME/KEY: misc_feature
<222> LOCATION: (16)..(16)
<223> OTHER INFORMATION: May be deoxy adenosine

<400> SEQUENCE: 69
ccttttgctc gtctta                                                     16

<210> SEQ ID NO 70
<211> LENGTH: 16
<212> TYPE: DNA
<213> ORGANISM: Artificial Sequence
<220> FEATURE:
<223> OTHER INFORMATION: Anti-miR-208 oligonucleotide
<220> FEATURE:
<221> NAME/KEY: misc_feature
<222> LOCATION: (1)..(1)
<223> OTHER INFORMATION: May be locked nucleic acid cytidine
      phosphorothioate
<220> FEATURE:
<221> NAME/KEY: misc_feature
<222> LOCATION: (2)..(2)
<223> OTHER INFORMATION: May be deoxy cytidine phosphorothioate
<220> FEATURE:
```

```
<221> NAME/KEY: misc_feature
<222> LOCATION: (3)..(3)
<223> OTHER INFORMATION: May be locked nucleic acid thymidine
      phosphorothioate
<220> FEATURE:
<221> NAME/KEY: misc_feature
<222> LOCATION: (4)..(4)
<223> OTHER INFORMATION: May be deoxy thymidine phosphorothioate
<220> FEATURE:
<221> NAME/KEY: misc_feature
<222> LOCATION: (5)..(6)
<223> OTHER INFORMATION: May be locked nucleic acid thymidine
      phosphorothioate
<220> FEATURE:
<221> NAME/KEY: misc_feature
<222> LOCATION: (7)..(7)
<223> OTHER INFORMATION: May be deoxy guanosine phosphorothioate
<220> FEATURE:
<221> NAME/KEY: misc_feature
<222> LOCATION: (8)..(8)
<223> OTHER INFORMATION: May be locked nucleic acid cytidine
      phosphorothioate
<220> FEATURE:
<221> NAME/KEY: misc_feature
<222> LOCATION: (9)..(9)
<223> OTHER INFORMATION: May be deoxy thymidine phosphorothioate
<220> FEATURE:
<221> NAME/KEY: misc_feature
<222> LOCATION: (10)..(10)
<223> OTHER INFORMATION: May be locked nucleic acid cytidine
      phosphorothioate
<220> FEATURE:
<221> NAME/KEY: misc_feature
<222> LOCATION: (11)..(11)
<223> OTHER INFORMATION: May be deoxy guanosine phosphorothioate
<220> FEATURE:
<221> NAME/KEY: misc_feature
<222> LOCATION: (12)..(12)
<223> OTHER INFORMATION: May be locked nucleic acid thymidine
      phosphorothioate
<220> FEATURE:
<221> NAME/KEY: misc_feature
<222> LOCATION: (13)..(13)
<223> OTHER INFORMATION: May be deoxy cytidine phosphorothioate
<220> FEATURE:
<221> NAME/KEY: misc_feature
<222> LOCATION: (14)..(15)
<223> OTHER INFORMATION: May be locked nucleic acid thymidine
      phosphorothioate
<220> FEATURE:
<221> NAME/KEY: misc_feature
<222> LOCATION: (16)..(16)
<223> OTHER INFORMATION: May be deoxy adenosine

<400> SEQUENCE: 70 cctttgctc gtctta                                                      16

<210> SEQ ID NO 71
<211> LENGTH: 16
<212> TYPE: DNA
<213> ORGANISM: Artificial Sequence
<220> FEATURE:
<223> OTHER INFORMATION: Anti-miR-208 oligonucleotide
<220> FEATURE:
<221> NAME/KEY: misc_feature
<222> LOCATION: (1)..(1)
<223> OTHER INFORMATION: May be locked nucleic acid cytidine
      phosphorothioate
<220> FEATURE:
<221> NAME/KEY: misc_feature
<222> LOCATION: (2)..(2)
<223> OTHER INFORMATION: May be deoxy cytidine phosphorothioate
<220> FEATURE:
<221> NAME/KEY: misc_feature
<222> LOCATION: (3)..(6)
<223> OTHER INFORMATION: May be locked nucleic acid thymidine
      phosphorothioate
<220> FEATURE:
```

```
<221> NAME/KEY: misc_feature
<222> LOCATION: (7)..(7)
<223> OTHER INFORMATION: May be deoxy guanosine phosphorothioate
<220> FEATURE:
<221> NAME/KEY: misc_feature
<222> LOCATION: (8)..(8)
<223> OTHER INFORMATION: May be locked nucleic acid cytidine
      phosphorothioate
<220> FEATURE:
<221> NAME/KEY: misc_feature
<222> LOCATION: (9)..(9)
<223> OTHER INFORMATION: May be deoxy thymidine phosphorothioate
<220> FEATURE:
<221> NAME/KEY: misc_feature
<222> LOCATION: (10)..(10)
<223> OTHER INFORMATION: May be locked nucleic acid cytidine
      phosphorothioate
<220> FEATURE:
<221> NAME/KEY: misc_feature
<222> LOCATION: (11)..(11)
<223> OTHER INFORMATION: May be deoxy guanosine phosphorothioate
<220> FEATURE:
<221> NAME/KEY: misc_feature
<222> LOCATION: (12)..(12)
<223> OTHER INFORMATION: May be deoxy thymidine phosphorothioate
<220> FEATURE:
<221> NAME/KEY: misc_feature
<222> LOCATION: (13)..(13)
<223> OTHER INFORMATION: May be locked nucleic acid cytidine
      phosphorothioate
<220> FEATURE:
<221> NAME/KEY: misc_feature
<222> LOCATION: (14)..(15)
<223> OTHER INFORMATION: May be deoxy thymidine phosphorothioate
<220> FEATURE:
<221> NAME/KEY: misc_feature
<222> LOCATION: (16)..(16)
<223> OTHER INFORMATION: May be locked nucleic acid adenosine

<400> SEQUENCE: 71 cctttttgctc gtctta                                                  16

<210> SEQ ID NO 72
<211> LENGTH: 15
<212> TYPE: DNA
<213> ORGANISM: Artificial Sequence
<220> FEATURE:
<223> OTHER INFORMATION: Anti-miR-208 oligonucleotide
<220> FEATURE:
<221> NAME/KEY: misc_feature
<222> LOCATION: (1)..(4)
<223> OTHER INFORMATION: May be locked nucleic acid thymidine
      phosphorothioate
<220> FEATURE:
<221> NAME/KEY: misc_feature
<222> LOCATION: (5)..(5)
<223> OTHER INFORMATION: May be deoxy guanosine phosphorothioate
<220> FEATURE:
<221> NAME/KEY: misc_feature
<222> LOCATION: (6)..(6)
<223> OTHER INFORMATION: May be locked nucleic acid thymidine
      phosphorothioate
<220> FEATURE:
<221> NAME/KEY: misc_feature
<222> LOCATION: (7)..(7)
<223> OTHER INFORMATION: May be deoxy thymidine phosphorothioate
<220> FEATURE:
<221> NAME/KEY: misc_feature
<222> LOCATION: (8)..(8)
<223> OTHER INFORMATION: May be locked nucleic acid cytidine
      phosphorothioate
<220> FEATURE:
<221> NAME/KEY: misc_feature
<222> LOCATION: (9)..(9)
<223> OTHER INFORMATION: May be deoxy guanosine phosphorothioate
<220> FEATURE:
<221> NAME/KEY: misc_feature
<222> LOCATION: (10)..(10)
```

```
<223> OTHER INFORMATION: May be deoxy thymidine phosphorothioate
<220> FEATURE:
<221> NAME/KEY: misc_feature
<222> LOCATION: (11)..(11)
<223> OTHER INFORMATION: May be locked nucleic acid cytidine
      phosphorothioate
<220> FEATURE:
<221> NAME/KEY: misc_feature
<222> LOCATION: (12)..(12)
<223> OTHER INFORMATION: May be deoxy thymidine phosphorothioate
<220> FEATURE:
<221> NAME/KEY: misc_feature
<222> LOCATION: (13)..(13)
<223> OTHER INFORMATION: May be locked nucleic acid thymidine
      phosphorothioate
<220> FEATURE:
<221> NAME/KEY: misc_feature
<222> LOCATION: (14)..(14)
<223> OTHER INFORMATION: May be deoxy adenosine phosphorothioate
<220> FEATURE:
<221> NAME/KEY: misc_feature
<222> LOCATION: (15)..(15)
<223> OTHER INFORMATION: May be locked nucleic acid thymidine

<400> SEQUENCE: 72
ttttgttcgt cttat                                                        15

<210> SEQ ID NO 73
<211> LENGTH: 15
<212> TYPE: DNA
<213> ORGANISM: Artificial Sequence
<220> FEATURE:
<223> OTHER INFORMATION: Anti-miR-208 oligonucleotide
<220> FEATURE:
<221> NAME/KEY: misc_feature
<222> LOCATION: (1)..(4)
<223> OTHER INFORMATION: May be locked nucleic acid thymidine
      phosphorothioate
<220> FEATURE:
<221> NAME/KEY: misc_feature
<222> LOCATION: (5)..(5)
<223> OTHER INFORMATION: May be deoxy guanosine phosphorothioate
<220> FEATURE:
<221> NAME/KEY: misc_feature
<222> LOCATION: (6)..(6)
<223> OTHER INFORMATION: May be locked nucleic acid thymidine
      phosphorothioate
<220> FEATURE:
<221> NAME/KEY: misc_feature
<222> LOCATION: (7)..(7)
<223> OTHER INFORMATION: May be deoxy thymidine phosphorothioate
<220> FEATURE:
<221> NAME/KEY: misc_feature
<222> LOCATION: (8)..(8)
<223> OTHER INFORMATION: May be locked nucleic acid cytidine
      phosphorothioate
<220> FEATURE:
<221> NAME/KEY: misc_feature
<222> LOCATION: (9)..(9)
<223> OTHER INFORMATION: May be deoxy guanosine phosphorothioate
<220> FEATURE:
<221> NAME/KEY: misc_feature
<222> LOCATION: (10)..(10)
<223> OTHER INFORMATION: May be deoxy thymidine phosphorothioate
<220> FEATURE:
<221> NAME/KEY: misc_feature
<222> LOCATION: (11)..(11)
<223> OTHER INFORMATION: May be locked nucleic acid cytidine
      phosphorothioate
<220> FEATURE:
<221> NAME/KEY: misc_feature
<222> LOCATION: (12)..(12)
<223> OTHER INFORMATION: May be deoxy thymidine phosphorothioate
<220> FEATURE:
<221> NAME/KEY: misc_feature
<222> LOCATION: (13)..(13)
<223> OTHER INFORMATION: May be locked nucleic acid thymidine
      phosphorothioate
```

```
<220> FEATURE:
<221> NAME/KEY: misc_feature
<222> LOCATION: (14)..(14)
<223> OTHER INFORMATION: May be locked nucleic acid adenosine
      phosphorothioate
<220> FEATURE:
<221> NAME/KEY: misc_feature
<222> LOCATION: (15)..(15)
<223> OTHER INFORMATION: May be locked nucleic acid thymidine

<400> SEQUENCE: 73
ttttgttcgt cttat                                                        15

<210> SEQ ID NO 74
<211> LENGTH: 15
<212> TYPE: DNA
<213> ORGANISM: Artificial Sequence
<220> FEATURE:
<223> OTHER INFORMATION: Anti-miR-208 oligonucleotide
<220> FEATURE:
<221> NAME/KEY: misc_feature
<222> LOCATION: (1)..(4)
<223> OTHER INFORMATION: May be locked nucleic acid thymidine
      phosphorothioate
<220> FEATURE:
<221> NAME/KEY: misc_feature
<222> LOCATION: (5)..(5)
<223> OTHER INFORMATION: May be deoxy guanosine phosphorothioate
<220> FEATURE:
<221> NAME/KEY: misc_feature
<222> LOCATION: (6)..(6)
<223> OTHER INFORMATION: May be locked nucleic acid thymidine
      phosphorothioate
<220> FEATURE:
<221> NAME/KEY: misc_feature
<222> LOCATION: (7)..(7)
<223> OTHER INFORMATION: May be deoxy thymidine phosphorothioate
<220> FEATURE:
<221> NAME/KEY: misc_feature
<222> LOCATION: (8)..(8)
<223> OTHER INFORMATION: May be locked nucleic acid cytidine
      phosphorothioate
<220> FEATURE:
<221> NAME/KEY: misc_feature
<222> LOCATION: (9)..(9)
<223> OTHER INFORMATION: May be deoxy guanosine phosphorothioate
<220> FEATURE:
<221> NAME/KEY: misc_feature
<222> LOCATION: (10)..(10)
<223> OTHER INFORMATION: May be locked nucleic acid thymidine
      phosphorothioate
<220> FEATURE:
<221> NAME/KEY: misc_feature
<222> LOCATION: (11)..(11)
<223> OTHER INFORMATION: May be locked nucleic acid cytidine
      phosphorothioate
<220> FEATURE:
<221> NAME/KEY: misc_feature
<222> LOCATION: (12)..(12)
<223> OTHER INFORMATION: May be deoxy thymidine phosphorothioate
<220> FEATURE:
<221> NAME/KEY: misc_feature
<222> LOCATION: (13)..(13)
<223> OTHER INFORMATION: May be locked nucleic acid thymidine
      phosphorothioate
<220> FEATURE:
<221> NAME/KEY: misc_feature
<222> LOCATION: (14)..(14)
<223> OTHER INFORMATION: May be deoxy adenosine phosphorothioate
<220> FEATURE:
<221> NAME/KEY: misc_feature
<222> LOCATION: (15)..(15)
<223> OTHER INFORMATION: May be locked nucleic acid thymidine

<400> SEQUENCE: 74
ttttgttcgt cttat                                                        15
```

<210> SEQ ID NO 75
<211> LENGTH: 15
<212> TYPE: DNA
<213> ORGANISM: Artificial Sequence
<220> FEATURE:
<223> OTHER INFORMATION: Anti-miR-208 oligonucleotide
<220> FEATURE:
<221> NAME/KEY: misc_feature
<222> LOCATION: (1)..(2)
<223> OTHER INFORMATION: May be locked nucleic acid thymidine
      phosphorothioate
<220> FEATURE:
<221> NAME/KEY: misc_feature
<222> LOCATION: (3)..(3)
<223> OTHER INFORMATION: May be deoxy thymidine phosphorothioate
<220> FEATURE:
<221> NAME/KEY: misc_feature
<222> LOCATION: (4)..(4)
<223> OTHER INFORMATION: May be locked nucleic acid thymidine
      phosphorothioate
<220> FEATURE:
<221> NAME/KEY: misc_feature
<222> LOCATION: (5)..(5)
<223> OTHER INFORMATION: May be deoxy guanosine phosphorothioate
<220> FEATURE:
<221> NAME/KEY: misc_feature
<222> LOCATION: (6)..(7)
<223> OTHER INFORMATION: May be deoxy thymidine phosphorothioate
<220> FEATURE:
<221> NAME/KEY: misc_feature
<222> LOCATION: (8)..(8)
<223> OTHER INFORMATION: May be locked nucleic acid cytidine
      phosphorothioate
<220> FEATURE:
<221> NAME/KEY: misc_feature
<222> LOCATION: (9)..(9)
<223> OTHER INFORMATION: May be locked nucleic acid guanosine
      phosphorothioate
<220> FEATURE:
<221> NAME/KEY: misc_feature
<222> LOCATION: (10)..(10)
<223> OTHER INFORMATION: May be locked nucleic acid thymidine
      phosphorothioate
<220> FEATURE:
<221> NAME/KEY: misc_feature
<222> LOCATION: (11)..(11)
<223> OTHER INFORMATION: May be locked nucleic acid cytidine
      phosphorothioate
<220> FEATURE:
<221> NAME/KEY: misc_feature
<222> LOCATION: (12)..(13)
<223> OTHER INFORMATION: May be locked nucleic acid thymidine
      phosphorothioate
<220> FEATURE:
<221> NAME/KEY: misc_feature
<222> LOCATION: (14)..(14)
<223> OTHER INFORMATION: May be locked nucleic acid adenosine
      phosphorothioate
<220> FEATURE:
<221> NAME/KEY: misc_feature
<222> LOCATION: (15)..(15)
<223> OTHER INFORMATION: May be locked nucleic acid thymidine

<400> SEQUENCE: 75
ttttgttcgt cttat                                              15

<210> SEQ ID NO 76
<211> LENGTH: 15
<212> TYPE: DNA
<213> ORGANISM: Artificial Sequence
<220> FEATURE:
<223> OTHER INFORMATION: Anti-miR-208 oligonucleotide
<220> FEATURE:
<221> NAME/KEY: misc_feature
<222> LOCATION: (1)..(4)
<223> OTHER INFORMATION: May be locked nucleic acid thymidine
      phosphorothioate

```
<220> FEATURE:
<221> NAME/KEY: misc_feature
<222> LOCATION: (5)..(5)
<223> OTHER INFORMATION: May be deoxy guanosine phosphorothioate
<220> FEATURE:
<221> NAME/KEY: misc_feature
<222> LOCATION: (6)..(6)
<223> OTHER INFORMATION: May be locked nucleic acid thymidine
      phosphorothioate
<220> FEATURE:
<221> NAME/KEY: misc_feature
<222> LOCATION: (7)..(7)
<223> OTHER INFORMATION: May be deoxy thymidine phosphorothioate
<220> FEATURE:
<221> NAME/KEY: misc_feature
<222> LOCATION: (8)..(8)
<223> OTHER INFORMATION: May be locked nucleic acid cytidine
      phosphorothioate
<220> FEATURE:
<221> NAME/KEY: misc_feature
<222> LOCATION: (9)..(9)
<223> OTHER INFORMATION: May be deoxy guanosine phosphorothioate
<220> FEATURE:
<221> NAME/KEY: misc_feature
<222> LOCATION: (10)..(10)
<223> OTHER INFORMATION: May be deoxy thymidine phosphorothioate
<220> FEATURE:
<221> NAME/KEY: misc_feature
<222> LOCATION: (11)..(11)
<223> OTHER INFORMATION: May be locked nucleic acid cytidine
      phosphorothioate
<220> FEATURE:
<221> NAME/KEY: misc_feature
<222> LOCATION: (12)..(12)
<223> OTHER INFORMATION: May be deoxy thymidine phosphorothioate
<220> FEATURE:
<221> NAME/KEY: misc_feature
<222> LOCATION: (13)..(13)
<223> OTHER INFORMATION: May be locked nucleic acid thymidine
      phosphorothioate
<220> FEATURE:
<221> NAME/KEY: misc_feature
<222> LOCATION: (14)..(14)
<223> OTHER INFORMATION: May be locked nucleic acid adenosine
      phosphorothioate
<220> FEATURE:
<221> NAME/KEY: misc_feature
<222> LOCATION: (15)..(15)
<223> OTHER INFORMATION: May be deoxy thymidine

<400> SEQUENCE: 76
ttttgttcgt cttat                                              15

<210> SEQ ID NO 77
<211> LENGTH: 15
<212> TYPE: DNA
<213> ORGANISM: Artificial Sequence
<220> FEATURE:
<223> OTHER INFORMATION: Anti-miR-208 oligonucleotide
<220> FEATURE:
<221> NAME/KEY: misc_feature
<222> LOCATION: (1)..(4)
<223> OTHER INFORMATION: May be locked nucleic acid thymidine
      phosphorothioate
<220> FEATURE:
<221> NAME/KEY: misc_feature
<222> LOCATION: (5)..(5)
<223> OTHER INFORMATION: May be deoxy guanosine phosphorothioate
<220> FEATURE:
<221> NAME/KEY: misc_feature
<222> LOCATION: (6)..(6)
<223> OTHER INFORMATION: May be locked nucleic acid thymidine
      phosphorothioate
<220> FEATURE:
<221> NAME/KEY: misc_feature
<222> LOCATION: (7)..(7)
<223> OTHER INFORMATION: May be deoxy thymidine phosphorothioate
<220> FEATURE:
```

```
<221> NAME/KEY: misc_feature
<222> LOCATION: (8)..(8)
<223> OTHER INFORMATION: May be locked nucleic acid cytidine
      phosphorothioate
<220> FEATURE:
<221> NAME/KEY: misc_feature
<222> LOCATION: (9)..(9)
<223> OTHER INFORMATION: May be deoxy guanosine phosphorothioate
<220> FEATURE:
<221> NAME/KEY: misc_feature
<222> LOCATION: (10)..(10)
<223> OTHER INFORMATION: May be locked nucleic acid thymidine
      phosphorothioate
<220> FEATURE:
<221> NAME/KEY: misc_feature
<222> LOCATION: (11)..(11)
<223> OTHER INFORMATION: May be locked nucleic acid cytidine
      phosphorothioate
<220> FEATURE:
<221> NAME/KEY: misc_feature
<222> LOCATION: (12)..(12)
<223> OTHER INFORMATION: May be deoxy thymidine phosphorothioate
<220> FEATURE:
<221> NAME/KEY: misc_feature
<222> LOCATION: (13)..(13)
<223> OTHER INFORMATION: May be locked nucleic acid thymidine
      phosphorothioate
<220> FEATURE:
<221> NAME/KEY: misc_feature
<222> LOCATION: (14)..(14)
<223> OTHER INFORMATION: May be locked nucleic acid adenosine
      phosphorothioate
<220> FEATURE:
<221> NAME/KEY: misc_feature
<222> LOCATION: (15)..(15)
<223> OTHER INFORMATION: May be deoxy thymidine

<400> SEQUENCE: 77
ttttgttcgt cttat                                              15

<210> SEQ ID NO 78
<211> LENGTH: 15
<212> TYPE: DNA
<213> ORGANISM: Artificial Sequence
<220> FEATURE:
<223> OTHER INFORMATION: Anti-miR-208 oligonucleotide
<220> FEATURE:
<221> NAME/KEY: misc_feature
<222> LOCATION: (1)..(2)
<223> OTHER INFORMATION: May be locked nucleic acid thymidine
      phosphorothioate
<220> FEATURE:
<221> NAME/KEY: misc_feature
<222> LOCATION: (3)..(3)
<223> OTHER INFORMATION: May be deoxy thymidine phosphorothioate
<220> FEATURE:
<221> NAME/KEY: misc_feature
<222> LOCATION: (4)..(4)
<223> OTHER INFORMATION: May be locked nucleic acid thymidine
      phosphorothioate
<220> FEATURE:
<221> NAME/KEY: misc_feature
<222> LOCATION: (5)..(5)
<223> OTHER INFORMATION: May be deoxy guanosine phosphorothioate
<220> FEATURE:
<221> NAME/KEY: misc_feature
<222> LOCATION: (6)..(6)
<223> OTHER INFORMATION: May be locked nucleic acid thymidine
      phosphorothioate
<220> FEATURE:
<221> NAME/KEY: misc_feature
<222> LOCATION: (7)..(7)
<223> OTHER INFORMATION: May be deoxy thymidine phosphorothioate
<220> FEATURE:
<221> NAME/KEY: misc_feature
<222> LOCATION: (8)..(8)
<223> OTHER INFORMATION: May be locked nucleic acid cytidine
      phosphorothioate
```

```
<220> FEATURE:
<221> NAME/KEY: misc_feature
<222> LOCATION: (9)..(9)
<223> OTHER INFORMATION: May be locked nucleic acid guanosine
      phosphorothioate
<220> FEATURE:
<221> NAME/KEY: misc_feature
<222> LOCATION: (10)..(10)
<223> OTHER INFORMATION: May be locked nucleic acid thymidine
      phosphorothioate
<220> FEATURE:
<221> NAME/KEY: misc_feature
<222> LOCATION: (11)..(11)
<223> OTHER INFORMATION: May be locked nucleic acid cytidine
      phosphorothioate
<220> FEATURE:
<221> NAME/KEY: misc_feature
<222> LOCATION: (12)..(13)
<223> OTHER INFORMATION: May be locked nucleic acid thymidine
      phosphorothioate
<220> FEATURE:
<221> NAME/KEY: misc_feature
<222> LOCATION: (14)..(14)
<223> OTHER INFORMATION: May be locked nucleic acid adenosine
      phosphorothioate
<220> FEATURE:
<221> NAME/KEY: misc_feature
<222> LOCATION: (15)..(15)
<223> OTHER INFORMATION: May be deoxy thymidine

<400> SEQUENCE: 78
ttttgttcgt cttat                                                    15

<210> SEQ ID NO 79
<211> LENGTH: 15
<212> TYPE: DNA
<213> ORGANISM: Artificial Sequence
<220> FEATURE:
<223> OTHER INFORMATION: Anti-miR-208 oligonucleotide
<220> FEATURE:
<221> NAME/KEY: misc_feature
<222> LOCATION: (1)..(4)
<223> OTHER INFORMATION: May be locked nucleic acid thymidine
      phosphorothioate
<220> FEATURE:
<221> NAME/KEY: misc_feature
<222> LOCATION: (5)..(5)
<223> OTHER INFORMATION: May be deoxy guanosine phosphorothioate
<220> FEATURE:
<221> NAME/KEY: misc_feature
<222> LOCATION: (6)..(7)
<223> OTHER INFORMATION: May be deoxy thymidine phosphorothioate
<220> FEATURE:
<221> NAME/KEY: misc_feature
<222> LOCATION: (8)..(8)
<223> OTHER INFORMATION: May be locked nucleic acid cytidine
      phosphorothioate
<220> FEATURE:
<221> NAME/KEY: misc_feature
<222> LOCATION: (9)..(9)
<223> OTHER INFORMATION: May be deoxy guanosine phosphorothioate
<220> FEATURE:
<221> NAME/KEY: misc_feature
<222> LOCATION: (10)..(10)
<223> OTHER INFORMATION: May be deoxy thymidine phosphorothioate
<220> FEATURE:
<221> NAME/KEY: misc_feature
<222> LOCATION: (11)..(11)
<223> OTHER INFORMATION: May be locked nucleic acid cytidine
      phosphorothioate
<220> FEATURE:
<221> NAME/KEY: misc_feature
<222> LOCATION: (12)..(13)
<223> OTHER INFORMATION: May be locked nucleic acid thymidine
      phosphorothioate
<220> FEATURE:
<221> NAME/KEY: misc_feature
<222> LOCATION: (14)..(14)
```

-continued

```
<223> OTHER INFORMATION: May be deoxy adenosine phosphorothioate
<220> FEATURE:
<221> NAME/KEY: misc_feature
<222> LOCATION: (15)..(15)
<223> OTHER INFORMATION: May be locked nucleic acid thymidine

<400> SEQUENCE: 79
ttttgttcgt cttat                                                     15

<210> SEQ ID NO 80
<211> LENGTH: 15
<212> TYPE: DNA
<213> ORGANISM: Artificial Sequence
<220> FEATURE:
<223> OTHER INFORMATION: Anti-miR-208 oligonucleotide
<220> FEATURE:
<221> NAME/KEY: misc_feature
<222> LOCATION: (1)..(4)
<223> OTHER INFORMATION: May be locked nucleic acid thymidine
      phosphorothioate
<220> FEATURE:
<221> NAME/KEY: misc_feature
<222> LOCATION: (5)..(5)
<223> OTHER INFORMATION: May be deoxy guanosine phosphorothioate
<220> FEATURE:
<221> NAME/KEY: misc_feature
<222> LOCATION: (6)..(7)
<223> OTHER INFORMATION: May be deoxy thymidine phosphorothioate
<220> FEATURE:
<221> NAME/KEY: misc_feature
<222> LOCATION: (8)..(8)
<223> OTHER INFORMATION: May be locked nucleic acid cytidine
      phosphorothioate
<220> FEATURE:
<221> NAME/KEY: misc_feature
<222> LOCATION: (9)..(9)
<223> OTHER INFORMATION: May be deoxy guanosine phosphorothioate
<220> FEATURE:
<221> NAME/KEY: misc_feature
<222> LOCATION: (10)..(10)
<223> OTHER INFORMATION: May be deoxy thymidine phosphorothioate
<220> FEATURE:
<221> NAME/KEY: misc_feature
<222> LOCATION: (11)..(11)
<223> OTHER INFORMATION: May be locked nucleic acid cytidine
      phosphorothioate
<220> FEATURE:
<221> NAME/KEY: misc_feature
<222> LOCATION: (12)..(13)
<223> OTHER INFORMATION: May be locked nucleic acid thymidine
      phosphorothioate
<220> FEATURE:
<221> NAME/KEY: misc_feature
<222> LOCATION: (14)..(14)
<223> OTHER INFORMATION: May be locked nucleic acid adenosine
      phosphorothioate
<220> FEATURE:
<221> NAME/KEY: misc_feature
<222> LOCATION: (15)..(15)
<223> OTHER INFORMATION: May be deoxy thymidine

<400> SEQUENCE: 80
ttttgttcgt cttat                                                     15

<210> SEQ ID NO 81
<211> LENGTH: 14
<212> TYPE: DNA
<213> ORGANISM: Artificial Sequence
<220> FEATURE:
<223> OTHER INFORMATION: Anti-miR-208 oligonucleotide
<220> FEATURE:
<221> NAME/KEY: misc_feature
<222> LOCATION: (1)..(3)
<223> OTHER INFORMATION: May be locked nucleic acid thymidine
      phosphorothioate
<220> FEATURE:
```

```
<221> NAME/KEY: misc_feature
<222> LOCATION: (4)..(4)
<223> OTHER INFORMATION: May be deoxy guanosine phosphorothioate
<220> FEATURE:
<221> NAME/KEY: misc_feature
<222> LOCATION: (5)..(5)
<223> OTHER INFORMATION: May be locked nucleic acid thymidine
      phosphorothioate
<220> FEATURE:
<221> NAME/KEY: misc_feature
<222> LOCATION: (6)..(6)
<223> OTHER INFORMATION: May be deoxy thymidine phosphorothioate
<220> FEATURE:
<221> NAME/KEY: misc_feature
<222> LOCATION: (7)..(7)
<223> OTHER INFORMATION: May be locked nucleic acid cytidine
      phosphorothioate
<220> FEATURE:
<221> NAME/KEY: misc_feature
<222> LOCATION: (8)..(8)
<223> OTHER INFORMATION: May be deoxy guanosine phosphorothioate
<220> FEATURE:
<221> NAME/KEY: misc_feature
<222> LOCATION: (9)..(9)
<223> OTHER INFORMATION: May be deoxy thymidine phosphorothioate
<220> FEATURE:
<221> NAME/KEY: misc_feature
<222> LOCATION: (10)..(10)
<223> OTHER INFORMATION: May be locked nucleic acid cytidine
      phosphorothioate
<220> FEATURE:
<221> NAME/KEY: misc_feature
<222> LOCATION: (11)..(11)
<223> OTHER INFORMATION: May be deoxy thymidine phosphorothioate
<220> FEATURE:
<221> NAME/KEY: misc_feature
<222> LOCATION: (12)..(12)
<223> OTHER INFORMATION: May be locked nucleic acid thymidine
      phosphorothioate
<220> FEATURE:
<221> NAME/KEY: misc_feature
<222> LOCATION: (13)..(13)
<223> OTHER INFORMATION: May be deoxy adenosine phosphorothioate
<220> FEATURE:
<221> NAME/KEY: misc_feature
<222> LOCATION: (14)..(14)
<223> OTHER INFORMATION: May be locked nucleic acid thymidine

<400> SEQUENCE: 81
tttgttcgtc ttat                                                    14

<210> SEQ ID NO 82
<211> LENGTH: 14
<212> TYPE: DNA
<213> ORGANISM: Artificial Sequence
<220> FEATURE:
<223> OTHER INFORMATION: Anti-miR-208 oligonucleotide
<220> FEATURE:
<221> NAME/KEY: misc_feature
<222> LOCATION: (1)..(3)
<223> OTHER INFORMATION: May be locked nucleic acid thymidine
      phosphorothioate
<220> FEATURE:
<221> NAME/KEY: misc_feature
<222> LOCATION: (4)..(4)
<223> OTHER INFORMATION: May be deoxy guanosine phosphorothioate
<220> FEATURE:
<221> NAME/KEY: misc_feature
<222> LOCATION: (5)..(5)
<223> OTHER INFORMATION: May be locked nucleic acid thymidine
      phosphorothioate
<220> FEATURE:
<221> NAME/KEY: misc_feature
<222> LOCATION: (6)..(6)
<223> OTHER INFORMATION: May be deoxy thymidine phosphorothioate
<220> FEATURE:
<221> NAME/KEY: misc_feature
<222> LOCATION: (7)..(7)
```

```
<223> OTHER INFORMATION: May be locked nucleic acid cytidine
      phosphorothioate
<220> FEATURE:
<221> NAME/KEY: misc_feature
<222> LOCATION: (8)..(8)
<223> OTHER INFORMATION: May be deoxy guanosine phosphorothioate
<220> FEATURE:
<221> NAME/KEY: misc_feature
<222> LOCATION: (9)..(9)
<223> OTHER INFORMATION: May be deoxy thymidine phosphorothioate
<220> FEATURE:
<221> NAME/KEY: misc_feature
<222> LOCATION: (10)..(10)
<223> OTHER INFORMATION: May be locked nucleic acid cytidine
      phosphorothioate
<220> FEATURE:
<221> NAME/KEY: misc_feature
<222> LOCATION: (11)..(11)
<223> OTHER INFORMATION: May be deoxy thymidine phosphorothioate
<220> FEATURE:
<221> NAME/KEY: misc_feature
<222> LOCATION: (12)..(12)
<223> OTHER INFORMATION: May be locked nucleic acid thymidine
      phosphorothioate
<220> FEATURE:
<221> NAME/KEY: misc_feature
<222> LOCATION: (13)..(13)
<223> OTHER INFORMATION: May be locked nucleic acid adenosine
      phosphorothioate
<220> FEATURE:
<221> NAME/KEY: misc_feature
<222> LOCATION: (14)..(14)
<223> OTHER INFORMATION: May be locked nucleic acid thymidine

<400> SEQUENCE: 82
tttgttcgtc ttat                                                     14

<210> SEQ ID NO 83
<211> LENGTH: 14
<212> TYPE: DNA
<213> ORGANISM: Artificial Sequence
<220> FEATURE:
<223> OTHER INFORMATION: Anti-miR-208 oligonucleotide
<220> FEATURE:
<221> NAME/KEY: misc_feature
<222> LOCATION: (1)..(3)
<223> OTHER INFORMATION: May be locked nucleic acid thymidine
      phosphorothioate
<220> FEATURE:
<221> NAME/KEY: misc_feature
<222> LOCATION: (4)..(4)
<223> OTHER INFORMATION: May be deoxy guanosine phosphorothioate
<220> FEATURE:
<221> NAME/KEY: misc_feature
<222> LOCATION: (5)..(5)
<223> OTHER INFORMATION: May be locked nucleic acid thymidine
      phosphorothioate
<220> FEATURE:
<221> NAME/KEY: misc_feature
<222> LOCATION: (6)..(6)
<223> OTHER INFORMATION: May be deoxy thymidine phosphorothioate
<220> FEATURE:
<221> NAME/KEY: misc_feature
<222> LOCATION: (7)..(7)
<223> OTHER INFORMATION: May be locked nucleic acid cytidine
      phosphorothioate
<220> FEATURE:
<221> NAME/KEY: misc_feature
<222> LOCATION: (8)..(8)
<223> OTHER INFORMATION: May be deoxy guanosine phosphorothioate
<220> FEATURE:
<221> NAME/KEY: misc_feature
<222> LOCATION: (9)..(9)
<223> OTHER INFORMATION: May be locked nucleic acid thymidine
      phosphorothioate
<220> FEATURE:
<221> NAME/KEY: misc_feature
<222> LOCATION: (10)..(10)
```

```
<223> OTHER INFORMATION: May be locked nucleic acid cytidine
      phosphorothioate
<220> FEATURE:
<221> NAME/KEY: misc_feature
<222> LOCATION: (11)..(11)
<223> OTHER INFORMATION: May be deoxy thymidine phosphorothioate
<220> FEATURE:
<221> NAME/KEY: misc_feature
<222> LOCATION: (12)..(12)
<223> OTHER INFORMATION: May be locked nucleic acid thymidine
      phosphorothioate
<220> FEATURE:
<221> NAME/KEY: misc_feature
<222> LOCATION: (13)..(13)
<223> OTHER INFORMATION: May be deoxy adenosine phosphorothioate
<220> FEATURE:
<221> NAME/KEY: misc_feature
<222> LOCATION: (14)..(14)
<223> OTHER INFORMATION: May be locked nucleic acid thymidine

<400> SEQUENCE: 83
tttgttcgtc ttat                                                       14

<210> SEQ ID NO 84
<211> LENGTH: 14
<212> TYPE: DNA
<213> ORGANISM: Artificial Sequence
<220> FEATURE:
<223> OTHER INFORMATION: Anti-miR-208 oligonucleotide
<220> FEATURE:
<221> NAME/KEY: misc_feature
<222> LOCATION: (1)..(1)
<223> OTHER INFORMATION: May be locked nucleic acid thymidine
      phosphorothioate
<220> FEATURE:
<221> NAME/KEY: misc_feature
<222> LOCATION: (2)..(2)
<223> OTHER INFORMATION: May be deoxy thymidine phosphorothioate
<220> FEATURE:
<221> NAME/KEY: misc_feature
<222> LOCATION: (3)..(3)
<223> OTHER INFORMATION: May be locked nucleic acid thymidine
      phosphorothioate
<220> FEATURE:
<221> NAME/KEY: misc_feature
<222> LOCATION: (4)..(4)
<223> OTHER INFORMATION: May be deoxy guanosine phosphorothioate
<220> FEATURE:
<221> NAME/KEY: misc_feature
<222> LOCATION: (5)..(6)
<223> OTHER INFORMATION: May be deoxy thymidine phosphorothioate
<220> FEATURE:
<221> NAME/KEY: misc_feature
<222> LOCATION: (7)..(7)
<223> OTHER INFORMATION: May be locked nucleic acid cytidine
      phosphorothioate
<220> FEATURE:
<221> NAME/KEY: misc_feature
<222> LOCATION: (8)..(8)
<223> OTHER INFORMATION: May be locked nucleic acid guanosine
      phosphorothioate
<220> FEATURE:
<221> NAME/KEY: misc_feature
<222> LOCATION: (9)..(9)
<223> OTHER INFORMATION: May be locked nucleic acid thymidine
      phosphorothioate
<220> FEATURE:
<221> NAME/KEY: misc_feature
<222> LOCATION: (10)..(10)
<223> OTHER INFORMATION: May be locked nucleic acid cytidine
      phosphorothioate
<220> FEATURE:
<221> NAME/KEY: misc_feature
<222> LOCATION: (11)..(12)
<223> OTHER INFORMATION: May be locked nucleic acid thymidine
      phosphorothioate
<220> FEATURE:
<221> NAME/KEY: misc_feature
```

```
<222> LOCATION: (13)..(13)
<223> OTHER INFORMATION: May be locked nucleic acid adenosine
      phosphorothioate
<220> FEATURE:
<221> NAME/KEY: misc_feature
<222> LOCATION: (14)..(14)
<223> OTHER INFORMATION: May be locked nucleic acid thymidine

<400> SEQUENCE: 84
tttgttcgtc ttat                                                       14

<210> SEQ ID NO 85
<211> LENGTH: 14
<212> TYPE: DNA
<213> ORGANISM: Artificial Sequence
<220> FEATURE:
<223> OTHER INFORMATION: Anti-miR-208 oligonucleotide
<220> FEATURE:
<221> NAME/KEY: misc_feature
<222> LOCATION: (1)..(3)
<223> OTHER INFORMATION: May be locked nucleic acid thymidine
      phosphorothioate
<220> FEATURE:
<221> NAME/KEY: misc_feature
<222> LOCATION: (4)..(4)
<223> OTHER INFORMATION: May be deoxy guanosine phosphorothioate
<220> FEATURE:
<221> NAME/KEY: misc_feature
<222> LOCATION: (5)..(5)
<223> OTHER INFORMATION: May be locked nucleic acid thymidine
      phosphorothioate
<220> FEATURE:
<221> NAME/KEY: misc_feature
<222> LOCATION: (6)..(6)
<223> OTHER INFORMATION: May be deoxy thymidine phosphorothioate
<220> FEATURE:
<221> NAME/KEY: misc_feature
<222> LOCATION: (7)..(7)
<223> OTHER INFORMATION: May be locked nucleic acid cytidine
      phosphorothioate
<220> FEATURE:
<221> NAME/KEY: misc_feature
<222> LOCATION: (8)..(8)
<223> OTHER INFORMATION: May be deoxy guanosine phosphorothioate
<220> FEATURE:
<221> NAME/KEY: misc_feature
<222> LOCATION: (9)..(9)
<223> OTHER INFORMATION: May be deoxy thymidine phosphorothioate
<220> FEATURE:
<221> NAME/KEY: misc_feature
<222> LOCATION: (10)..(10)
<223> OTHER INFORMATION: May be locked nucleic acid cytidine
      phosphorothioate
<220> FEATURE:
<221> NAME/KEY: misc_feature
<222> LOCATION: (11)..(11)
<223> OTHER INFORMATION: May be deoxy thymidine phosphorothioate
<220> FEATURE:
<221> NAME/KEY: misc_feature
<222> LOCATION: (12)..(12)
<223> OTHER INFORMATION: May be locked nucleic acid thymidine
      phosphorothioate
<220> FEATURE:
<221> NAME/KEY: misc_feature
<222> LOCATION: (13)..(13)
<223> OTHER INFORMATION: May be locked nucleic acid adenosine
      phosphorothioate
<220> FEATURE:
<221> NAME/KEY: misc_feature
<222> LOCATION: (14)..(14)
<223> OTHER INFORMATION: May be deoxy thymidine

<400> SEQUENCE: 85
tttgttcgtc ttat                                                       14

<210> SEQ ID NO 86
```

```
<211> LENGTH: 14
<212> TYPE: DNA
<213> ORGANISM: Artificial Sequence
<220> FEATURE:
<223> OTHER INFORMATION: Anti-miR-208 oligonucleotide
<220> FEATURE:
<221> NAME/KEY: misc_feature
<222> LOCATION: (1)..(3)
<223> OTHER INFORMATION: May be locked nucleic acid thymidine
      phosphorothioate
<220> FEATURE:
<221> NAME/KEY: misc_feature
<222> LOCATION: (4)..(4)
<223> OTHER INFORMATION: May be deoxy guanosine phosphorothioate
<220> FEATURE:
<221> NAME/KEY: misc_feature
<222> LOCATION: (5)..(5)
<223> OTHER INFORMATION: May be locked nucleic acid thymidine
      phosphorothioate
<220> FEATURE:
<221> NAME/KEY: misc_feature
<222> LOCATION: (6)..(6)
<223> OTHER INFORMATION: May be deoxy thymidine phosphorothioate
<220> FEATURE:
<221> NAME/KEY: misc_feature
<222> LOCATION: (7)..(7)
<223> OTHER INFORMATION: May be locked nucleic acid cytidine
      phosphorothioate
<220> FEATURE:
<221> NAME/KEY: misc_feature
<222> LOCATION: (8)..(8)
<223> OTHER INFORMATION: May be deoxy guanosine phosphorothioate
<220> FEATURE:
<221> NAME/KEY: misc_feature
<222> LOCATION: (9)..(9)
<223> OTHER INFORMATION: May be locked nucleic acid thymidine
      phosphorothioate
<220> FEATURE:
<221> NAME/KEY: misc_feature
<222> LOCATION: (10)..(10)
<223> OTHER INFORMATION: May be locked nucleic acid cytidine
      phosphorothioate
<220> FEATURE:
<221> NAME/KEY: misc_feature
<222> LOCATION: (11)..(11)
<223> OTHER INFORMATION: May be deoxy thymidine phosphorothioate
<220> FEATURE:
<221> NAME/KEY: misc_feature
<222> LOCATION: (12)..(12)
<223> OTHER INFORMATION: May be locked nucleic acid thymidine
      phosphorothioate
<220> FEATURE:
<221> NAME/KEY: misc_feature
<222> LOCATION: (13)..(13)
<223> OTHER INFORMATION: May be locked nucleic acid adenosine
      phosphorothioate
<220> FEATURE:
<221> NAME/KEY: misc_feature
<222> LOCATION: (14)..(14)
<223> OTHER INFORMATION: May be deoxy thymidine

<400> SEQUENCE: 86
tttgttcgtc ttat                                                     14

<210> SEQ ID NO 87
<211> LENGTH: 14
<212> TYPE: DNA
<213> ORGANISM: Artificial Sequence
<220> FEATURE:
<223> OTHER INFORMATION: Anti-miR-208 oligonucleotide
<220> FEATURE:
<221> NAME/KEY: misc_feature
<222> LOCATION: (1)..(1)
<223> OTHER INFORMATION: May be locked nucleic acid thymidine
      phosphorothioate
<220> FEATURE:
<221> NAME/KEY: misc_feature
<222> LOCATION: (2)..(2)
```

```
<223> OTHER INFORMATION: May be deoxy thymidine phosphorothioate
<220> FEATURE:
<221> NAME/KEY: misc_feature
<222> LOCATION: (3)..(3)
<223> OTHER INFORMATION: May be locked nucleic acid thymidine
      phosphorothioate
<220> FEATURE:
<221> NAME/KEY: misc_feature
<222> LOCATION: (4)..(4)
<223> OTHER INFORMATION: May be deoxy guanosine phosphorothioate
<220> FEATURE:
<221> NAME/KEY: misc_feature
<222> LOCATION: (5)..(5)
<223> OTHER INFORMATION: May be locked nucleic acid thymidine
      phosphorothioate
<220> FEATURE:
<221> NAME/KEY: misc_feature
<222> LOCATION: (6)..(6)
<223> OTHER INFORMATION: May be deoxy thymidine phosphorothioate
<220> FEATURE:
<221> NAME/KEY: misc_feature
<222> LOCATION: (7)..(7)
<223> OTHER INFORMATION: May be locked nucleic acid cytidine
      phosphorothioate
<220> FEATURE:
<221> NAME/KEY: misc_feature
<222> LOCATION: (8)..(8)
<223> OTHER INFORMATION: May be locked nucleic acid guanosine
      phosphorothioate
<220> FEATURE:
<221> NAME/KEY: misc_feature
<222> LOCATION: (9)..(9)
<223> OTHER INFORMATION: May be locked nucleic acid thymidine
      phosphorothioate
<220> FEATURE:
<221> NAME/KEY: misc_feature
<222> LOCATION: (10)..(10)
<223> OTHER INFORMATION: May be locked nucleic acid cytidine
      phosphorothioate
<220> FEATURE:
<221> NAME/KEY: misc_feature
<222> LOCATION: (11)..(12)
<223> OTHER INFORMATION: May be locked nucleic acid thymidine
      phosphorothioate
<220> FEATURE:
<221> NAME/KEY: misc_feature
<222> LOCATION: (13)..(13)
<223> OTHER INFORMATION: May be locked nucleic acid adenosine
      phosphorothioate
<220> FEATURE:
<221> NAME/KEY: misc_feature
<222> LOCATION: (14)..(14)
<223> OTHER INFORMATION: May be deoxy thymidine

<400> SEQUENCE: 87
tttgttcgtc ttat                                                       14

<210> SEQ ID NO 88
<211> LENGTH: 14
<212> TYPE: DNA
<213> ORGANISM: Artificial Sequence
<220> FEATURE:
<223> OTHER INFORMATION: Anti-miR-208 oligonucleotide
<220> FEATURE:
<221> NAME/KEY: misc_feature
<222> LOCATION: (1)..(3)
<223> OTHER INFORMATION: May be locked nucleic acid thymidine
      phosphorothioate
<220> FEATURE:
<221> NAME/KEY: misc_feature
<222> LOCATION: (4)..(4)
<223> OTHER INFORMATION: May be deoxy guanosine phosphorothioate
<220> FEATURE:
<221> NAME/KEY: misc_feature
<222> LOCATION: (5)..(6)
<223> OTHER INFORMATION: May be deoxy thymidine phosphorothioate
<220> FEATURE:
<221> NAME/KEY: misc_feature
```

```
<222> LOCATION: (7)..(7)
<223> OTHER INFORMATION: May be locked nucleic acid cytidine
      phosphorothioate
<220> FEATURE:
<221> NAME/KEY: misc_feature
<222> LOCATION: (8)..(8)
<223> OTHER INFORMATION: May be deoxy guanosine phosphorothioate
<220> FEATURE:
<221> NAME/KEY: misc_feature
<222> LOCATION: (9)..(9)
<223> OTHER INFORMATION: May be deoxy thymidine phosphorothioate
<220> FEATURE:
<221> NAME/KEY: misc_feature
<222> LOCATION: (10)..(10)
<223> OTHER INFORMATION: May be locked nucleic acid cytidine
      phosphorothioate
<220> FEATURE:
<221> NAME/KEY: misc_feature
<222> LOCATION: (11)..(12)
<223> OTHER INFORMATION: May be locked nucleic acid thymidine
      phosphorothioate
<220> FEATURE:
<221> NAME/KEY: misc_feature
<222> LOCATION: (13)..(13)
<223> OTHER INFORMATION: May be deoxy adenosine phosphorothioate
<220> FEATURE:
<221> NAME/KEY: misc_feature
<222> LOCATION: (14)..(14)
<223> OTHER INFORMATION: May be locked nucleic acid thymidine

<400> SEQUENCE: 88
tttgttcgtc ttat                                                      14

<210> SEQ ID NO 89
<211> LENGTH: 14
<212> TYPE: DNA
<213> ORGANISM: Artificial Sequence
<220> FEATURE:
<223> OTHER INFORMATION: Anti-miR-208 oligonucleotide
<220> FEATURE:
<221> NAME/KEY: misc_feature
<222> LOCATION: (1)..(3)
<223> OTHER INFORMATION: May be locked nucleic acid thymidine
      phosphorothioate
<220> FEATURE:
<221> NAME/KEY: misc_feature
<222> LOCATION: (4)..(4)
<223> OTHER INFORMATION: May be deoxy guanosine phosphorothioate
<220> FEATURE:
<221> NAME/KEY: misc_feature
<222> LOCATION: (5)..(6)
<223> OTHER INFORMATION: May be deoxy thymidine phosphorothioate
<220> FEATURE:
<221> NAME/KEY: misc_feature
<222> LOCATION: (7)..(7)
<223> OTHER INFORMATION: May be locked nucleic acid cytidine
      phosphorothioate
<220> FEATURE:
<221> NAME/KEY: misc_feature
<222> LOCATION: (8)..(8)
<223> OTHER INFORMATION: May be deoxy guanosine phosphorothioate
<220> FEATURE:
<221> NAME/KEY: misc_feature
<222> LOCATION: (9)..(9)
<223> OTHER INFORMATION: May be deoxy thymidine phosphorothioate
<220> FEATURE:
<221> NAME/KEY: misc_feature
<222> LOCATION: (10)..(10)
<223> OTHER INFORMATION: May be locked nucleic acid cytidine
      phosphorothioate
<220> FEATURE:
<221> NAME/KEY: misc_feature
<222> LOCATION: (11)..(12)
<223> OTHER INFORMATION: May be locked nucleic acid thymidine
      phosphorothioate
<220> FEATURE:
<221> NAME/KEY: misc_feature
<222> LOCATION: (13)..(13)
```

```
<223> OTHER INFORMATION: May be locked nucleic acid adenosine
      phosphorothioate
<220> FEATURE:
<221> NAME/KEY: misc_feature
<222> LOCATION: (14)..(14)
<223> OTHER INFORMATION: May be deoxy thymidine

<400> SEQUENCE: 89
tttgttcgtc ttat                                                         14

<210> SEQ ID NO 90
<211> LENGTH: 16
<212> TYPE: DNA
<213> ORGANISM: Artificial Sequence
<220> FEATURE:
<223> OTHER INFORMATION: Anti-miR-208 oligonucleotide
<220> FEATURE:
<221> NAME/KEY: misc_feature
<222> LOCATION: (1)..(1)
<223> OTHER INFORMATION: May be locked nucleic acid cytidine
      phosphorothioate
<220> FEATURE:
<221> NAME/KEY: misc_feature
<222> LOCATION: (2)..(2)
<223> OTHER INFORMATION: May be deoxy thymidine phosphorothioate
<220> FEATURE:
<221> NAME/KEY: misc_feature
<222> LOCATION: (3)..(5)
<223> OTHER INFORMATION: May be locked nucleic acid thymidine
      phosphorothioate
<220> FEATURE:
<221> NAME/KEY: misc_feature
<222> LOCATION: (6)..(6)
<223> OTHER INFORMATION: May be locked nucleic acid guanosine
      phosphorothioate
<220> FEATURE:
<221> NAME/KEY: misc_feature
<222> LOCATION: (7)..(7)
<223> OTHER INFORMATION: May be deoxy thymidine phosphorothioate
<220> FEATURE:
<221> NAME/KEY: misc_feature
<222> LOCATION: (8)..(8)
<223> OTHER INFORMATION: May be locked nucleic acid thymidine
      phosphorothioate
<220> FEATURE:
<221> NAME/KEY: misc_feature
<222> LOCATION: (9)..(9)
<223> OTHER INFORMATION: May be deoxy cytidine phosphorothioate
<220> FEATURE:
<221> NAME/KEY: misc_feature
<222> LOCATION: (10)..(10)
<223> OTHER INFORMATION: May be locked nucleic acid guanosine
      phosphorothioate
<220> FEATURE:
<221> NAME/KEY: misc_feature
<222> LOCATION: (11)..(11)
<223> OTHER INFORMATION: May be deoxy thymidine phosphorothioate
<220> FEATURE:
<221> NAME/KEY: misc_feature
<222> LOCATION: (12)..(12)
<223> OTHER INFORMATION: May be deoxy cytidine phosphorothioate
<220> FEATURE:
<221> NAME/KEY: misc_feature
<222> LOCATION: (13)..(13)
<223> OTHER INFORMATION: May be locked nucleic acid thymidine
      phosphorothioate
<220> FEATURE:
<221> NAME/KEY: misc_feature
<222> LOCATION: (14)..(14)
<223> OTHER INFORMATION: May be deoxy thymidine phosphorothioate
<220> FEATURE:
<221> NAME/KEY: misc_feature
<222> LOCATION: (15)..(15)
<223> OTHER INFORMATION: May be locked nucleic acid adenosine
      phosphorothioate
<220> FEATURE:
<221> NAME/KEY: misc_feature
<222> LOCATION: (16)..(16)
```

```
<223> OTHER INFORMATION: May be deoxy thymidine

<400> SEQUENCE: 90
cttttgttcg tcttat                                                    16

<210> SEQ ID NO 91
<211> LENGTH: 16
<212> TYPE: DNA
<213> ORGANISM: Artificial Sequence
<220> FEATURE:
<223> OTHER INFORMATION: Anti-miR-208 oligonucleotide
<220> FEATURE:
<221> NAME/KEY: misc_feature
<222> LOCATION: (1)..(1)
<223> OTHER INFORMATION: May be locked nucleic acid cytidine
      phosphorothioate
<220> FEATURE:
<221> NAME/KEY: misc_feature
<222> LOCATION: (2)..(2)
<223> OTHER INFORMATION: May be deoxy thymidine phosphorothioate
<220> FEATURE:
<221> NAME/KEY: misc_feature
<222> LOCATION: (3)..(4)
<223> OTHER INFORMATION: May be locked nucleic acid thymidine
      phosphorothioate
<220> FEATURE:
<221> NAME/KEY: misc_feature
<222> LOCATION: (5)..(6)
<223> OTHER INFORMATION: May be deoxy thymidine phosphorothioate
<220> FEATURE:
<221> NAME/KEY: misc_feature
<222> LOCATION: (7)..(7)
<223> OTHER INFORMATION: May be locked nucleic acid guanosine
      phosphorothioate
<220> FEATURE:
<221> NAME/KEY: misc_feature
<222> LOCATION: (8)..(8)
<223> OTHER INFORMATION: May be locked nucleic acid cytidine
      phosphorothioate
<220> FEATURE:
<221> NAME/KEY: misc_feature
<222> LOCATION: (9)..(9)
<223> OTHER INFORMATION: May be deoxy thymidine phosphorothioate
<220> FEATURE:
<221> NAME/KEY: misc_feature
<222> LOCATION: (10)..(10)
<223> OTHER INFORMATION: May be locked nucleic acid cytidine
      phosphorothioate
<220> FEATURE:
<221> NAME/KEY: misc_feature
<222> LOCATION: (11)..(11)
<223> OTHER INFORMATION: May be deoxy guanosine phosphorothioate
<220> FEATURE:
<221> NAME/KEY: misc_feature
<222> LOCATION: (12)..(12)
<223> OTHER INFORMATION: May be locked nucleic acid thymidine
      phosphorothioate
<220> FEATURE:
<221> NAME/KEY: misc_feature
<222> LOCATION: (13)..(13)
<223> OTHER INFORMATION: May be deoxy cytidine phosphorothioate
<220> FEATURE:
<221> NAME/KEY: misc_feature
<222> LOCATION: (14)..(14)
<223> OTHER INFORMATION: May be locked nucleic acid thymidine
      phosphorothioate
<220> FEATURE:
<221> NAME/KEY: misc_feature
<222> LOCATION: (15)..(15)
<223> OTHER INFORMATION: May be deoxy thymidine phosphorothioate
<220> FEATURE:
<221> NAME/KEY: misc_feature
<222> LOCATION: (16)..(16)
<223> OTHER INFORMATION: May be locked nucleic acid adenosine
      phosphorothioate

<400> SEQUENCE: 91
```

```
cttttttgctc gtctta                                                    16

<210> SEQ ID NO 92
<211> LENGTH: 23
<212> TYPE: RNA
<213> ORGANISM: Caenorhabditis elegans

<400> SEQUENCE: 92
uaucacagcc agcuuugaug ugc                                             23

<210> SEQ ID NO 93
<211> LENGTH: 21
<212> TYPE: RNA
<213> ORGANISM: Caenorhabditis elegans

<400> SEQUENCE: 93
ucccugagac cucaagugug a                                               21

<210> SEQ ID NO 94
<211> LENGTH: 22
<212> TYPE: RNA
<213> ORGANISM: Artificial Sequence
<220> FEATURE:
<223> OTHER INFORMATION: Anti-miR-208 oligonucleotide

<400> SEQUENCE: 94
auaagacgag caaaaagcuu gu                                              22

<210> SEQ ID NO 95
<211> LENGTH: 22
<212> TYPE: DNA
<213> ORGANISM: Artificial Sequence
<220> FEATURE:
<223> OTHER INFORMATION: Anti-miR-208 oligonucleotide

<400> SEQUENCE: 95
acaagctttt tgctcgtctt at                                              22

<210> SEQ ID NO 96
<211> LENGTH: 17
<212> TYPE: DNA
<213> ORGANISM: Artificial Sequence
<220> FEATURE:
<223> OTHER INFORMATION: Anti-miR-208 oligonucleotide

<400> SEQUENCE: 96 cttttttgctc gtcttat                                                   17

<210> SEQ ID NO 97
<211> LENGTH: 22
<212> TYPE: RNA
<213> ORGANISM: Artificial Sequence
<220> FEATURE:
<223> OTHER INFORMATION: Anti-miR-208 oligonucleotide

<400> SEQUENCE: 97
auaagacgaa caaaagguuu gu                                              22

<210> SEQ ID NO 98
<211> LENGTH: 22
<212> TYPE: DNA
<213> ORGANISM: Artificial Sequence
<220> FEATURE:
<223> OTHER INFORMATION: Anti-miR-208 oligonucleotide

<400> SEQUENCE: 98
```

```
acaaaccttt tgttcgtctt at                                              22

<210> SEQ ID NO 99
<211> LENGTH: 17
<212> TYPE: DNA
<213> ORGANISM: Artificial Sequence
<220> FEATURE:
<223> OTHER INFORMATION: Anti-miR-208 oligonucleotide

<400> SEQUENCE: 99 cctttgttc gtcttat                                                     17
```

MICRORNA INHIBITORS COMPRISING LOCKED NUCLEOTIDES

CROSS-REFERENCE TO RELATED APPLICATIONS

This application claims priority to and the benefit of U.S. Provisional Application No. 61/423,456, filed Dec. 15, 2010, and of U.S. Provisional Application No. 61/495,224, filed Jun. 9, 2011, each of which are hereby incorporated by reference in its entirety.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: MIRG_023_01US_SeqList_ST25.txt, date recorded: Dec. 15, 2011, file size 117 kilobytes).

FIELD OF THE INVENTION

The present invention relates to chemical motifs for microRNA (miRNA or miR) inhibitors, and particularly to chemically modified miRNA antisense oligonucleotides having advantages in potency, efficiency of delivery, target specificity, stability, and/or toxicity when administered to a patient.

BACKGROUND

MicroRNAs (miRs) have been implicated in a number of biological processes including regulation and maintenance of cardiac function (see, Eva Van Rooij and Eric Olson, *MicroRNAs: Powerful new regulators of heart disease and proactive therapeutic targets, J. Clin. Invest.* 117(9):2369-2376 (2007); Chien K R, *Molecular Medicine: MicroRNAs and the tell-tale heart, Nature* 447, 389-390 (2007)). Therefore, miRs represent a relatively new class of therapeutic targets for conditions such as cardiac hypertrophy, myocardial infarction, heart failure, vascular damage, and pathologic cardiac fibrosis, among others. miRs are small, non-protein coding RNAs of about 18 to about 25 nucleotides in length, and act as repressors of target mRNAs by promoting their degradation, when their sequences are perfectly complementary, or by inhibiting translation, when their sequences contain mismatches. The mechanism involves incorporation of the mature miRNA strand into the RNA-induced silencing complex (RISC), where it associates with its target RNAs by base-pair complementarity.

miRNA function may be targeted therapeutically by antisense polynucleotides or by polynucleotides that mimic miRNA function ("miRNA mimetic"). However, targeting miRNAs therapeutically with oligonucleotide-based agents poses several challenges, including RNA-binding affinity and specificity, efficiency of cellular uptake, and nuclease resistance. For example, when polynucleotides are introduced into intact cells they are attacked and degraded by nucleases leading to a loss of activity. While polynucleotide analogues have been prepared in an attempt to avoid their degradation, e.g. by means of 2' substitutions (B. Sproat et al., *Nucleic Acids Research* 17 (1989), 3373-3386), the modifications often affect the polynucleotide's potency for its intended biological action. Such reduced potency, in each case, may be due to an inability of the modified polynucleotide to form a stable duplex with the target RNA and/or a loss of interaction with the cellular machinery. Other modifications include the use of locked nucleic acid, which has the potential to improve RNA-binding affinity. Veedu R N and Wengel J, *Locked nucleic acid as a novel class of therapeutic agent. RNA Biology* 6:3, 321-323 (2009).

Oligonucleotide chemistry patterns or motifs for miRNA inhibitors have the potential to improve the delivery, stability, potency, specificity, and/or toxicity profile of the inhibitors, and such are needed for effectively targeting miRNA function in a therapeutic context.

SUMMARY OF THE INVENTION

The invention provides chemically modified oligonucleotides capable of inhibiting the expression (e.g., abundance) of miR-208 family miRNAs, including miR-208a, miR-208b, and/or miR-499. The invention further provides pharmaceutical compositions comprising the oligonucleotides, and methods of treating patients having conditions or disorders relating to, or involving, a miR-208 family miRNA. Such conditions include various cardiovascular conditions. In various embodiments, the oligonucleotides provide advantages in one or more of potency, efficiency of delivery, target specificity, toxicity, and/or stability.

In one aspect, the invention provides a chemically-modified oligonucleotide capable of reducing the expression or abundance of miR-208 family miRNAs. The activity or potency of the oligonucleotides may be determined in vitro and/or in vivo. For example, the oligonucleotide may significantly inhibit (e.g., about 50% inhibition) the activity of a miR-208 family miRNA (as determined in the dual luciferase assay) at a concentration of about 50 nM or less, or in other embodiments, 40 nM or less, 20 nM or less, or 10 nM or less. Alternatively, or in addition, the activity of the oligonucleotide may be determined in a suitable mouse or rat model, or non-human primate model, such as those described herein, where inhibition (e.g., by at least 50%) of a miR-208 family miRNA is observed at a dose of 50 mg/kg or less, such as 25 mg/kg or less, 10 mg/kg or less, or 5 mg/kg or less. In these embodiments, the oligonucleotide may be dosed subcutaneously or intravenously (and as described herein), and may be formulated in an aqueous preparation (e.g., saline).

The nucleotide sequence of the oligonucleotide is substantially complementary to a nucleotide sequence of human miR-208a or miR-208b (or corresponding pre- or pri-miRNA), and contains a mixture of locked and non-locked nucleotides. For example, the oligonucleotide may contain at least three, at least five, or at least seven, locked nucleotides, and at least one non-locked nucleotide. Generally, the length of the oligonucleotide and number and position of locked nucleotides is such that the oligonucleotide reduces miR-208a, miR-208b, and/or miR-499 activity at an oligonucleotide concentration of about 50 nM or less in an in vitro luciferase assay, or at a dose of 50 mg/kg or less in a suitable rat or mouse model or non-human primate model as described herein. In exemplary embodiments, the locked nucleotides have a 2' to 4' methylene bridge.

The oligonucleotide may comprise, consist essentially of, or consist of, a full length or truncated miR-208a, miR-208b, or miR-499 antisense sequence. In these embodiments, the oligonucleotide is from about 6 to 22 nucleotides in length, or is from about 10 to 18 nucleotides in length, or is about 11 to about 16 nucleotides in length. The oligonucleotide in some embodiments is about 14, 15, 16, or 17 nucleotides in length. The oligonucleotide may comprise the nucleotide sequence of 5'-TGCTCGTCTTA-3' (SEQ ID NO:1) or may comprise the nucleotide sequence of 5'-TGTTCGTCTTA-3' (SEQ ID NO:2). In particular embodiments, the oligonucleotide comprises, consists essentially of, or consists of the nucleotide sequence 5'-CTTTTTGCTCGTCTTA-3' (SEQ ID NO:3) or 5'-CCTTTTGTTCGTCTTA-3' (SEQ ID NO:4).

The oligonucleotide may contain at least about 3, at least about 5, or at least about 7 locked nucleotides, or at least 9 locked nucleotides, but in various embodiments is not fully comprised of locked nucleotides. Generally, the number and position of locked nucleotides is such that the oligonucleotide reduces or inhibits miR-208a, miR-208b, and/or miR-499 activity at high potency. In certain embodiments, the oligonucleotide does not contain a stretch of nucleotides with more than four, or more than three, or more than two, contiguous non-locked nucleotides. In exemplary embodiments, the oligonucleotide has exactly 9 locked nucleotides and 7 non-locked nucleotides. For example, the pattern of locked nucleotides may be such that at least positions 1, 6, 10, 13, and 15 are locked nucleotides. In certain embodiments, at least positions 1, 5, 10, and 16 are locked nucleotides. In certain embodiments, positions 1, 5, 6, 8, 10, 11, 13, 15, and 16 are locked nucleotides, and the remaining positions are non-locked nucleotides. In other embodiments, positions 1, 3, 4, 5, 6, 8, 10, 13, 15, and 16 are locked nucleotides, with the remaining positions being non-locked nucleotides. In still other embodiments, positions 1, 4, 5, 7, 9, 10, 12, 14, and 16 are locked nucleotides, with remaining positions being non-locked nucleotides. These patterns of locked nucleotides may be employed, in certain embodiments, using the nucleotide sequence of SEQ ID NO:3 or SEQ ID NO:4, or variant thereof described herein. Where the inhibitor consists of, or consists essentially of, the nucleotide sequence of SEQ ID NO:3 or SEQ ID NO:4, the oligonucleotide may contain all locked nucleotides.

For non-locked nucleotides, the nucleotide may contain a 2' modification with respect to a 2' hydroxyl. In some embodiments the 2' modification may be independently selected from O-alkyl (which may be substituted), halo, and deoxy (H).

The oligonucleotide may also contain one or more phosphorothioate linkages. For example, the oligonucleotide may be fully phosphorothioate-linked or may contain about half or ¾ phosphorothioate linkages.

Exemplary oligonucleotide inhibitors are shown in Table 1.

In another aspect, the invention provides pharmaceutical compositions and formulations comprising the oligonucleotides of the invention, which may involve incorporation of the oligonucleotide within a variety of macromolecular assemblies, micelle, or liposome compositions for cellular delivery. In certain embodiments, the oligonucleotides are formulated for conventional intravenous, subcutaneous, or intramuscular dosing. Such formulations may be conventional aqueous preparations, such as formulation in saline. In certain embodiments, the compositions are suitable or formulated for intradermal, subcutaneous, intramuscular, intraperitoneal or intravenous injection, or by direct injection into target tissue (e.g., cardiac tissue).

In still other aspects, the invention provides a method for delivering oligonucleotides and the pharmaceutical compositions to mammalian cells either in vitro or ex vivo, e.g., for treating, ameliorating, or preventing the progression of a condition in a mammalian patient. The method may comprise administering the oligonucleotide or composition comprising the same to a mammalian patient or population of target cells. The patient may have a condition associated with, mediated by, or resulting from, miR-208 family expression. Such conditions include, for example, cardiac hypertrophy, myocardial infarction, heart failure (e.g., congestive heart failure), vascular damage, restenosis, or pathologic cardiac fibrosis.

Thus, the invention provides a use of the modified oligonucleotides and compositions of the invention for treating such conditions, and for the preparation of medicaments for such treatments.

Other aspects and embodiments of the invention will be apparent from the following detailed description of the invention.

DESCRIPTION OF THE FIGURES

FIG. 2. miR-208 inhibitor efficacy measured by Dual Luciferase assay for miR-208a. FIG. 2 shows the effect of adding LNAs: 10673 has 9 LNAs of 16 nucleotides (9/16), 10674 has 11/16, 10677 has 13/16, and 10101 and 10591 have 9/16. "208 alone" refers to the luciferase construct alone having the miR-208a recognition site cloned 3' to the renilla luciferase gene. "208+ mimic" includes cotransfection of mir-208a.

FIG. 9. Chart showing placement of Locked Nucleic Acids in the top 10 miR-208 inhibitor designs (SEQ ID NOS:94-99).

FIG. 12 shows Real-time PCR analysis on murine hearts one week after intravenous (i.v.) delivery of increasing doses of antimiR-208a, and demonstrates a dose-dependent reduction in miR-208a levels. n=4 for each dose.

FIG. 13 shows that i.v., intraperitoneal (i.p) or subcutaneous (s.c.) delivery of 25 mg/kg of antimiR-208a (M-10101) induces potent silencing of miR-208a. n=4 for each group.

FIG. 14A shows Real-time PCR analysis demonstrating that antimiR-208a (M-10101) potently reduces cardiac levels of miR-208a up to 6 weeks after injection, which leads to a time-responsive reduction in miR-499. Dosing with both an antimiR against miR-208a and -499 induces an immediate reduction in cardiac levels of both miR-208a and miR-499. FIG. 14B shows (by real-time PCR) that Myh7 is reduced 4 weeks after miR-208a inhibition, while inhibition of miR-208a and miR-499 reduces Myh7 after 2 weeks. FIG. 14C is a Western blot analysis for Myh7 showing reduced Myh7 expression at the indicated time-points following antimiR-208a or antimiR-208a/-499 treatment. Gapdh serves as a loading control. For FIGS. 14A and B, error bars depict SEM. n=4 for each time-point and dose.

FIG. 16A shows Kaplan-Meier survival curves in the Dahl hypertensive rat model, and shows a pronounced decrease in survival in response to a HS diet for both HS/Saline and HS/Control groups, which is significantly improved in response to antimiR-208a (M-10101) treatment. FIG. 16B shows body weight analysis, and indicates that Dahl hypertensive rats on 8% HS diet exhibit reduced weight gain compared to animals on LS diet, while HS/antimiR-208a treated rats show a significantly better maintenance in weight gain. For (a) and (b), n=6 for LS/Saline; n=15 for HS/Saline and HS/Control; and n=14 for HS/antimiR-208a. The "n" on the graph represents total survivors remaining at week 8 post-diet.

FIG. 17B shows echocardiography measurements, indicating that the increase in IVRT and decrease in MV E/A in response to 4% HS diet are significantly improved in response to antimiR-208a treatment 8 weeks after the onset of the diet. IVRT, isovolumic relaxation time; MV E/A, mitral valve early to active filling velocity ratio. n=10 for all groups.

FIG. 18B is a bar-graph representation of histological quantification showing significantly less hypertrophy and fibrosis in the presence of antimiR-208a. Error bars depict SEM, * p<0.05 vs. HS saline, # p<0.05 vs. LS saline.

FIG. 19A shows real-time PCR analysis indicating a dose-dependent reduction of miR-208a in both left ventricle (LV) and right ventricle (RV), which corresponds to a dose-dependent decrease in miR-499. While miR-208b is increased in response to the HS diet, antimiR-208a significantly blunts this response. Administration of a control chemistry (directed against a C. elegans miR) has no effect on the expression of either miR-208a, miR-499 or miR-208b. Error bars depict SEM, * p<0.05 vs. HS saline, # p<0.05 vs. LS saline. FIG. 19B shows that regulation of miR-499 and miR-208b in response to antimiR-208a treatment can be confirmed by Northern blot analysis. U6 serves as a loading control.

FIG. 20B shows a Western blot analysis for Myh7 from ventricular tissue confirms the dose-dependent reduction in response to antimiR-208a treatment. Gapdh is used as a loading control.

FIG. 21 shows real-time PCR analysis on plasma samples, indicating an increase in miR-499 in response to HS diet, while antimiR-208a significantly lowers the detection of miR-499 in plasma 8 weeks following the onset of 4% HS diet and 7 weeks after the onset of antimiR treatment. Further miRNA analysis additionally indicates a decrease in plasma detectable miR-423-5p in response to antimiR-208a.

DETAILED DESCRIPTION OF THE INVENTION

Figure 1:
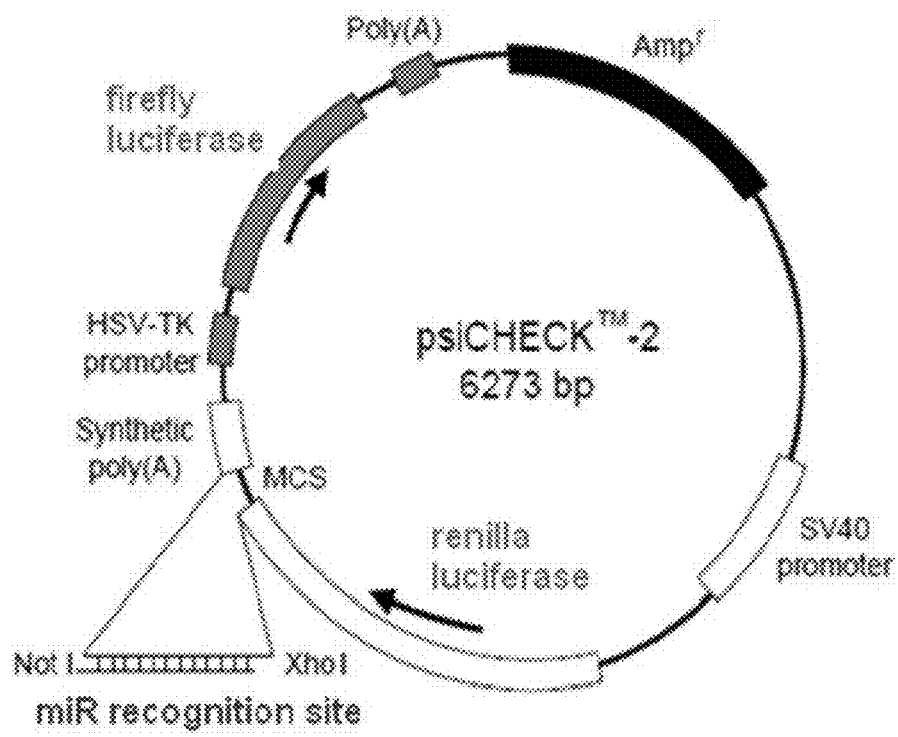
FIG. 1. The psiCHECK™-2 construct (Promega) for quantifying inhibitor activity in vitro using the dual luciferase assay.

The invention provides chemically modified oligonucleotides capable of inhibiting the expression (e.g., abundance) of miR-208 family miRNAs, including miR-208a, miR-208b, and/or miR-499. The invention provides in some embodiments, oligonucleotides capable of inhibiting, in a specific fashion, the expression or abundance of each of miR-208a, miR-208b, and miR-499. The invention further provides pharmaceutical compositions comprising the oligonucleotides, and methods of treating patients having conditions or disorders relating to or involving a miR-208 family miRNA, such as a various cardiovascular conditions. In various embodiments, the oligonucleotides provide advantages in one or more of potency, efficiency of delivery, target specificity, toxicity, and/or stability.

Chemically-Modified miR-208a Antisense Oligonucleotides

In one aspect, the invention provides an oligonucleotide capable of reducing the expression or abundance of miR-208 family miRNAs. The activity of the oligonucleotides may be determined in vitro and/or in vivo. For example, when inhibition of miR-208a, miR-208b, or miR-499 activity is determined in vitro, the activity may be determined using a dual luciferase assay as described herein. The oligonucleotide significantly inhibits such activity, as determined in the dual luciferase activity, at a concentration of about 50 nM or less, or in other embodiments, 40 nM or less, 20 nM or less, or 10 nM or less. For example, the oligonucleotide may have an IC50 for inhibition of miR-208a, miR-208b, and/or miR-499 activity of about 50 nM or less, 40 nM or less, 30 nM or less, or 20 nM or less, as determined in the dual luciferase assay.

The dual luciferase assay, as exemplified by the commercially available product PsiCHECK™ (Promega), involves placement of the miR recognition site in the 3' UTR of a gene for a detectable protein (e.g., renilla luciferase). The construct is co-expressed with the target miRNA, such that inhibitor activity can be determined by change in signal. A second gene encoding a detectable protein (e.g., firefly luciferase) can be included on the same plasmid, and the ratio of signals determined as an indication of antimiR activity.

Alternatively, or in addition, the activity of the oligonucleotide may be determined in a suitable mouse or rat model, such as those described herein, where inhibition (e.g., by at least 50%) of a miR-208 family miRNA is observed at an oligonucleotide dose of 50 mg/kg or less, 25 mg/kg or less, such as 10 mg/kg or less or 5 mg/kg or less. In some embodiments, the activity of the oligonucleotides is determined in an animal model described in WO 2008/016924, which descriptions are hereby incorporated by reference. For example, the oligonucleotide may exhibit at least 50% target miRNA inhibition or target de-repression at a dose of 50 mg/kg or less, 25 mg/kg or less, such as 10 mg/kg or less or 5 mg/kg or less. In such embodiments, the oligonucleotide may be dosed intravenously or subcutaneously to mice, and the oligonucleotide may be formulated in saline.

In these or other embodiments, the oligonucleotides of the invention are stable after administration, being detectable in the circulation and/or target organ for at least three weeks, at least four weeks, at least five weeks, or at least six weeks, or more, following administration. Thus, the oligonucleotides of the invention have the potential to provide for less frequent administration, lower doses, and/or longer duration of therapeutic effect.

The nucleotide sequence of the oligonucleotide is substantially complementary to a nucleotide sequence of human miR-208a and/or miR-208b, and contains a mix of locked and non-locked nucleotides. For example, the oligonucleotide may contain at least five or at least seven or at least nine locked nucleotides, and at least one non-locked nucleotide. Generally, the length of the oligonucleotide and number and position of locked nucleotides is such that the oligonucleotide reduces miR-208a, miR-208b, and/or miR-499 activity at an oligonucleotide concentration of about 50 nM or less in the in vitro luciferase assay, or at a dose of about 50 mg/kg or less, or about 25 mg/kg or less in a suitable mouse or rat model, each as described. A substantially complementary oligonucleotide may have from 1 to 4 mismatches (e.g., 1 or 2 mismatches) with respect to its target sequence of miR-208a or miR-208b.

miR-208a, including its structure and processing, and its potential for treating cardiac hypertrophy, heart failure, or myocardial infarction (among other conditions), are described in WO 2008/016924, which is hereby incorporated by reference in its entirety. The pre-miRNA sequence for human miR-208a, which may be used for designing inhibitory miRNAs in accordance with the invention, is (the underlined sequence is the mature form):

```
                                            (SEQ ID NO: 5)
5'-ACGGGCGAGC UUUUGGCCCG GGUUAUACCU GAUGCUCACG

UAUAAGACGA GCAAAAAGCU UGUUGGUCAG A-3'.
```

The structure and processing of miR-208b and miR-499 are also described in WO 2009/018492, which is hereby incorporated by reference. Mature miR-208b has the nucleotide sequence 5'-AUAAGACGAACAAAAGGUUUGU-3' (SEQ ID NO:6), and mature miR-499 has the nucleotide sequence 5'-UUAAGACUUGCAGUGAUGUUU-3' (SEQ ID NO:7). These sequences may be used to design complementary inhibitors in accordance with the invention.

The oligonucleotide contains one or more locked nucleic acid (LNAs) residues, or "locked nucleotides". LNAs are described, for example, in U.S. Pat. No. 6,268,490, U.S. Pat. No. 6,316,198, U.S. Pat. No. 6,403,566, U.S. Pat. No. 6,770,748, U.S. Pat. No. 6,998,484, U.S. Pat. No. 6,670,461, and U.S. Pat. No. 7,034,133, all of which are hereby incorporated by reference in their entireties. LNAs are modified nucleotides or ribonucleotides that contain an extra bridge between the 2' and 4' carbons of the ribose sugar moiety resulting in a "locked" conformation, and/or bicyclic structure. In one embodiment, the oligonucleotide contains one or more LNAs having the structure shown by structure A below. Alternatively or in addition, the oligonucleotide may contain one or more LNAs having the structure shown by structure B below. Alternatively or in addition, the oligonucleotide contains one or more LNAs having the structure shown by structure C below.

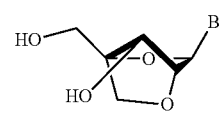

A

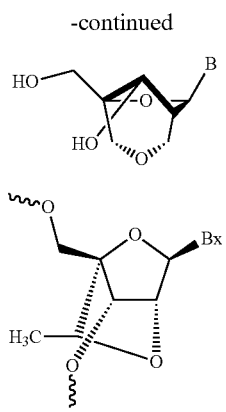

Other suitable locked nucleotides that can be incorporated in the oligonucleotides of the invention include those described in U.S. Pat. No. 6,403,566 and U.S. Pat. No. 6,833,361, both of which are hereby incorporated by reference in their entireties.

In exemplary embodiments, the locked nucleotides have a 2' to 4' methylene bridge, as shown in structure A, for example.

The oligonucleotide may comprise, consist essentially of, or consist of, a full length or truncated miR-208a or miR-208b antisense sequence. As used herein, the term "full length" in reference to a miRNA sequence refers to the length of the mature miRNA antisense counterpart. Thus, the inhibitors described herein may be truncated or full-length, antisense, mature miRNA sequences, or may comprise these sequences in combination with other polynucleotide sequences. In certain embodiments, the chemical modification motif described herein renders full length antisense miRNA (mature) sequences unnecessary. In these embodiments, the oligonucleotide is from 8 to 20 nucleotides in length, or is from 10 to 18 nucleotides in length, or is from 11 to 16 nucleotides in length. The oligonucleotide in some embodiments is about 12, about 13, about 14, about 15, about 16, about 17, or about 18 nucleotides in length. The truncated oligonucleotide may have a sequence that targets, by antisense inhibition, a miR-208a sequence within 5'-UAAGACGAGCAAAAAG-3' (SEQ ID NO:8) or a miR-208b sequence within UAAGAC-GAACAAAAAG-3' (SEQ ID NO:9).

The oligonucleotide generally has a nucleotide sequence designed to target mature miR-208a, miR-208b, and/or miR-499. The oligonucleotide may, in these or other embodiments, also or alternatively be designed to target the pre- or pri-miRNA forms. In certain embodiments, the oligonucleotide may be designed to have a sequence containing from 1 to 5 (e.g., 1, 2, 3, or 4) mismatches relative to the fully complementary (mature) miR-208 sequence. In certain embodiments, such antisense sequences may be incorporated into shRNAs or other RNA structures containing stem and loop portions, for example.

In certain embodiments, the oligonucleotide comprises a nucleotide sequence that is completely complementary to a nucleotide sequence of miR-208a or miR-208b. For example, the oligonucleotide may comprise the nucleotide sequence of 5'-TGCTCGTCTTA-3' (SEQ ID NO:1) or may comprise the nucleotide sequence of 5'-TGTTCGTCTTA-3' (SEQ ID NO:2). In particular embodiments, the oligonucleotide comprises, consists essentially of, or consists of the nucleotide sequence 5'-CTTTTTGCTCGTCTTA-3' (SEQ ID NO:3) or '5-CCTTTTGTTCGTCTTA (SEQ ID NO:4). In this context, "consists essentially of" includes the optional addition of nucleotides (e.g., one or two) on either or both of the 5' and 3' ends, so long as the additional nucleotide(s) do not substantially affect (as defined by an increase in IC50 of no more than 20%) the oligonucleotide's inhibition of the target miRNA activity in the dual luciferase assay or mouse model.

The oligonucleotide generally contains at least 3, at least 5, at least 7, or at least 9 locked nucleotides, but in various embodiments is not fully comprised of locked nucleotides. Generally, the number and position of locked nucleotides is such that the oligonucleotide reduces miR-208a, miR-208b, and/or miR-499 activity as determined in vitro or in vivo as described. In certain embodiments, the oligonucleotide does not contain a stretch of nucleotides with more than four, or more than three, contiguous non-locked nucleotides. In certain embodiments, the oligonucleotide does not contain a stretch of nucleotides with more than two contiguous non-locked nucleotides. For example, the oligonucleotide may have just one occurrence of contiguous non-locked nucleotides. In these or other embodiments, the region complementary to the miR-208a, miR-208b, and/or miR-499 seed region comprises at least three or at least four locked nucleotides. These embodiments may, for example, employ a nucleotide sequence of SEQ ID NO:3 or SEQ ID NO:4.

Thus, in various embodiments, the oligonucleotide contains at least nine locked nucleotides, or at least eleven locked nucleotides. The oligonucleotide may contain at least three or at least 5 non-locked nucleotides. For example, the oligonucleotide may contain nine locked nucleotides and seven non-locked nucleotides, or may contain eleven locked nucleotides and five non-locked nucleotides.

The pattern of locked nucleotides may be such that at least positions 1, 6, 10, 13, and 15 are locked nucleotides. In certain embodiments, positions 1, 5, 6, 8, 10, 11, 13, 15, and 16 are locked nucleotides, and the remaining positions are non-locked nucleotides. In other embodiments, positions 1, 3, 4, 5, 6, 8, 10, 13, 15, and 16 are locked nucleotides, with the remaining positions being non-locked nucleotides. In some embodiments, positions 1, 4, 5, 7, 9, 10, 12, 14, and 16 are locked nucleotides, and remaining positions are non-locked nucleotides. In exemplary embodiments, such patterns find use with an oligonucleotide having the sequence of SEQ ID NO:3 or SEQ ID NO:4.

For non-locked nucleotides, the nucleotide may contain a 2' modification with respect to a 2' hydroxyl. For example, the 2' modification may be 2' deoxy. Incorporation of 2'-modified nucleotides in antisense oligonucleotides may increase both resistance of the oligonucleotides to nucleases and their thermal stability with complementary RNA. Various modifications at the 2' positions may be independently selected from those that provide increased nuclease sensitivity, without compromising molecular interactions with the RNA target or cellular machinery. Such modifications may be selected on the basis of their increased potency in vitro or in vivo. Exemplary methods for determining increased potency (e.g., IC50) for miRNA inhibition are described herein, including the dual luciferase assay and in vivo miRNA expression or target de-repression.

In some embodiments the 2' modification may be independently selected from O-alkyl (which may be substituted), halo, and deoxy (H). Substantially all, or all, nucleotide 2' positions of the non-locked nucleotides may be modified in certain embodiments, e.g., as independently selected from O-alkyl (e.g., O-methyl), halo (e.g., fluoro), deoxy (H), and amino. For example, the 2' modifications may each be independently selected from O-methyl and fluoro. In exemplary embodiments, purine nucleotides each have a 2' OMe and pyrimidine nucleotides each have a 2'-F. In certain embodiments, from one to about five 2' positions, or from about one to about three 2' positions are left unmodified (e.g., as 2' hydroxyls).

2' modifications in accordance with the invention also include small hydrocarbon substituents. The hydrocarbon substituents include alkyl, alkenyl, alkynyl, and alkoxyalkyl, where the alkyl (including the alkyl portion of alkoxy), alkenyl and alkynyl may be substituted or unsubstituted. The alkyl, alkenyl, and alkynyl may be C1 to C10 alkyl, alkenyl or alkynyl, such as C1, C2, or C3. The hydrocarbon substituents may include one or two or three non-carbon atoms, which may be independently selected from N, O, and/or S. The 2' modifications may further include the alkyl, alkenyl, and alkynyl as O-alkyl, O-alkenyl, and O-alkynyl.

Exemplary 2' modifications in accordance with the invention include 2'-O-alkyl (C1-3 alkyl, such as 2'OMe or 2'OEt), 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-NMA) substitutions.

In certain embodiments, the oligonucleotide contains at least one 2'-halo modification (e.g., in place of a 2' hydroxyl), such as 2'-fluoro, 2'-chloro, 2'-bromo, and 2'-iodo. In some embodiments, the 2' halo modification is fluoro. The oligonucleotide may contain from 1 to about 5 2'-halo modifications (e.g., fluoro), or from 1 to about 3 2'-halo modifications (e.g., fluoro). In some embodiments, the oligonucleotide contains all 2'-fluoro nucleotides at non-locked positions, or 2'-fluoro on all non-locked pyrimidine nucleotides. In certain embodiments, the 2'-fluoro groups are independently di-, tri-, or un-methylated.

The oligonucleotide may have one or more 2'-deoxy modifications (e.g., H for 2' hydroxyl), and in some embodiments, contains from 2 to about 10 2'-deoxy modifications at non-locked positions, or contains 2' deoxy at all non-locked positions.

In exemplary embodiments, the oligonucleotide contains 2' positions modified as 2'OMe in non-locked positions. Alternatively, non-locked purine nucleotides are modified at the 2' position as 2'OMe, with non-locked pyrimidine nucleotides modified at the 2' position as 2'-fluoro.

In certain embodiments, the oligonucleotide further comprises at least one terminal modification or "cap". The cap may be a 5' and/or a 3'-cap structure. The terms "cap" or "end-cap" include chemical modifications at either terminus of the oligonucleotide (with respect to terminal ribonucleotides), and including modifications at the linkage between the last two nucleotides on the 5' end and the last two nucleotides on the 3' end. The cap structure as described herein may increase resistance of the oligonucleotide to exonucleases without compromising molecular interactions with the RNA target or cellular machinery. Such modifications may be selected on the basis of their increased potency in vitro or in vivo. The cap can be present at the 5'-terminus (5'-cap) or at the 3'-terminus (3'-cap) or can be present on both ends. In certain embodiments, the 5'- and/or 3'-cap is independently selected from phosphorothioate monophosphate, abasic residue (moiety), phosphorothioate linkage, 4'-thio nucleotide, carbocyclic nucleotide, phosphorodithioate linkage, inverted nucleotide or inverted abasic moiety (2'-3' or 3'-3'), phosphorodithioate monophosphate, and methylphosphonate moiety. The phosphorothioate or phosphorodithioate linkage(s), when part of a cap structure, are generally positioned between the two terminal nucleotides on the 5' end and the two terminal nucleotides on the 3' end.

In certain embodiments, the oligonucleotide has at least one terminal phosphorothioate monophosphate. The phosphorothioate monophosphate may support a higher potency by inhibiting the action of exonucleases. The phosphorothioate monophosphate may be at the 5' and/or 3' end of the oligonucleotide. A phosphorothioate monophosphate is defined by the following structures, where B is base, and R is a 2' modification as described above:

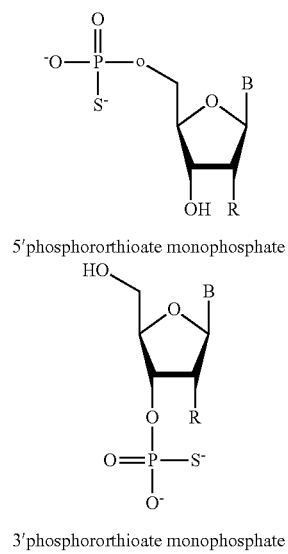

5'phosphorothioate monophosphate

3'phosphorothioate monophosphate

Where the cap structure can support the chemistry of a locked nucleotide, the cap structure may incorporate a locked nucleotide as described herein.

Phosphorothioate linkages may be present in some embodiments, such as between the last two nucleotides on the 5' and the 3' end (e.g., as part of a cap structure), or as alternating with phosphodiester bonds. In these or other embodiments, the oligonucleotide may contain at least one terminal abasic residue at either or both the 5' and 3' ends. An abasic moiety does not contain a commonly recognized purine or pyrimidine nucleotide base, such as adenosine, guanine, cytosine, uracil or thymine. Thus, such abasic moieties lack a nucleotide base or have other non-nucleotide base chemical groups at the 1' position. For example, the abasic nucleotide may be a reverse abasic nucleotide, e.g., where a reverse abasic phosphoramidite is coupled via a 5' amidite (instead of 3' amidite) resulting in a 5'-5' phosphate bond. The structure of a reverse abasic nucleoside for the 5' and the 3' end of a polynucleotide is shown below.

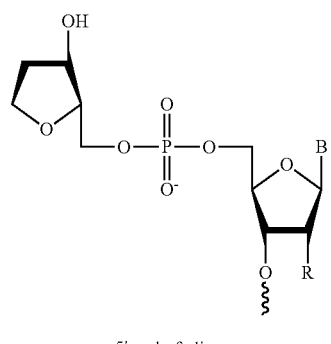

5' end of oligo

-continued

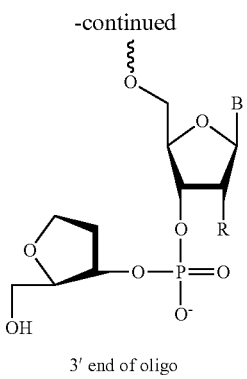

3' end of oligo

The oligonucleotide may contain one or more phosphorothioate linkages. Phosphorothioate linkages have been used to render oligonucleotides more resistant to nuclease cleavage. For example, the polynucleotide may be partially phosphorothioate-linked, for example, phosphorothioate linkages may alternate with phosphodiester linkages. In certain embodiments, however, the oligonucleotide is fully phosphorothioate-linked. In other embodiments, the oligonucleotide has from one to five or one to three phosphate linkages.

In some embodiments, the nucleotide has one or more carboxamido-modified bases as described in PCT/US11/59588, which is hereby incorporated by reference, including with respect to all exemplary pyrimidine carboxamido modifications disclosed therein with heterocyclic substituents.

In exemplary embodiments, the oligonucleotide has the structure of a Compound listed in Table 1, below.

TABLE 1

Exemplary Oligonucleotides

| Cmpd# (M) | Alias | Sequence | | Length |
|---|---|---|---|---|
| 10101 | 208a_DNA_LNA_16_PS | 5' lCs; dTs; dTs; dTs; lTs; lTs; dGs; lCs; dTs; lCs; lGs; dTs; lCs; dTs; lTs; lA (SEQ ID NO: 10) | 3' | 16 |
| 10570 | 208fam optdes1 | 5' lTs; dGs; lCs; lTs; lCs; dGs; lTs; lCs; dTs; lTs; lA (SEQ ID NO: 11) | 3' | 11 |
| 10571 | 208fam optdes2 | 5' lTs; dGs; lCs; lTs; lCs; dGs; dTs; lCs; dTs; lTs; lA (SEQ ID NO: 12) | 3' | 11 |
| 10572 | 208fam optdes3 | 5' lTs; dGs; lCs; dAs; lCs; dGs; lTs; dCs; lTs; lTs; lA (SEQ ID NO: 13) | 3' | 11 |
| 10573 | 208fam optdes4 | 5' lTs; lGs; dCs; dAs; lCs; lGs; dTs; lCs; dTs; lTs; lA (SEQ ID NO: 14) | 3' | 11 |
| 10673 | 208a LNA C T DNA 16 1 | 5' lCs; dTs; lTs; lTs; lTs; lTs; dGs; lCs; dTs; lCs; dGs; dTs; lCs; dTs; lTs; dA (SEQ ID NO: 15) | 3' | 16 |
| 10674 | 208a_LNA C T DNA 16 2 | 5' lCs; dTs; dTs; lTs; lTs; lTs; dGs; lCs; lTs; lCs; dGs; lTs; lCs; lTs; lTs; dA (SEQ ID NO: 16) | 3' | 16 |
| 10677 | 208a_LNA C T DNA 16 3 | 5' lCs; lTs; lTs; lTs; lTs; lTs; dGs; lCs; lTs; lCs; dGs; lTs; lCs; lTs; lTs; dA (SEQ ID NO: 17) | 3' | 16 |
| 10679 | 208 LNA opt 1 | 5' lCs; dTs; lTs; dTs; lTs; lTs; dGs; lCs; dTs; lCs; dGs; lTs; dCs; lTs; lTs; dA (SEQ ID NO: 18) | 3' | 16 |
| 10680 | 208 LNA opt 2 | 5' lCs; dTs; lTs; lTs; lTs; lTs; dGs; lCs; dTs; lCs; dGs; dTs; lCs; dTs; dTs; lA (SEQ ID NO: 19) | 3' | 16 |
| 10681 | 208 LNA opt 3 | 5' lCs; dTs; lTs; lTs; dTs; lTs; dGs; lCs; lTs; lCs; dGs; dTs; lCs; dTs; lTs; dA (SEQ ID NO: 20) | 3' | 16 |
| 10682 | 208 LNA opt 4 | 5' lCs; dTs; lTs; dTs; lTs; dTs; lGs; dCs; lTs; dCs; lGs; dTs; lCs; dTs; lTs; lA (SEQ ID NO: 21) | 3' | 16 |
| 10683 | 208 LNA opt 5 | 5' lCs; dTs; dTs; lTs; lTs; dTs; lGs; dCs; lTs; lCs; dGs; lTs; dCs; lTs; dTs; lA (SEQ ID NO: 22) | 3' | 16 |
| 10707 | 208b_DNA_LNA_16_PS | 5' lCs; dGs; dTs; dTs; lTs; lTs; dGs; lTs; dTs; lCs; lGs; dTs; lCs; dTs; lTs; lA (SEQ ID NO: 23) | 3' | 16 |
| 10718 | 208a like 15 1 | 5' lTs; lTs; lTs; lTs; lTs; dGs; lCs; dTs; lCs; dGs; dTs; lCs; dTs; lTs; dA (SEQ ID NO: 24) | 3' | 15 |
| 10719 | 208a like 15 2 | 5' lTs; lTs; dTs; lTs; lTs; dGs; lCs; dTs; lCs; dGs; dTs; lCs; dTs; lTs; dA (SEQ ID NO: 25) | 3' | 15 |
| 10720 | 208a like 15 3 | 5' lTs; lTs; lTs; lTs; lTs; dGs; dCs; dTs; lCs; dGs; lTs; lCs; dTs; lTs; dA (SEQ ID NO: 26) | 3' | 15 |
| 10721 | 208a like 15 4 | 5' lTs; dTs; lTs; lTs; lTs; dGs; lCs; dTs; lCs; dGs; dTs; lCs; lTs; lTs; dA (SEQ ID NO: 27) | 3' | 15 |
| 10722 | 208a like_15_5 | 5' lTs; lTs; lTs; lTs; lTs; dGs; lCs; dTs; lCs; dGs; dTs; lCs; lTs; lTs; lA (SEQ ID NO: 28) | 3' | 15 |
| 10723 | 208a like 15 6 | 5' lTs; dTs; lTs; lTs; lTs; dGs; lCs; dTs; lCs; dGs; dTs; lCs; lTs; lTs; lA (SEQ ID NO: 29) | 3' | 15 |
| 10724 | 208b like 15 1 | 5' lCs; lTs; lTs; lTs; lTs; dGs; lCs; dTs; lCs; dGs; dTs; lCs; dTs; lTs; dA (SEQ ID NO: 30) | 3' | 15 |
| 10725 | 208b like 15 2 | 5' lCs; dTs; lTs; lTs; lTs; dGs; lCs; dTs; lCs; dGs; dTs; lCs; dTs; lTs; dA (SEQ ID NO: 31) | 3' | 15 |
| 10726 | 208b like 15 3 | 5' lCs; dTs; lTs; lTs; lTs; dGs; lCs; dTs; lCs; dGs; dTs; lCs; lTs; lTs; dA (SEQ ID NO: 32) | 3' | 15 |
| 10727 | 208b like 15 4 | 5' lCs; lTs; lTs; lTs; lTs; dGs; lCs; dTs; lCs; dGs; dTs; lCs; dTs; lTs; lA (SEQ ID NO: 33) | 3' | 15 |
| 10728 | 208b like 15 5 | 5' lCs; dTs; lTs; lTs; lTs; dGs; lCs; dTs; lCs; dGs; dTs; lCs; dTs; lTs; lA (SEQ ID NO: 34) | 3' | 15 |
| 10729 | 208b like 15 6 | 5' lCs; lTs; lTs; lTs; lTs; dGs; dCs; dTs; lCs; dGs; lTs; lCs; dTs; lTs; dA (SEQ ID NO: 35) | 3' | 15 |
| 10730 | 208b 15 1 | 5' lCs; lTs; lTs; lTs; dGs; lTs; dTs; lCs; dGs; dTs; lCs; dTs; lTs; dA (SEQ ID NO: 36) | 3' | 15 |

TABLE 1-continued

Exemplary Oligonucleotides

| Cmpd# (M) | Alias | Sequence | | Length |
|---|---|---|---|---|
| 10731 | 208b 15 2 | 5' lCs; lTs; lTs; lTs; lTs; dGs; lTs; dTs; lCs; dGs; dTs; lCs; dTs; lTs; lA (SEQ ID NO: 37) | 3' | 15 |
| 10732 | 208b 15 3 | 5' lCs; lTs; lTs; lTs; lTs; dGs; lTs; dTs; lCs; dGs; lTs; lCs; dTs; lTs; dA (SEQ ID NO: 38) | 3' | 15 |
| 10733 | 208a like 15 7 | 5' lTs; dTs; lTs; dTs; lTs; dGs; dCs; dTs; lCs; lGs; lTs; lCs; lTs; lTs; lA (SEQ ID NO: 39) | 3' | 15 |
| 10734 | 208b like 15 7 | 5' lCs; lTs; lTs; lTs; lTs; dGs; dCs; dTs; lCs; lGs; lTs; lCs; lTs; lTs; lA (SEQ ID NO: 40) | 3' | 15 |
| 10735 | 208b 15 4 | 5' lCs; dTs; dTs; lTs; dGs; dTs; dTs; lCs; lGs; lTs; lCs; lTs; lTs; lA (SEQ ID NO: 41) | 3' | 15 |
| 10736 | 208a like 14 1 | 5' lTs; lTs; lTs; lTs; dGs; lCs; dTs; lCs; dGs; dTs; lCs; dTs; lTs; dA (SEQ ID NO: 42) | 3' | 14 |
| 10737 | 208a like 14 2 | 5' lTs; lTs; lTs; lTs; dGs; lCs; dTs; lCs; dGs; dTs; lCs; dTs; lTs; lA (SEQ ID NO: 43) | 3' | 14 |
| 10738 | 208a like 14 3 | 5' lTs; lTs; lTs; lTs; dGs; dCs; dTs; lCs; dGs; dTs; lCs; dTs; lTs; lA (SEQ ID NO: 44) | 3' | 14 |
| 10739 | 208a like 14 4 | 5' lTs; lTs; lTs; lTs; dGs; dCs; dTs; lCs; dGs; dTs; lCs; dTs; lTs; lA (SEQ ID NO: 45) | 3' | 14 |
| 10740 | 208a like 14 5 | 5' lTs; lTs; lTs; lTs; dGs; dCs; lTs; lCs; dGs; dCs; lTs; lTs; dA (SEQ ID NO: 46) | 3' | 14 |
| 10741 | 208a like 14 6 | 5' lTs; dTs; lTs; dTs; dGs; lCs; dTs; lCs; lGs; lTs; lCs; lTs; lTs; lA (SEQ ID NO: 47) | 3' | 14 |
| 10742 | 208b 14 1 | 5' lTs; lTs; lTs; lTs; dGs; lTs; dTs; lCs; dGs; dTs; lCs; dTs; lTs; dA (SEQ ID NO: 48) | 3' | 14 |
| 10743 | 208b 14 2 | 5' lTs; lTs; lTs; lTs; dGs; lTs; dTs; lCs; dGs; dTs; lCs; dTs; lTs; lA (SEQ ID NO: 49) | 3' | 14 |
| 10744 | 208b 14 3 | 5' lTs; lTs; lTs; lTs; dGs; dTs; lTs; lCs; dGs; dTs; lCs; dTs; lTs; lA (SEQ ID NO: 50) | 3' | 14 |
| 10745 | 208b 14 4 | 5' lTs; lTs; lTs; lTs; dGs; dTs; dTs; lCs; dGs; dTs; lCs; dTs; lTs; lA (SEQ ID NO: 51) | 3' | 14 |
| 10746 | 208b 14 5 | 5' lTs; lTs; lTs; lTs; dGs; dTs; lTs; lCs; dGs; lTs; dCs; lTs; lTs; dA (SEQ ID NO: 52) | 3' | 14 |
| 10747 | 208b 14 6 | 5' lTs; dTs; lTs; dTs; dGs; lTs; dTs; lCs; lGs; lTs; lCs; lTs; lTs; lA (SEQ ID NO: 53) | 3' | 14 |
| 10748 | 208a like 13 1 | 5' lTs; lTs; lTs; dGs; lCs; dTs; lCs; dGs; dTs; lCs; dTs; lTs; dA (SEQ ID NO: 54) | 3' | 13 |
| 10749 | 208a like 13 2 | 5' lTs; lTs; lTs; dGs; lCs; dTs; lTs; dGs; dTs; lCs; dTs; lTs; lA (SEQ ID NO: 55) | 3' | 13 |
| 10750 | 208a like 13 3 | 5' lTs; lTs; lTs; dGs; lCs; dTs; lCs; lGs; lTs; lCs; lTs; lTs; lA (SEQ ID NO: 56) | 3' | 13 |
| 10751 | 208a like 13 4 | 5' lTs; dTs; lTs; dGs; lCs; dTs; lCs; lGs; lTs; lCs; lTs; lTs; lA (SEQ ID NO: 57) | 3' | 13 |
| 10752 | 208b 13 1 | 5' lTs; lTs; lTs; dGs; lTs; dTs; lCs; dGs; dTs; lCs; dTs; lTs; dA (SEQ ID NO: 58) | 3' | 13 |
| 10753 | 208b 13 2 | 5' lTs; lTs; lTs; dGs; lTs; dTs; lCs; dGs; dTs; lCs; dTs; lTs; lA (SEQ ID NO: 59) | 3' | 13 |
| 10754 | 208b 13 3 | 5' lTs; lTs; lTs; dGs; lTs; dTs; lCs; lGs; lTs; lCs; lTs; lTs; lA (SEQ ID NO: 60) | 3' | 13 |
| 10755 | 208b 13 4 | 5' lTs; dTs; lTs; dGs; lTs; dTs; lCs; lGs; lTs; lCs; lTs; lTs; lA (SEQ ID NO: 61) | 3' | 13 |
| 10756 | 208a like 11 1 | 5' lTs; dGs; lCs; dTs; lCs; dGs; dTs; lCs; dTs; lTs; dA (SEQ ID NO: 62) | 3' | 11 |
| 10757 | 208a like 11 2 | 5' lTs; dGs; lCs; dTs; lCs; dGs; dTs; lCs; dTs; lTs; lA (SEQ ID NO: 63) | 3' | 11 |
| 10758 | 208b_11_1 | 5' lTs; dGs; lTs; dTs; lCs; dGs; dTs; lCs; dTs; lTs; dA (SEQ ID NO: 64) | 3' | 11 |
| 10759 | 208b 11 2 | 5' lTs; dGs; lTs; dTs; lCs; dGs; dTs; lCs; dTs; lTs; lA (SEQ ID NO: 65) | 3' | 11 |
| 10760 | 208b 16 1 | 5' lCs; dCs; lTs; lTs; lTs; dGs; lTs; dTs; lCs; dGs; dTs; lCs; dTs; lTs; dA (SEQ ID NO: 66) | 3' | 16 |
| 10761 | 208b 16 2 | 5' lCs; dCs; lTs; lTs; lTs; dGs; lTs; dTs; dGs; lTs; dCs; lTs; lTs; dA (SEQ ID NO: 67) | 3' | 16 |
| 10762 | 208b 16 3 | 5' lCs; dCs; lTs; lTs; lTs; dGs; lTs; dTs; dGs; dTs; lCs; dTs; dTs; lA (SEQ ID NO: 68) | 3' | 16 |
| 10763 | 208b like 16 1 | 5' lCs; dCs; lTs; lTs; lTs; dGs; lCs; dTs; lCs; dGs; dTs; lCs; dTs; lTs; dA (SEQ ID NO: 69) | 3' | 16 |
| 10764 | 208b like 16 2 | 5' lCs; dCs; lTs; lTs; lTs; dGs; lCs; dTs; lCs; dGs; lTs; dCs; lTs; lTs; dA (SEQ ID NO: 70) | 3' | 16 |
| 10765 | 208b like 16 3 | 5' lCs; dCs; lTs; lTs; lTs; dGs; lCs; dTs; lCs; dGs; dTs; lCs; dTs; dTs; lA (SEQ ID NO: 71) | 3' | 16 |
| 10775 | 208b 15 5 | 5' lTs; lTs; lTs; lTs; dGs; lTs; dTs; lCs; dGs; dTs; lCs; dTs; lTs; dAs; lT (SEQ ID NO: 72) | 3' | 15 |
| 10776 | 208b 15 6 | 5' lTs; lTs; lTs; lTs; dGs; lTs; dTs; lCs; dGs; dTs; lCs; dTs; lTs; lAs; lT (SEQ ID NO: 73) | 3' | 15 |

TABLE 1-continued

Exemplary Oligonucleotides

| Cmpd# (M) | Alias | Sequence | | Length |
|---|---|---|---|---|
| 10777 | 208b 15 7 | 5' lTs; lTs; lTs; lTs; dGs; lTs; dTs; lCs; dGs; lTs; lCs; dTs; lTs; dAs; lT (SEQ ID NO: 74) | 3' | 15 |
| 10778 | 208b 15 8 | 5' lTs; lTs; dTs; lTs; dGs; dTs; dTs; lCs; lGs; lTs; lCs; lTs; lTs; lAs; lT (SEQ ID NO: 75) | 3' | 15 |
| 10779 | 208b 15 9 | 5' lTs; lTs; lTs; lTs; dGs; lTs; dTs; lCs; dGs; dTs; lCs; dTs; lTs; lAs; dT (SEQ ID NO: 76) | 3' | 15 |
| 10780 | 208b 15 10 | 5' lTs; lTs; lTs; lTs; dGs; lTs; dTs; lCs; dGs; lTs; lCs; dTs; lTs; lAs; dT (SEQ ID NO: 77) | 3' | 15 |
| 10781 | 208b 15 11 | 5' lTs; lTs; dTs; lTs; dGs; lTs; dTs; lCs; lGs; lTs; lCs; lTs; lTs; lAs; dT (SEQ ID NO: 78) | 3' | 15 |
| 10782 | 208b 15 12 | 5' lTs; lTs; lTs; lTs; dGs; dTs; dTs; lCs; dGs; dTs; lCs; lTs; lTs; dAs; lT (SEQ ID NO: 79) | 3' | 15 |
| 10783 | 208b_15_13 | 5' lTs; lTs; lTs; lTs; dGs; dTs; dTs; lCs; dGs; dTs; lCs; lTs; lTs; lAs; dT (SEQ ID NO: 80) | 3' | 15 |
| 10784 | 208b 14 7 | 5' lTs; lTs; lTs; dGs; lTs; dTs; lCs; dGs; dTs; lCs; dTs; lTs; dAs; lT (SEQ ID NO: 81) | 3' | 14 |
| 10785 | 208b 14 8 | 5' lTs; lTs; lTs; dGs; lTs; dTs; lCs; dGs; dTs; lCs; dTs; lTs; lAs; lT (SEQ ID NO: 82) | 3' | 14 |
| 10786 | 208b 14 9 | 5' lTs; lTs; lTs; dGs; lTs; dTs; lCs; dGs; lTs; lCs; dTs; lTs; dAs; lT (SEQ ID NO: 83) | 3' | 14 |
| 10787 | 208b 14 10 | 5' lTs; dTs; lTs; dGs; dTs; dTs; lCs; lGs; lTs; lCs; lTs; lTs; lAs; lT (SEQ ID NO: 84) | 3' | 14 |
| 10788 | 208b 14 11 | 5' lTs; lTs; lTs; dGs; lTs; dTs; lCs; dGs; dTs; lCs; dTs; lTs; lAs; dT (SEQ ID NO: 85) | 3' | 14 |
| 10789 | 208b 14 12 | 5' lTs; lTs; lTs; dGs; lTs; dTs; lCs; dGs; lTs; lCs; dTs; lTs; lAs; dT (SEQ ID NO: 86) | 3' | 14 |
| 10790 | 208b 14 13 | 5' lTs; dTs; lTs; dGs; lTs; dTs; lCs; lGs; lTs; lCs; lTs; lTs; lAs; dT (SEQ ID NO: 87) | 3' | 14 |
| 10791 | 208b 14 14 | 5' lTs; lTs; lTs; dGs; dTs; dTs; lCs; dGs; dTs; lCs; lTs; lTs; dAs; lT (SEQ ID NO: 88) | 3' | 14 |
| 10792 | 208b 14 15 | 5' lTs; lTs; lTs; dGs; dTs; dTs; lCs; dGs; dTs; lCs; lTs; lTs; lAs; dT (SEQ ID NO: 89) | 3' | 14 |
| 10793 | 208b 16 4 | 5' lCs; dTs; lTs; lTs; lTs; lGs; dTs; lTs; dCs; lGs; dTs; dCs; lTs; dTs; lAs; dT (SEQ ID NO: 90) | 3' | 16 |
| 11184 | | 5' lCs; dTs; lTs; lTs; dTs; dTs; lGs; lCs; dTs; lCs; dGs; lTs; dCs; lTs; dTs; lAs (SEQ ID NO: 91) | 3' | 16 |

TABLE 2

Description of Notations

| | |
|---|---|
| deoxy A | dA |
| deoxy G | dG |
| deoxy C | dC |
| deoxy T | dT |
| lna A | lA |
| lnaG | lG |
| lna C | lC |
| lna T | lT |
| deoxy A P═S | dAs |
| deoxy G P═S | dGs |
| deoxy C P═S | dCs |
| deoxy T P═S | dTs |
| lna A P═S | lAs |
| lnaG P═S | lGs |
| lna C P═S | lCs |
| lna T P═S | lTs |

In particular embodiments, the oligonucleotide is 10101, 10673, 10674, 10677, 10679, 10683, 10707, or 10680, or other oligonucleotide described in Table 1.

The synthesis of oligonucleotides, including modified polynucleotides, by solid phase synthesis is well known and is reviewed in *New Chemical Methods for Synthesizing Polynucleotides*. Caruthers M H, Beaucage S L, Efcavitch J W, Fisher E F, Matteucci M D, Stabinsky Y. Nucleic Acids Symp. Ser. 1980; (7):215-23.

Compositions, Formulations, and Delivery

The oligonucleotide may be incorporated within a variety of macromolecular assemblies or compositions. Such complexes for delivery may include a variety of liposomes, nanoparticles, and micelles, formulated for delivery to a patient. The complexes may include one or more fusogenic or lipophilic molecules to initiate cellular membrane penetration. Such molecules are described, for example, in U.S. Pat. No. 7,404,969 and U.S. Pat. No. 7,202,227, which are hereby incorporated by reference in their entireties. Alternatively, the oligonucleotide may further comprise a pendant lipophilic group to aid cellular delivery, such as those described in WO 2010/129672, which is hereby incorporated by reference.

The composition or formulation may employ a plurality of therapeutic oligonucleotides, including at least one described herein. For example, the composition or formulation may employ at least 2, 3, 4, or 5 miRNA inhibitors described herein.

The oligonucleotides of the invention may be formulated as a variety of pharmaceutical compositions. Pharmaceutical compositions will be prepared in a form appropriate for the intended application. Generally, this will entail preparing compositions that are essentially free of pyrogens, as well as other impurities that could be harmful to humans or animals. Exemplary delivery/formulation systems include colloidal dispersion systems, macromolecule complexes, nanocapsules, microspheres, beads, and lipid-based systems including oil-in-water emulsions, micelles, mixed micelles, and liposomes. Commercially available fat emulsions that are suitable for delivering the nucleic acids of the invention to cardiac and skeletal muscle tissues include Intralipid®, Liposyn®, Liposyn® II, Liposyn® III, Nutrilipid, and other similar lipid emulsions. A preferred colloidal system for use as a delivery vehicle in vivo is a liposome (i.e., an artificial membrane vesicle). The preparation and use of such systems is well known in the art. Exemplary formulations are also disclosed in U.S. Pat. No. 5,981,505; U.S. Pat. No. 6,217,900; U.S. Pat. No. 6,383,512; U.S. Pat. No. 5,783,565; U.S. Pat. No. 7,202,227; U.S. Pat. No. 6,379,965; U.S. Pat. No. 6,127,170; U.S. Pat. No. 5,837,533; U.S. Pat. No. 6,747,014; and WO03/093449, which are hereby incorporated by reference in their entireties.

In some embodiments, the oligonucleotide is formulated for conventional subcutaneous or intravenous administration, for example, by formulating with appropriate aqueous diluent, including sterile water and normal saline.

The pharmaceutical compositions and formulations may employ appropriate salts and buffers to render delivery vehicles stable and allow for uptake by target cells. Aqueous compositions of the present invention comprise an effective amount of the delivery vehicle comprising the inhibitor oligonucleotide (e.g. liposomes or other complexes), dissolved or dispersed in a pharmaceutically acceptable carrier or aqueous medium. The phrases "pharmaceutically acceptable" or "pharmacologically acceptable" refers to molecular entities and compositions that do not produce adverse, allergic, or other untoward reactions when administered to an animal or a human. As used herein, "pharmaceutically acceptable carrier" may include one or more solvents, buffers, solutions, dispersion media, coatings, antibacterial and antifungal agents, isotonic and absorption delaying agents and the like acceptable for use in formulating pharmaceuticals, such as pharmaceuticals suitable for administration to humans. The use of such media and agents for pharmaceutically active substances is well known in the art. Supplementary active ingredients also can be incorporated into the compositions.

Administration or delivery of the pharmaceutical compositions according to the present invention may be via any route so long as the target tissue is available via that route. For example, administration may be by intradermal, subcutaneous, intramuscular, intraperitoneal or intravenous injection, or by direct injection into target tissue (e.g., cardiac tissue). The stability and/or potency of the oligonucleotides disclosed herein allows for convenient routes of administration, including subcutaneous, intradermal, and intramuscular. Pharmaceutical compositions comprising miRNA inhibitors may also be administered by catheter systems or systems that isolate coronary circulation for delivering therapeutic agents to the heart. Various catheter systems for delivering therapeutic agents to the heart and coronary vasculature are known in the art. Some non-limiting examples of catheter-based delivery methods or coronary isolation methods suitable for use in the present invention are disclosed in U.S. Pat. No. 6,416,510; U.S. Pat. No. 6,716,196; U.S. Pat. No. 6,953,466, WO 2005/082440, WO 2006/089340, U.S. Patent Publication No. 2007/0203445, U.S. Patent Publication No. 2006/0148742, and U.S. Patent Publication No. 2007/0060907, which are all hereby incorporated by reference in their entireties.

The compositions or formulations may also be administered parenterally or intraperitoneally. By way of illustration, solutions of the conjugates as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations generally contain a preservative to prevent the growth of microorganisms.

The pharmaceutical forms suitable for injectable use or catheter delivery include, for example, sterile aqueous solutions or dispersions and sterile powders for the extemporaneous preparation of sterile injectable solutions or dispersions. Generally, these preparations are sterile and fluid to the extent that easy injectability exists. Preparations should be stable under the conditions of manufacture and storage and should be preserved against the contaminating action of microorganisms, such as bacteria and fungi. Appropriate solvents or dispersion media may contain, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial an antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions may be prepared by incorporating the conjugates in an appropriate amount into a solvent along with any other ingredients (for example as enumerated above) as desired. Generally, dispersions are prepared by incorporating the various sterilized active ingredients into a sterile vehicle which contains the basic dispersion medium and the desired other ingredients, e.g., as enumerated above. In the case of sterile powders for the preparation of sterile injectable solutions, the preferred methods of preparation include vacuum-drying and freeze-drying techniques which yield a powder of the active ingredient(s) plus any additional desired ingredient from a previously sterile-filtered solution thereof.

Upon formulation, solutions are preferably administered in a manner compatible with the dosage formulation and in such amount as is therapeutically effective. The formulations may easily be administered in a variety of dosage forms such as injectable solutions, drug release capsules and the like. For parenteral administration in an aqueous solution, for example, the solution generally is suitably buffered and the liquid diluent first rendered isotonic for example with sufficient saline or glucose. Such aqueous solutions may be used, for example, for intravenous, intramuscular, subcutaneous and intraperitoneal administration. Preferably, sterile aqueous media are employed as is known to those of skill in the art, particularly in light of the present disclosure. By way of illustration, a single dose may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

Methods of Treatment

The invention provides a method for delivering oligonucleotides to a mammalian cell (e.g., as part of a composition or formulation described herein), and methods for treating, ameliorating, or preventing the progression of a condition in a mammalian patient. The oligonucleotide or pharmaceutical composition may be contacted in vitro or in vivo with a target cell (e.g., a mammalian cell). The cell may be a heart cell.

The method generally comprises administering the oligonucleotide or composition comprising the same to a mammalian patient or population of target cells. The oligonucleotide, as already described, is a miRNA inhibitor (e.g., having a nucleotide sequence designed to inhibit expression or activity of a miR-208 family miRNA). Thus, the patient may have a condition associated with, mediated by, or resulting from, miR-208 family expression. Such conditions include, for example, cardiac hypertrophy, myocardial infarction, heart failure (e.g., congestive heart failure), vascular damage, restenosis, or pathologic cardiac fibrosis. Thus, the invention provides a use of the modified oligonucleotides and compositions of the invention for treating such conditions, and for the preparation of medicaments for such treatments.

In certain embodiments, the patient (e.g., human patient) has one or more risk factors including, for example, long standing uncontrolled hypertension, uncorrected valvular disease, chronic angina, recent myocardial infarction, congestive heart failure, congenital predisposition to heart disease and pathological hypertrophy. Alternatively or in addition, the patient may have been diagnosed as having a genetic predisposition to, for example, cardiac hypertrophy, or may have a familial history of, for example, cardiac hypertrophy.

In this aspect, the present invention may provide for an improved exercise tolerance, reduced hospitalization, better quality of life, decreased morbidity, and/or decreased mortality in a patient with heart failure or cardiac hypertrophy.

In certain embodiments, the activity of miR-208a, miR-208b, and/or miR-499 in cardiac tissue, or as determined in patient serum, is reduced or inhibited.

In various embodiments, the pharmaceutical composition is administered by parenteral administration or by direct injection into heart tissue. The parenteral administration may be intravenous, subcutaneous, or intramuscular. In some embodiments, the composition is administered by oral, transdermal, sustained release, controlled release, delayed release, suppository, catheter, or sublingual administration. In certain embodiments, the oligonucleotide is administered at a dose of 25 mg/kg or less, or a dose of 10 mg/kg or less, or a dose of 5 mg/kg or less. In these embodiments, the oligonucleotide or composition may be administered by intramuscular or subcutaneous injection, or intravenously.

In some embodiments, the methods further comprise scavenging or clearing the miRNA inhibitors following treatment. For example, a oligonucleotide having a nucleotide sequence that is complementary to the inhibitor may be administered after therapy to attenuate or stop the function of the inhibitor.

EXAMPLES

Example 1

In Vitro Activity of miRNA Inhibitors Targeting the miRNA 208 Family

A panel of miRNA inhibitors (single stranded oligonucleotides) was synthesized targeting the miRNA 208 family (miR208a, miR-208b and miR-499). The sequences and modification patterns are shown in Table 1. A description of the base codes is provided in Table 2. The panel included multiple lengths of reverse complement inhibitors ranging from 11 nucleotides to 16 nucleotides. The number of LNA modifications was varied as well as the location of the LNA modification in the oligonucleotide.

A small panel was initially tested in HeLa cells utilizing the dual-luciferase assay readout. The assay used the psiCHECK™-2 construct (Promega) (FIG. 1). HeLa cells do not express the miR-208 family; therefore the corresponding mimic was also co-transfected with the plasmid.

Figure 2:
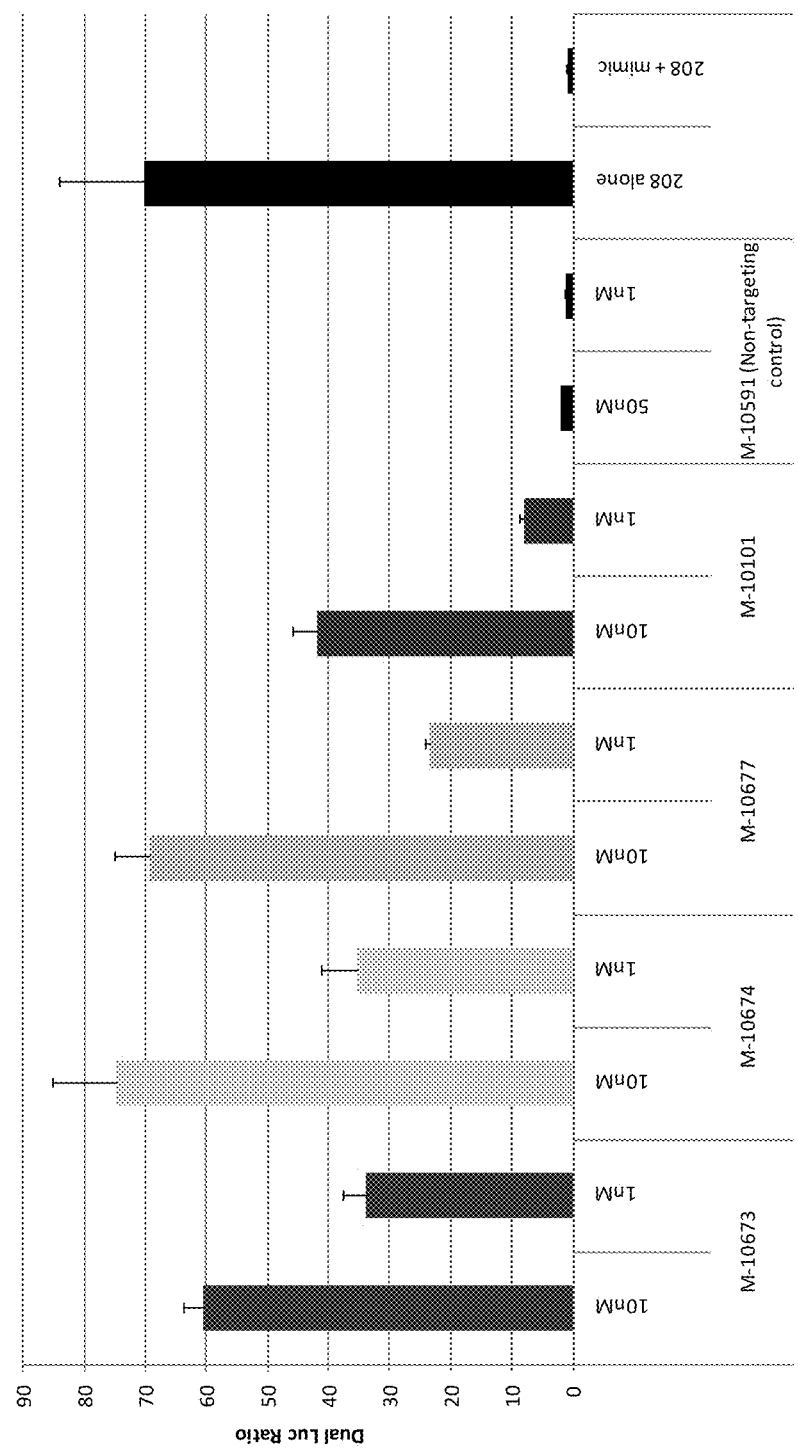
Figure 3:
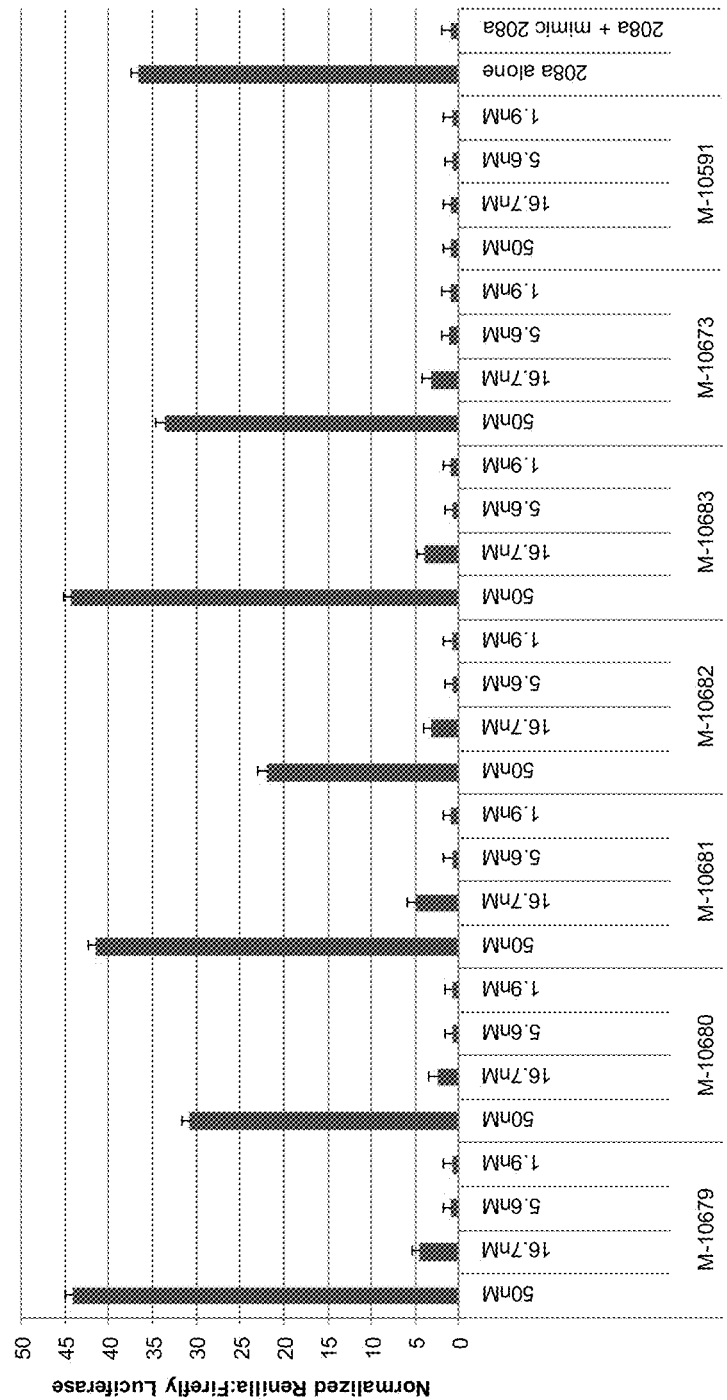
FIG. 3. miR-208 inhibitor efficacy measured by Dual Luciferase assay for miR-208a. M-10591 is a non-targeting control.
Figure 4:
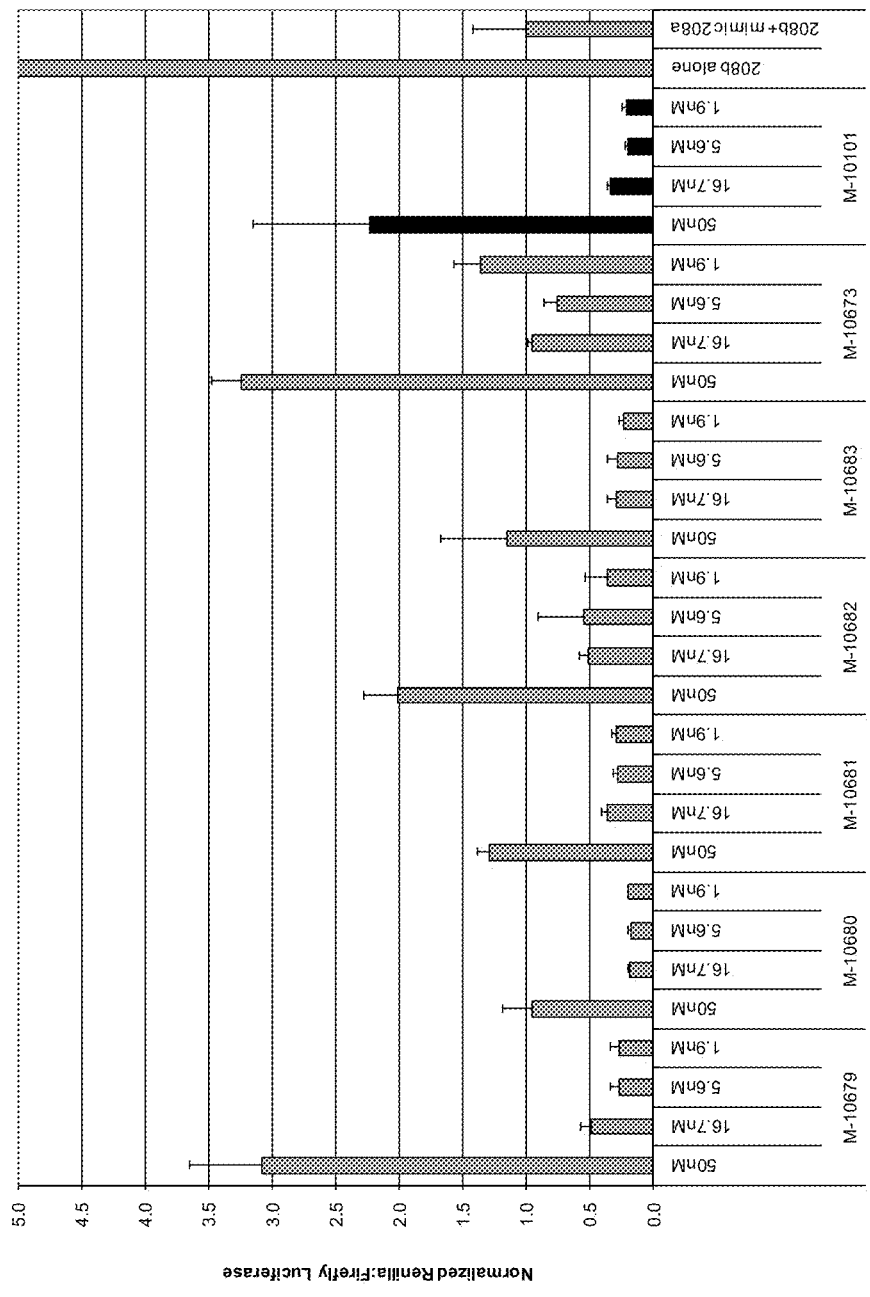
FIG. 4. miR-208 inhibitor efficacy measured by Dual Luciferase assay for miR-208b.
Figure 5:
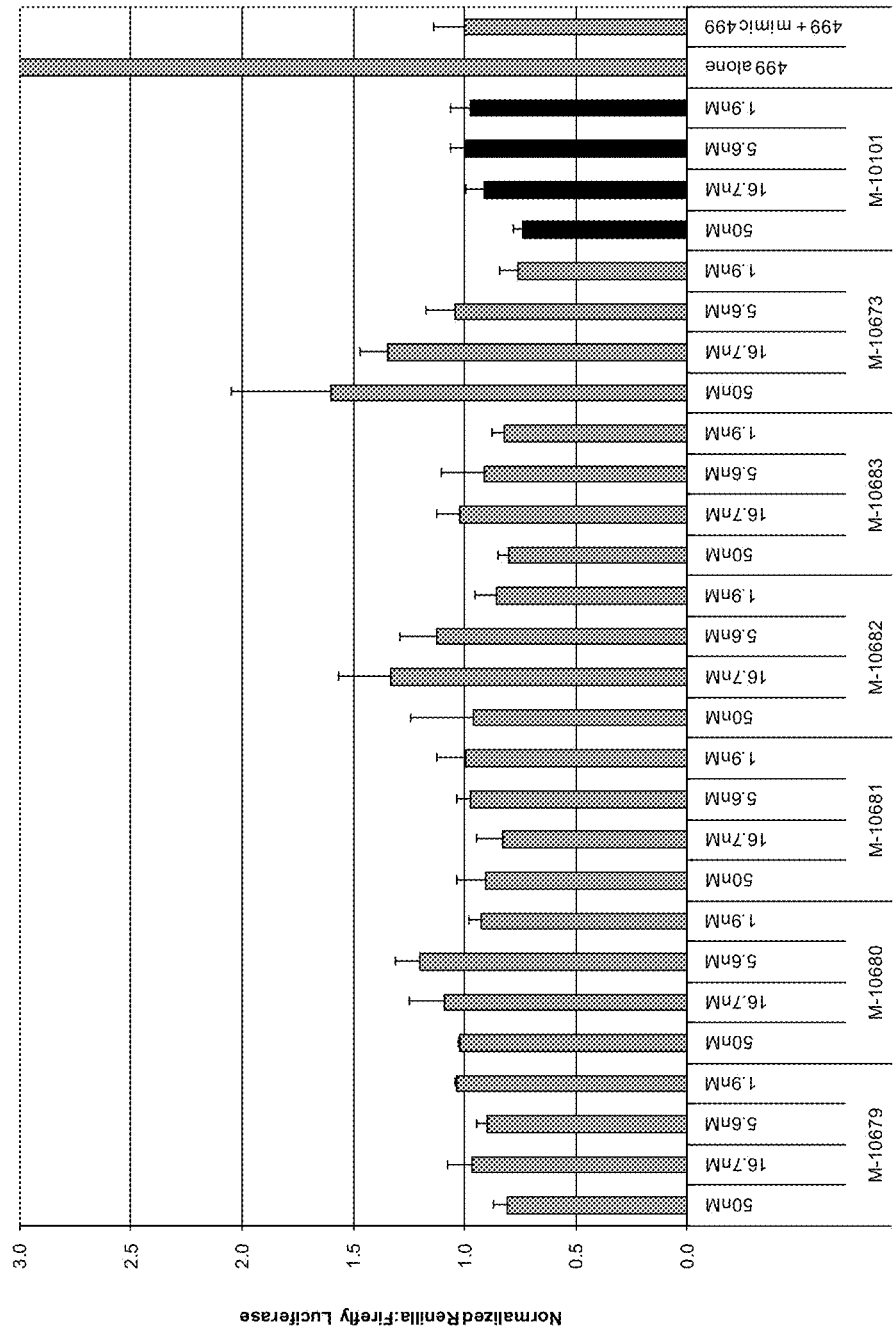
FIG. 5. miR-208 inhibitor efficacy measured by Dual Luciferase assay for miR-499.

The results show that LNA patterns have disparate activities in vitro as inhibitors of miR-208 family miRNAs. Some particularly potent designs are shown in FIG. 2. For example, M-10673 has the same number of LNA modifications (9 out of 16) as M-10101, yet at 1 nM showed higher inhibition of miR-208a. In view of these results, another limited panel of inhibitors was synthesized and tested, with all being 16 nucleotides in length with 9 LNA modifications (the remaining being DNA nucleosides). FIGS. 3-5 show the results of these inhibitors in dual luciferase reports for miR-208a, miR-208b, and miR-499 (respectively). M-10673 showed inhibition for not just miR-208a, but also against miR-208b and miR-499. There are two mismatches between miR-208a and miR-208b in the 16-mer inhibitors.

A more complete panel of inhibitor designs was then constructed. The structure of these molecules are shown in Table 1.

Example 2

In Vivo Activity of miRNA Inhibitors Targeting the miRNA 208 Family

Figure 6:
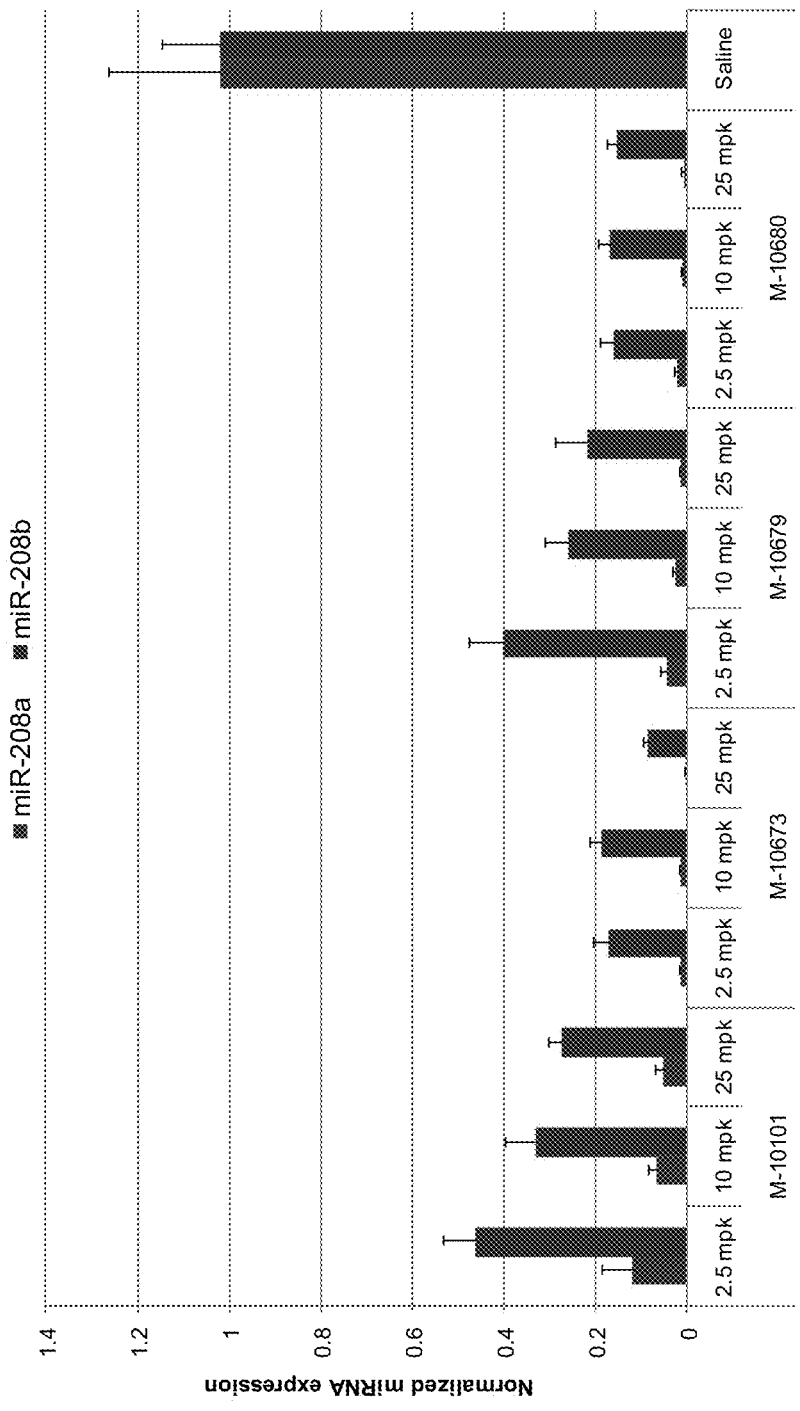
FIG. 6. miR-208a and miR-208b expression levels in the heart after in vivo dosing of miRNA inhibitor designs in normal mice. Left bars are miR-208a expression levels and right bars are miR-208b expression levels.

Three inhibitors targeting miR-208 family were synthesized and tested in normal mice for the effect on miR-208a and miR-208b levels. The mice (n=4) were dosed 2.5, 10 and 25 mg/kg through a low pressure tail vein injection and heart tissue was analyzed four days later by qPCR for miRNA levels. The results (FIG. 6) correlated well to the in vitro dual luciferase results. These results suggest that it may be possible to lower the dose at least 10-fold for a therapeutic effect (25 mpk to 2.5 mpk).

The above initial experiments demonstrate that there are unique LNA-containing modification motifs (including number and position of LNA) that enhance potency for miR-208 family miRNAs.

Figure 7:
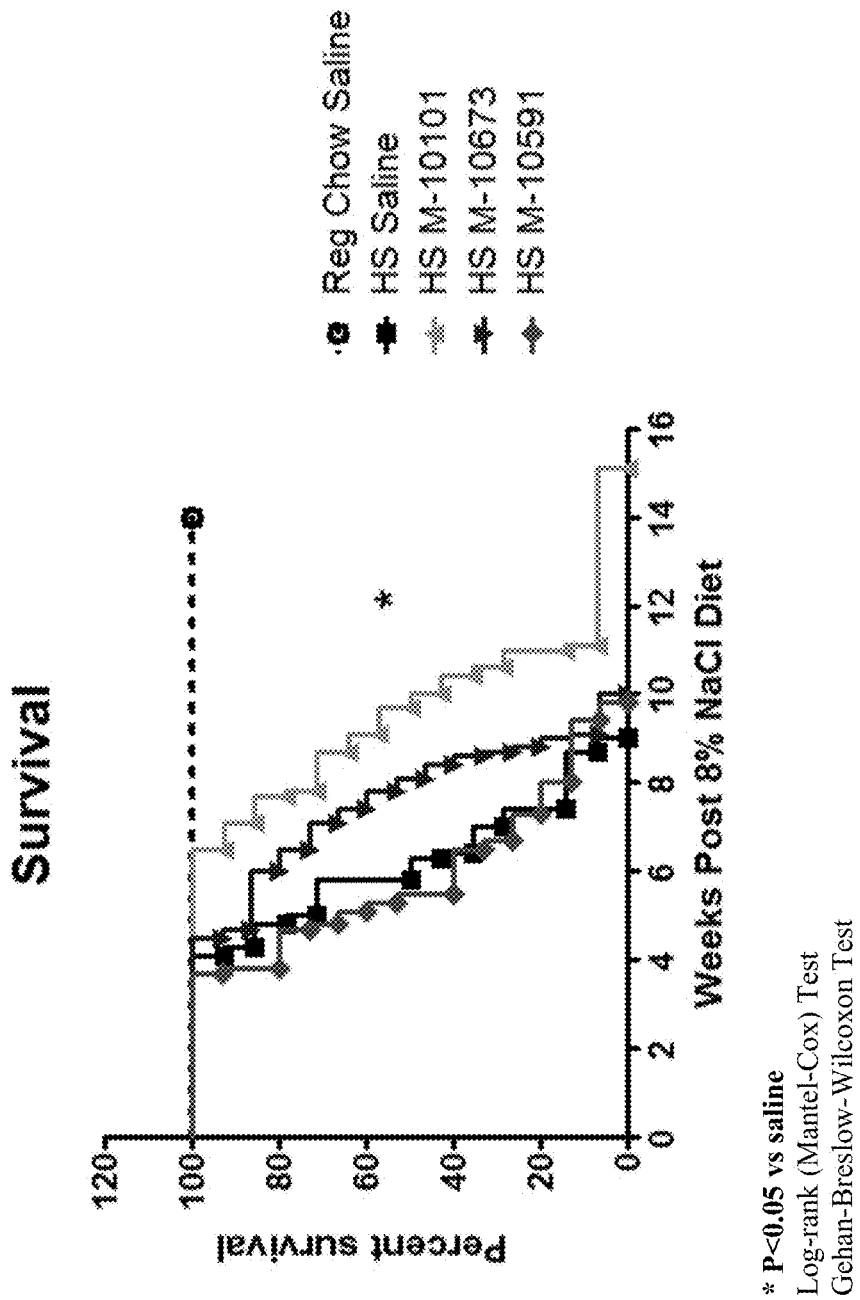
FIG. 7. Survival of Dahl salt-sensitive rats after in vivo dosing of miRNA inhibitor designs at 25 mg/kg subcutaneously every two weeks.
Figure 8:
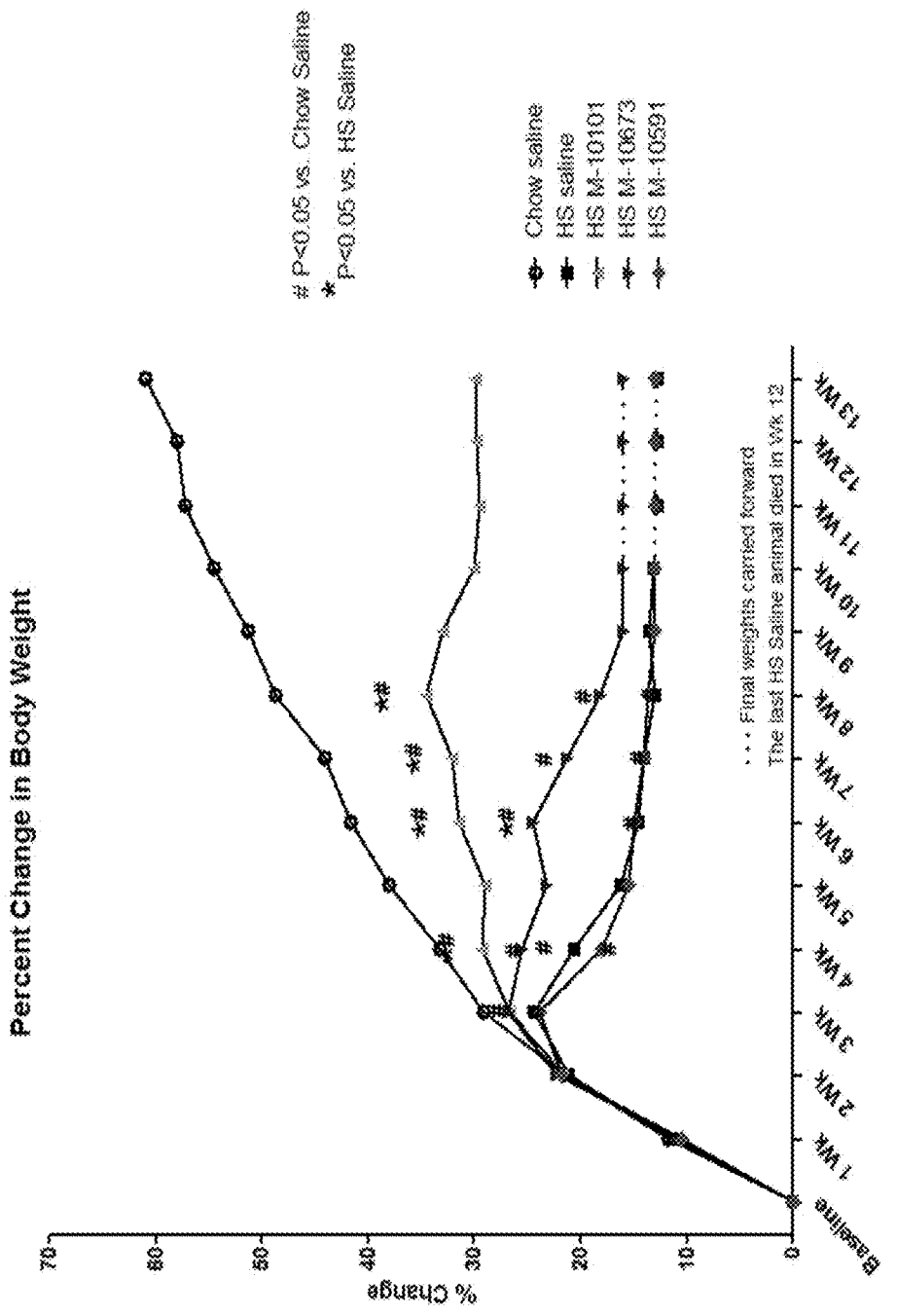
FIG. 8. Percent body weight changes for Dahl salt-sensitive rats dosed with inhibitor designs as in FIG. 7.
Figure 10:
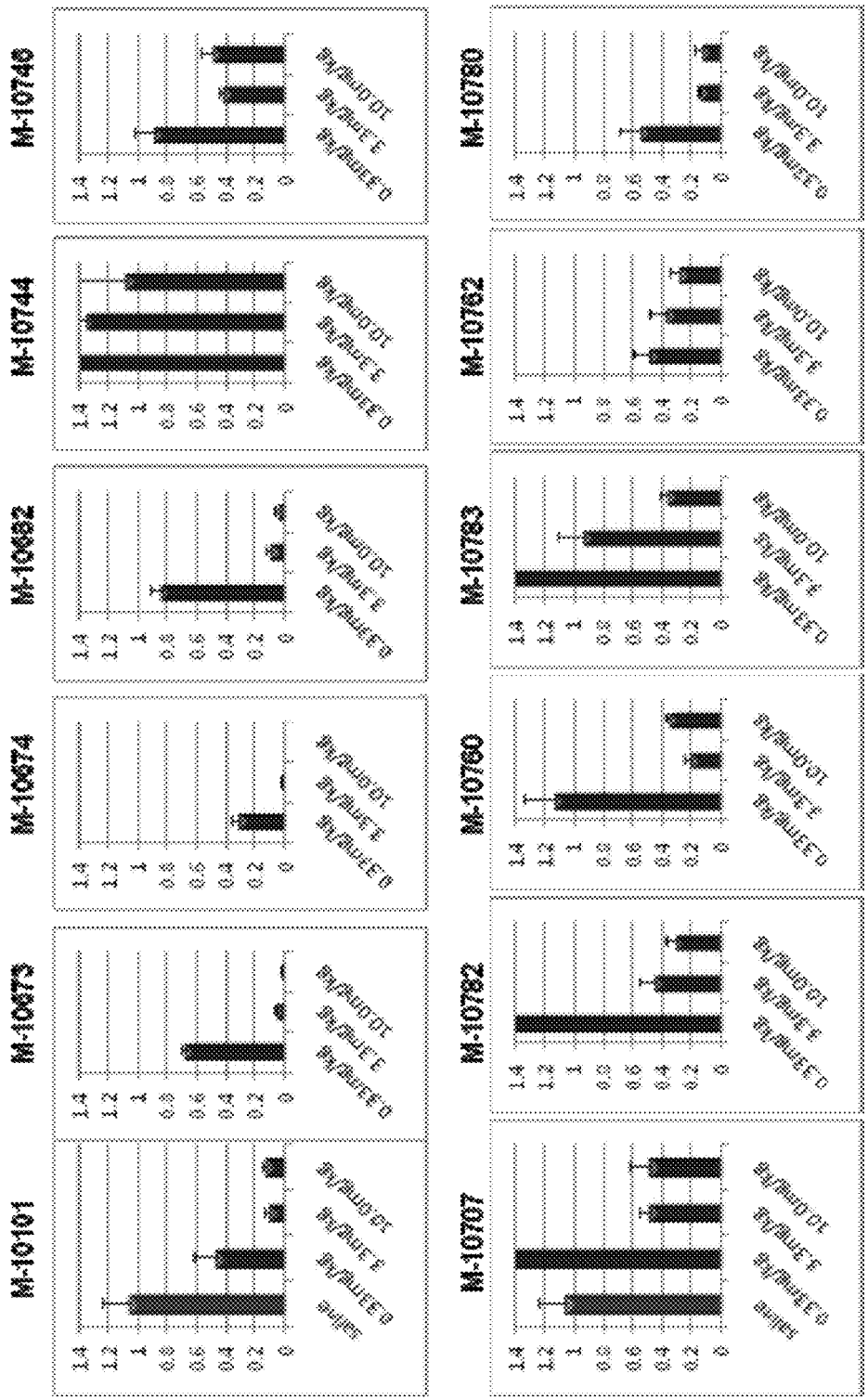
FIG. 10. miR-208a abundance in heart determined by Real-time PCR after in vivo dosing of miR-208a inhibitor designs in normal mice.
Figure 11:
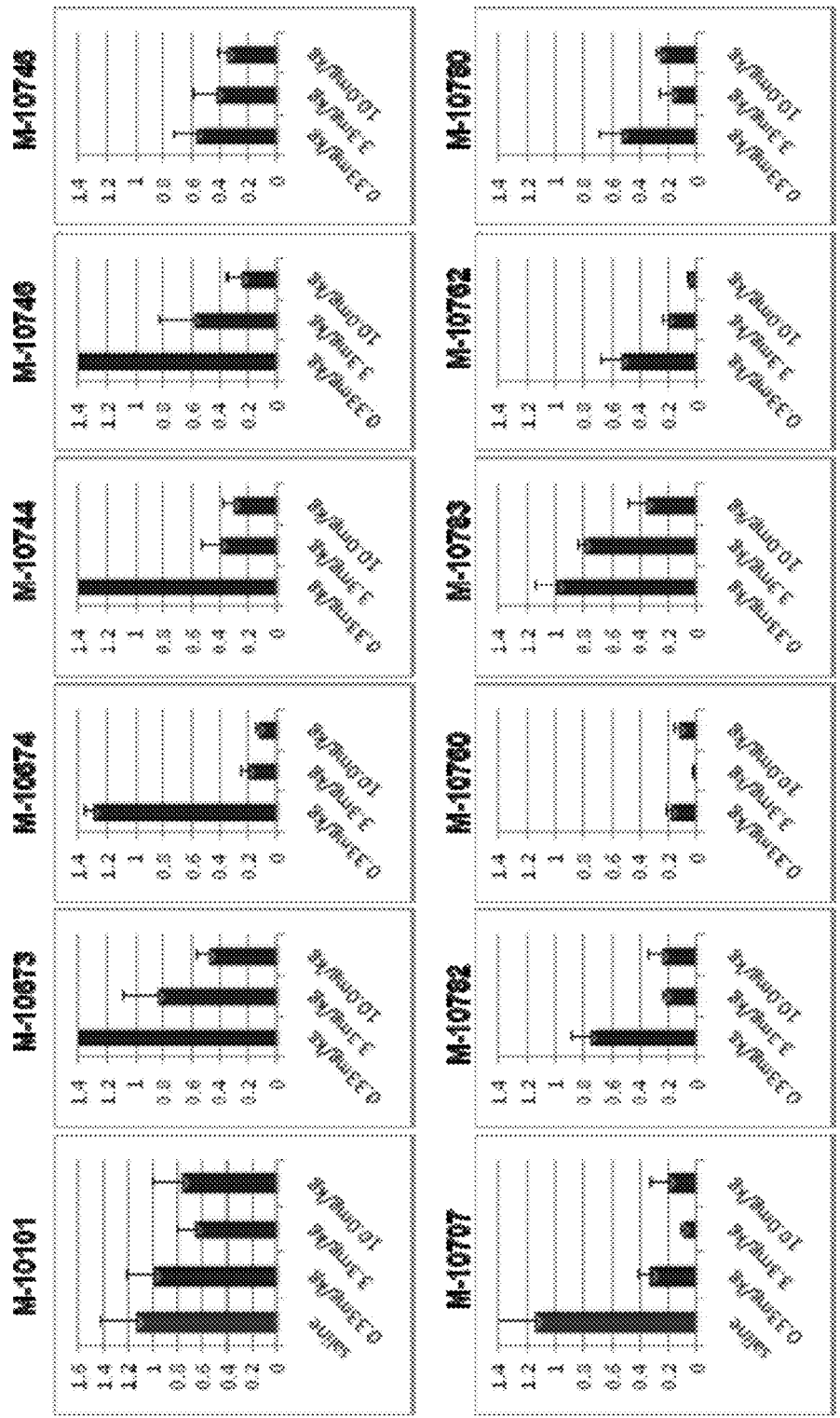
FIG. 11. miR-208b abundance in heart determined by Real-time PCR after in vivo dosing of miR-208a inhibitor designs in normal mice.

M-10101 and M-10673 were tested in the Dahl salt-sensitive rat model, which is described further below. FIGS. 7 and 8 show the best survival and body weight control with M-10101.

Example 3

Therapeutic Inhibition of miR-208 Improves Cardiac Function and Survival During Heart Failure Previously, it was reported that genetic deletion of the cardiac specific miR-208a prevents pathological cardiac remodeling and up-regulation of Myh7 in response to stress. This example shows that systemic delivery of an antisense oligonucleotide (M-10101 from Table 1) induces potent and sustained silencing of miR-208a in the heart. Therapeutic inhibition of miR-208a by subcutaneous delivery of antimiR-208a during hypertension-induced heart failure in Dahl hypertensive rats dose-dependently prevents pathological myosin switching and cardiac remodeling, while improving cardiac function, overall health and survival. Transcriptional profiling indicates antimiR-208a evokes prominent effects on cardiac gene expression, while plasma analysis indicates significant changes in circulating levels of miRNAs upon antimiR-208a treatment. These studies indicate the potential of oligonucleotide-based therapies for modulating cardiac miRNAs, and validate miR-208 as a potent therapeutic target for the manipulation of cardiac function and remodeling during heart disease.

Chronic and acute stress to the heart results in a pathological remodeling response accompanied by cardiomyocyte hypertrophy, fibrosis, pump failure, myocyte degeneration and apoptosis, which often culminate in heart failure and sudden death (1). While classical pharmacological treatment strategies can reduce remodeling and prolong survival in heart failure patients, these therapies are ultimately ineffective in preventing progression of the disease. A hallmark of pathological hypertrophy and heart failure is the re-activation of a set of fetal cardiac genes, including those encoding atrial natriuretic factor (ANF), B-type natriuretic peptide (BNP) and fetal isoforms of contractile proteins, such as skeletal α-actin and Myh7 (β-myosin heavy chain, β-MHC) (2). Down-regulation of Myh6 (α-MHC) and up-regulation of Myh7 is a common response to cardiac injury irrespective of the species (3-5). Relatively minor increases in the ratio of Myh6 to Myh7 have been shown to have beneficial effects on cardiac contractility and performance in humans and rodents (6-8). Much attention has been focused on understanding the mechanisms that regulate cardiac remodeling and myosin switching in search for potential approaches to therapeutically manipulate these processes.

Previously, signature expression patterns of microRNAs (miRNAs) were identified that were associated with pathological cardiac hypertrophy, heart failure and myocardial infarction in humans and mouse models of heart disease (9-10). Gain- and loss-of-function studies in mice have revealed profound and unexpected functions for these miRNAs in numerous facets of cardiac biology, including the control of myocyte growth, contractility, fibrosis, and angiogenesis (reviewed in 11). Especially intriguing is miR-208, a miRNA encoded within an intron of the Myh6 gene which regulates the cardiac stress response (12-13). Although genetic deletion of miR-208 in mice failed to induce an overt phenotype at baseline, in response to several forms of cardiac stress, miR-208 null mice showed virtually no cardiomyocyte hypertrophy or fibrosis and were unable to up-regulate Myh7 expression (12).

In the adult heart, miR-208 is essential for the expression of not only Myh7, but also of a closely related myosin isoform, Myh7b (14). Remarkably, both of these genes encode slow myosins and contain intronic miRNAs (miR-208b and miR-499, respectively) (15-16). Since miR-208 (which we will refer to as miR-208a), -208b and miR-499 are related miRNAs that arise from myosin genes, we collectively refer to as myomiRs (17). Through gain- and loss-of-function experiments in mice, we have shown that genetic deletion of miR-208a dose-dependently reduces Myh7b/miR-499 expression within the adult heart (18). Since miR-499 mutant animals show no effect on Myh7 expression or cardiac remodeling in response to stress, and reintroduction of miR-499 removes the cardiac effects seen in the miR-208a mutant mice (18), we conclude that the combined reduction in miR-208a and miR-499 is responsible for the cardioprotective effects seen in miR-208a mutant animals.

The importance of miRNAs for cardiac function and dysfunction suggests opportunities for therapeutically exploiting the biology of miRNAs in the setting of heart disease. Single-stranded RNA oligonucleotides have been shown to be effective in inactivating miRNAs in vivo through complementary base pairing (19-23), and represent a potentially effective means of inactivating pathological miRNAs. Here we show that systemic delivery of unconjugated, Locked Nucleic Acid (LNA)-modified antisense oligonucleotides against miR-208a is sufficient to induce specific, potent and sustained silencing of miR-208a in the heart. Moreover, antimiR-208a dose-dependently prevents stress-induced remodeling, functional deterioration, and cardiac myosin switching, while improving general health and survival in a rat model of heart failure (Dahl salt-sensitive rats). Gene expression analysis showed specific gene expression changes in response to antimiR-208a treatment, including changes in previously defined target genes. Intriguingly, these physiological effects of antimiR-208a in hypertensive rats are mirrored by significant changes in plasma levels of circulating miRNAs. Together, these studies indicate the potency of systemically delivered antimiRs in the settings of heart disease, and validate miR-208 as an important therapeutic target during heart failure.

AntimiR Mediated Silencing of miR-208a In Vivo

Figure 12:
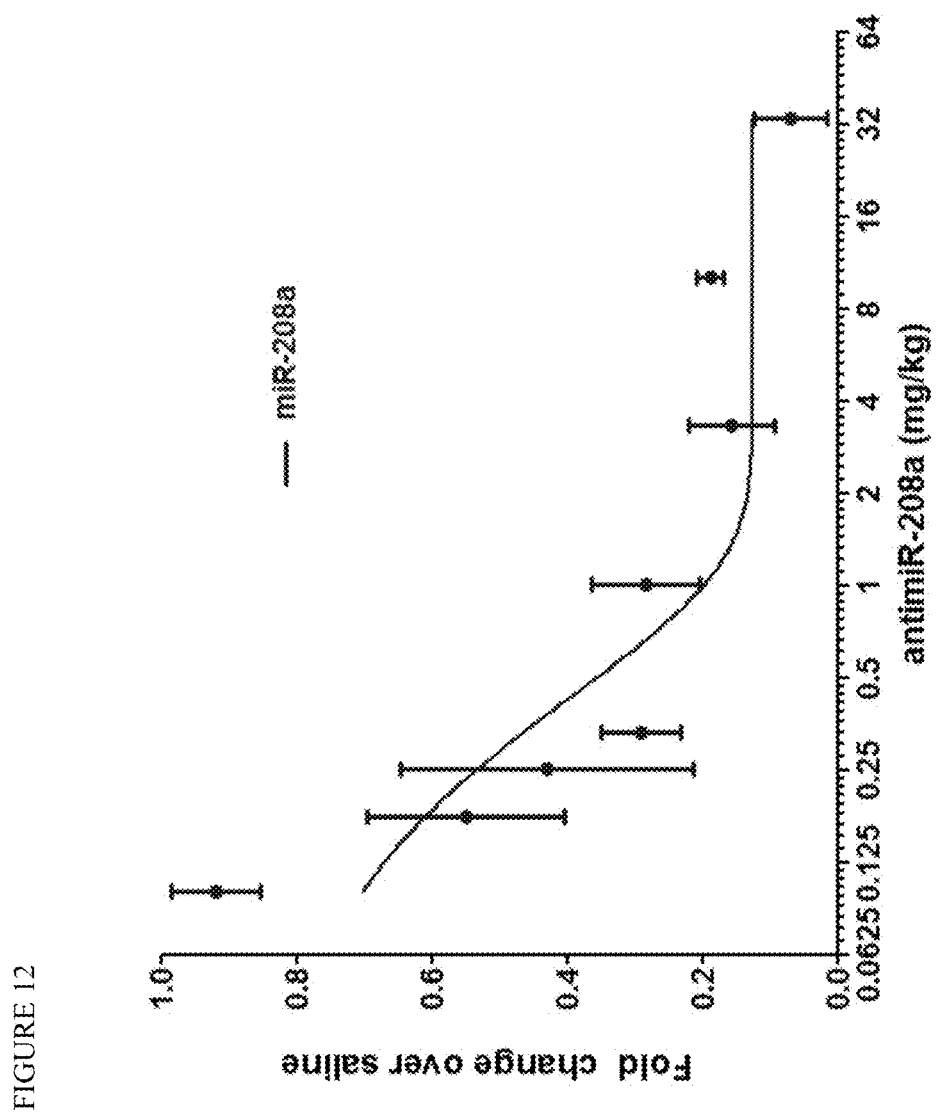
FIG. 12. Systemic delivery of antimiR-208a (M-10101) induces potent and sustained silencing of miR-208 in the heart.

To determine the therapeutic potential of miR-208a inhibition in cardiomyocytes in vivo, we designed an unconjugated LNA-containing antimiR against miR-208a (antimiR-208a, M-10101 in Table 2). AntimiR-208a targets bases 2-17 of the 5' region of mature miR-208a, and contains a combination of LNA and DNA linked by phosphorothioate bonds. Real-time PCR and Northern blot analysis one week after intravenous (i.v.) delivery of antimiR-208a to mice at doses ranging from 0.1 to 33 mg/kg indicated a dose-responsive silencing of miR-208a, while injection of a mismatch antimiR of similar chemistry showed no inhibition of miR-208a (FIG. 12). Notably, we observed an up-shift of miR-208 in the presence of the 16 mer LNA antimiR, reflecting the formation of a stable heteroduplex between miR-208a and the LNA antimiR. Real-time analysis of the other two myomiRs, miR-208b and miR-499, showed no inhibition following a single injection after seven days, nor did we observe any changes in Myh7 (data not shown).

Figure 13:
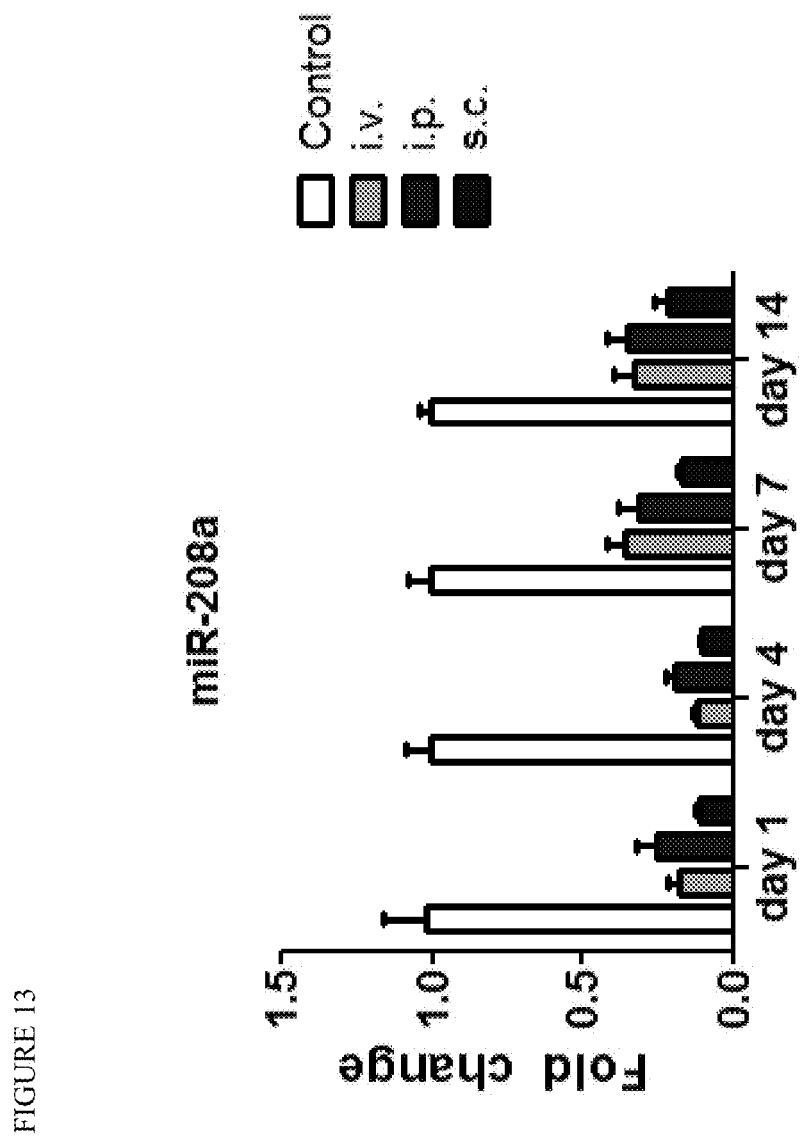
FIG. 13. Real-time PCR analysis on cardiac tissue collected at the indicated time-points.

To investigate the potential to deliver antimiR-208a via additional routes of administration, we injected mice i.v., intraperitoneally (i.p.), or subcutaneously (s.c.) with 25 mg/kg antimiR-208a and measured miR-208a inhibition at days 1, 4, 7, and 14. All 3 routes of administration showed robust inhibition of miR-208a (FIG. 13), with no significant differences in antimiR-208a detection in plasma, heart, liver and kidney between the different delivery methods (not shown).

Extended miR-208a Inhibition Leads to Myh7 Regulation In Vivo

Figure 14:
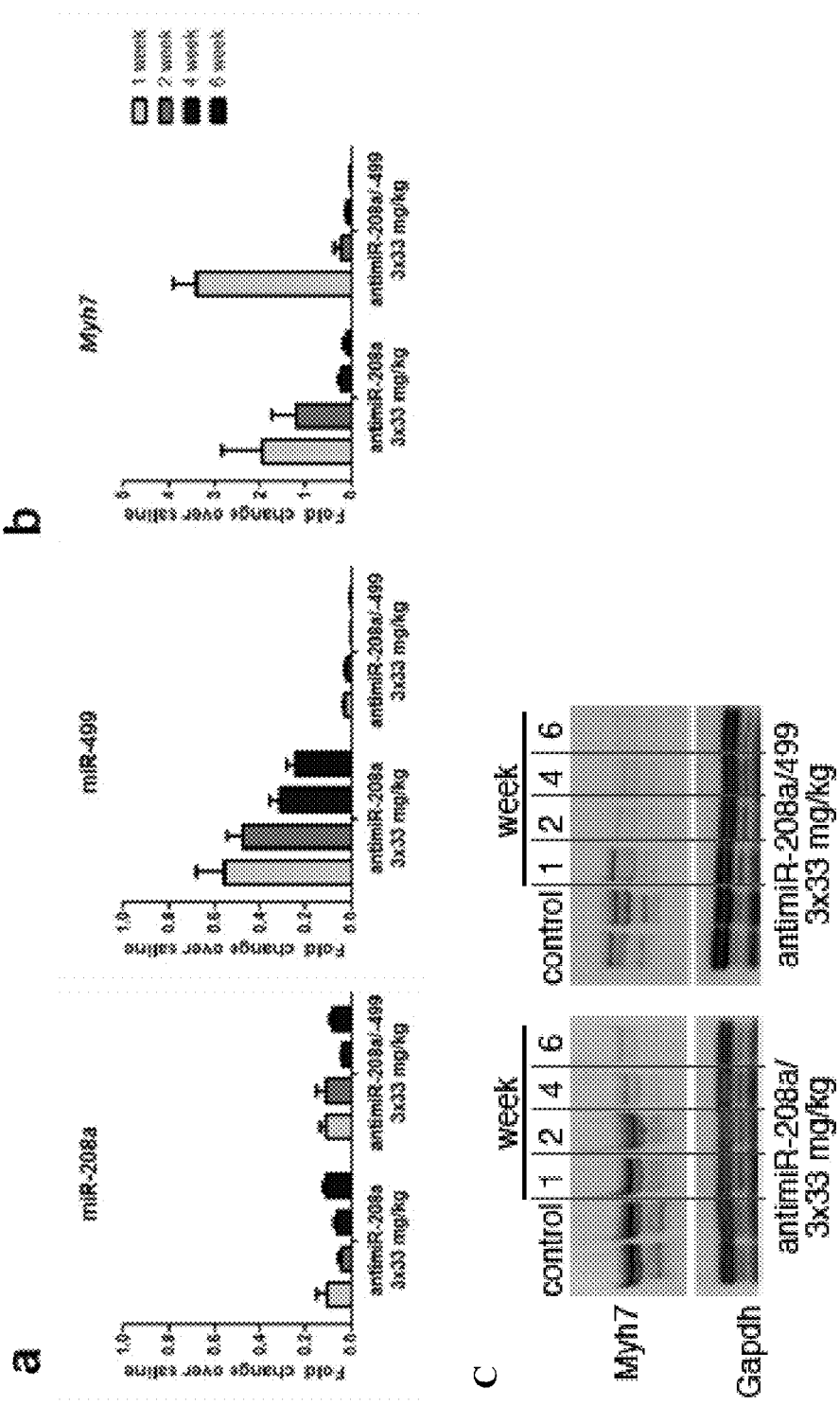
FIG. 14. miR-208a silencing reduces miR-499 and Myh7.

Since a single dose of antimiR-208a after seven days was unable to establish an effect on Myh7, as was seen in the miR-208a knockout mice, we set out to determine the dose and time required for efficient Myh7 regulation following antimiR-208a administration. Three consecutive doses of 33 mg/kg antimiR-208a robustly inhibited miR-208a for at least six weeks (FIG. 14). miR-499, which is known to be regulated by miR-208 (18), showed a time-dependent decrease in expression from one to six-weeks after administration of antimiR-208a, going from a 35 to 75% reduction in miR-499 (FIG. 14A). Furthermore, Myh7 mRNA expression was significantly reduced starting at four weeks after antimiR-208a treatment, suggesting a specific threshold of miR-208a and miR-499 levels is necessary for Myh7 expression (FIG. 14B), which was paralleled by a reduction in Myh7 protein (FIG. 14C). The initial spike in Myh7 mRNA in response to antimiR-208a is not translated into increased Myh7 protein.

Figure 15:
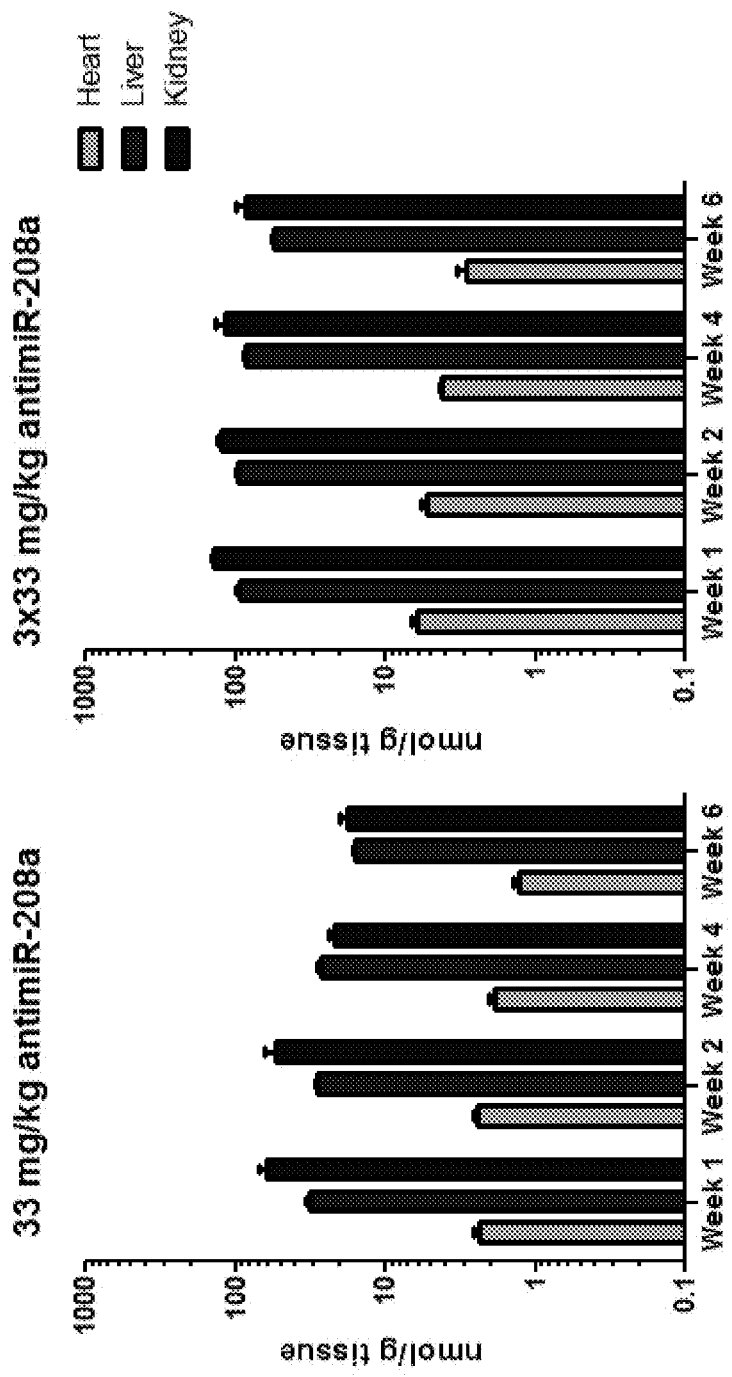
FIG. 15. Tissue distribution analysis indicates that significant amounts of antimiR-208a (M-10101) are detectable in plasma, heart, liver of kidney up to 6 weeks after injection. Error bars depict SEM. n=4 for each time-point and dose.

To establish whether the effect on Myh7 expression is based on a reduction in both miR-208a and miR-499, we injected mice for 3 consecutive days with a cocktail of antimiR-208a and antimiR-499, each at 33 mg/kg. Treatment with antimiR-208a/-499 caused robust inhibition of miR-208a and miR-499 for six weeks, and demonstrated a much more rapid regulation of Myh7 mRNA and protein, with reduced expression before two weeks after treatment (FIG. 14A-C). AntimiR distribution data using a sandwich hybridization assay to quantify antimiR-208a in heart, liver, kidney, and plasma, indicated that considerable amounts of antimiR-208a are still detectable 6 weeks after administration of either 33 mg/kg or 3×33 mg/kg of antimiR-208a (FIG. 15)

Figure 16:
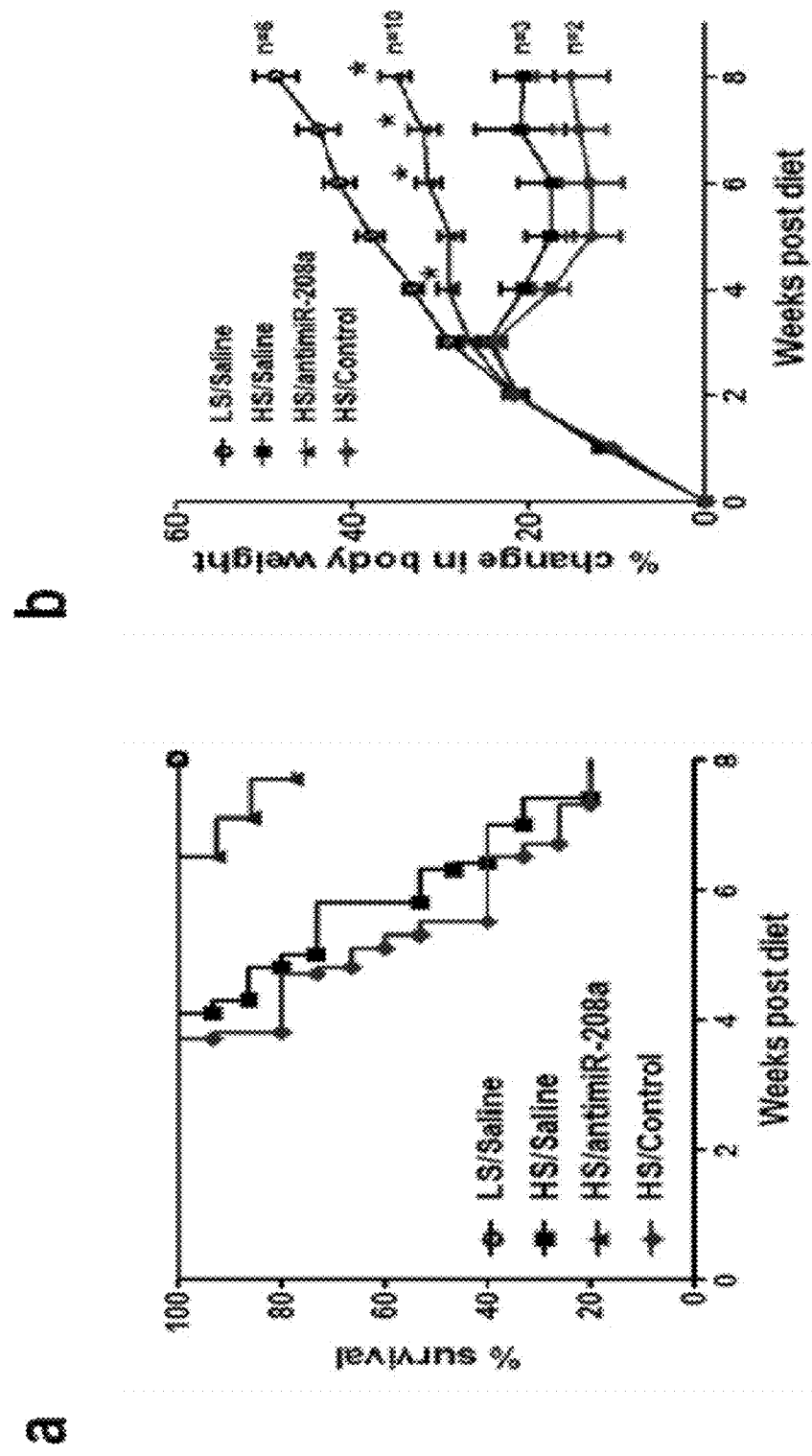
FIG. 16. Therapeutic silencing of miR-208a is beneficial during heart failure.

Therapeutic Silencing of miR-208 Reduces Cardiac Remodeling, while Improving Cardiac Function and Survival During Heart Failure Since previous data showed that genetic deletion of miR-208a results in a cardioprotective effect, we aimed to test the therapeutic relevance of miR-208a inhibition. To this end, we used Dahl salt-sensitive rats that were either fed a low-salt (LS) diet (0.25% NaCl) or a high-salt (HS) diet (8.0% NaCl) starting at 8 weeks of age. After one week on HS, rats were administered saline, 25 mg/kg antimiR-208a, or 25 mg/kg scrambled control oligo subcutaneously every two weeks. Following 3-4 weeks on the HS diet, the saline and control treated animals showed visible signs of immobility and discomfort and death, while subcutaneous delivery of antimiR-208a was able to significantly alleviate these symptoms (FIG. 16). As an indication of health, we monitored body weight during the duration of the study. Dahl rats on the HS diet injected with either saline or the control oligo exhibited significant reductions in weight gain compared to LS diet controls. HS/antimiR-208a treated rats, however, showed comparable weight gain (FIG. 16B). To exclude the possibility antimiR-208a treated animals were maintaining weight through ingesting less of the 8% HS diet, food intake was monitored, which showed a comparable ingestion between all HS fed groups (not shown).

Figure 17:
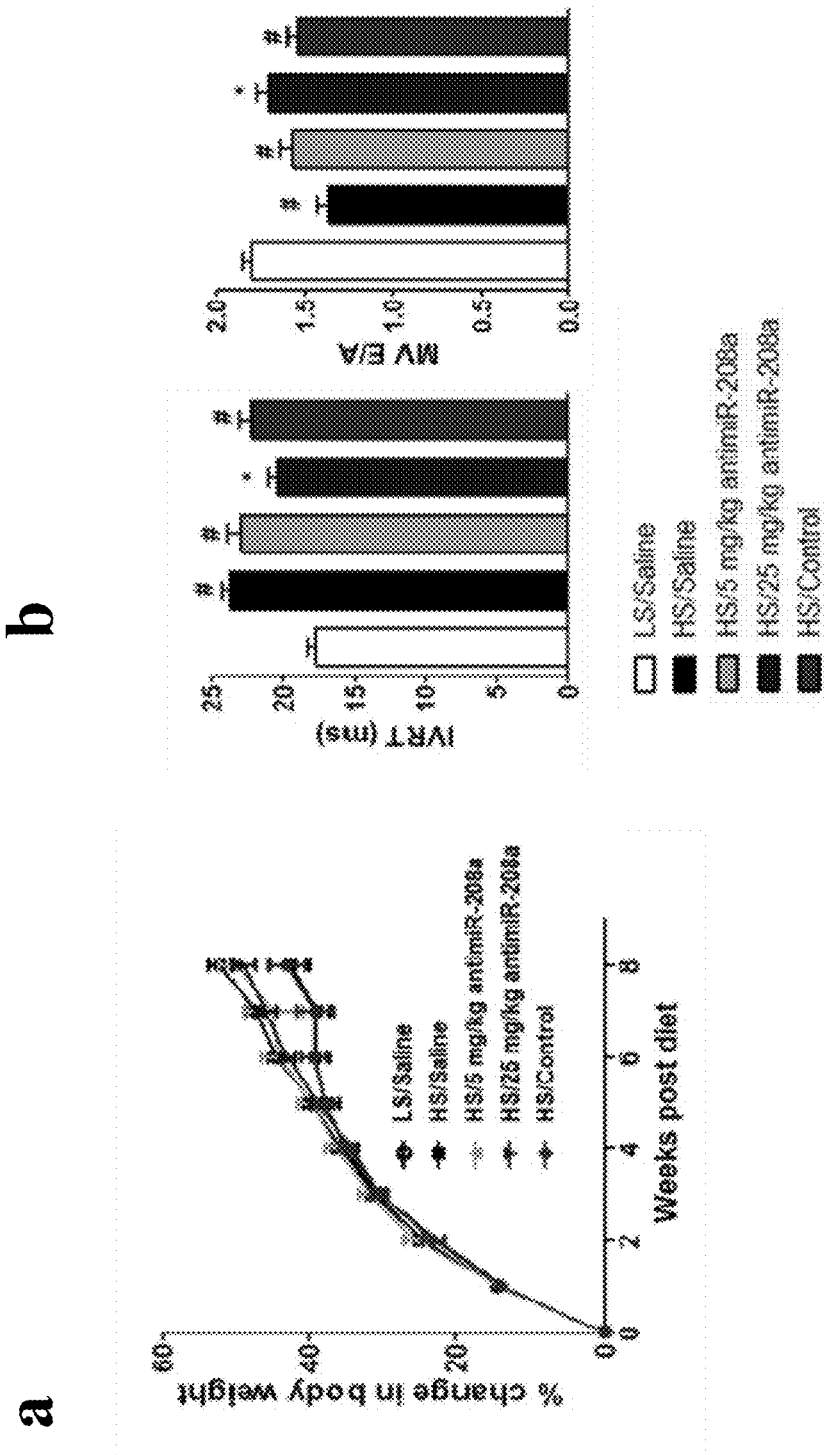
FIG. 17. Body weight analysis of Dahl rats on the 4% HS diet (FIG. 17A), showing significant reductions in weight gain compared to LS diet controls, while both 5 and 25 mg/kg injections every 2 weeks is sufficient to maintain weight gain comparable to animals on a normal diet. Error bars depict SEM, * p<0.05 vs. HS saline, # p<0.05 vs. LS saline.
Figure 18:
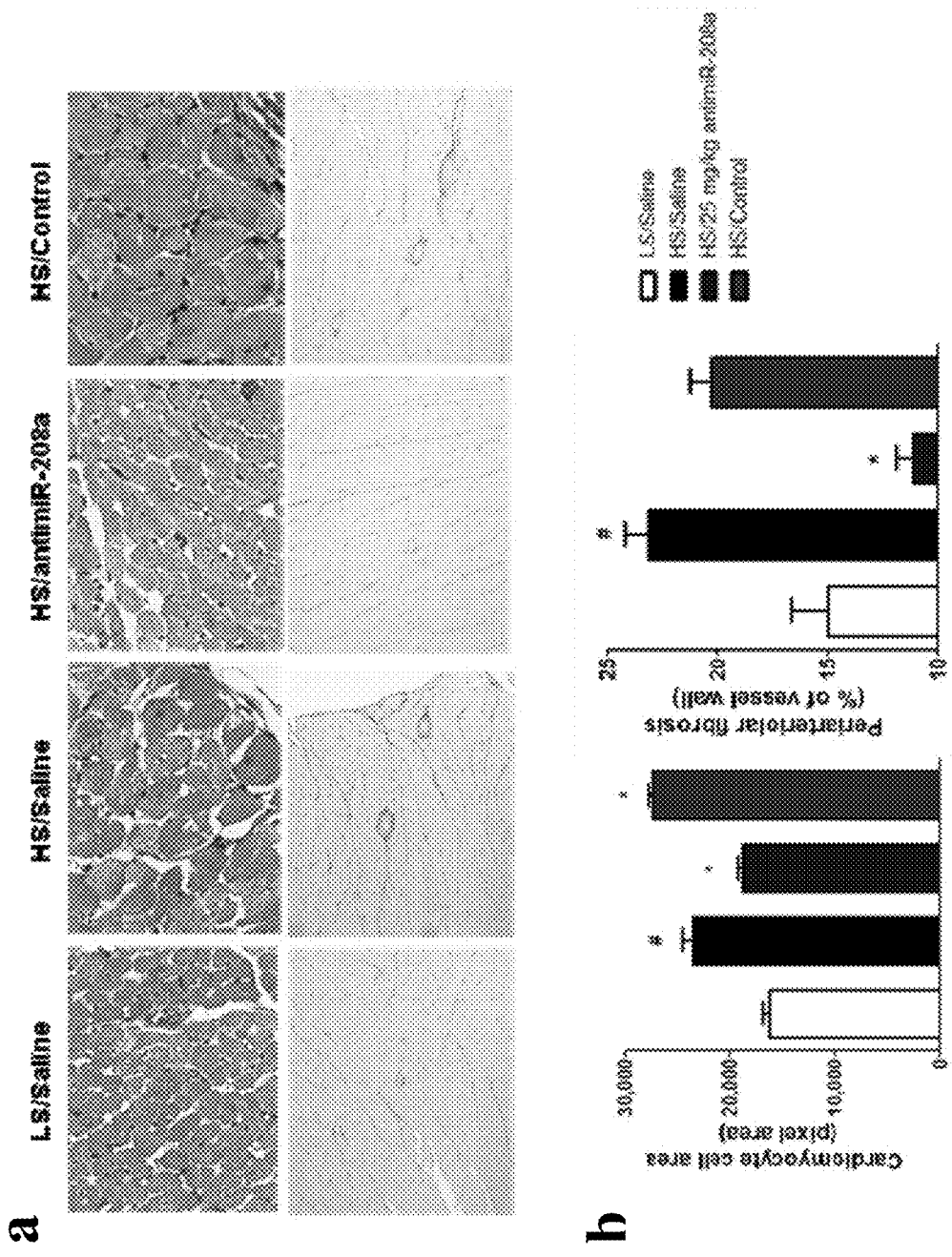
FIG. 18. Representative images of H&E and picrosirius red stained left ventricular histological sections indicate an increase in cardiomyocyte hypertrophy and perivascular fibrosis in response to the 4% HS diet for 8 weeks, while both parameters are reduced in response to antimiR-208a (M-10101) treatment (FIG. 18A).

To obtain additional insight into the protective effects seen in response to antimiR-208a, subsequent studies were done using a 4.0% NaCl diet for 9 weeks, during which the rats received either saline, 5 or 25 mg/kg of antimiR-208a, or 25 mg/kg of antimiR control every 2 weeks. Body weight analysis indicated that Dahl rats on the HS diet exhibited significant reductions in weight gain compared to LS diet controls, while HS/antimiR-208a treated rats maintained their increase in weight gain (FIG. 17A). Functional assessment using echocardiography of antimiR-208a treated Dahl rats showed a dose-dependent, significant improvement in measurements of diastolic function. AntimiR-208a treated rats exhibited a significant reduction in isovolumic relaxation time (IVRT) compared to HS/saline controls, as well as a normalization of the mitral valve early to active filling velocity ratio (MV E/A) compared to HS/Saline controls eight weeks post HS diet (FIG. 17B). Quantification of cardiomyocyte size showed a significant reduction in cardiomyocyte hypertrophy following treatment with antimiR-208a (FIG. 18A, B). Additionally, antimiR-208a treatment reduced periarteriolar fibrosis induced by HS diet as assessed by quantification of picrosirius red staining (FIG. 18A, B).

miR-208a Inhibition Reverses the Myosin Switch During Heart Failure

Figure 19:
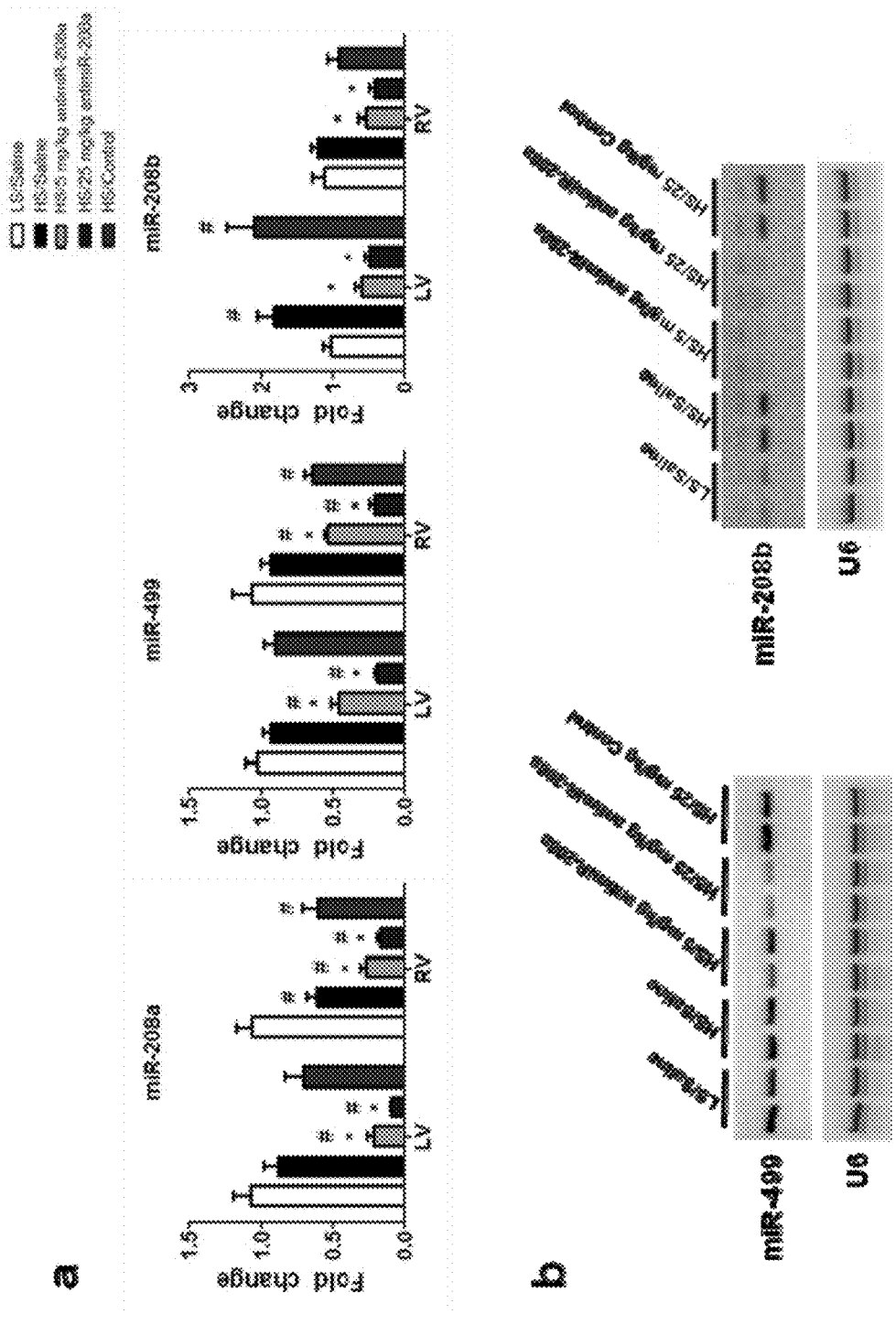
FIG. 19. antimiR-208a (M-10101) treatment reduces miR-499 and Myh7 in Dahl salt-sensitive rats. All analyses were performed 8 weeks following the onset of 4% HS diet and 7 weeks after the onset of antimiR treatment. n=10 for all groups in (a) and (c).

To compare the physiological changes observed after antimiR-208a treatment with molecular and cellular changes, we examined myomiR expression following HS treatment. AntimiR-208a caused a dose-dependent inhibition of miR-208a in both left and right ventricles 2 weeks after the last injection, whereas a control oligo showed no difference compared to saline (FIG. 19A, left panel). miR-499 also showed a dose-dependent decrease in expression following sustained inhibition of miR-208a (FIG. 19A, middle panel). miR-208b was induced in both HS/Saline and HS/Control treated animals, however antimiR-208a treatment resulted in a dose-dependent decrease in miR-208b levels (FIG. 19A, right panel). This regulation of miR-499 and miR-208b was confirmed by Northern blot analysis (FIG. 19B).

Figure 20:
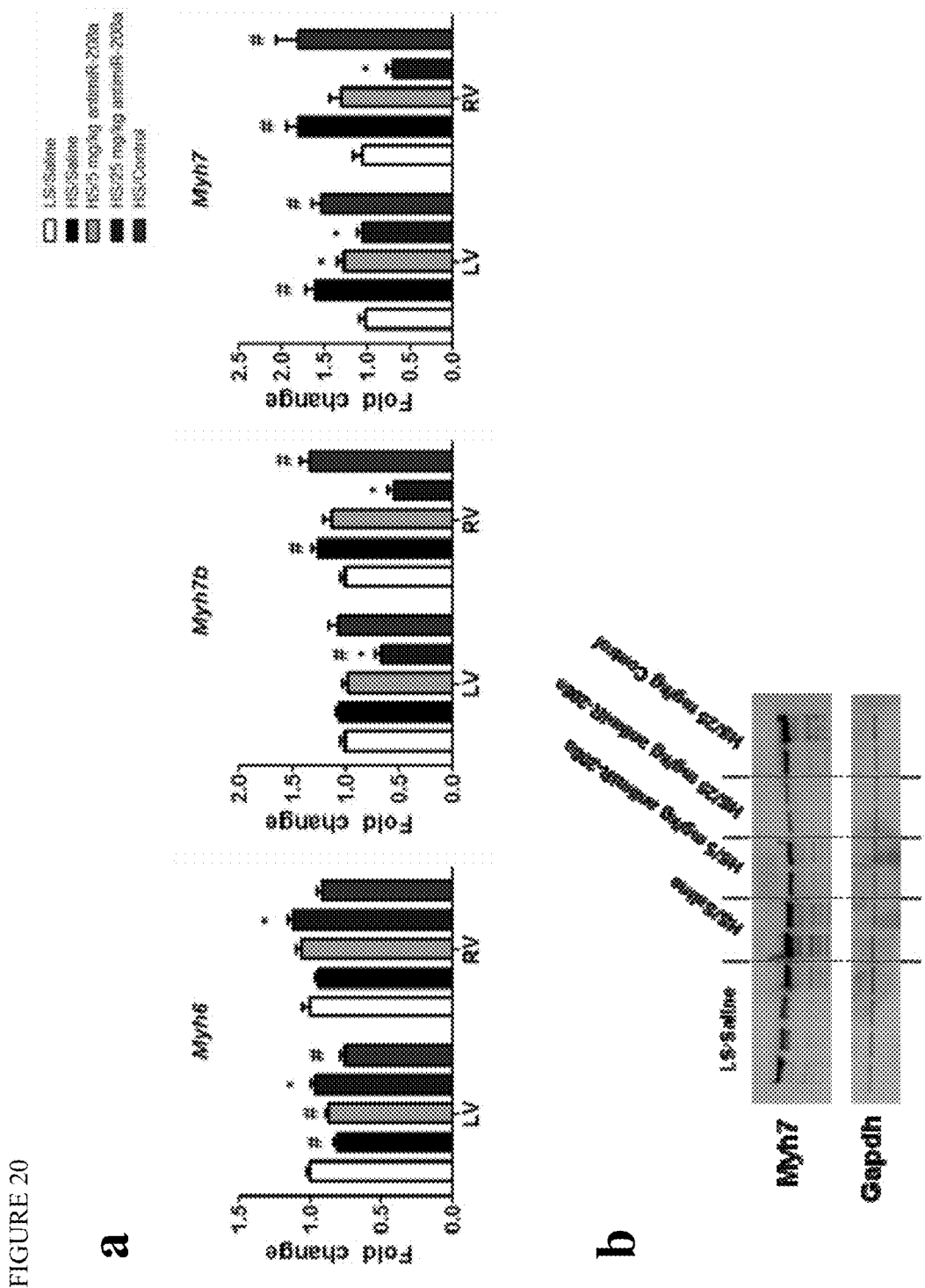
FIG. 20. Real-time PCR analysis showing that HS diet reduces Myh6, while it increases Myh7 (FIG. 20A). AnitmiR-208a (M-10101) treatment dose-dependently increases Myh6 expression while it reduces Myh7b expression. The HS diet-induced increase in Myh7 is dose-dependently reduced by antimiR-208a. Error bars depict SEM, * p<0.05 vs. HS saline, # p<0.05 vs. LS saline.
Figure 21:
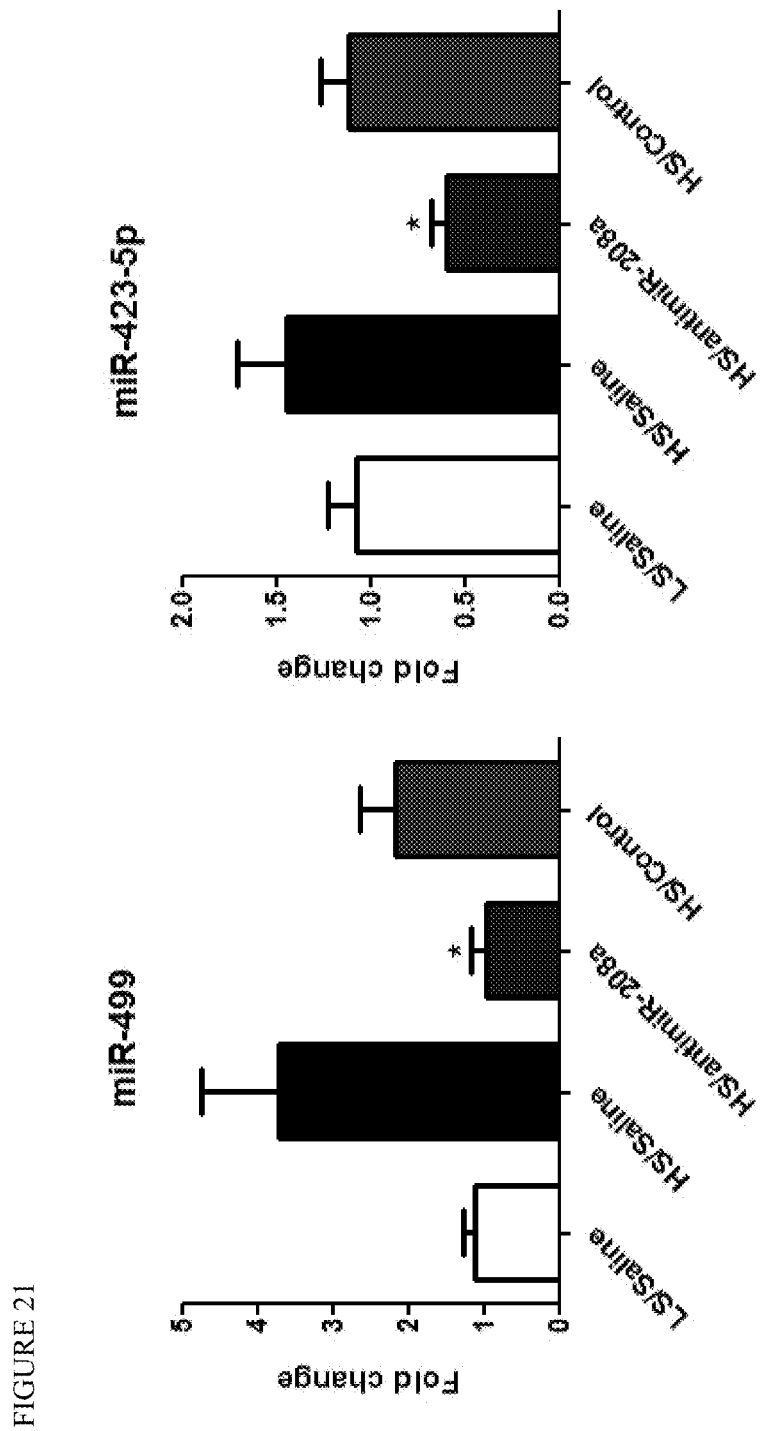
FIG. 21. miR-499 in plasma serves a biomarker for antimiR-208a efficacy.

To assess the regulation of the host genes, we examined Myh6, Myh7, and Myh7b mRNA levels. Myh7 was significantly increased in response to HS in both the HS/saline and HS/control groups. This increase was dose-dependently blunted in response to antimiR-208a. Additionally, antimiR-208a treatment normalized the decreased expression of Myh6 mRNA observed in both HS/saline and HS/control groups (FIG. 20A). Expression of Myh7b mirrored miR-499 levels, exhibiting a dose-dependent reduction upon antimiR-208a treatment. Furthermore, the dose-dependent regulation of Myh7 was confirmed by western blot (FIG. 20B).

AntimiR-208a does not Induce Changes in Cardiac Conductance or Signs of Toxicity While genetic deletion of miR-208a does not affect viability or cause gross morphological heart defects, a previous report mentioned that miR-208a might be required for proper heart electrophysiology. Although we never observed any overt abnormalities in the miR-208 knockout animals, to verify whether antimiR-208a treatment resulted in cardiac conductance effects we measured ECGs in both wild-type mice and diseased rats. Both species showed proper cardiac electrophysiology after antimiR-208a treatment for an extended period of time (not shown).

Independent of the route of administration, all mice and rats tolerated the antimiR-208a or control oligo well and exhibited normal behaviors, as determined by activity level and grooming throughout the study. Compared to saline, antimiR-208a or the control oligo did not induce baseline changes in body or additional tissue weights, including heart, kidney, liver, lungs or spleen up to 6 weeks after dosing (not shown). Neither antimiR-208a, nor control oligo treatment changed serum levels of the alanine aminotransferase (ALT) and aspartate aminotransferase (AST) liver enzymes in rats (not shown), suggesting that the oligonucleotides do not induce any overt liver toxicities.

AntimiR-208a Induces Specific Gene Expression Changes

To establish the effect of miR-208a inhibition on gene expression changes, we performed microarray analysis on Dahl rats on HS diet that were either injected with saline, antimiR-208a or control oligo. Compared to control oligo treated animals, antimiR-208a treated animals showed that 131 genes were significantly changed. Only 15 genes (with a false positive discovery rate of 67%) were significantly different between saline and control oligo injected animals, indicating the lack of effect on gene expression by the oligonucleotide chemistry itself. As visually demonstrated in a heat map, hierarchical clustering of the expression of the 131 significantly changed genes between control oligo and antimiR-208a treated hearts showed robust clustering of up- and down-regulated genes following antimiR-208a treatment, and validated there to be no gene expression response following control oligo treatment (not shown). Gene array analysis confirmed the significant down-regulation of Myh7 and Myh7b in response to antimiR-208a compared to control oligo ($-1.31$, $p=0.005$ and $-2.38$, $p=0.037$, respectively), while Thrap1, a previously characterized target, was increased ($1.56$, $p=0.49$). Out of the 13518 genes that were detected on the array, 289 genes were bioinformatically predicted to be miR-208 targets. Of these predicted targets, 28 genes showed increased expression with antimiR-208 treatment by microarray, of which several were confirmed by real-time PCR (not shown). Since the gene expression analysis was performed on cardiac samples from Dahl hypertensive rats that had been treated with saline, antimiR-208a or control oligo for 8 weeks, we suspect the remainder of the gene expression changes might be secondary to the direct gene regulatory effects of miR-208a inhibition.

BLAST analysis of the antimiR sequence against the rat genome indicated that the sequence of antimiR-208a shows close homology (at least 14 bases of complementarity) to four coding sequences; however none of these genes were regulated as determined by microarray analysis. Together these analyses indicate that the LNA-modified oligos are highly specific in targeting miR-208a without any gene expression changes induced by the chemistry class.

miR-499 is a Plasma Biomarker for antimiR-208a Efficacy

Detection of miRNAs in plasma during various disease settings is showing increasing diagnostic promise. To determine if there is a specific miRNA to correlate with antimiR-208a efficacy, we examined a panel of muscle related miRNAs during HS treatment. Several muscle specific miRNAs tested, such as miR-1 and -133, did not show significant differences between the groups tested (not shown). Strikingly, miR-499, while only showing modest increases in plasma detection under high salt, was significantly reduced in antimiR-208a treated animals, suggesting miR-499 can act as a plasma based marker for antimiR-208a efficacy. Additionally, miR-423-5p, plasma levels of which were previously correlated to human heart failure (24), was found to be reduced in animals treated with antimiR-208a.

Discussion

Data presented here indicate that therapeutic inhibition of miR-208 leads to a profound reduction in cardiac remodeling, which coincides with a significant improvement in survival and cardiac function during heart disease.

Antisense oligonucleotides can be used to effectively silence miRNAs in vivo (19-23). These antimiRs are chemically modified to ensure in vivo stability, specificity and high binding affinity to the miRNA of interest. LNA is a nucleic acid modification that introduces a thermodynamically strong duplex formation with oligonucleotides while enhancing specificity toward complementary RNA or DNA oligonucleotides (19-20). As a consequence of the high binding affinity, biological activity for LNA-modified antimiRs is attained with shorter oligonucleotides (8-16 bases) (25). Recently, the therapeutic applicability has been reported in rodents and non-human primates, where systemic delivery of unconjugated LNA-antimiR potently antagonized the liver-expressed miR-122 leading to an improvement in Hepatitis C Virus-induced liver pathology in chronically infected chimpanzees (23).

A key finding in the current study is that systemic delivery of LNA-modified oligonucleotides is effective in inducing potent and sustained silencing of miR-208 in the heart. Sustained miR-208a inhibition and the absence of an effect on the closely related miR-208b upon systemic delivery of antimiR-208a indicate in vivo stability and specificity. Based on the sustained miR-208a silencing and the downstream Myh7 regulation in time, it seems probable that antimiR-208a can accumulate in cardiac cells to silence all newly formed copies of miR-208a that are being produced by Myh6 transcription. This effect might be reinforced further by the general lack of turnover of cardiomyocytes, preventing dilution due to a decrease in the portion of cells that are targeted with the antimiR.

Although gene regulatory effects of miRNAs on direct targets are fairly immediate, miR-208a inhibition requires several weeks before it establishes an effect on Myh7b and Myh7 expression. We hypothesize that the delay in downstream biological effects is due to the requirement of alterations in the expression of many direct and indirect target genes of which the combined effects are required to induce the change. A comparable phenomenon was observed in response to miR-122 inhibition, which induces a lowering in plasma cholesterol, but not until weeks after antimiR treatment while gene expression changes were immediate (19-20). Nonetheless, the effect on Myh7b and Myh7 expression phenocopies the effects seen in the miR-208 genetic deletion (12), indicating miR-208a is effectively silenced.

The therapeutic effects of antimiR-208a in the Dahl hypertensive rat provide strong evidence that subcutaneous delivery is sufficient to effectively deliver antimiRs to the heart in vivo and that miR-208a inhibition prevents cardiac remodeling, functional deterioration and lethality during heart disease. Although it remains unclear whether these effects arise solely from effects on the cardiomyocyte due to miR-208a inhibition, or whether there are extra-cardiac effects in response to miR-208a inhibition currently unknown, the dose-responsiveness and the absence of an effect in animals treated with a control chemistry strongly suggest the observed effects are due to a lowering in miR-208a levels. Ongoing experiments will indicate whether this therapeutic benefit can be established in multiple models of heart failure and whether combined antimiR dosing against miR-208a and miR-499 in parallel will elucidate the observed effects more rapidly. While the initial rodent data look very encouraging and no adverse side-effects were observed upon antimiR treatment, extensive analyses will be required to determine the long-term safety of such agents in various settings.

Recently, miRNAs were detected in serum and plasma of humans and animals, opening the possibility of using miRNAs as diagnostic biomarkers of various diseases, including heart disease (24, 26-28). Plasma miRNA analysis shows that, in addition to several other miRNAs changing, antimiR-208a treatment results in a diminished detection of miR-499 in blood serum, which parallels the decrease in cardiac expression of Myh7b/miR-499 in response to antimiR-208a treatment. Given the correlation between cardiac and plasma based miR-499 levels and efficacy of antimiR-208a, these data suggest plasma miR-499 levels might act as a biomarker of effective delivery of antimiR-208a to the heart when moving into patients.

Myosin and subsequent myomiR expression differs significantly between species. While Myh6/miR-208a is the predominant myosin/myomiR isoform in the hearts of smaller rodents, larger mammals express more Myh7/miR208b (17). While miR-208a and 208b have overlapping seed sequence, they differ 3 bases in their 3' region. Subsequent pharmacokinetic and efficacy studies in larger mammals will be required to establish whether inhibition of miR-208a, miR-208b or both miR-208 isoforms is required to establish a comparable therapeutic effect in larger species. Additionally, since therapeutic use of miR-208 inhibition will likely be a combination therapy with current standard of care in heart failure patients, it will be important to assess whether anti-miR-208a, in conjunction with these current treatments, adds to the beneficial effects of these drugs.

Taken together, this study demonstrates that subcutaneous delivery of LNA-based antimiRs can effectively target the heart, and further validates miR-208 as a target during cardiac disease.

Methods

Animal Procedures.

All animal protocols were approved by the Institutional Animal Care and Use Committee of miRagen Therapeutics, Inc.

Animals and Delivery of LNA-Modified antimiRs.

The LNA-antimiR oligonucleotides were synthesized at miRagen Therapeutics, Inc. as unconjugated and fully phosphorothiolated oligonucleotides perfectly complementary to the 5' region of the mature miR-208a sequence. The LNA control oligonucleotide consisted of a sequence directed against a *C. elegans* specific miRNA. Unless else indicated, in vivo delivery of the oligonucleotide chemistries was achieved by low pressure intravenous (i.v.) injections via the tail vein of either adult male C56Bl6 mice or adult male Dahl Salt-sensitive rats (Harlan, Indianapolis). All chemistries were dissolved and injected in a comparable end volume of saline after which the animals were examined for obvious side effects of the chemistries. Tissue samples were collected at the indicated timepoints for molecular or histological examination. Dahl rats were maintained on 0.25 NaCl or placed on 4% or 8% NaCl diet at 8 weeks of age (Harlan, Indianapolis).

Quantitative Real-Time PCR Analysis.

For in vivo real-time PCR analysis, RNA was extracted from cardiac tissue using Trizol (Invitrogen) after which two µg RNA from each tissue sample was used to generate cDNA using Super Script II reverse transcriptase per manufacturer's specifications (Invitrogen). To detect the level of miR-208 RT-PCR was performed using the Taqman MicroRNA assay (Applied Biosystems, ABI) according the manufacturer's recommendations, using 10-100 ng of total RNA. The expression of a subset of genes was analyzed by quantitative real time PCR using Taqman probes purchased from ABI.

Northern Blot Analysis.

Total RNA was isolated from cardiac tissue samples by using Trizol reagent (Gibco/BRL). Northern blots to detect microRNAs were performed as described previously described. A U6 probe served as a loading control (IDT). 10 ug of total RNA from cardiomyocytes or heart tissue was loaded on 20% acrylamide denaturing gels and transferred to Zeta-probe GT genomic blotting membranes (Bio-Rad) by electrophoresis. After transfer, the blots were cross-linked and baked at 80° C. for 1 hr. To maximize the sensitivity of miRNA detection, oligonucleotide probes were labeled with the Starfire Oligos Kit (IDT, Coralville, Iowa) and $\alpha$-$^{32}$P dATP (Amersham or Perkin Elmer). Probes were hybridized to the membranes overnight at 39° C. in Rapid-hyb buffer (Amersham), after which they were washed twice for 10 minutes at 39° C. with 0.5×SSC containing 0.1% SDS. The blots were exposed and quantified by PhosphorImager analysis (GE HealthCare Life Sciences) and a U6 probe served as a loading control (ABI). The intensity of the radioactive signal was used to quantify the fold change in expression using a phosphorimager and ImageQuant (Bio-Rad).

Western Blot Analysis.

For Western blot analysis, Myosin was extracted from cardiac cells or tissue as described (29). MHC isoforms were detected by loading 0.1 ug protein lysate on a 4-15% gradient gel and separated by SDS PAGE and Western blotting was performed with mouse monoclonal anti-myosin (slow, skeletal M8421) (Sigma, Mo.), which is highly specific for Myh7.

Biodistribution Assay.

A sandwich hybridization assay was used for the quantification of antimiR-208a in plasma and tissue samples. Probes for the hybridization assay were synthesized using 2'Ome, and LNA modified nucleotides and are: bTEG-mU;1A;mA; 1G;mA;1C;mG (capture probe) and mA;1G;mC;1A;mA;1A; mA;1A;mG-6FAM (detection probe). Detection was accomplished using anti-fluorescence-POD, Fab fragments (Roche) and TMB Peroxidase Substrate (KPL). Standard curves were generated using non-linear logistic regression analysis with 4 parameters (4-PL). The working concentration range of the assay was 2-536 ng/ml. Tissue samples were prepared at 100 mg/ml by homogenizing in 3M GITC buffer (3 M guanidine isothiocyanate, 0.5 M NaCl, 0.1 M Tris pH 7.5, 10 mM EDTA) for 2×30 seconds using an MP FastPre-24 at a speed setting of 6.0. Plasma samples and tissue homogenates were diluted a minimum of 50-fold in 1 M GITC Buffer (1 M guanidine isothiocyanate, 0.5 M NaCl, 0.1 M Tris pH 7.5, 10 mM EDTA) for testing.

Echocardiography.

Cardiac function was evaluated by two-dimensional transthoracic echocardiography on sedated rats (2-2.5% isoflurane) using a Visual Sonic Ultrasound system with a 30 MHz transducer. The heart was imaged in a parasternal short-axis view at the level of the papillary muscles, to record M-mode measurements, determine heart rate, wall thickness, and end-diastolic and end-systolic dimensions. Fractional shortening (defined as the end-diastolic dimension minus the end-systolic dimension normalized for the end-diastolic dimension) was used as an index of cardiac contractile function. Diastolic function was assessed using trans-mitral flow Doppler from an apical 4-chamber view to measure E/A ratio, isovolumic relaxation time and deceleration time of E wave velocity.

Surface ECG Measurement.

Mice were anesthetized with 2% isoflurane in 200 mL/min $O_2$ and rats were anesthetized with 2% isoflurane in 500 mL/min breathing air via nosecone. Body temperature for mice and rats was maintained at 37°-38° C. via a Homeothermic Warming System (Kent Scientific) or a heat lamp and warming platform (Visual Sonics). Lead II electrocardiograms were recorded for 10 min using subcutaneous needle electrodes and an Iworx data acquisition system sampling at 1 kHz. Using Labscribe software (Iworx), tracing were analyzed after 2, 4, 6, 8 and 10 minutes and were inspected for normal sinus rhythm; approximately 40 beats at each timepoint were analyzed using computerized techniques to quantify signal intervals (HR, PR, QRS, QT and QTc).

Histology.

Tissues used for histology were incubated in Krebs-Henselheit solution, fixed in 4% paraformaldehyde, sectioned, and processed for hematoxylin and eosin (H&E) and picrosirius red staining or in situ hybridization by standard techniques (30). Images of approximately 100 cardiomyocytes per animal in cross section were captured from the H&E stained sections. Cardiomyocyte cross sectional areas were measured with Image-Pro Plus software and a mean was determined for each animal. Perivascular fibrosis images were taken from epi, mid and endocardial regions from the pricrosirius red stained sections from each animal. Image-Pro plus software was used to determine the total vessel wall area including perivascular fibrosis. The luminal area was subtracted from total vessel wall area. Perivascular fibrosis was determined via color segmentation and reported as a % of the total vessel wall area.

Gene Expression Analysis.

Microarray profiling was performed on Illumina RatRef-12 BeadChip arrays by a service provider (Expression Analysis, Durham, N.C.). Total RNA was isolated from cardiac tissue as described above. Analysis of differential gene expression was performed by the service provider using PADE (Permutation Analysis of Differential Expression). Note that if a gene probe does not have detection p-value≤0.05 in all 12 arrays, then that gene is omitted from subsequent analysis. Differential expression graphs were provided by the service provider. Gene clustering was performed using Cluster 3.0 and heat map images were generated in Java TreeView. Gene ontology was performed using the online tool found at www.pantherdb.org. Predicted miR-208 gene targets in the rat were found using targetscan.org (TargetScan), pictar.mdc-berlin.de (Pictar), and microrna.org (miRanda). Of all the gene targets predicted by miRanda, only those with a mirsvr score of <−0.1 were included in the analysis. For the identification of miR-208 targets, a p-value cut-off for differential expression of ≤0.05 was used.

Quantitative Real-Time PCR Analysis from Plasma.

RNA from plasma samples was isolated using Trizol LS Reagent (Invitrogen), using the manufacturer's protocol. Prior to RNA isolation, 250 pmol of two different synthetic *C. elegans* miRNA sequences were added to serve as internal controls for normalization of target miRNAs. The *C. elegans* sequences used were cel-miR-2 (UAUCACAGCCAGCU-UUGAUGUGC (SEQ ID NO:92)), and cel-lin-4 (UC-CCUGAGACCUCAAGUGUGA (SEQ ID NO:93)) (Dharmacon). The final RNA pellet was re-suspended in a final volume equal to the initial plasma volume and 5 µl was used for subsequent RT-PCR reactions, as described above.

Statistical Analysis.

One-way ANOVA and Newman-Keuls Multiple Comparison Post-test were used to determine significance. P<0.05 was considered statistically significant.

Example 4

Inhibitor Dosing in Non-Human Primates

Figure 22:
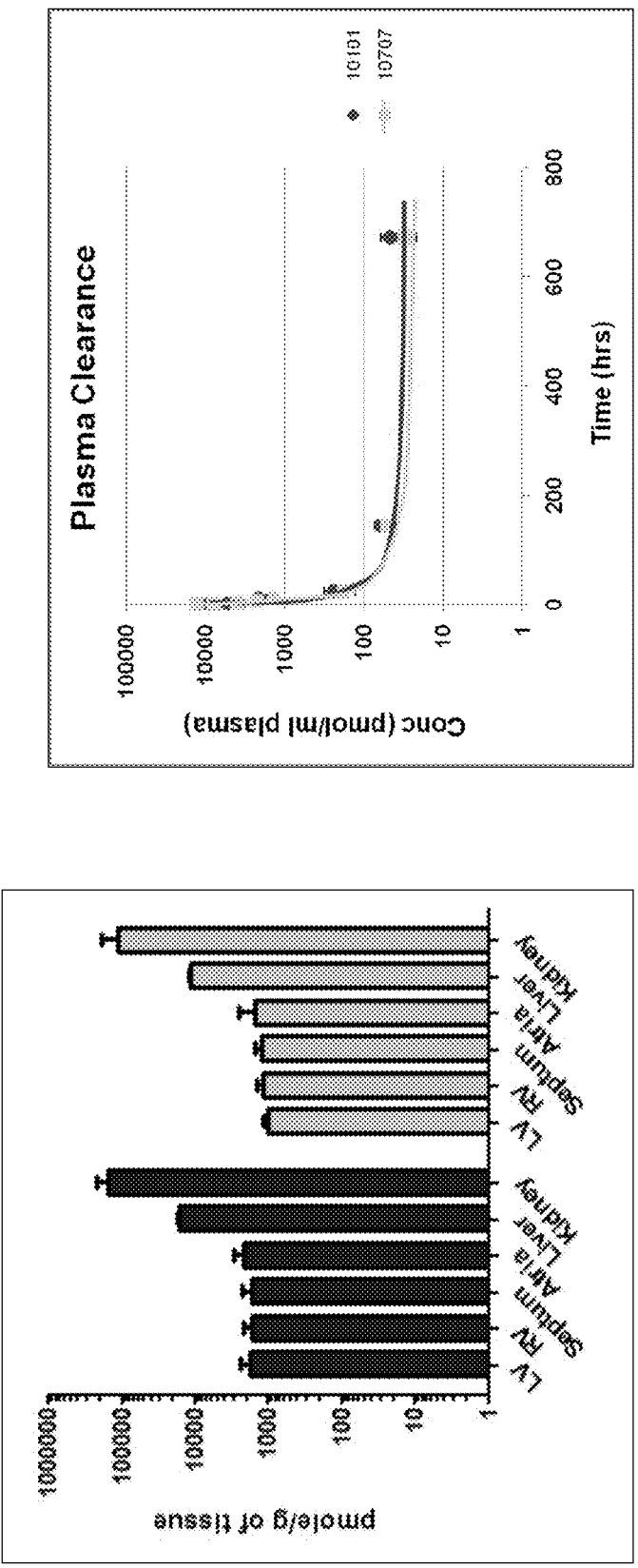
FIG. 22. Tissue and plasma distribution in African Green Monkeys (~3 kg). Antimirs 10101 (antimiR-208a) and 10707 (antimiR-208b) were administered three times at a dose of 25 mg/kg by the saphenous vein, and drug plasma clearance determined (right panel). Tissue was collected after four weeks and assayed for inhibitor (dark bars, M-10101; light bars, M-10707).

Antimirs 10101 and 10707 were administered three times at a dose of 25 mg/kg to African Green Monkeys (~3 kg) by the saphenous vein. Tissue was collected after four weeks and assayed for inhibitor. Results are shown in FIG. 22. Right panel shows drug plasma clearance. Left panel shows tissue and plasma distribution (dark bars, M-10101; light bars, M-10707).

Figure 23:
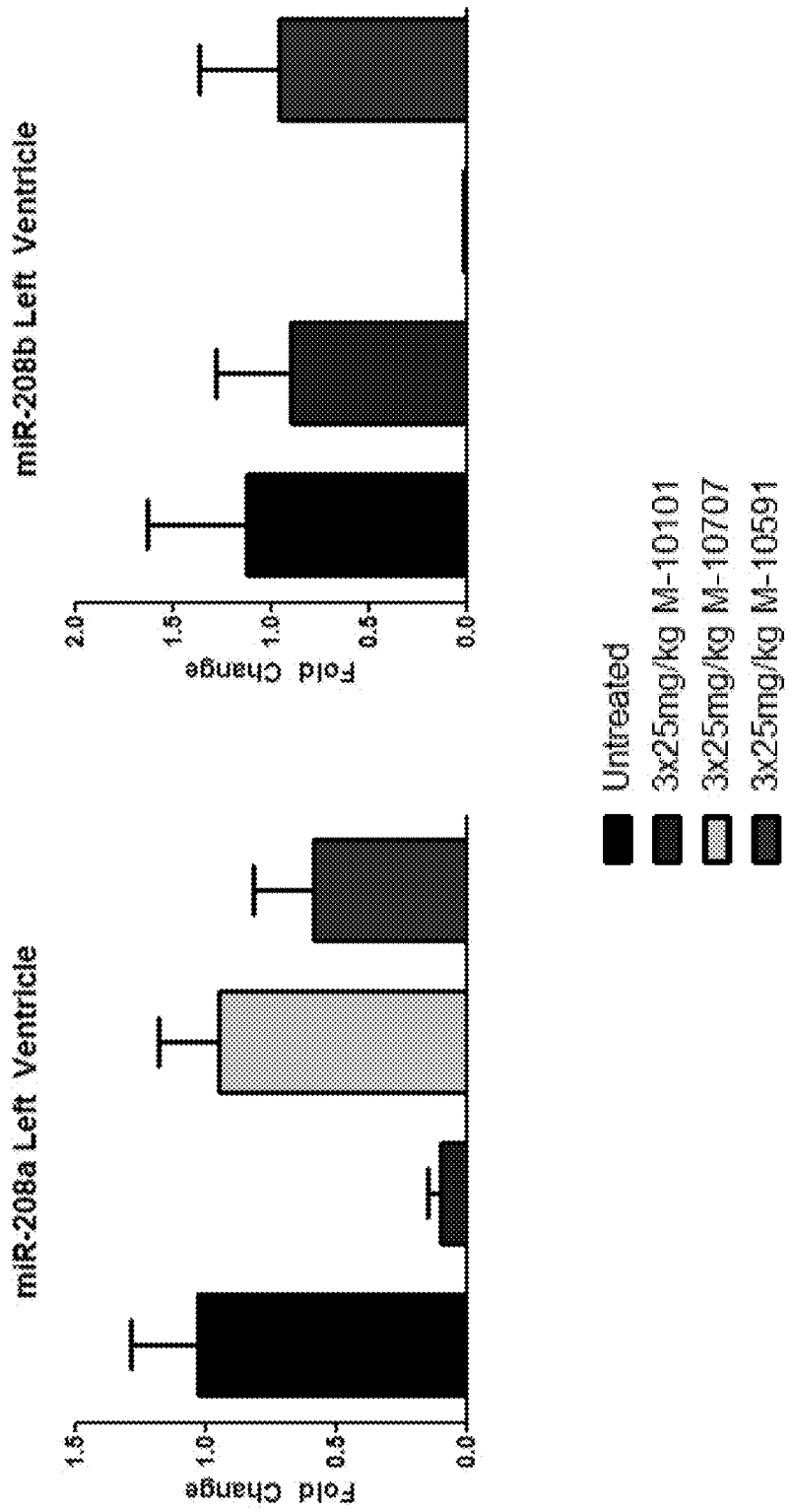
FIG. 23. Specific miRNA target inhibition in African Green Monkeys. Left panel shows changes in miR-208a expression in left ventricle (left to right: untreated, M-10101, M-10707, M-10591). Right panel shows changes in miR-208b in left ventricle (left to right: untreated, M-10101, M-10707, M-10591). As shown, with only two nucleotide differences between M-10101 and M-10707, the antimiRs are specific for their target miR (miR-208a and miR-208b, respectively).

FIG. 23 shows miRNA target inhibition. Left panel shows changes in miR-208a expression in left ventricle (left to right: untreated, M-10101, 10707, 10591). Right panel shows changes in miR-208b in left ventricle (left to right: untreated, M-10101, M-10707, M-10591). With only two nucleotide differences between M-10101 and M-10707, the antimiRs are specific for their target miR (miR-208a and miR-208b, respectively).

Figure 24:
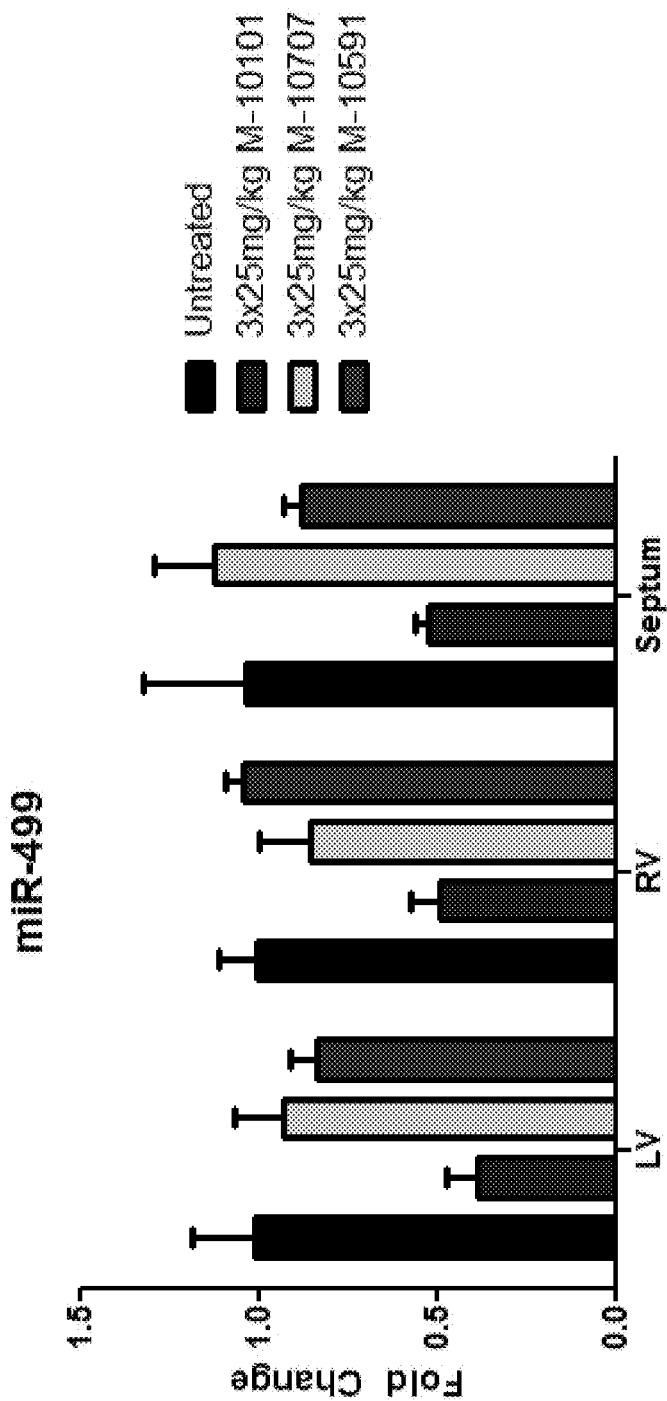
FIG. 24. Mir-499 levels after treatment. Levels are shown for left ventricle (LV), right ventricle (RV), and septum. Bars are, from left to right, untreated, M-10101, M-10707, and M-10591.

FIG. 24 shows Mir-499 levels after treatment. Levels are shown for left ventricle (LV), right ventricle (RV), and septum. Bars are, from left to right, untreated, M-10101, M-10707, and M-10591.

Example 5

Molecular Analysis of antimiR-208a Treatment

Seven antimiR-208a chemistries where selected that showed efficacy in vivo, each having 9 LNAs and 7 DNA nucleotides. The compounds were dosed at 25 mg/kg s.c. in mice, with takedown at day 4. miRs and target expression were measured. Compounds were: M-10101, M-10680, M-10681, M-10682, M-10683, M-10673, and M-11184 (see Table 1).

Hepatic and renal toxicology markers did not show significant increases from saline (data not shown).

Figure 25:
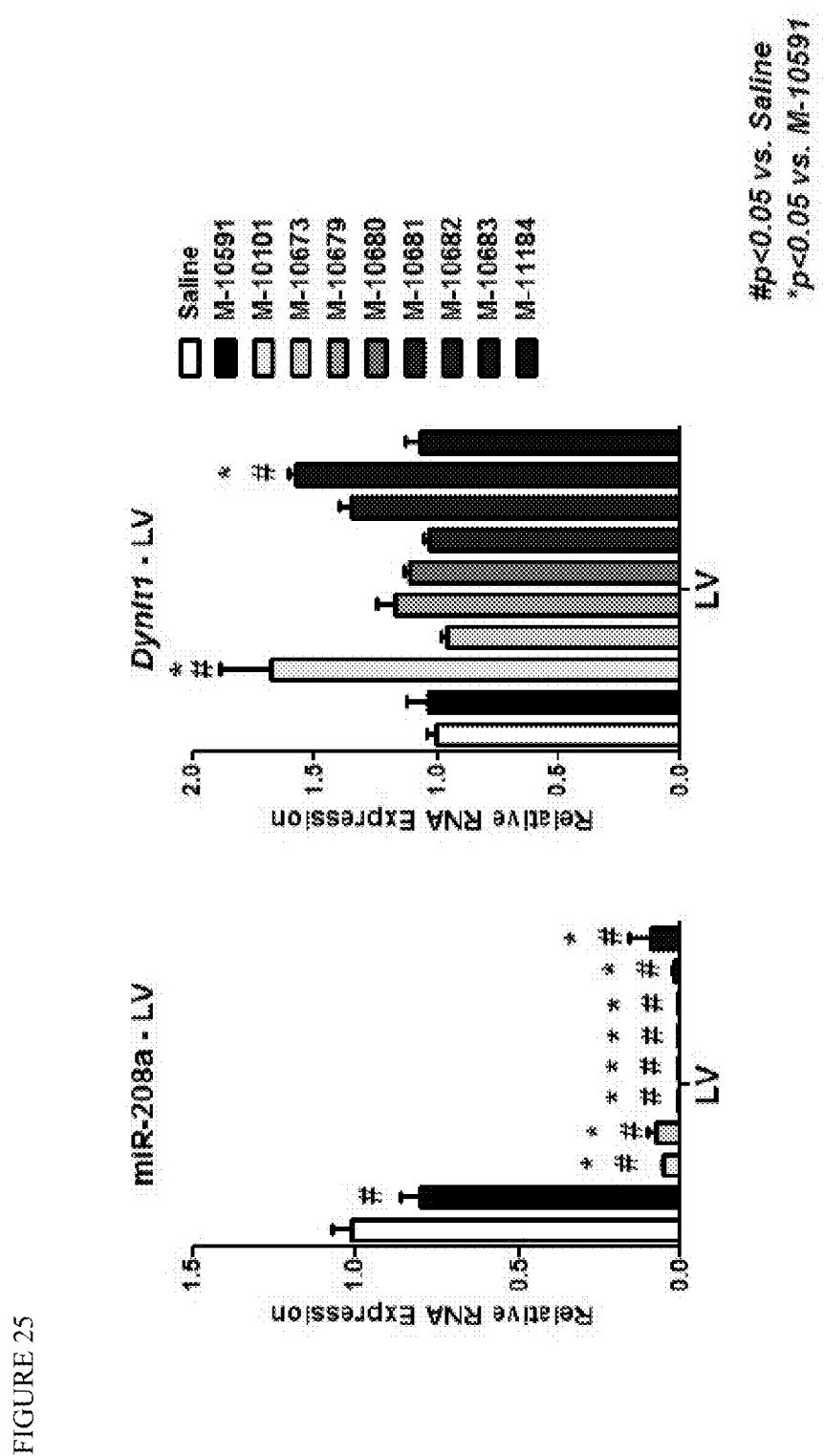
FIG. 25. antimiR-208a compounds with different chemistry patterns show miR-208a knockdown in the left ventricle when administered to rats at 25 mg/kg subcutaneously. The compounds show different levels of target de-repression.

The compounds show varying levels of target de-repression. M-10101 and M-10683 were particularly effective. FIG. 25 shows expression of miR-208a and Dynit1.

Figure 26:
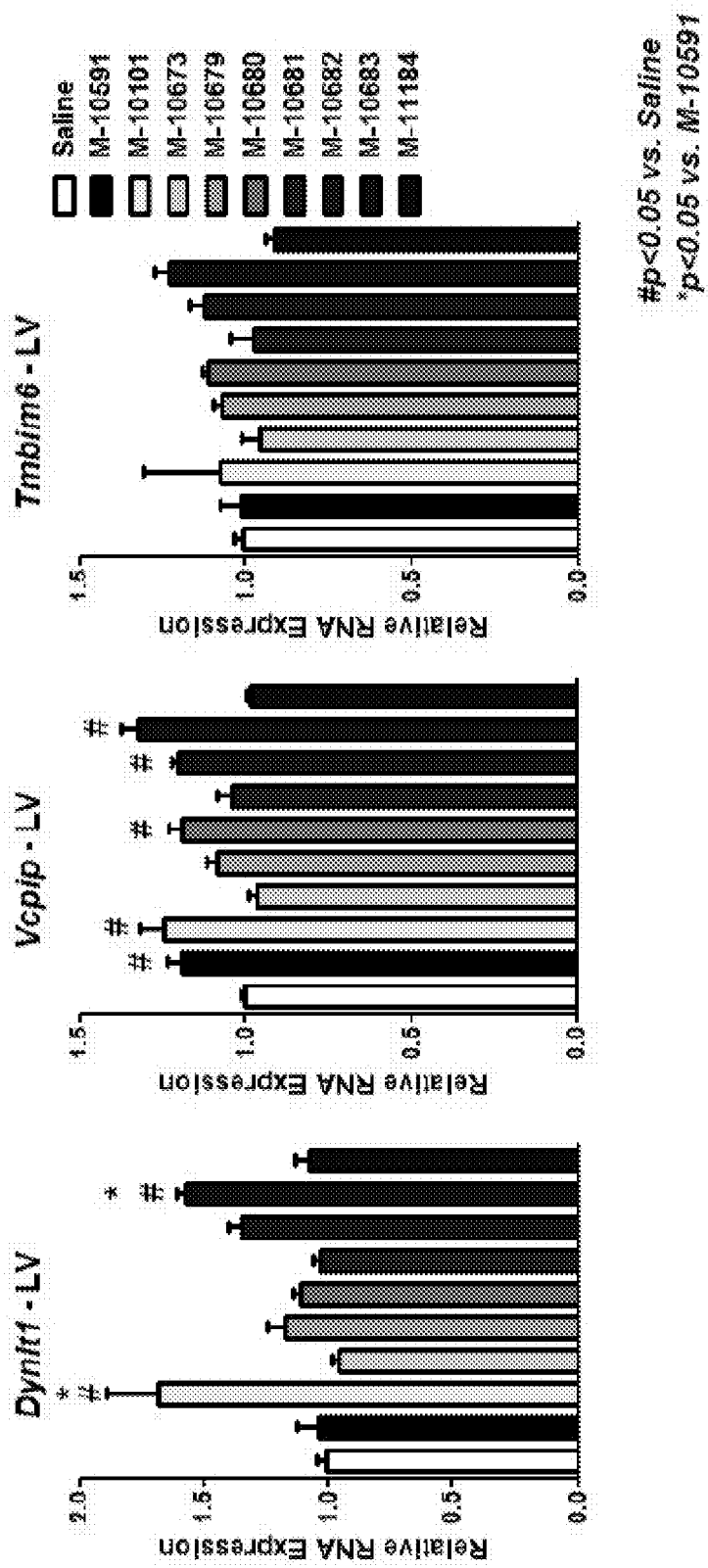
FIGS. 26 to 28. Target de-repression with antimiR-208a compounds as in FIG. 25.
Figure 27:
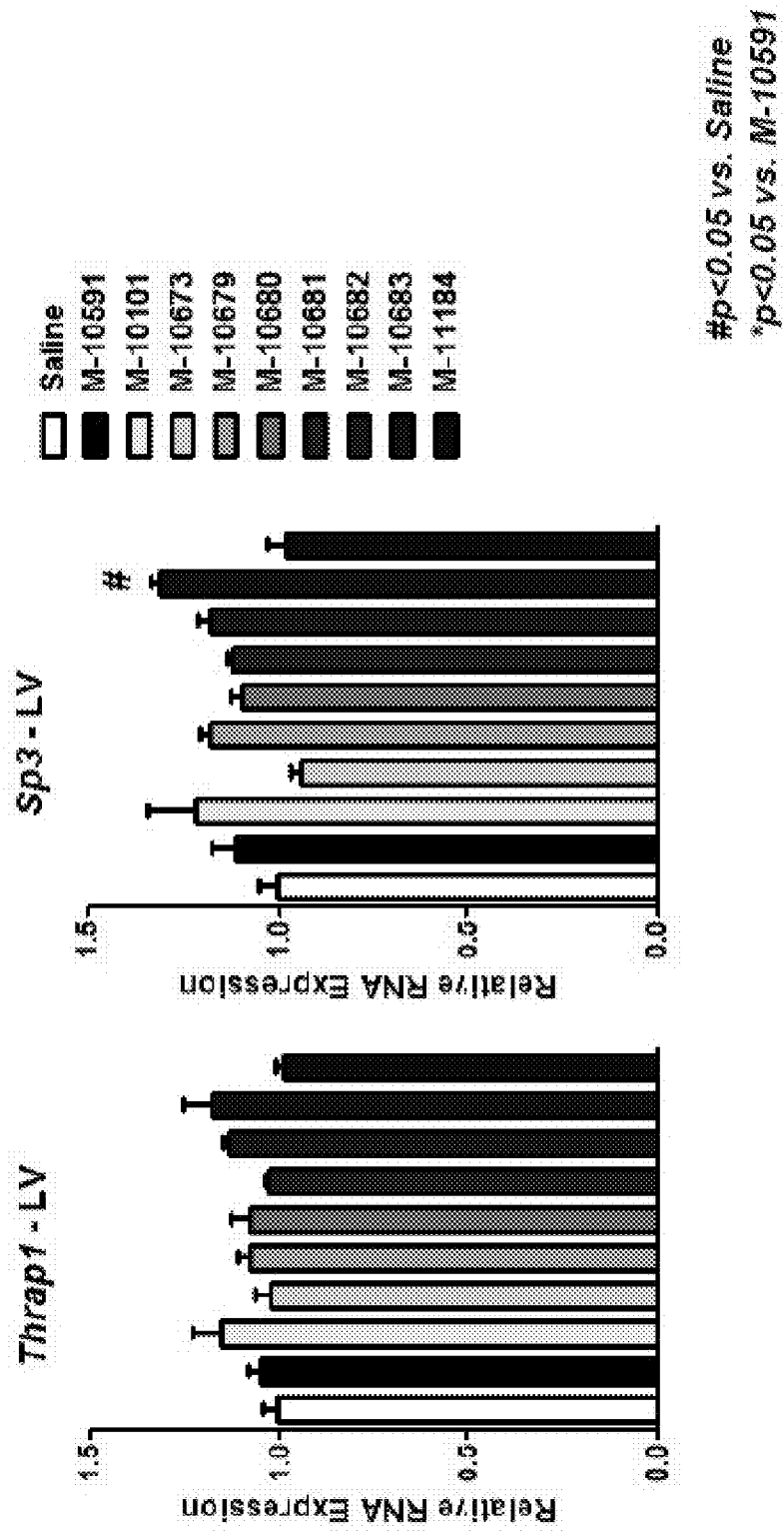
Figure 28:
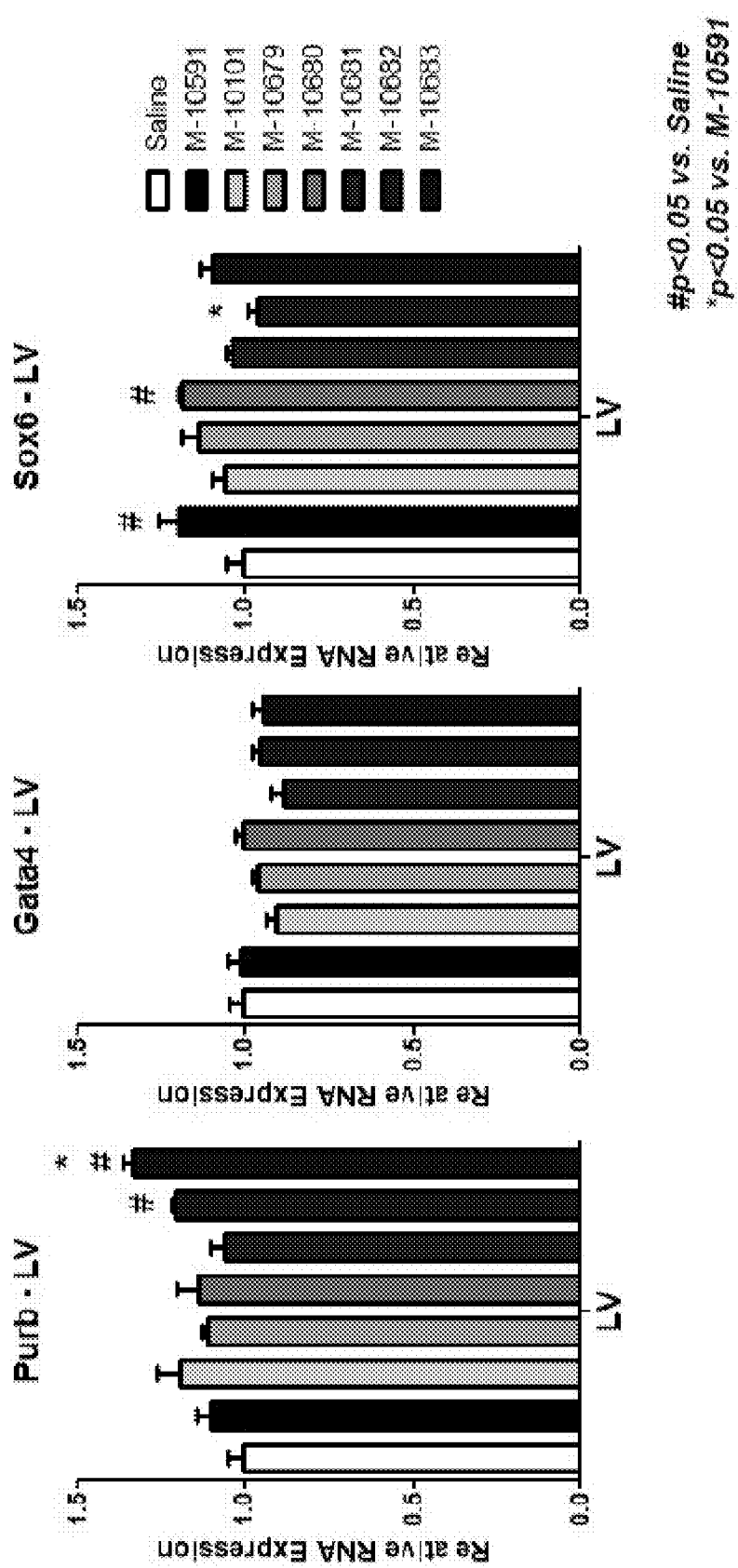

FIG. 26 shows expression of Dynit1, Vcpip, and Tmbim6. FIG. 27 shows expression of Thrap1 and Sp3. FIG. 28 shows expression of Purb, Gata4, and Sox6.

Figure 29:
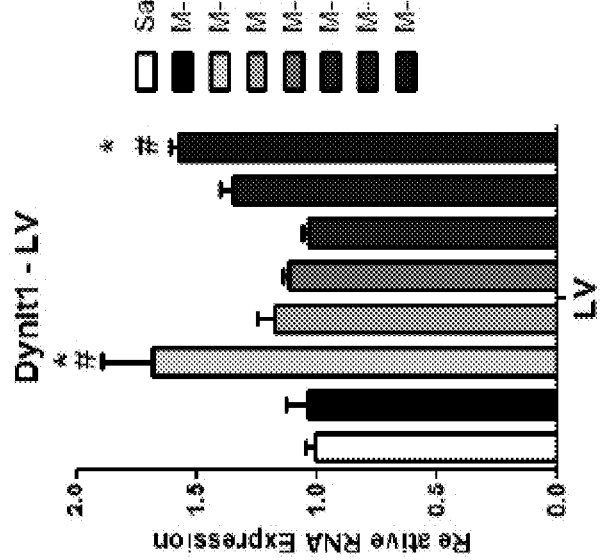
FIG. 29. Antimir-208a treatment increases miR-19b plasma levels in unstressed rodents (SD rats).
Figure 29:
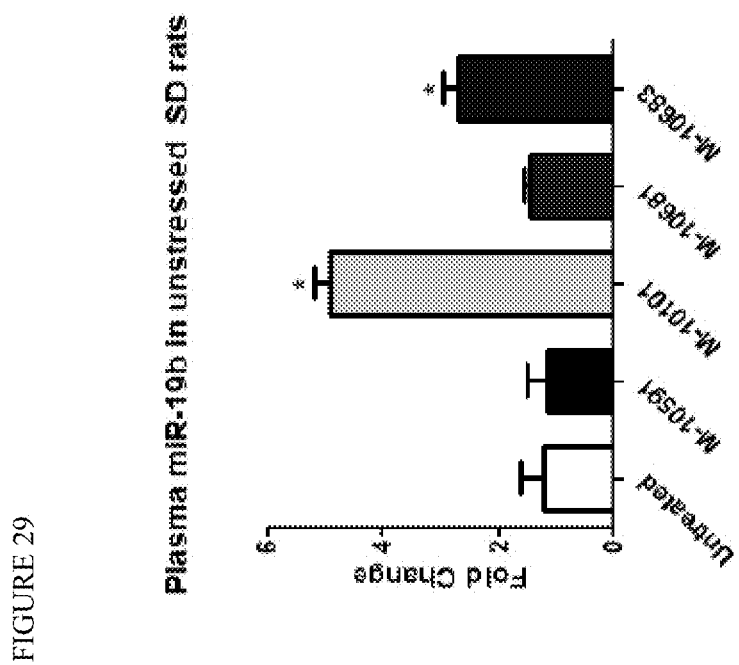

As shown in FIG. 29, antimir-208a treatment increases miR-19b plasma levels in unstressed rodents (SD rats).

Figure 30:
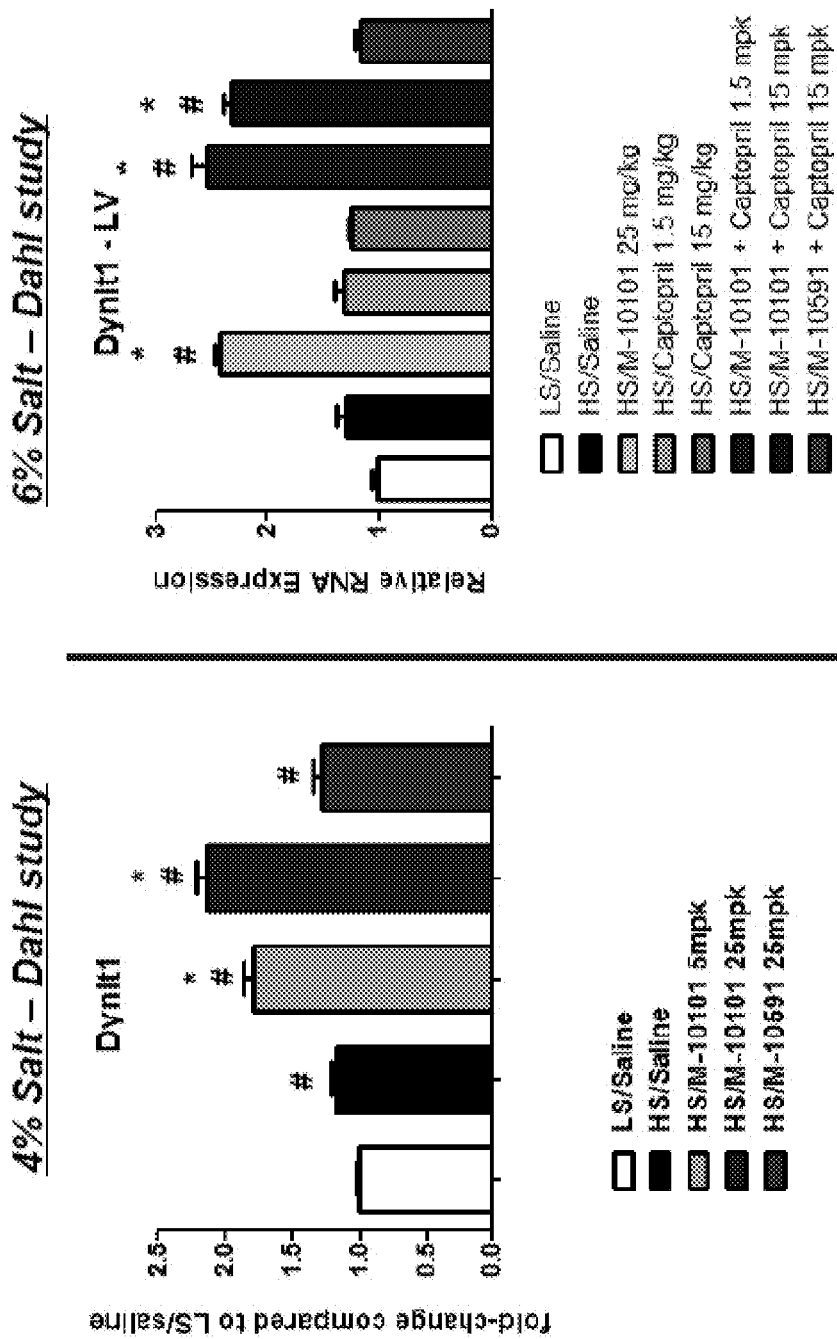
FIG. 30. Studies with salt-sensitive rats show that the degree of target de-repression depends on degree of stress. Dynit1 shows more robust de-repression with 6% salt stress.
Figure 31:
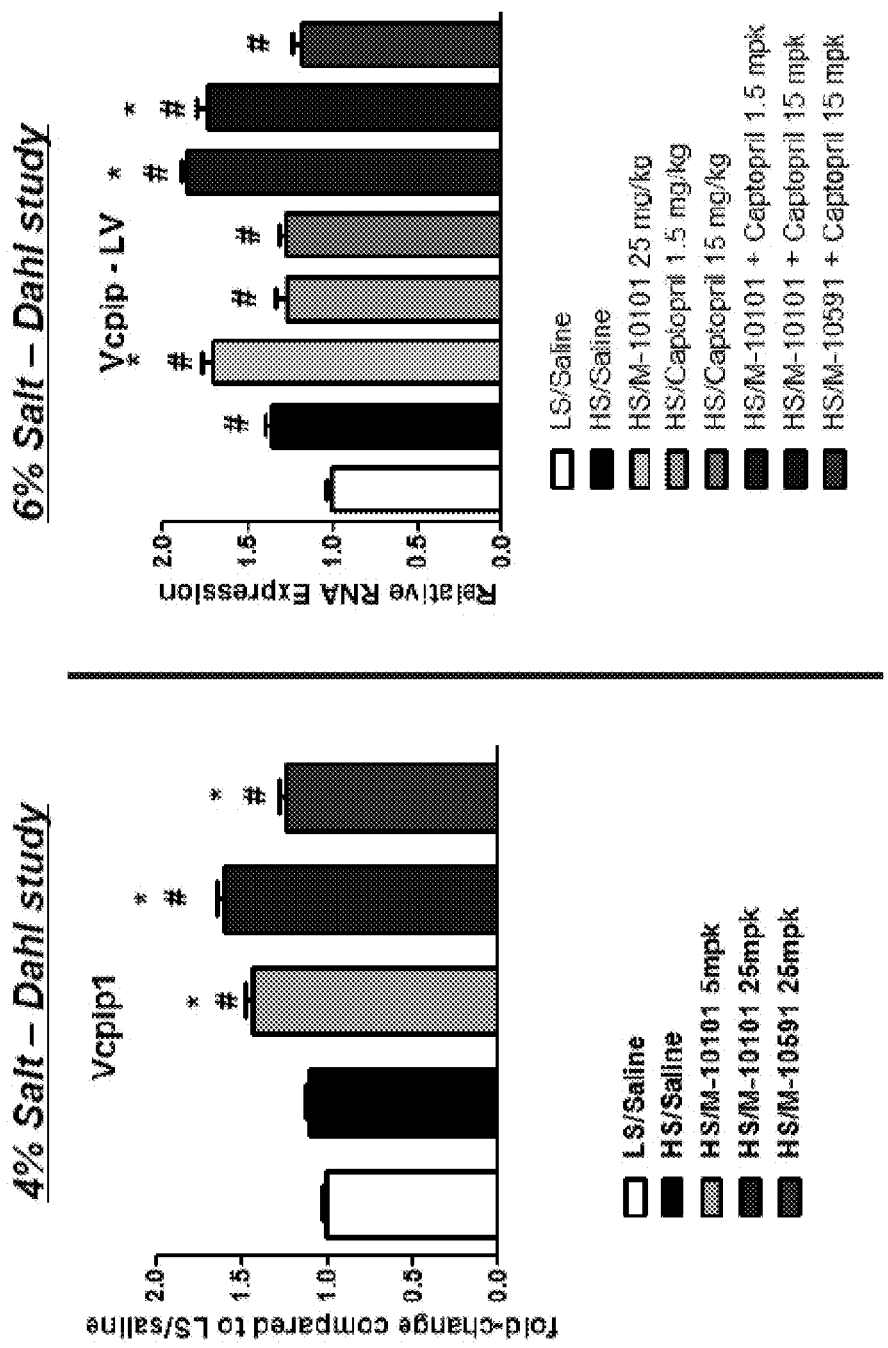
FIG. 31. Degree of target de-repression (Vcpip1) at different degrees of stress (4% and 6% salt diets) in salt sensitive rat model.
Figure 32:
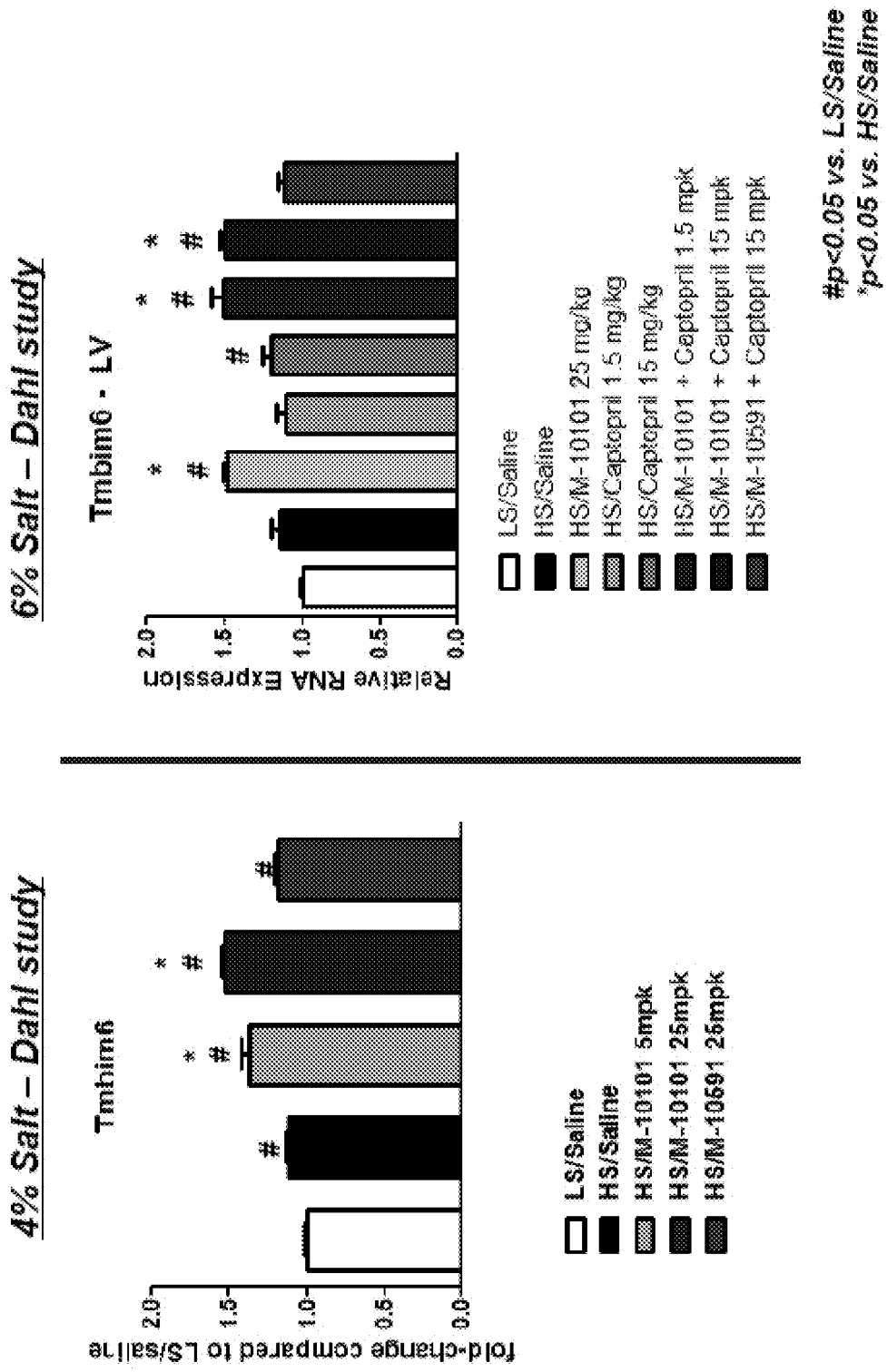
FIG. 32. Degree of target de-repression (Tmbim6) at different degrees of stress (4% and 6% salt diets) in salt sensitive rat model.

The degree of target de-repression depends on the degree of stress, as shown using the Dahl salt-sensitive rat model. FIG. 30 shows the results for Dynit1 expression at 4% salt and 6% salt. Dynit1 shows more robust de-repression at 6%. FIG. 31 shows results for the target Vcpip1. FIG. 32 shows results for the target Tmbim6.

Figure 33:
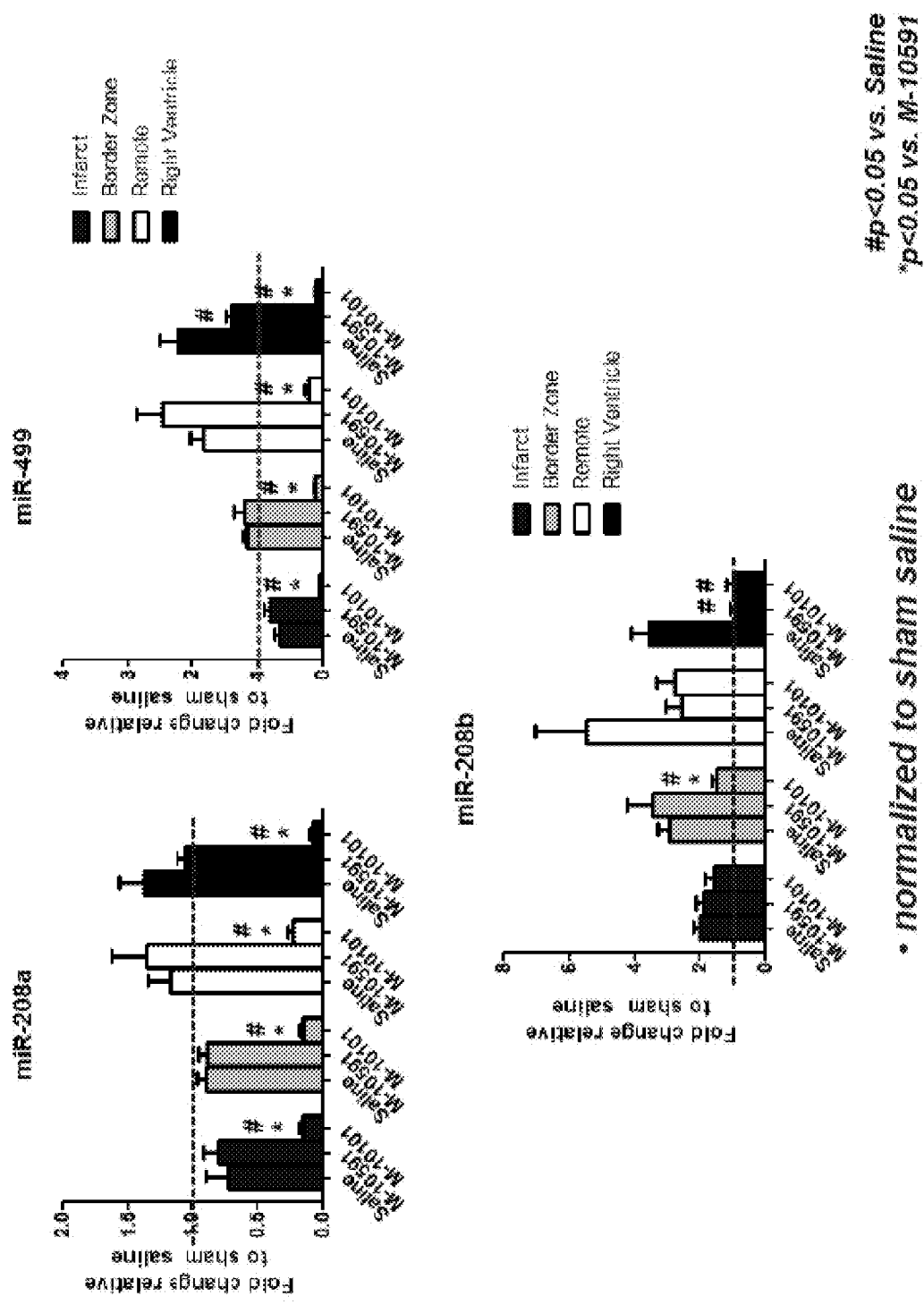
FIG. 33. Degree of miR inhibition in different regions of the heart, showing that more stressed regions show greater effect.
Figure 34:
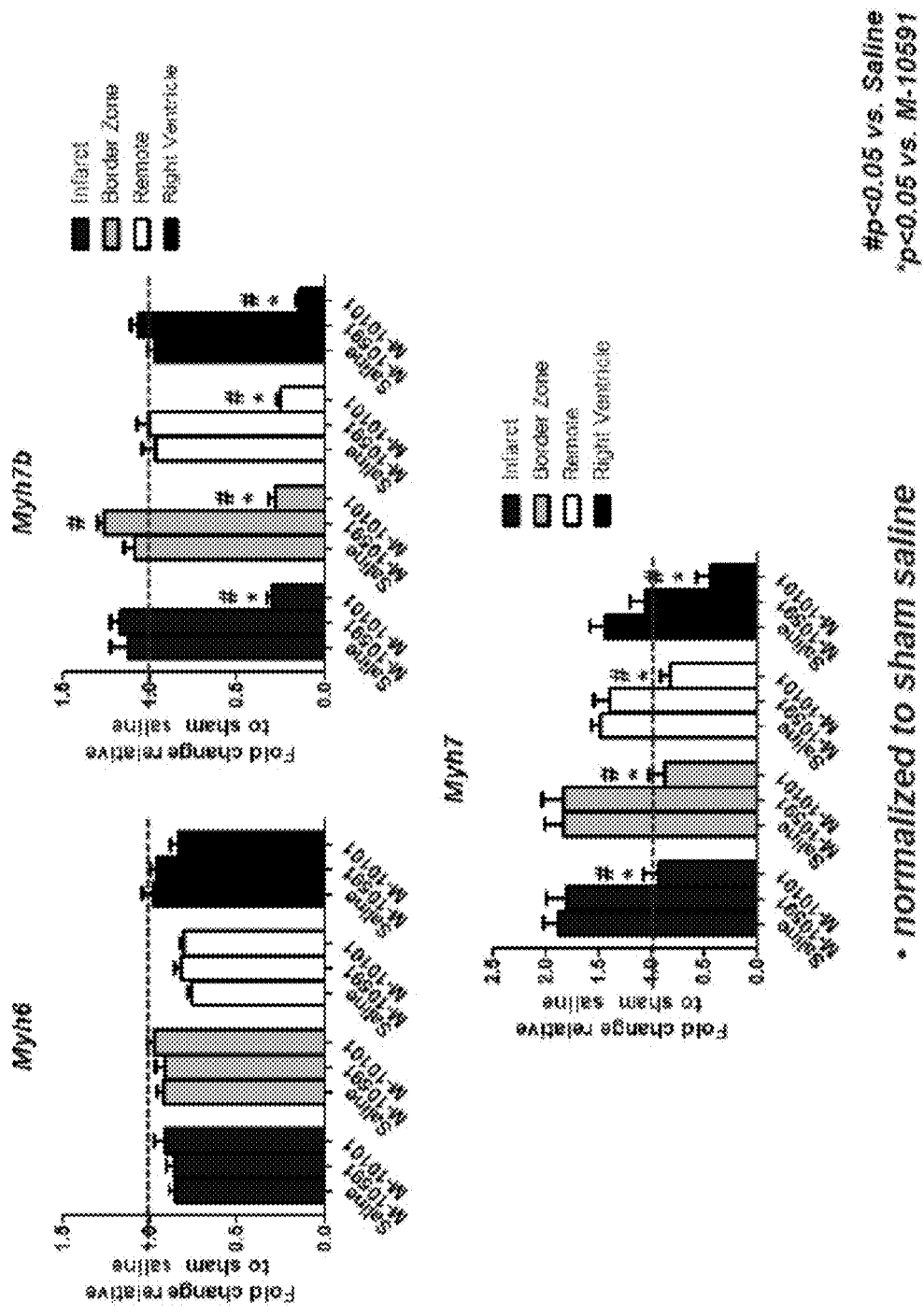
FIG. 34. Degree of myosin expression in different regions of the heart upon antimiR-208a treatment, showing that more stressed regions show greater effect.
Figure 35:
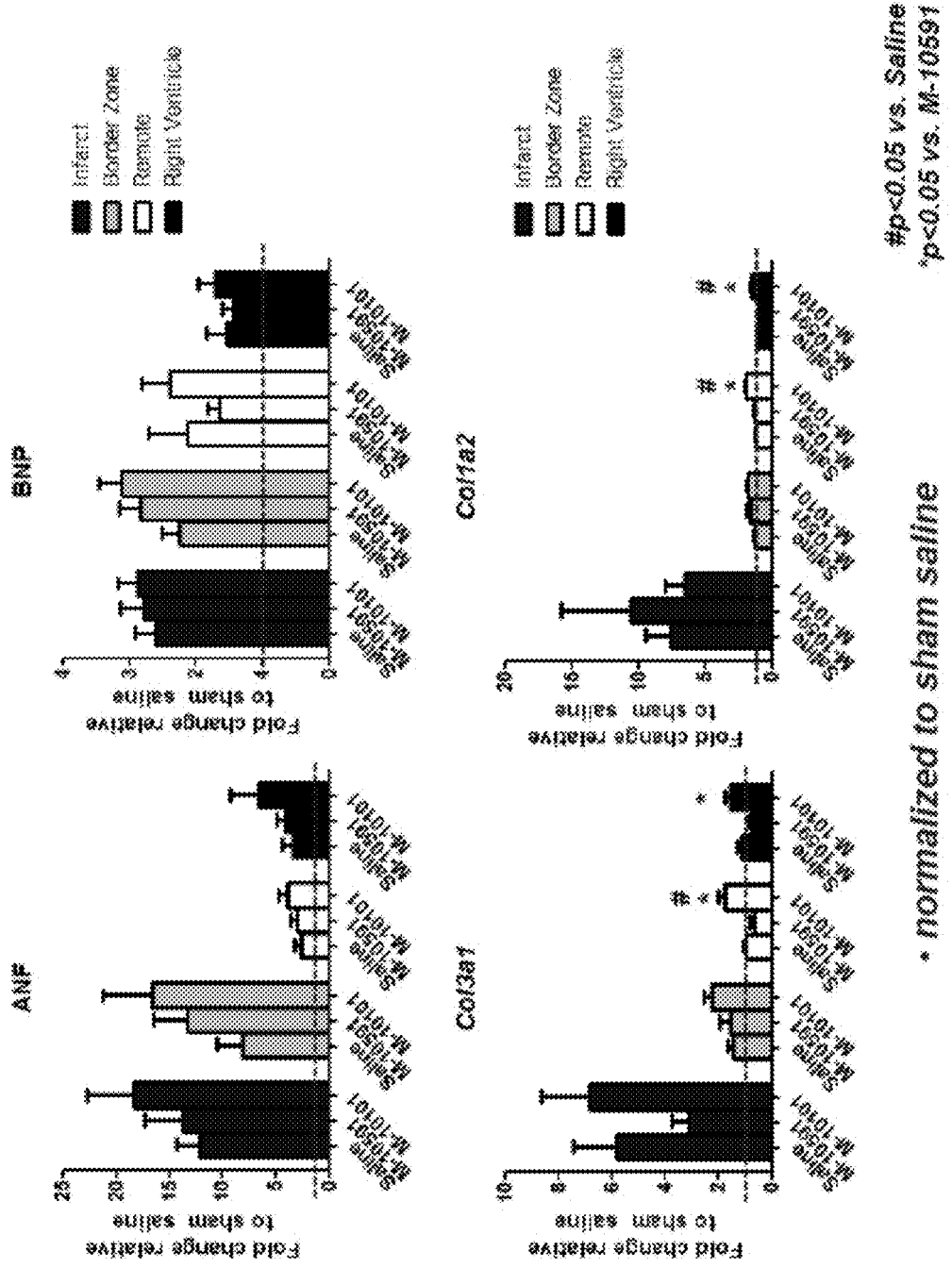
FIG. 35. Degree of expression of certain cardiac stress markers in different regions of the heart upon antimiR-208a treatment.
Figure 36:
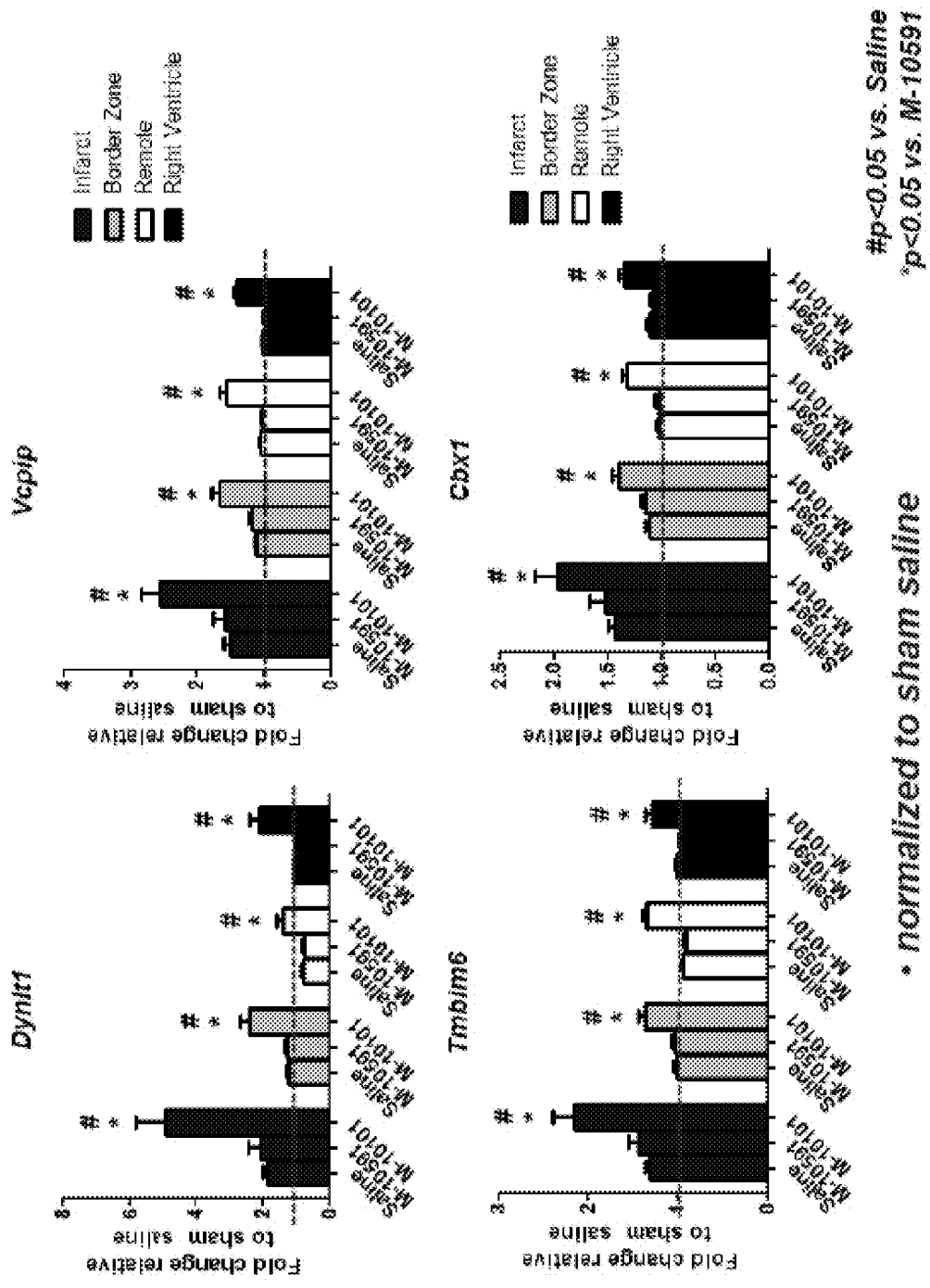
FIG. 36. Degree of target expression in different regions of the heart upon antimiR-208a treatment, showing that more stressed regions show greater effect.
Figure 37:
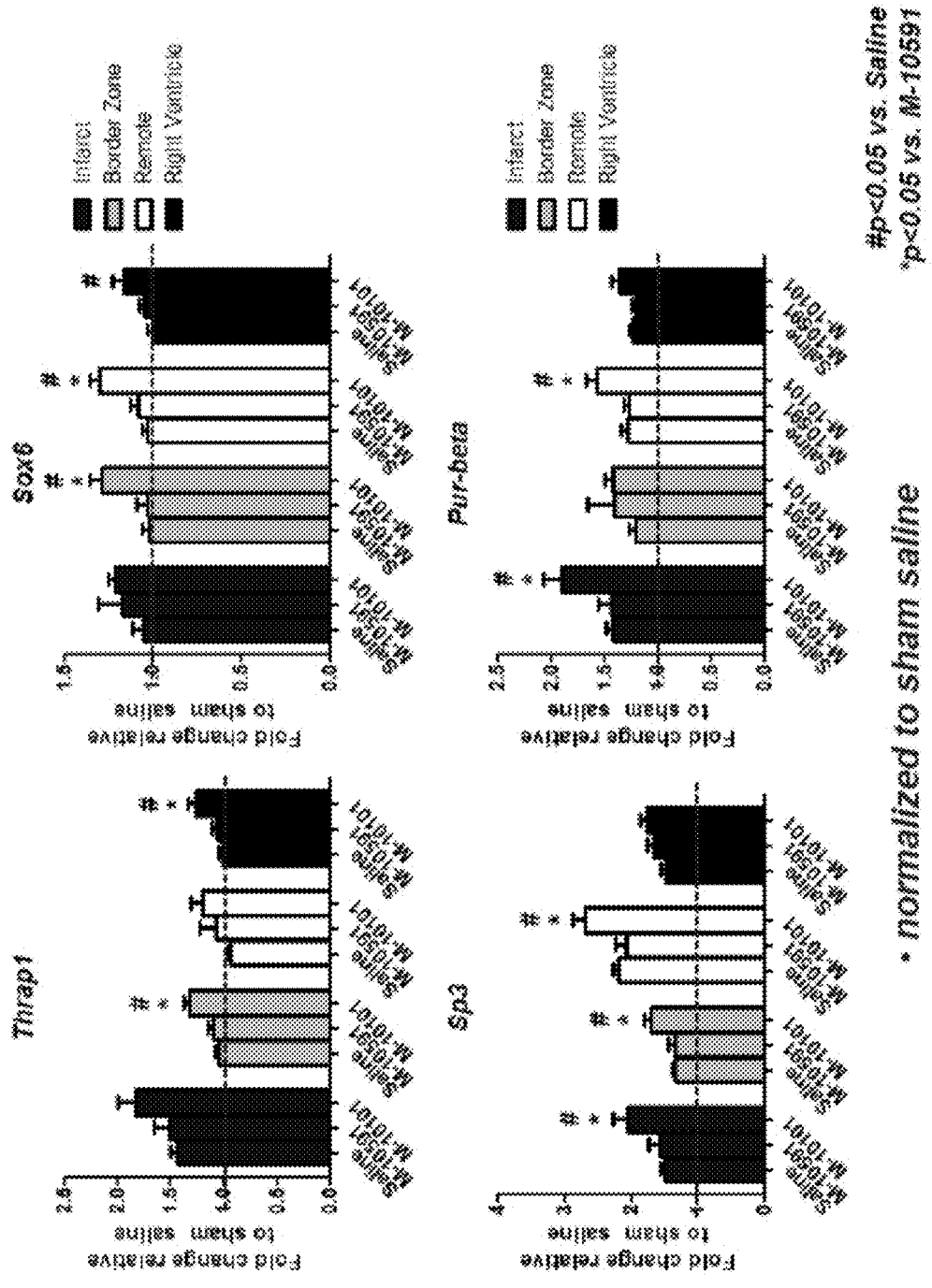
FIG. 37. Degree of target expression in different regions of the heart upon antimiR-208a treatment, showing that more stressed regions show greater effect.
Figure 38:
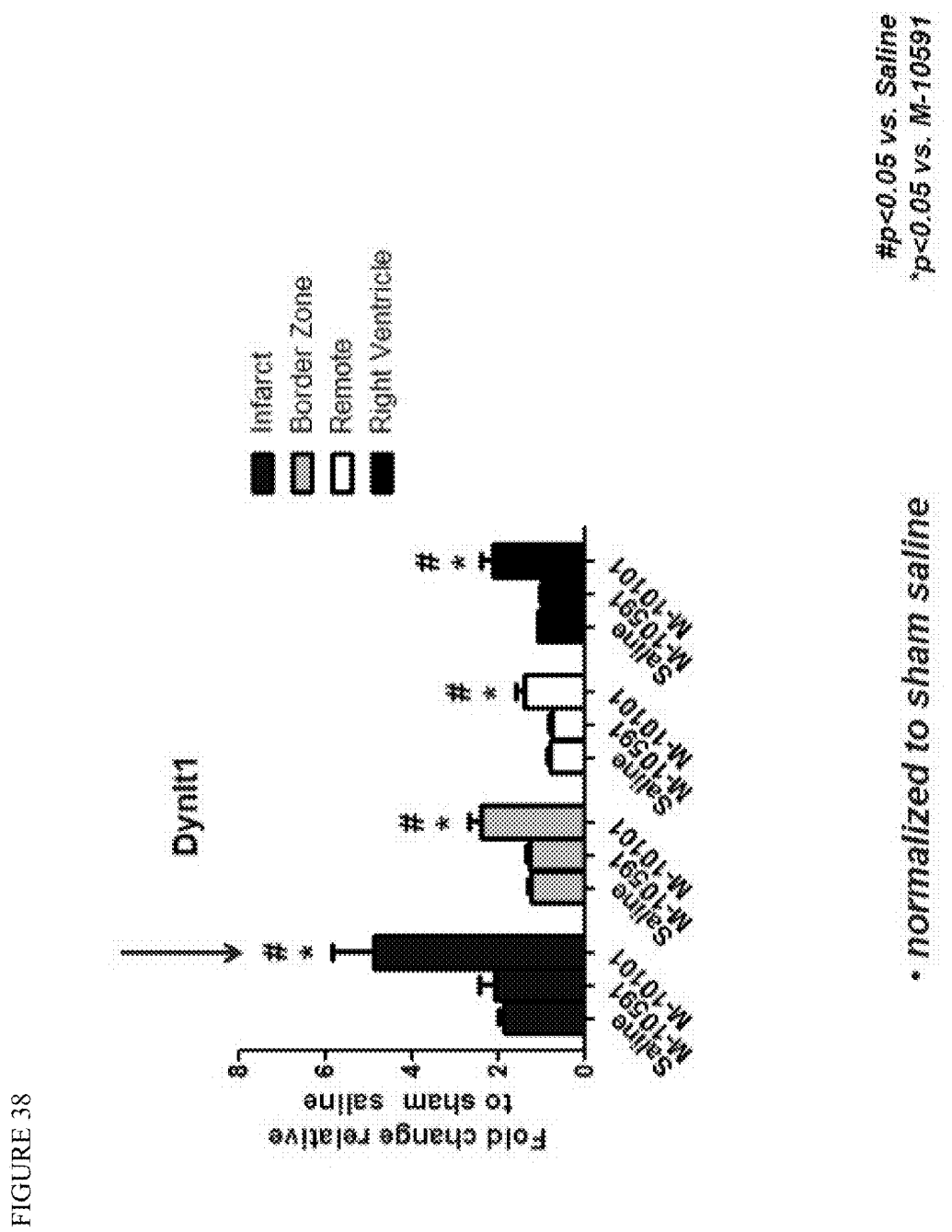
FIG. 38. Degree of Dynit1 de-repression in different regions of the heart upon atimiR-208a treatment, showing that more stressed regions show greater effect.
Figure 39:
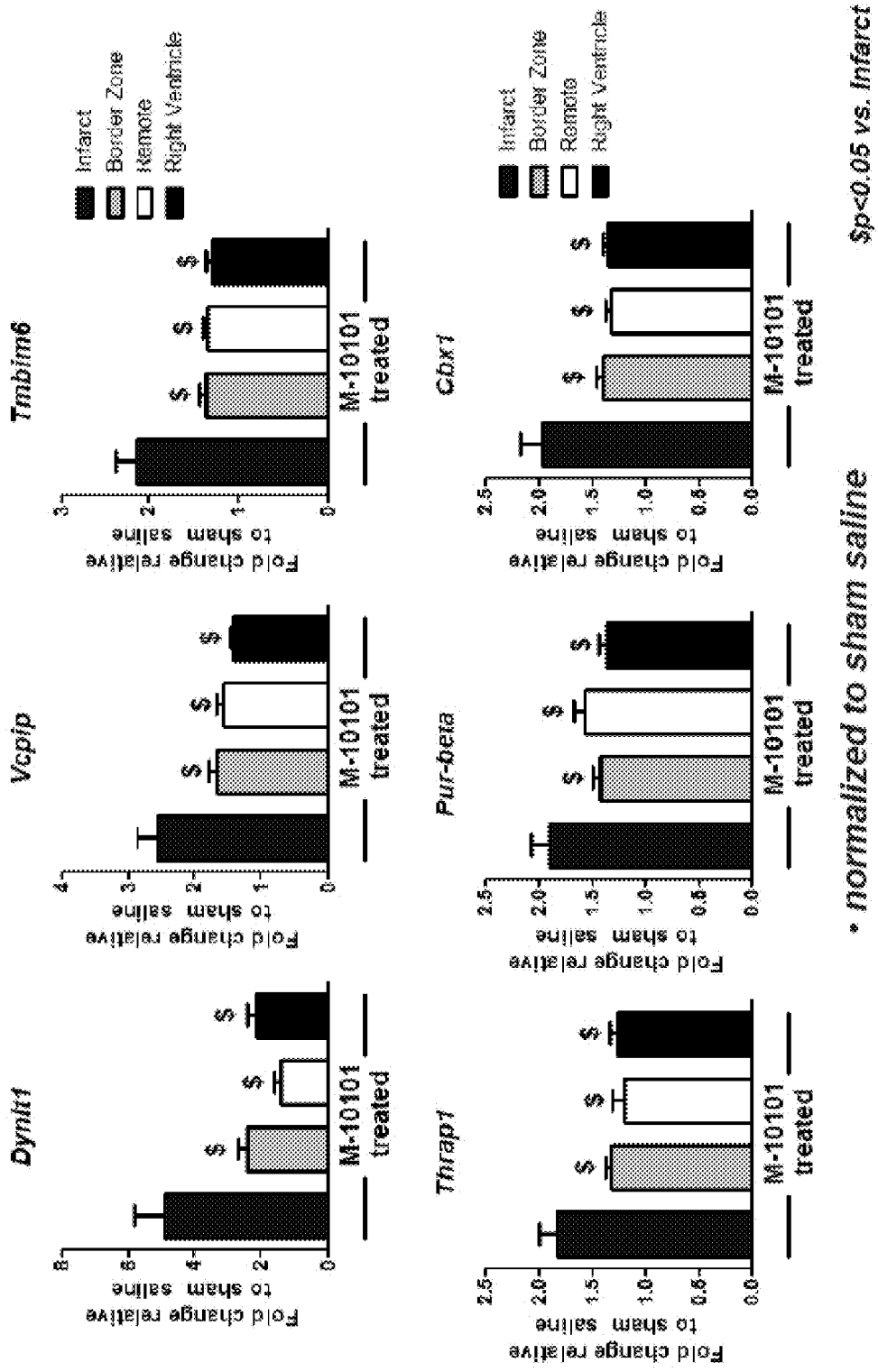
FIG. 39. Degree of target de-repression in different regions of the heart upon atimiR-208a treatment, showing that more stressed regions show greater effect.

FIGS. 33 to 39 show degrees of miR inhibition in different regions of the heart, showing that more stressed regions show greater effect. FIG. 33 shows inhibition of miR-208a, miR-208b, and miR-499. FIG. 34 shows de-repression of myosin markers. FIG. 35 shows degree of expression of certain cardiac stress markers. FIG. 36 shows de-repression of Dynit1, Vcpip, Tmbim6 and Cbx1. FIG. 37 shows expression of Thrap1, Sox6, Sp3, and pur-beta. As shown in FIG. 38, the infarted area showed the greatest de-repression of Dynit1. FIG. 39 shows the de-repression of targets in different regions of the heart with M-10101.

REFERENCES

1. Hill, J. A. & Olson, E. N. Cardiac plasticity. *N Engl J Med* 358, 1370-1380 (2008).
2. Frey, N., Katus, H. A., Olson, E. N. & Hill, J. A. Hypertrophy of the heart: a new therapeutic target? *Circulation* 109, 1580-1589 (2004).
3. Fatkin, D., et al. An abnormal Ca(2+) response in mutant sarcomere protein-mediated familial hypertrophic cardiomyopathy. *J Clin Invest* 106, 1351-1359 (2000).
4. Gupta, M. P. Factors controlling cardiac myosin-isoform shift during hypertrophy and heart failure. *J Mol Cell Cardiol* 43, 388-403 (2007).
5. Vanderheyden, M., et al. Myocardial gene expression in heart failure patients treated with cardiac resynchronization therapy responders versus nonresponders. *J Am Coll Cardiol* 51, 129-136 (2008).
6. Lowes, B. D., et al. Changes in gene expression in the intact human heart. Downregulation of alpha-myosin heavy chain in hypertrophied, failing ventricular myocardium. *J Clin Invest* 100, 2315-2324 (1997).
7. Miyata, S., Minobe, W., Bristow, M. R. & Leinwand, L. A. Myosin heavy chain isoform expression in the failing and nonfailing human heart. *Circ Res* 86, 386-390 (2000).
8. Stelzer, J. E., Brickson, S. L., Locher, M. R. & Moss, R. L. Role of myosin heavy chain composition in the stretch activation response of rat myocardium. *J Physiol* 579, 161-173 (2007).
9. van Rooij, E., et al. A signature pattern of stress-responsive microRNAs that can evoke cardiac hypertrophy and heart failure. *Proc Natl Acad Sci USA* 103, 18255-18260 (2006).
10. van Rooij, E., et al. Dysregulation of microRNAs after myocardial infarction reveals a role of miR-29 in cardiac fibrosis. *Proc Natl Acad Sci USA* 105, 13027-13032 (2008).
11. Montgomery, R. L. & van Rooij, E. MicroRNA regulation as a therapeutic strategy for cardiovascular disease. *Curr Drug Targets* 11, 936-942 (2010).
12. van Rooij, E., et al. Control of stress-dependent cardiac growth and gene expression by a microRNA. *Science* 316, 575-579 (2007).
13. Callis, T. E., et al. MicroRNA-208a is a regulator of cardiac hypertrophy and conduction in mice. *J Clin Invest* 119, 2772-2786 (2009).
14. McGuigan, K., Phillips, P. C. & Postlethwait, J. H. Evolution of sarcomeric myosin heavy chain genes: evidence from fish. *Mol Biol Evol* 21, 1042-1056 (2004).
15. Berezikov, E., et al. Diversity of microRNAs in human and chimpanzee brain. *Nat Genet* 38, 1375-1377 (2006).
16. Landgraf, P., et al. A mammalian microRNA expression atlas based on small RNA library sequencing. *Cell* 129, 1401-1414 (2007).

17. van Rooij, E., Liu, N. & Olson, E. N. MicroRNAs flex their muscles. *Trends Genet* 24, 159-166 (2008).
18. van Rooij, E., et al. A family of microRNAs encoded by myosin genes governs myosin expression and muscle performance. *Dev Cell* 17, 662-673 (2009).
19. Elmen, J., et al. LNA-mediated microRNA silencing in non-human primates. *Nature* 452, 896-899 (2008).
20. Elmen, J., et al. Antagonism of microRNA-122 in mice by systemically administered LNA-antimiR leads to up-regulation of a large set of predicted target mRNAs in the liver. *Nucleic Acids Res* 36, 1153-1162 (2008).
21. Krutzfeldt, J., et al. Specificity, duplex degradation and subcellular localization of antagomirs. *Nucleic Acids Res* 35, 2885-2892 (2007).
22. Krutzfeldt, J., et al. Silencing of microRNAs in vivo with 'antagomirs'. *Nature* 438, 685-689 (2005).
23. Lanford, R. E., et al. Therapeutic silencing of microRNA-122 in primates with chronic hepatitis C virus infection. *Science* 327, 198-201 (2010).
24. Tijsen, A. J., et al. MiR423-5p as a circulating biomarker for heart failure. *Circ Res* 106, 1035-1039 (2010).
25. Petersen, M. & Wengel, J. LNA: a versatile tool for therapeutics and genomics. *Trends Biotechnol* 21, 74-81 (2003).
26. Adachi, T., et al. Plasma microRNA 499 as a biomarker of acute myocardial infarction. *Clin Chem* 56, 1183-1185 (2010).
27. D'Alessandra, Y., et al. Circulating microRNAs are new and sensitive biomarkers of myocardial infarction. *Eur Heart J* (2010).
28. Ji, X., et al. Plasma miR-208 as a biomarker of myocardial injury. *Clin Chem* 55, 1944-1949 (2009).
29. Hamalainen, N. & Pette, D. Patterns of myosin isoforms in mammalian skeletal muscle fibres. *Microsc Res Tech* 30, 381-389 (1995).
30. Shelton, J. M., Lee, M. H., Richardson, J. A. & Patel, S. B. Microsomal triglyceride transfer protein expression during mouse development. *J Lipid Res* 41, 532-537 (2000).

---

The invention claimed is:

1. An oligonucleotide comprising an inhibitor nucleotide sequence that is complementary to a nucleotide sequence of human miR-208a or miR-208b, and having a mix of locked and non-locked nucleotides, wherein the inhibitor nucleotide sequence consists essentially of 5'-CTTTTTGCTCGTCTTA-3'(SEQ ID NO: 3) or 5'-CCTTTTGTTCGTCTTA-3' (SEQ ID NO: 4), and at least positions 1, 5, 6, 8, 10, 11, 13, 15, and 16 of SEQ ID NO: 3 or SEQ ID NO: 4 are locked nucleotides, with remaining positions being non-locked nucleotides.

2. The oligonucleotide of claim 1, wherein the oligonucleotide does not contain a stretch of nucleotides with more than three contiguous non-locked nucleotides.

3. The oligonucleotide of claim 2, wherein the oligonucleotide has exactly one occurrence of contiguous non-locked nucleotides.

4. The oligonucleotide of claim 1, containing nine locked nucleotides and seven non-locked nucleotides.

5. The oligonucleotide of claim 1, wherein the nucleotides not in a locked configuration are 2' deoxy.

6. The oligonucleotide of claim 1, wherein at least one non-locked nucleotide is 2' O-alkyl or 2' halo.

7. The oligonucleotide of claim 1, wherein the locked nucleotides have a 2' to 4' methylene bridge.

8. The oligonucleotide of claim 1, containing one or more phosphorothioate linkages.

9. The oligonucleotide of claim 8, wherein the oligonucleotide is fully phosphorothioate-linked.

10. The oligonucleotide of claim 8, having from one to three phosphate linkages.

11. The oligonucleotide of claim 1, having the structure of Compound 10101 or 10707.

12. The oligonucleotide of claim 1, further comprising a pendent lipophilic group.

13. A pharmaceutical composition comprising an effective amount of the oligonucleotide of claim 1, or a pharmaceutically-acceptable salt thereof, and a pharmaceutically-acceptable carrier or diluent.

* * * * *